US010206952B2

(12) United States Patent
Turner et al.

(10) Patent No.: US 10,206,952 B2
(45) Date of Patent: *Feb. 19, 2019

(54) ENHANCED RECONSTITUTION AND AUTORECONSTITUTION OF THE HEMATOPOIETIC COMPARTMENT

(71) Applicant: Taiga Biotechnologies, Inc., Aurora, CO (US)

(72) Inventors: Brian C. Turner, Aurora, CO (US); Yosef Refaeli, Aurora, CO (US); Gregory Alan Bird, Aurora, CO (US)

(73) Assignee: TAIGA BIOTECHNOLOGIES, INC., Aurora, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/785,000

(22) Filed: Oct. 16, 2017

(65) Prior Publication Data
US 2018/0117089 A1 May 3, 2018

Related U.S. Application Data

(63) Continuation of application No. 14/415,325, filed as application No. PCT/US2013/051384 on Jul. 19, 2013, now Pat. No. 9,789,135.

(60) Provisional application No. 61/674,224, filed on Jul. 20, 2012, provisional application No. 61/785,691, filed on Mar. 14, 2013.

(51) Int. Cl.
A61K 35/12 (2015.01)
A61K 35/14 (2015.01)
A61K 35/28 (2015.01)
A61K 38/17 (2006.01)
C07K 14/47 (2006.01)
C12N 5/074 (2010.01)
C12N 5/078 (2010.01)
C12N 5/0789 (2010.01)
C07K 14/82 (2006.01)

(52) U.S. Cl.
CPC .......... A61K 35/28 (2013.01); A61K 38/1709 (2013.01); A61K 38/1761 (2013.01); C07K 14/4747 (2013.01); C07K 14/82 (2013.01); C12N 5/0647 (2013.01); A61K 35/12 (2013.01); A61K 35/14 (2013.01); A61K 38/17 (2013.01); A61K 2035/124 (2013.01); C07K 2319/10 (2013.01); C07K 2319/21 (2013.01); C07K 2319/40 (2013.01); C12N 5/0634 (2013.01); C12N 2501/60 (2013.01); C12N 2501/606 (2013.01)

(58) Field of Classification Search
CPC .... A61K 2300/00; A61K 35/28; A61K 28/16; A61K 38/17; A61K 2035/124; C12N 5/0647; C12N 5/0634; C07K 14/4747; C07K 14/47
See application file for complete search history.

(56) References Cited

U.S. PATENT DOCUMENTS

| 4,963,489 A | 10/1990 | Naughton et al. |
| 5,476,996 A | 12/1995 | Wilson et al. |
| 5,652,122 A | 7/1997 | Frankel et al. |
| 5,674,980 A | 10/1997 | Frankel et al. |
| 5,698,767 A | 12/1997 | Wilson et al. |
| 5,811,301 A | 9/1998 | Cameron |
| 5,824,837 A | 10/1998 | Chen et al. |
| 5,847,082 A | 12/1998 | Rother et al. |
| 5,849,288 A | 12/1998 | Reisner |
| 6,358,739 B1 | 3/2002 | Baetge et al. |
| 6,451,558 B1 | 9/2002 | Cooke et al. |
| 6,451,601 B1 | 9/2002 | Baetge et al. |
| 6,645,501 B2 | 11/2003 | Dowdy |
| 7,135,287 B1 | 11/2006 | Lonberg et al. |
| 7,311,920 B1 | 12/2007 | Devico et al. |
| 7,582,745 B2 | 9/2009 | Sah et al. |
| 7,767,453 B2 | 8/2010 | Zhang |
| 8,481,492 B2 | 7/2013 | Edenhofer et al. |
| 8,784,825 B2 | 7/2014 | Refaeli et al. |
| 8,828,723 B2 | 9/2014 | Refaeli et al. |
| 9,150,831 B2 | 10/2015 | Cambier et al. |
| 9,365,825 B2 | 6/2016 | Turner et al. |
| 9,789,135 B2 * | 10/2017 | Turner ................. C12N 5/0647 |
| 2001/0049393 A1 | 12/2001 | Coller et al. |

(Continued)

FOREIGN PATENT DOCUMENTS

| AU | 2762802 | 5/2002 |
| AU | 2006304392 B2 | 5/2014 |

(Continued)

OTHER PUBLICATIONS

Non-Final Office Action on U.S. Appl. No. 15/179,735, dated Feb. 26, 2018.
Examination Report issued on EP Application 13820331.0, dated Apr. 24, 2018.
Examination Report issued on EP Application 14778538.0, dated Apr. 16, 2018.
Non-Final Office Action on U.S. Appl. No. 13/797,648, dated Apr. 19, 2018, includes Accession NP 002458.2, 2018.
Aubry et al., "N-Myc Shares Cellular Functions with c-Myc", DNA and Cell Biology, vol. 19, No. 6, Jun. 2000, pp. 353-364.

(Continued)

Primary Examiner — Bridget E Bunner
(74) Attorney, Agent, or Firm — Foley & Lardner LLP

(57) ABSTRACT

The present disclosure relates to the acceleration of hematopoietic compartment reconstitution in a subject in need of hematopoietic stem cell transplantation by administering a composition having a protein transduction domain-MYC (PTD-MYC) fusion protein in combination with hematopoietic stem cell transplantation and to the enhancement of hematopoietic compartment autoreconstitution in a subject in need thereof by administering a composition having a protein transduction domain-MYC (PTD-MYC) fusion protein.

20 Claims, 37 Drawing Sheets
Specification includes a Sequence Listing.

(56) References Cited

U.S. PATENT DOCUMENTS

| | | |
|---|---|---|
| 2002/0076787 A1 | 6/2002 | Baetge et al. |
| 2002/0098166 A1 | 7/2002 | Havemann et al. |
| 2002/0155502 A1 | 10/2002 | Balint et al. |
| 2003/0072794 A1 | 4/2003 | Boulikas |
| 2003/0138859 A1 | 7/2003 | Barbera-Guillem et al. |
| 2003/0220286 A1 | 11/2003 | Abruzzese et al. |
| 2005/0220705 A1 | 10/2005 | Brooks et al. |
| 2005/0281816 A1 | 12/2005 | Lamping et al. |
| 2006/0068469 A1 | 3/2006 | Payne et al. |
| 2006/0115898 A1 | 6/2006 | Zhang et al. |
| 2006/0154331 A1 | 7/2006 | Avidan et al. |
| 2006/0156422 A1 | 7/2006 | Dalrymple et al. |
| 2007/0011753 A1 | 1/2007 | Ito et al. |
| 2007/0047583 A1 | 3/2007 | Assa et al. |
| 2007/0067854 A1 | 3/2007 | Habu et al. |
| 2007/0093420 A1 | 4/2007 | Yeomans et al. |
| 2007/0098715 A1 | 5/2007 | Ettenberg et al. |
| 2007/0116691 A1 | 5/2007 | Cambier et al. |
| 2007/0130628 A1 | 6/2007 | Brown |
| 2007/0248618 A1 | 10/2007 | Cohen |
| 2009/0291094 A1 | 11/2009 | Refaeli et al. |
| 2010/0047217 A1 | 2/2010 | Refaeli et al. |
| 2010/0055129 A1 | 3/2010 | Refaeli et al. |
| 2010/0233804 A1 | 9/2010 | Zhou et al. |
| 2010/0279351 A1 | 11/2010 | Refaeli |
| 2010/0297763 A1 | 11/2010 | Cambier et al. |
| 2011/0218210 A1 | 9/2011 | Refaeli et al. |

FOREIGN PATENT DOCUMENTS

| | | |
|---|---|---|
| CN | 1357620 | 7/2002 |
| EP | 1 103 615 A1 | 5/2001 |
| EP | 1 357 184 | 10/2003 |
| EP | 1 792 627 | 6/2007 |
| GB | 2 387 599 | 10/2003 |
| JP | 2000-189157 | 7/2000 |
| JP | 2001-518300 | 10/2001 |
| JP | 2002-541786 | 12/2002 |
| JP | 2003-513672 | 4/2003 |
| JP | 2003-514565 | 4/2003 |
| JP | 2004-519245 | 7/2004 |
| JP | 2005-523012 | 8/2005 |
| JP | 2005-525085 | 8/2005 |
| JP | 2005-527211 | 9/2005 |
| JP | 2009-511081 | 3/2009 |
| WO | WO-94/04686 | 3/1994 |
| WO | WO-94/19465 | 9/1994 |
| WO | WO-95/14078 | 5/1995 |
| WO | WO-98/10058 | 3/1998 |
| WO | WO-98/52614 | 11/1998 |
| WO | WO-99/16884 | 4/1999 |
| WO | WO-99/45962 | 9/1999 |
| WO | WO-99/53023 | 10/1999 |
| WO | WO-99/53028 | 10/1999 |
| WO | WO-00/09669 | 2/2000 |
| WO | WO-00/61617 | 10/2000 |
| WO | WO-00/62067 | 10/2000 |
| WO | WO-01/34824 | 5/2001 |
| WO | WO-01/38548 | 5/2001 |
| WO | WO-02/057436 | 7/2002 |
| WO | WO-02/074968 | 9/2002 |
| WO | WO-03/033701 | 4/2003 |
| WO | WO-03/038057 | 5/2003 |
| WO | WO-03/039462 | 5/2003 |
| WO | WO-03/089580 | 10/2003 |
| WO | WO-03/089630 | 10/2003 |
| WO | WO-03/094849 | 11/2003 |
| WO | WO-03/097675 | 11/2003 |
| WO | WO-2004/035535 | 4/2004 |
| WO | WO-2004/050885 | 6/2004 |
| WO | WO-2004/084805 | 10/2004 |
| WO | WO-2005/014785 | 2/2005 |
| WO | WO-2005/084158 | 9/2005 |
| WO | WO-2006/032876 | 3/2006 |
| WO | WO-2006/116512 | 11/2006 |
| WO | WO-2007/047583 | 4/2007 |
| WO | WO-2007/067183 | 6/2007 |
| WO | WO-2008/112922 | 9/2008 |
| WO | WO-2009/059304 | 5/2009 |
| WO | WO-2009/139930 A2 | 11/2009 |
| WO | WO-2010/011644 | 1/2010 |
| WO | WO-2010/025421 | 3/2010 |
| WO | WO-2012/055170 | 5/2012 |
| WO | WO-2014/164606 | 10/2014 |

OTHER PUBLICATIONS

Austrian Search Report and Written Opinion received for Singapore Patent Application No. 2011013679, dated Mar. 23, 2012, 17 pages.

Baum, Christopher, "Insertional Mutagenesis in Gene Therapy and Stem Cell Biology", Current Opinion in Hematology, vol. 14, Jul. 2007, pp. 337-342.

Beerens et al., "Protein Transduction Domains and their Utility in Gene Therapy", Current Gene Therapy, vol. 3, No. 5, 2003, pp. 486-494.

Benassayag et al., "Human c-Myc Isoforms Differentially Regulate Cell Growth and Apoptosis in *Drosophila melanogaster*," Molecular and Cellular Biology 25(22): 9897-9909 (2005).

Berkson et al., "Pilot Screening Programme for Small Molecule Activators of p53", International Journal of Cancer, vol. 115, 2005, pp. 701-710.

Bird et al., Expansion of Human and Murine Hematopoietic Stem and Progenitor Cells Ex Vivo without Genetic Modification Using MYC and Bcl-2 Fusion Proteins, PLOS ONE, vol. 9, No. 8, Aug. 29, 2014 p. 20 pages.

Bissonnette et al., "Apoptotic cell death induced by c-myc is inhibited by bc1-2," Nature, vol. 359, Oct. 8, 1992, pp. 552-554.

Bouchard et al., "Control of cell proliferation by Myc", Trends in Cell Biology, vol. 8, pp. 202-206, (1998).

Bunting et al., "Restoration of lymphocyte function in Janus kinase 3-deficient mice by retro-viral-mediated gene transfer," Nature Medicine 4:58-64 (1998).

Buske et al., "Deregulated Expression of HOXB4 Enhances the Primitive Growth Activity of Human Hematopoietic Cells", Blood, vol. 100, No. 3, Aug. 1, 2002, pp. 862-868.

Capecchi, Mario R., "Altering the Genome by Homologous Recombination", Science, vol. 244, No. 4910, Jun. 16, 1989, pp. 1288-1292.

Caron, et al., "Endosome disruption enhances the functional nuclear delivery of Tat-fusion proteins", Biochem Biophys Res Commun, (2004), vol. 319, pp. 12-20.

Carotta et al., "Directed Differentiation and Mass Cultivation of Pure Erythorid Progenitors from Mouse Embryonic Stem Cells", Blood, vol. 104, No. 6, Sep. 15, 2004, pp. 1873-1880.

Chadwick, et al., "Notch Signaling Induces Apoptosis in Primary Human CD34 Hematopoietic Progenitor Cells", Stem Cells, (2007), vol. 24, pp. 203-210.

Chen et al., "Small-Molecule Anthracene-Induced Cytotoxicity and Induction of Apoptosis through Generation of Reactive Oxygen Species", Biological & Pharmaceutical Bulletin, vol. 27, No. 6, Jun. 2004, pp. 838-845.

Cheng et al., "BCL-2, BCL-XL, Sequester BH3 Domain-Only Molecules Preventing BAX- and BAK-Mediated Mitochondrial Apoptosis", Molecular Cell (2001) vol. 8, pp. 705-711.

Chin et al., "Essential Role for Oncogenic Ras in Tumour Maintenance", Nature, vol. 400, 1999, pp. 468-472.

Chinese 3rd Office Action dated Nov. 28, 2016 in Chinese Patent Application No. 201410168106.2.

Choi et al., "Myc Protein is Stabilized by Suppression of a Novel E3 Ligase Complex in Cancer Cells", Genes & Development, vol. 24, 2010, pp. 1236-1241.

Choi, et al., "Status Epilepticus-Induced Somatostatinergic Hilar Interneuron Degeneration Is Regulated by Striatal Enriched Protein Tyrosine Phosphatase", Journal of Neuroscience, (2007), vol. 27, No. 11, pp. 2999-3009.

Coeytaux et al., "The Cationic Amphipathic alpha-Helix of HIV-1 Viral Protein R (Vpr) Binds to Nucleic Acids, Permeabilizes Membranes, and Efficiently Transfects Cells," The Journal of Biological Chemistry, vol. 278, No. 20, May 16, 2003, pp. 18110-18116.

(56) References Cited

OTHER PUBLICATIONS

Coller, et al., "Expression Analysis with Oligonucleotide Microarrays Reveals that MYC Regulates Genes Involved in Growth, Cell Cycle, Signaling, and Adhesion", PNAS, (2000), 97(7):3260-3265.
Communication issued on EP Application 09747016.5, dated Jun. 12, 2017.
Conti, et al., "Gene therapy using neural stem cells," Methods Mol. Biol. 198:233-244 (2002).
Coppola et al., "Constitutive c-myc oncogene expression blocks mouse erythroleukaemia cell differentiation but not commitment," Nature, vol. 320, Apr. 24, 1986, pp. 760-763.
D'Alessandro et al, "Red blood cell storage: the story so far," Blood Transfus, Mar. 29, 2010, pp. 82-88.
Dang et al., "Identification of the Human c-myc Protein Nuclear Translocation Signal", Molecular and Cellular Biology, vol. 8, No. 10, Oct. 1988, pp. 4048-4054.
Dang et al., "Nuclear and Nucleolar Targeting Sequences of c-erb-A, c-myb, N-myc, p53, HSP70 and HIV tat Proteins". Journal of Biological Chemistry, vol. 264, No. 30, pp. 18019-18023 (1989).
Dang, Chi V., "c-Myc Target Genes Involved in Cell Growth, Apoptosis, and Metabolism", Molecular and Cellular Biology, vol. 19, No. 1, Jan. 1999, pp. 1-11.
Daugas et al, "Erythrocytes: Death of a Mummy," Cell Death and Differentiation, vol. 8, 2001, pp. 1131-1133.
Decision of Rejection issued on Japanese application 2014-108137, dated Jun. 2, 2016, English translation only.
Delgado et al., "Myc Roles in Hematopoiesis and Leukemia," Genes and Cancer, 2010, pp. 605-616.
Deocampo, et al., "Cooperation of BCL-2 and MYC in the Neoplastic Transformation of Normal Rat Lever Epithelial Cells is Related to the Down-Regulation of Gap Junction-Mediated Intercellular Communication", Carcinogenesis, vol. 21, No. 8, pp. 1501-1506,(2000).
Dmitrovsky et al., "A Transfected c-myc Oncogene Inhibits Mouse Erytholeukemic Differentiation," Current Topics in Microbiology and Immunology, vol. 132, 1986, 4 pages.
Domashenko et al., "TAT-mediated transduction of NF-Ya peptide induces the ex vivo proliferation and egraftment potential of human hematopoietic progenitor cells," Blood, Oct. 14, 2010, vol. 116, No. 15, pp. 2676-2683.
Dvorak et al., "Cytochemical Localization of Peroxidase Activity in the Developing Erythrocyte," Am. J. Pathol. 1972, 67(2), pp. 303-326.
Eilers, et al., "Chimeras of MYC Oncoprotein and Steroid Receptors Cause Hormone-Dependent Transformation of Cells," Nature 340(6228):66-68 (1989).
Eischen, et al., "Apoptosis Triggered by Myc-Induced Suppression of Bcl-XL or Bcl-2 Is Bypassed during Lymphomagenesis", Molecular Cell Biology, 2001, 21: 5063-5070.
English Translation of Decision of Rejection on Japanese Application No. 2011-520133, dated Nov. 26, 2014, 6 pages.
English Translation of Decision of Rejection on Japanese Application No. 2011-525258, dated Dec. 3, 2014, 11 pages.
English Translation of Fourth Office Action received for Chinese Patent Application No. 200880015602.7 dated Nov. 11, 2013, 6 pages.
English Translation of Notification of Reasons of Refusal for Japanese Patent Application No. 2012-221023 dated Jun. 24, 2014, 2 pages.
English Translation of Office Action on Chinese Appl. No. 200980127166.7 dated Apr. 11, 2014, 3 pages.
English Translation of Office Action on Israeli Application No. 208810 dated Jan. 13, 2015, 3 pages.
English Translation of Office Action on Israeli Application No. 232432 dated Mar. 8, 2015, 3 pages.
English Translation of Office Action on Israeli Patent Application No. 200919 dated May 19, 2014, 3 pages.
English Translation of Office Action on Japanese Patent Application. No. 2012-221023 dated Apr. 22, 2014, 3 pages.
English Translation of Office Action on Korean Patent Application No. 10-2013-7020078 dated Sep. 17, 2014, 5 pages.
English Translation of Office Action received for Chinese Patent Application No. 200980126312.4 dated Jan. 22, 2014, 3 pages.
English Translation of Office Action received for Eurasian Patent Application No. 201001762/28, dated Oct. 16, 2013, 1 page.
English translation of Office Action received for Israeli Patent Application No. 190946, dated Apr. 22, 2013, 1 page.
English Translation of Office Action received for Israeli Patent Application No. 209968 dated Jan. 2, 2014, 2 pages.
English translation of Office Action received for Japanese Application No. 2008-536713 dated Aug. 5, 2013, 2 pages.
English Translation of Office Action received for Japanese Patent Application No. 2011-525258 dated Feb. 17, 2014, 4 pages.
English Translation of Office Action received for Korean Patent Application No. 10-2008-7011791 dated Jan. 15, 2014, 3 pages.
English Translation of Office Action received for Korean Patent Application No. 10-2013-7028338, dated Jan. 15, 2014, 3 pages.
English Translation of Second Office Action received for Chinese Patent Application No. 200980127166.7, dated Jun. 10, 2013, 1 page.
English Translation of the Third Office Action on Chinese Patent Application No. 200680045545.8 dated Feb. 15, 2015, 4 pages.
English Translation of Third Office Action on Japanese Patent Application No. 2009-553785 dated Apr. 22, 2014, 3 pages.
Esdar, C., et al., "Differentiation-associated apoptosis of neural stem cells is effected by Bcl-2 overexpression: impact on cell lineage determination," Eur. J. Cell Biol.,(2001), vol. 80, No. 8, pp. 539-553.
Exam Report issued on European Application 14779483.8, dated Oct. 16, 2017.
Examination Report for Indian Patent Application No. 3332/DELNP/2008 dated Aug. 23, 2013, 6 pages.
Examination Report issued on Australian Application 2013292330, dated Sep. 6, 2017.
Examination Report issued on Australian Application 2015205879, dated Mar. 15, 2016.
Examination Report issued on Australian Application 2016203892, dated Apr. 12, 2017.
Examination Report issued on EP Application 09747016.5, dated Jul. 26, 2016.
Examination Report issued on EP Application 15175802.6, dated Jan. 31, 2017.
Examination Report issued on Indian Application 2048/DELNP/2011, dated Sep. 15, 2016.
Examination Report issued on Indian Application 634/DELNP/2011, dated Jun. 8, 2017.
Examination Report issued on Indian Application 9033/DELNP/2010, dated May 19, 2017.
Examination Report No. 1 on Australian Application No. 2014202016 dated May 12, 2015, 3 pages.
Examination Report on Australian application 2009274172, dated Jul. 24, 2014, 3 pages.
Examination Report on Australian Patent Application No. 2012216462 dated Mar. 6, 2014, 3 pages.
Examination Report on Canadian Application 2,731,767, dated Sep. 5, 2014, 2 pages.
Examination Report on Canadian Application No. 2,735,522 dated Oct. 2, 2014, 2 pages.
Examination Report on European Application No. 09747016.5 dated Mar. 19, 2015, 5 pages.
Examiner's Report on Canadian Application No. 2680613 dated Nov. 28, 2014, 4 pages.
Examiner's Report on Canadian Application No. 2723114 dated Apr. 21, 2015, 4 pages.
Examiner's Report on European Application No. 12187097.6 dated Jan. 22, 2015, 6 pages.
Extended European Search Report and Search Opinion received for Patent Application No. 12187097.6, dated Mar. 27, 2013, 8 pages.
Extended European Search Report for EP Patent Application No. 13188850.0, dated May 27, 2014, 8 pages.
Extended European Search Report received for European Patent Application No. 09810692.5, dated Jul. 11, 2011, 5 pages.

(56) References Cited

OTHER PUBLICATIONS

Extended European Search Report received for European Patent Application No. 06826025.6, dated Aug. 13, 2009, 8 pages.
Extended European Search Report received for European Patent Application No. 09747016.5, dated May 30, 2012, 8 pages.
Extended European Search Report received for European Patent Application No. 09800871. 7, dated Jun. 24, 2011, 5 pages.
Extended European Search Report received for European Patent Application No. 12187077.8, dated Mar. 25, 2013, 7 pages.
Extended Search Report issued on EP Application 13820331.0, dated Nov. 10, 2016.
Extended Search Report issued on European Application 14778538. 0, dated Sep. 29, 2016.
Extended Search Report issued on European Application 14779483. 8, dated Dec. 23, 2016.
Extended Search Report issued on European Patent Application 15175802.6, dated Dec. 14, 2015.
Fanidi et al., "Cooperative interaction between c-myc and bcl-2 proto-oncogenes," Nature, vol. 359, Oct. 8, 1992, pp. 554-556.
Felsher, et al., "Reversible Tumorigenesis by MYC in Hematopoietic Lineages", (1999), Molecular Cell, 4: 199-207.
Final Office Action on U.S. Appl. No. 12/467,957, dated Sep. 17, 2014, 9 pages.
Final Office Action on U.S. Appl. No. 12/506,894 dated Oct. 9, 2014, 15 pages.
Final Office Action on U.S. Appl. No. 13/797,648 dated Feb. 8, 2017.
Final Office Action on U.S. Appl. No. 14/461,105 dated Sep. 15, 2016.
Final Office Action on U.S. Appl. No. 14/509,870 dated Feb. 3, 2017.
Final Office Action on U.S. Appl. No. 14/873,296, dated Jan. 24, 2018.
Final Office Action on U.S. Appl. No. 12/701,383 dated Nov. 13, 2014, 18 pages.
Final Office Action on U.S. Appl. No. 13/795,659 dated Jul. 11, 2014, 16 pages.
Final Office Action on U.S. Appl. No. 13/795,659 dated Mar. 26, 2015, 18 pages.
Final Office Action on U.S. Appl. No. 13/797,648 dated Apr. 1, 2015, 12 pages.
Final Office Action on U.S. Appl. No. 11/583,970 dated Apr. 9, 2014, 20 pages.
Final Office Action received for Korean Patent Application No. 10-2009-7021320, dated May 29, 2013, 6 pages (3 pages of English Translation and 3 pages of Office Action).
Final Office Action received for U.S. Appl. No. 11/583,970, dated Nov. 17, 2011, 15 pages.
Final Office Action received for U.S. Appl. No. 12/701,383 , dated Nov. 16, 2011, 13 pages.
Final Office Action received for U.S. Appl. No. 11/583,970, dated Nov. 26, 2008, 13 pages.
Final Office Action received for U.S. Appl. No. 12/048,148, dated Feb. 15, 2013, 17 pages.
Final Office Action received for U.S. Appl. No. 12/467,957 dated Feb. 28, 2011, 8 pages.
Final Office Action received for U.S. Appl. No. 12/550,166, dated May 11, 2012, 12 pages.
Final Office Action received on U.S. Appl. No. 11/583,970, dated Nov. 4, 2009, 10 pages.
Final Office Action Response filed for U.S. Appl. No. 11/583,970, dated Feb. 4, 2010, 10 pages.
Final Office Action Response filed for U.S. Appl. No. 11/583,970, dated Feb. 16, 2012, 14 pages.
First Office Action issued on Chinese Application 201410479685.2, dated Nov. 17, 2015.
Futaki, Chemistry and Biology (Kagaku to Seibutsu), vol. 43, No. 10, Oct. 1, 2005, p. 649-653 (English translation not available).

Gandarillas et al., "C-Myc promotes differentiation of human epidermal stem cells," Genes & Development, vol. 11, 1997, pp. 2869-2882.
Gauss et al., "DEAE-Dextran Enhances Electroportation of Mammalian Cells", Nucleic Acids Research, vol. 20, No. 4, pp. 6739-6740 (1992).
Grumont et al., "The Mitogen-Induced Increase in T Cell Size Involves PKC and NFAT Activation of Rel/NF-kB-Dependent c-myc Expression," Immunity, 2004, vol. 21, p. 19-30.
Guzman et al., "Preferential induction of apoptosis for primary human leukemic stem cells," PNAS 99(25):16220-16225 (2002).
Habib et al., "Myc Stimulates B Lymphocyte Differentiation and Amplifies Calcium Signaling", J.Cell Biol., vol. 179, No. 4, 2007, pp. 717-731.
Hann et al., "Proteins Encoded by the Human C-Myc Oncogene: Differential Expression in Neoplastic Cells", Mol. Cell. Biol., vol. 4, No. 11, Nov. 1984, pp. 2486-2497.
Hiramatsu et al., "Complete Reconstitution of Human Lymphocytes from Cord Blood CD34 Cells Using the NOD/SCID/ycnull Mice Model", Blood, vol. 102, No. 3, 2003, pp. 873-880.
Ho, et al., "Synthetic Protein Transduction Domains: Enhanced Transduction Potential in Vitro and in Vivo", Cancer Research, (2001), vol. 61, pp. 474-477.
Hoffman, "Progress in the develoment of systems for in vitro expansion of human hematopoietic stem cells," Curr. Op. Hematology 6(3): 14 pages (1999).
Horton, S.J. et al., "Continuous MLL-ENL expression is necessary to establish a "Hox Code" and maintain immortalization of hematopoietic progenitor cells," Cancer Res. 65(20):9245-9252 (2005).
Hoshimaru, M. et al., "Differentiation of the immortalized adult neuronal progenitor cell line HC2S2 into neurons by regulatable suppression of the V-MYC oncogene," Proceedings of the National Acadamy of Sciences of USA 93(4):1518-1523 (1996).
Howard, M.J. et al., "Transplantation of apoptosis-resistant embryonic stem cells into the injured rat spinal cord," Somatosensory & Motor Research 22(1-2):37-44 (2005).
Huang et al., "Dynamic Regulation of C-Myc Proto-Oncogene Expression during Lymphocyte Development Revealed by a GFP-c-Myc Knock-In Mouse", Eur. J. Immunol., vol. 38, No. 2, 2008, pp. 342-349.
Huettner et al., "Reversibility of Acute B-Cell Leukaemia Induced by BCR-ABL 1," Nature Genetics, vol. 24, 2000, pp. 57-60.
International Preliminary Report and Written Opinion for International Application No. PCT/US2014/022971, dated Sep. 24, 2015.
International Preliminary Report on Patentability for International Application No. PCT/US2013/051384, dated Jan. 29, 2015, 12 pages.
International Preliminary Report on Patentability issued on PCT/US2014/022977, dated Sep. 15, 2015.
International Preliminary Report on Patentability received for PCT Patent Application No. PCT/US2006/040379, dated Apr. 23, 2008, 5 pages.
International Preliminary Report on Patentability received for PCT Patent Application No. PCT/US2008/056896, dated Sep. 15, 2009, 4 pages.
International Preliminary Report on Patentability received for PCT Patent Application No. PCT/US2008/082263, dated May 4, 2010, 6 pages.
International Preliminary Report on Patentability Received for PCT Patent Application No. PCT/US2009/003105, dated Nov. 17, 2010, 6 pages.
International Preliminary Report on Patentability received for PCT Patent Application No. PCT/US2009/051242, dated Jan. 25, 2011, 6 pages.
International Preliminary Report on Patentability received for PCT Patent Application No. PCT/US2009/055443, dated Mar. 1, 2011, 6 pages.
International Search Report and Written Opinion for International (PCT) Patent Application No. PCT/US06/040379, dated Sep. 24, 2007, 6 pages.

(56) References Cited

OTHER PUBLICATIONS

International Search Report and Written Opinion for International Application No. PCT/US2013/051384, dated Nov. 13, 2013, 15 pages.
International Search Report and Written Opinion for International Application No. PCT/US2014/022971 dated Aug. 13, 2014, 12 pages.
International Search Report and Written Opinion on PCT/US2014/022977, dated Aug. 28, 2014, 13 pages.
International Search Report and Written Opinion received for PCT Patent Application No. PCT/US2008/056896 dated Aug. 14, 2008, 5 pages.
International Search Report and Written Opinion received for PCT Patent Application No. PCT/US2008/082263, dated Jun. 25, 2009, 8 pages.
International Search Report and Written Opinion received for PCT Patent Application No. PCT/US2009/003105, dated Jan. 15, 2010, 9 pages.
International Search Report and Written Opinion received for PCT Patent Application No. PCT/US2009/051242, dated Feb. 19, 2010, 9 pages.
International Search Report and Written Opinion received for PCT Patent Application No. PCT/US2009/055443, dated Jun. 30, 2010, 11 pages.
Invitation to Pay Additional Fees and, Where Applicable, Protest Fee for PCT Application No. PCT/US2014/22971, dated May 27, 2014, 2 pages.
Iritani et al., "Modulation of T-lymphocyte development, growth and cell size by the Myc antagonist and transcriptional repressor Mad 1", The EMBO Journal, vol. 21, No. 18, pp. 4820-4830, 1999.
Iritani, et al., "c-Myc enhances protein synthesis and cell size during B lymphocyte development", PNAS, (1999), vol. 96, No. 23, pp. 13180-13185.
Jadlowsky, et al., "Dominant negative mutant Cyclin T1 proteins inhibit HIV transcription by specifically degrading Tat", Retrovirology, (2008), vol. 5, Article 63, 12 pages.
Jayapal et al., "Down-regulation of Myc is Essential for Terminal Erythroid Maturation" The Journal of Biological Chemistry, vol. 285, No. 51, pp. 40252-40265, Dec. 17, 2010.
Johnson, N.A. et al., "Lymphomas with concurrent BCL2 and MYC translocations: the critical factors associated with survival", Blood, 2009, vol. 114, No. 11, pp. 2273-2279.
Ju, et al., "Anti-Apoptotic Therapy with a Tat Fusion Protein Protects Against Excitotoxic Insults in Vitro and in Vivo", Experimental Neurology, vol. 210, 2008, pp. 602-607.
Karon et al., "Temporal sequence of major biochemical events during Blood Bank storage of packed red blood cells," Blood Transfus, vol. 10, 2012, pp. 453-461.
Kashio, et al., "A Protein Derived From the Fusion of TAT Peptide and FNK, a Bcl-xL Derivative, Prevents Cochlear Hair Cell Death From Aminoglycoside Ototoxicity In Vivo", Journal of Neuroscience Research, (2007), vol. 85, No. 7, pp. 1403-1412.
Kelso et al., "Survival of the Myeloid Progenitor Cell Line FDC-P1 is Prolonged by Interferon-y or Interleukin-4", Growth Factors, vol. 6, No. 3, 1992, pp. 233-242.
Kitada, et al., "Reversal of Chemoresistance of Lymphoma Cells by Antisense-Mediated Reduction of bcl-2 Gene Expression", Antisense Research and Development, (1994), vol. 4, pp. 71-79.
Korbling et al., "Allogenic Blood Stem Cell Transplantation: Peripheralization and Yield of Donor-Derived Primitive Hematopoietic Progenitor Cells (CD34+Thy-Idim) and Lymphoid Subsets, and Possible Predictors of Engraftment and Graft-Versus-Host Disease," Blood 86:2842-2848 (1995).
Krosl et al., "In vitro expansion of hematopoietic stem cells by recombinant TAT-HOXB4 protein," Nature Mediciine 9(11):1428-1432 (2003).
Lang et al., "Mechanisms and Significance of Eryptosis, the Suicidal Death of Erythorocytes," Blood Purification, vol. 33, 2012, pp. 125-130.

Levesque, J-P et al., "The endosteal 'osteoblastic' niche and its role in hematopoietic stem cell homing and mobilization", Leukemia, 2010, vol. 24, pp. 1979-1992.
Li et al., "Reconstitution of Functional Human B Lymphocytes in NOD/SCID Mice Engrafted with ex vivo Expanded CD34 Cord Blood Cells", Experimental Hematology, vol. 30, 2002, pp. 1036-1043.
Littlewood, et. al., "A modified oestrogen receptor ligand-binding domain as an improved switch for the regulation of heterologous proteins", Nucleic Acids Research, (1995), vol. 23, No. 10, pp. 1686-1690.
Macpherson, P. et al., "Activity-dependent gene regulation in conditionally-immortalized muscle precursor cell lines," J. Cell. Biol. 91(4):821-839 (2004).
McCarthy, "Underground movement", Nature Reviews Cancer, (2007), vol. 7, 1 page, published online Oct. 11, 2007.
Melkonyan et al., "Electroporation efficiency in mammalian cells is increased by dimethyl sulfoxide (DMSO)," Nucleic Acids Research 24:4356-4357 (1996).
Merino et al., "Developmental Regulation of the Bcl-2 Protein and Susceptibility to Cell Death in B Lymphocytes", The EMBO Journal, vol. 13, No. 3, 1994, pp. 683-691.
Miharada et al., "Efficient enucleation of erythroblasts differentiated in vitro from hematopoietic stem and progenitor cells", Nature Biotechnology, 24(10): 1255-1256, 2006.
Miller et al., "Expansion in vitro of adult murine hematopoietic stem cells with transplantable lympho-myeloid reconstituting ability," PNAS USA 94: 13648-13653 (1997).
Moore et al., "In Vitro Maintenance of Highly Purified, Transplantable hematopoietic Stem Cells," Blood 89(12):4337-4347 (1997).
Mooslehner et al., Retroviral Integration Sites in Transgenic Mov Mice Frequently Map in the Vicinity of Transcribed DNA Regions,: J. Virology 64:3056-3058 (1990).
Muchmore et al., "X Ray and NMR Structure of Human Bcl-xL, an Inhibitor of Programmed Cell Death", Nature, vol. 381, May 23, 1996, pp. 335-341.
Non Final Office Action received for U.S. Appl. No. 11/583,970, dated May 9, 2011, 10 pages.
Non Final Office Action received for U.S. Appl. No. 12/048,148, dated Oct. 13, 2011, 9 pages.
Non Final Office Action received for U.S. Appl. No. 12/962,197, dated Aug. 26, 2011, 11 pages.
Non-Final Office Action on U.S. Appl. No. 14/461,105 dated Mar. 22, 2016.
Non-Final Office Action on U.S. Appl. No. 14/415,325 dated Dec. 23, 2016.
Non-Final Office Action on U.S. Appl. No. 14/509,870 dated Jul. 12, 2016.
Non-Final Office Action on U.S. Appl. No. 14/661,786, dated Aug. 27, 2015.
Non-Final Office Action on U.S. Appl. No. 14/873,296 dated Aug. 17, 2017.
Non-Final Office Action on U.S. Appl. No. 15/244,138 dated Jan. 22, 2018.
Non-Final Office Action on U.S. Appl. No. 12/506,894 dated Apr. 3, 2015, 16 pages.
Non-Final Office Action on U.S. Appl. No. 13/795,659 dated Nov. 26, 2014, 13 pages.
Non-Final Office Action on U.S. Appl. No. 13/797,648 dated Jun. 17, 2016.
Non-Final Office Action on U.S. Appl. No. 11/583,970 dated Sep. 20, 2013, 19 pages.
Non-final Office Action on U.S. Appl. No. 12/467,957 dated Apr. 4, 2014, 14 pages.
Non-Final Office Action on U.S. Appl. No. 12/701,383 dated Jun. 13, 2014, 26 pages.
Non-final Office Action on U.S. Appl. No. 13/795,659 dated Mar. 10, 2014, 11 pages.
Non-final Office Action on U.S. Appl. No. 13/797,648 dated Apr. 3, 2014, 13 pages.
Non-Final Office Action received for U.S. Appl. No. 11/583,970, dated Mar. 12, 2008, 13 pages.

(56) References Cited

OTHER PUBLICATIONS

Non-Final Office Action received for U.S. Appl. No. 12/467,957 dated Oct. 13, 2010, 15 pages.
Non-Final Office Action received for U.S. Appl. No. 12/701,383, dated Apr. 28, 2011, 9 pages.
Non-Final Office Action received for U.S. Appl. No. 11/583,970, dated Mar. 23, 2009, 11 pages.
Non-Final Office Action received for U.S. Appl. No. 12/048,148 dated Jan. 19, 2011, 6 pages.
Non-Final Office Action received for U.S. Appl. No. 12/048,148, dated May 11, 2012, 9 pages.
Non-Final Office Action received for U.S. Appl. No. 12/506,894, dated Apr. 27, 2012, 13 pages.
Non-Final Office Action received for U.S. Appl. No. 12/550,166 dated Jan. 11, 2012, 7 pages.
Notice of Acceptance issued on Australian Application 2009274172, dated Aug. 3, 2015.
Notice of Acceptance of Australian Application No. 2012216462, dated Apr. 10, 2015, 2 pages.
Notice of Allowance on U.S. Appl. No. 11/583,970, dated Aug. 29, 2014, 11 pages.
Notice of Allowance on U.S. Appl. No. 12/467,957, dated Nov. 26, 2014, 7 pages.
Notice of Allowance on U.S. Appl. No. 13/795,659 dated Mar. 1, 2016.
Notice of Allowance on U.S. Appl. No. 13/795,659, dated Sep. 29, 2015.
Notice of Allowance on U.S. Appl. No. 14/415,325 dated Jun. 9, 2017.
Notice of Allowance on U.S. Appl. No. 14/461,105 dated Jun. 2, 2017.
Notice of Allowance on U.S. Appl. No. 14/509,870 dated Jun. 22, 2017.
Notice of Allowance on U.S. Appl. No. 14/661,786 dated Apr. 25, 2016.
Notice of Allowance on U.S. Appl. No. 12/506,894 dated Jun. 16, 2015, 8 pages.
Notice of Allowance on U.S. Appl. No. 12/701,383 dated May 22, 2015, 9 pages.
Notice of Allowance on U.S. Appl. No. 13/777,967 dated Jul. 14, 2014.
Notice of Allowance on U.S. Appl. No. 12/550,166 dated Apr. 28, 2014, 4 pages.
Notice of Allowance received for U.S. Appl. No. 12/550,166, dated Nov. 26, 2012, 9 pages.
Notice of Reasons for Rejection (English translation) issued on Japanese application 2014-108137, dated Aug. 18, 2015.
Notice of Reasons for Rejection issued on Japanese Application 2014-108137, dated Nov. 1, 2017.
Notice of Reasons for Rejection issued on Japanese Application 2015-075703, dated Dec. 8, 2016, English translation only.
Notice of Reasons for Rejection issued on Japanese application 2015-523297, dated Jul. 19, 2017, English Translation only.
Notice of Reasons for Rejection issued on Japanese Application 2016-027812, dated Mar. 1, 2017.
Notice of Reasons for Rejection issued on Japanese Application 2016-501113, dated Dec. 28, 2017.
Notice of Reasons for Rejection issued on Japanese Application 2016-501117, dated Apr. 17, 2017.
Notice of Reasons for Rejectionissued on Japanese Application 2015-075703, dated May 11, 2016, English translation.
Notification prior to Allowance of Israeli Patent Application No. 209343 dated Apr. 7, 2014, 2 pages.
Office Action issued Korean Application 10-2010-7028384, dated Apr. 28, 2017, English Translation.
Office Action issued on Australian Application 2014249202, dated Nov. 18, 2015.
Office Action issued on Canadian Appl. 2626525, dated Jun. 6, 2016.
Office Action issued on Canadian Application 2,626,525 dated Jun. 13, 2017.
Office Action issued on Canadian Application 2723114, dated Jul. 7, 2016.
Office Action issued on Canadian Application 2731767, dated Oct. 5, 2015.
Office Action issued on Canadian Application 2735522, dated Nov. 16, 2015.
Office Action issued on Chinese Application 201410168106.2, dated Jun. 22, 2017 English translation only.
Office Action issued on Chinese Application 201410479865.2, dated Jul. 5, 2016, English Translation only.
Office Action issued on Chinese Application 201480026147.6, dated Apr. 20, 2017, English translation.
Office Action issued on Chinese Application 201480026147.6, dated Sep. 28, 2017.
Office Action issued on Japanese application 2015-523297, dated Apr. 3, 2017.
Office Action issued on Japanese Application 2016-501117, dated Nov. 15, 2017.
Office Action issued on Korean Appl. 10-2010-7028384, dated Aug. 18, 2016 English translation only.
Office Action on Canadian Application No. 2,626,525 dated Apr. 8, 2014, 4 pages.
Office Action on Canadian Application No. 2626525 dated May 8, 2015, 3 pages.
Office Action on Canadian Patent Application No. 2,680,613 dated Nov. 21, 2013, 3 pages.
Office Action received for Australian Patent Application No. 2006304392, dated Jul. 16, 2012, 3 pages.
Office Action received for Australian Patent Application No. 2009246876 dated Jan. 17, 2014, 6 pages.
Office Action received for Australian Patent Application No. 2009285547, dated Jul. 25, 2011, 2 pages.
Office Action received for Canadian Patent Application No. 2626525, dated Apr. 17, 2013, 4 pages.
Office Action received for Canadian Patent Application No. 2731767, dated Jul. 25, 2012, 3 pages.
Office Action received for Canadian Patent Application No. 2735522, dated Sep. 10, 2012, 3 pages.
Office Action received for Chinese Patent Application No. 200580031540.5, dated Jul. 3, 2012, English translation, 11 pages.
Office Action received for Chinese Patent Application No. 200680045545.8, dated Dec. 31, 2010, English translation, 8 pages.
Office Action received for Chinese Patent Application No. 200680045545.8, dated Sep. 15, 2011, English translation, 9 pages.
Office Action received for Chinese Patent Application No. 200880015602.7, dated Jan. 31, 2012, 16 pages (10 pages of English translation and 6 pages of Office Action).
Office Action received for Chinese Patent Application No. 200880015602.7, dated May 9, 2013, 13 pages (8 pages of English Translation and 5 pages of Official copy).
Office Action received for Chinese Patent Application No. 200880015602.7, dated Oct. 31, 2012, 10 pages (6 pages of English Translation and 4 pages of Chinese Office Action).
Office Action received for Chinese Patent Application No. 200980126312.4, dated Aug. 28, 2012, 12 pages (6 pages of English Translation and 6 pages of Office Action).
Office Action received for Chinese Patent Application No. 200980127166.7, dated Dec. 5, 2012, 4 pages (1 page of English Translation and 3 pages of Office Action).
Office Action received for Chinese Patent Application No. 200980126312.4, dated Jan. 30, 2012, 14 pages (7 pages of English translation and 7 pages of Office Action).
Office Action received for European Application No. 09810692.5 dated Feb. 25, 2014, 3 pages.
Office Action received for European Patent Application No. 06826025.6, dated Sep. 1, 2009, 3 pages.
Office Action received for European Patent Application No. 06826025.6, dated Sep. 22, 2009, 1 page.
Office Action received for European Patent Application No. 08743862.8, dated May 14, 2010, 6 pages.

(56) References Cited

OTHER PUBLICATIONS

Office Action received for European Patent Application No. 08743862.8, dated Sep. 23, 2010, 6 pages.
Office Action received for European Patent Application No. 09747016.5, dated Apr. 9, 2013, 6 pages.
Office Action received for European Patent Application No. 09810692.5, dated Mar. 28, 2012, 3 pages.
Office Action received for Indian Application No. 3332/DELNP/2008 dated Aug. 23, 2013, 3 pages.
Office Action received for Israel Patent Application No. 200919, dated Jan. 17, 2013, 4 pages (2 pages of English Translation and 2 pages of Official Copy).
Office Action received for Israel Patent Application No. 208810, dated Nov. 2, 2011, 3 pages of English Translation only.
Office Action received for Israel Patent Application No. 209343, dated Aug. 14, 2012, 3 pages (2 pages of English Translation and 1 page of Office Action).
Office Action received for Israel Patent Application No. 209343, dated Nov. 2, 2011, 3 pages of English Translation only.
Office Action received for Israel Patent Application No. 209968, dated Aug. 21, 2012, 4 pages (2 pages of English Translation and 2 pages of Office Action).
Office Action received for Israel Patent Application No. 209968, dated Nov. 2, 2011, 3 pages of English Translation only.
Office Action received for Israeli Patent Application No. 190946, dated Jul. 3, 2012, 1 page, (English Translation only).
Office Action received for Japanese Application No. 2011-520133, dated Feb. 5, 2014, 4 pages (in Japanese).
Office Action received for Japanese Patent Application No. 2008-536713, dated Jul. 3, 2012, 2 pages (No English Translation Provided).
Office Action received for Japanese Patent Application No. 2009-553785, dated Jun. 19, 2012, 6 pages (2 pages of English Translation and 4 pages of Office Action).
Office Action received for Korean Patent Application No. 10-2008-7011791, dated May 28, 2013, English translation, 3 pages.
Office Action received for Korean Patent Application No. 10-2009-7021320, dated Jul. 29, 2011, 7 pages (3 pages of English Translation and 4 pages of Office Action).
Office Action received for Korean Patent Application No. 10-2009-7021320, dated Sep. 18, 2012, 11 pages (7 pages of English Translation and 4 pages of Office Action).
Official Action on European Application No. 09810692.5 dated Oct. 22, 2014, 3 pages.
Oral Proceedings Summons received for European Patent Application No. 08743862.8, dated May 14, 2012, 6 pages.
Pan et al., "Reprogramming human fibroblasts using HIV-1 TAT recombinant proteins OCT4, SOX2, KLF4 and c-MYC," Mol. Biol Rep (2010) 37:2117-2124.
Partial Search Report issued on EP Appl. 14778538.0, dated Jul. 8, 2016.
Partial Supplementary European Search Report issued on EP Appl. 13820331.0, dated Jun. 30, 2016.
Pharmaceutics (Yakuzaigaku), 64(3), 2004, p. 164-167 (English translation not available).
Pierelli et al., "Modulation of bcl-2 and p27 in human primitive proliferating hematopoietic progenitors by autocrine TGF-B 1 is a cell cycle-independent effect and influences their hematopoietic potential," Blood 95:3001-3010 (2000).
Pinto et al., "Hematopoietic progenitor/stem cells immortalized by Lhx2 generate functional hematopoietic cells in vivo," Blood 99(11):3939-3946 (2002).
Podsypanina, K. et al., "Oncogene cooperation in tumor maintenance and tumor recurrence in mouse mammary tumors induced by MYC and mutant Kras," PNAS 105(13):5242-5247 (2008).
Polenakovic et al., "Is Erythropoietin a Survival Factor for Red Blood Cells," J. Am. Soc. Nephrol, vol. 7, 1996, pp. 1178-1182.
Pollock, K. et al., "A conditionally immortal clonal stem cell line from human cortical neuroepithelium for the treatment of ischemic stroke," Exp. Neurol., (2006), vol. 199, No. 1, pp. 143-155.

Pre-Appeal Examination Report on Japanese Application 2014-108137, dated Dec. 7, 2016, English translation only.
Prochownik et al., "Deregulated expression of c-myc by murine erythroleukaemia cells prevents differentiation," Nature, vol. 322, Aug. 28, 1986, pp. 848-850.
Qin et al., "Nuclear Factor KB Nuclear Translocation Upregulates c-Myc and p53 Expression during NMDA Receptor-Mediated Apoptosis in Rat Striatum", The Journal of Neuroscience, vol. 19, No. 10, May 15, 1999, pp. 4023-4033.
Rabbitts, et al., "Metabolism of c-myc gene products: c-myc mRNA and protein expression in the cell cycle", EMBO Journal, (1985), vol. 4, No. 8, pp. 2009-2015.
Radhakrishnan et al., "A Novel Transcriptional Inhibitor Induces Apoptosis in Tumor Cells and Exhibits Antiangiogenic Activity", Cancer Research, vol. 66, No. 6, Mar. 15, 2006, pp. 3264-3270.
Raymon, H.K. et al., "Immortalized human dorsal root ganglion cells differentiate into neurons with nociceptive properties," J. Neuroscience 19(13):5420-5428 (1999).
Re-Examination Report on Australian Patent No. 2009285547 dated Apr. 23, 2015, 3 pages.
Refaeli et al., "The protooncogene MYC can break B cell tolerance," PNAS, 102(11):4097-4102, (2005).
Refaeli, Y, "The B-Cell Antigen Receptor and Overexpression of MYC Can Cooperate in the Genesis of B-Cell Lymphomas", PLOS Biology, vol. 6, No. 6, e152, 2008, pp. 1208-1225.
Restriction Requirement received for U.S. Appl. No. 11/583,970, dated Nov. 13, 2007, 14 pages.
Restriction Requirement received for U.S. Appl. No. 12/701,383, dated Jan. 25, 2011, 10 pages.
Richter, et al., "Lhx.2 expression in hematopoietic progenitor/stem cells in vivo causes a chronic myeloproliferative disorder and altered globin expression," J. Hematol., (2003), 88(12):1336-1347.
Roh et al., "Transgenic Mice for Cre-Inducible Overexpression of the Oncogenes c-MYC and Pim-1 in Multiple Tissues", Genesis: The Journal of Genetics and Development, vol. 44 pp. 447-453, (2006).
Rosenwald, et al., "Increased Expression of Eukaryotic Translation Inhibition Factors eIF-4E and eIF-2alpha in Response to Growth Induction by C-MYC", Proc. Natl. Acad. Sci. USA, vol. 90, pp. 6175-6178, (1993).
Rudolph et al., "Expression of Mad1 in T cells leads to reduced thymic cellularity and impaired mitogen-induced proliferation", Oncogene, 2001, vol. 20, pp. 1164-1175.
Satoh et al, "Roles for c-Myc in Self-renewal of Hematopoietic Stem Cells," The Journal of Biological Chemistry, 2004, vol. 279, No. 24, p. 24986-24993.
Sauer, "Inducible Gene Targeting in Mice Using the Cre/lox System," Methods, (1998), vol. 14, No. 4, pp. 381-392.
Schiedlmeier et al., "High-level Ectopic HOXB4 Expression Confers a Profound in Vivo Competitive Growth Advantage on Human Cord Blood CD34 Cells, but Impairs Lymphomyeloid Differentiation", Blood, vol. 101, No. 5, Mar. 1, 2003, pp. 1759-1768.
Schmidt et al., "Transgenic Mice Bearing the Human c-myc Gene Activated by an Immunoglobulin Enhancer: A pre-B-cell Lymphoma Model", National Academy of Sciences, vol. 85, pp. 6047-6051 (1988).
Schroy, et al., "A Simple Method for Freezing and Thawing Cultured Cells," Methods in Cell Science (formerly known as TCA Manual), (1976), vol. 2, No. 1, pp. 309-310.
Schwarze et al., "Protein transduction: unrestricted delivery into all cells?" Trends Cell Biol. 10:290-295 (2000).
Seibutsugaku Jiten (Dictionary of Biology), Iwanami Shoten, 1997, The 4th edition, p. 1396, English translation not available.
Silva et al., "Erythropoietin Can Promote Erythroid Progenitor Survival by Repressing Apoptosis Through Bcl-xl, and Bcl-2," Blood, vol. 88, No. 5, Sep. 1, 1996, pp. 1576-1582.
Sipione, S. et al., "Modeling brain pathologies using neural stem cells," Methods Mol. Biol., (2002), vol. 198, pp. 245-262.
Snyder, et al., "Regulation of NMDA receptor trafficking by amyloid-3B2", Nature Neuroscience, (2005), vol. 8, No. 8, pp. 1051-1058.
Soane,L., et al., "TAT-mediated endocytotic delivery of the loop deletion Bcl-2 protein protects neurons against cell death", Journal of Neurochemistry, (2005), vol. 95, pp. 230-243.

(56) References Cited

OTHER PUBLICATIONS

Sunyer, "Evolutionary and Functional Relationships of B Cells from Fish and Mammals: Insights into their Novel Roles in Phagocytosis and Presentation of Particulate Antigen," Infect Disord Drug Targets 12(3):200-212 (2012).
Supplementary Search Report received for European Patent Application No. 08743862.8 dated Feb. 9, 2010, 1 page.
Taguchi et al., "Nuclear trafficking of macromolecules by an oligopeptide derived from Vpr of human immunodeficiency virus type-1" Biochem. Biophys. Res. Commun. 2004, 320(1) pp. 18-26.
Takahashi, et al., Induction of pluripotent stem cells from mouse embryonic and adult fibroblast cultures by defined factors, Cell, 126:663-676, 2006.
Theis, et al., "Expression of the myc/His-Tagged Human Peptide Transporter hPEPT1 in Yeast for Protein Purification and Functional Analysis", Protein Expression and Purification, (2001), vol. 22, pp. 436-442.
Thomas, et. al., "Progress and Problems with the Use of Viral Vectors for Gene Therapy", Nature, (May 2003), vol. 4, pp. 346-358.
Trumpp et al., "c-Myc Regulates Mammalian Body Size by Controlling Cell Number But Not Cell Size," Nature 414: 768-773 (2001).
Tsai et al., "Lymphohematopoietic progenitors immortalized by a retroviral vector harboring a dominant-negative retinoic acid receptor can recapitulate lymphoid, myeloid, and erythroid development," Genes & Dev. 8:2831-2841 (1994).
Varnum-Finney et al., "Pluripotent, cytokine-dependent, hematopoietic stem cells are immortalized by constitutive Notch1 signaling," Nature Medicine 6(11):1278-1281 (2000).
Vaux et al., "Bcl-2 gene promotes hemopoietic cell survival and cooperates with c-myc to immortalize pre-B cells," Nature 335:440-442 (1988).
Vaux, et al., "Immunologic competence of B cells subjected to constitutive c-myc oncogene expression in immunoglobulin heavy chain enhancer myc transgenic mice", J. Immunol., (1987), vol. 139, No. 11, pp. 3854-3860.
Wagner et al., "Myc-Mediated Apoptosis is Blocked by Ectopic Expression of Bcl-2," Molecular and Cellular Biology, Apr. 1993, pp. 2432-2440.
Wang et al., "Primitive Human Hematopoietic Cells Are Enriched in Cord Blood Compared with Adult Bone Marrow or Mobilized Peripheral Blood as Measured by the Quantitative In Vivo SCID-Repopulating Cell Assay," Blood 89:3919-3924 (1997).
Wechsler et al., "MXI1, a Putative Tumor Suppressor Gene, Suppresses Growth of Human Glioblastoma Cells", Cancer Research 57, pp. 4405-4912, (1997).
Wikipedia [online], "Stem Cell", 2008, [retrieved on Nov. 13, 2008]. Retrieved from the Internet: <URL: http//en.wikipedia.org/wiki/Stem_cell>, 11 pages.
Wilson, et al., "c-Myc controls the balance between hematopoietic stem cell self-renewal and differentiation", Genes and Development, 2004, vol. 18, pp. 2747-2763.
Wu et al., "Inhibition of c-myc Expression Induces Apoptosis of WEHI 231 Murine B Cells", Molecular and Cellular Biology, Sep. 1996, vol. 16, No. 9, pp. 5015-5025.
Wurm, et al., "Large-scale transient expression of mammalian cells for recombinant protein production," Curr. Op. Biotech., (1999), vol. 10, pp. 156-159.
Xi et al., "In Vitro Large Scale Production of Human Mature Red Blood Cells From Hematopoietic Stem Cells by Cocultuing with Human Fetal Liver Stromal Cells," Biomed. Res. Int. Epub Jan. 30, 2013, 2013:807863.
Xu Zhixiang, et al, "The Development of the Study on the Anti-Tumor Effect of Flt3 Ligand," Chinese Journal of Tumor Biological Therapy, vol. 7, No. 3, Sep. 30, 2000.
Yagihashi, et al., "Detection of Anti-Survivin Antibody in Gastro-intestinal Cancer Patients", Clinical Chemistry, (2001), vol. 47, No. 9, pp. 1729-1731.
Yanai et al., "A novel stromal cell-dependent hematopoietic cell line established from temperature-sensitive SV40 T-antigen transgenic mice," Exp. Hematol., 27:1087-1096 (1999).
Young et al., "B-Cell Receptor Signaling in the Genesis and Maintenance of B-Cell Lymphoma", Future Oncology, vol. 4, No. 5, 2008, pp. 591-594.
Zhang et al., "Cytokines Regulating Hematopoietic Stem Cell Function", Current Opinion Hematology, vol. 15, No. 4, Jul. 2008, pp. 307-311.
Zhang et al., "Reprogramming of somatic cells via TAT-mediated protein transduction of recombinant factors," Biomaterials 33 (2012) 5047-5055.
Notice of Allowance on U.S. Appl. No. 15/179,735 dated May 29, 2018.
Second Office Action issued on Chinese Application 201480026500.0, dated Apr. 27, 2018.
Final Office Action on U.S. Appl. No. 15/244,138 dated Jun. 4, 2018.
Office Action issued on Chinese Application 201510760532X, dated May 11, 2018.
Canadian Office Action, dated Jul. 4, 2018, issued in Canadian Patent Application No. 2,626,525.
European Office Action, dated May 15, 2018, issued in European Patent Application No. 09747016.5.
European Office Action, dated Jun. 29, 2018, issued in European Patent Application No. 14779483.8.
Israeli Office Action, dated Jun. 27, 2018, issued in Israeli Patent Application No. 208810.
Israeli Office Action, dated Jul. 29, 2018, issued in Israeli Patent Application No. 256512.
Israeli Office Action, dated Jul. 30, 2018, issued in Israeli Patent Application No. 241192.
Japanese Office Action, dated Jul. 18, 2018, issued in Japanese Patent Application No. 2017-123838.

\* cited by examiner

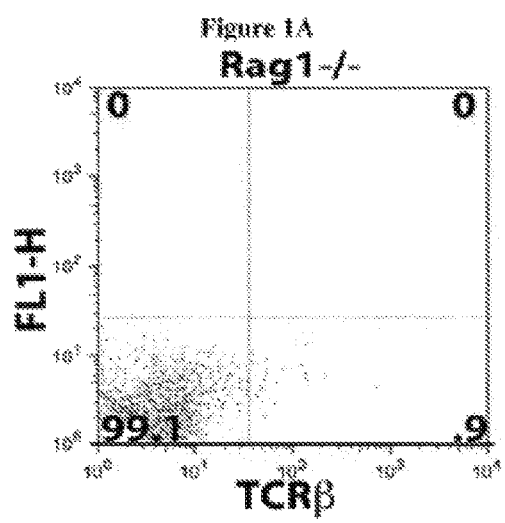
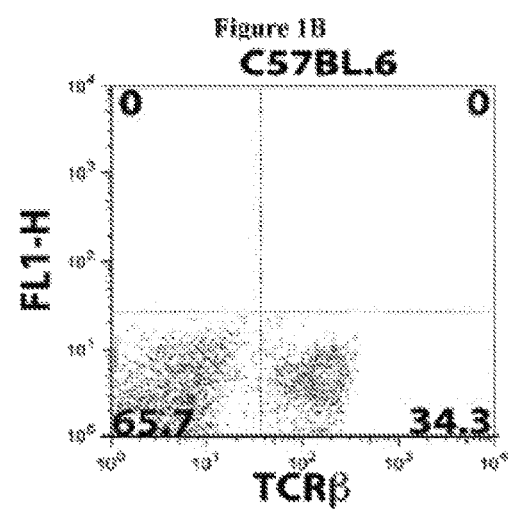
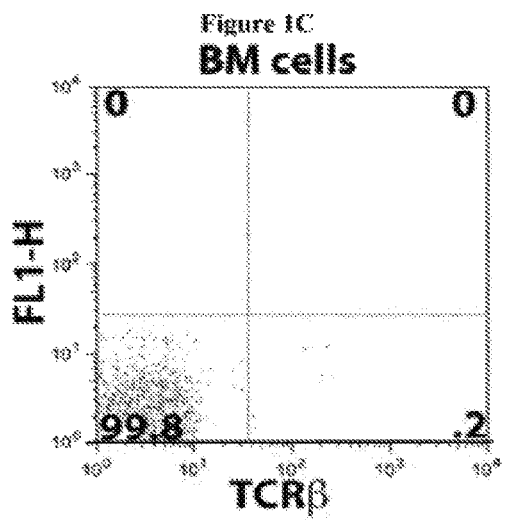
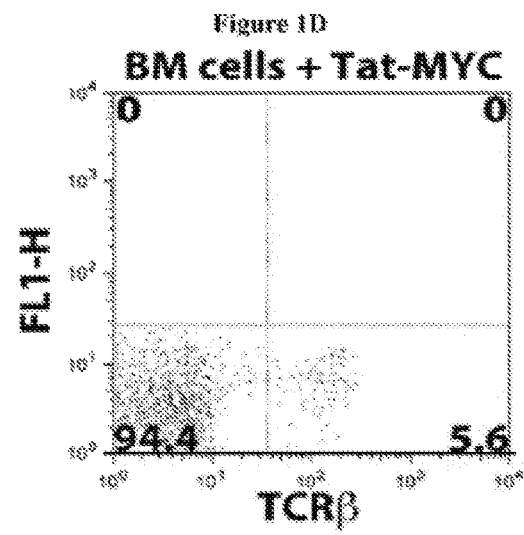

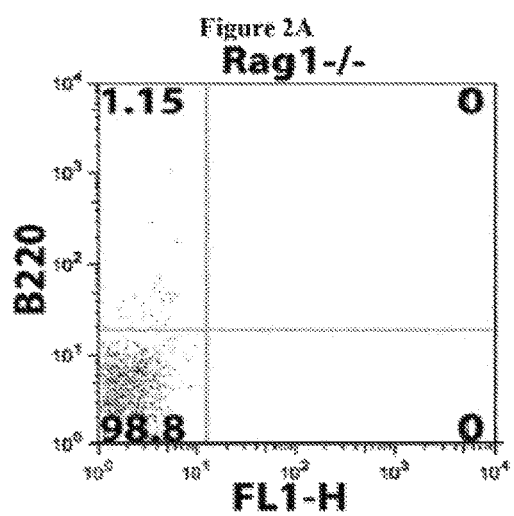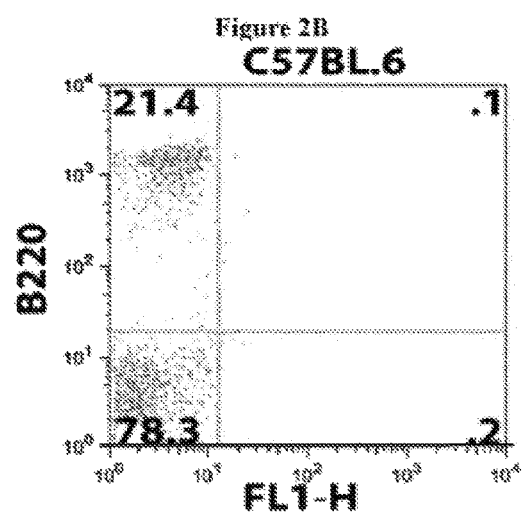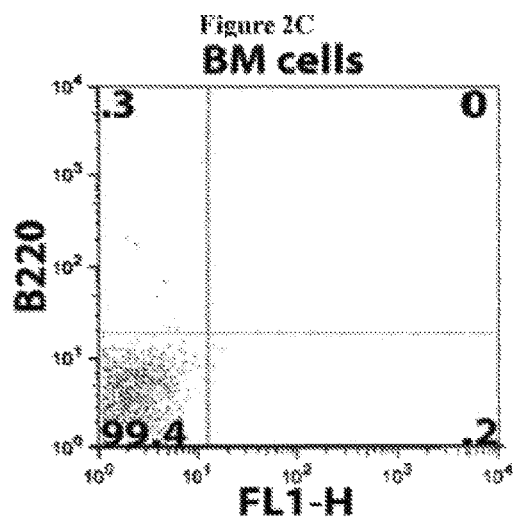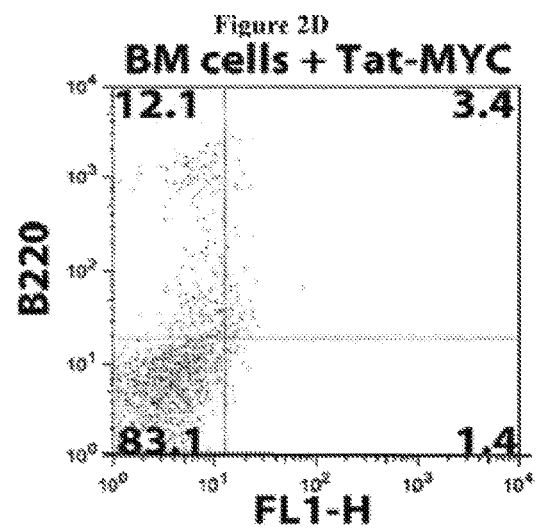

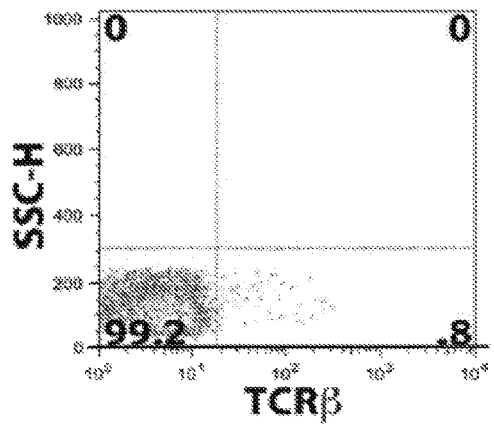
Figure 3A Rag1-/-
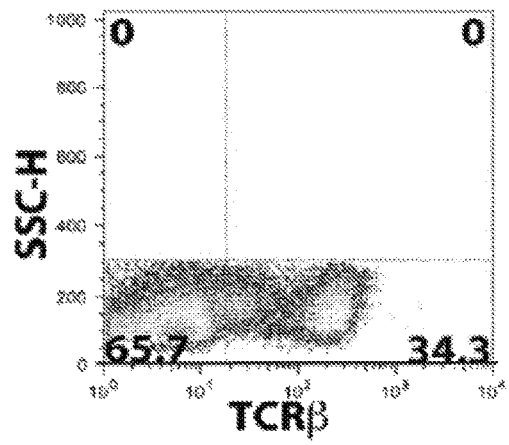
Figure 3B C57BL.6
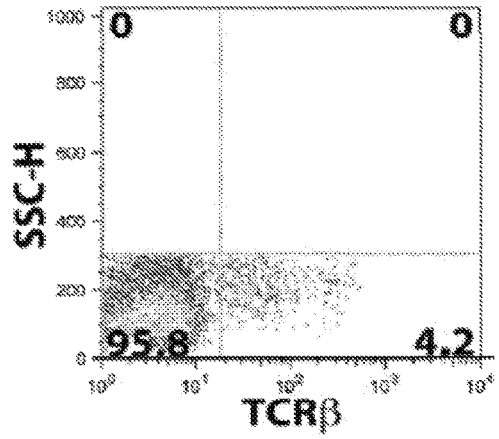
Figure 3C BM cells
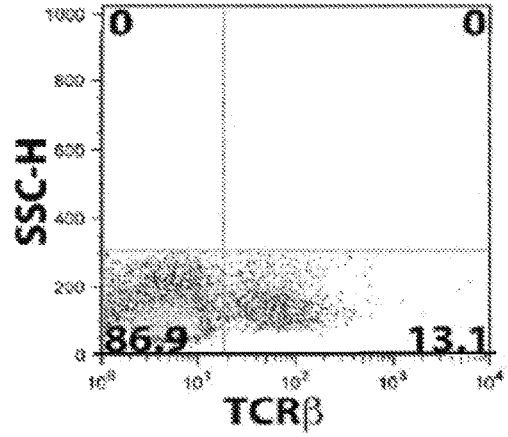
Figure 3D BM cells + Tat-MYC

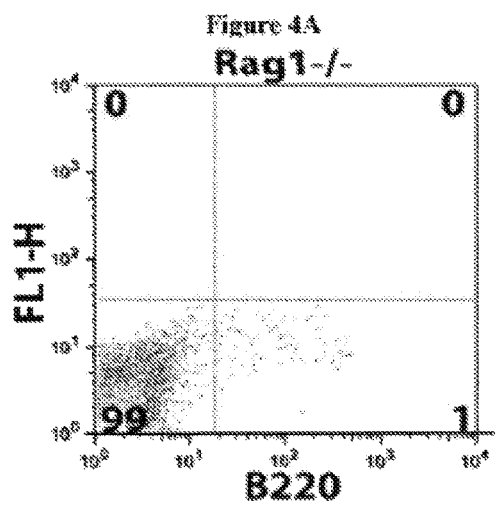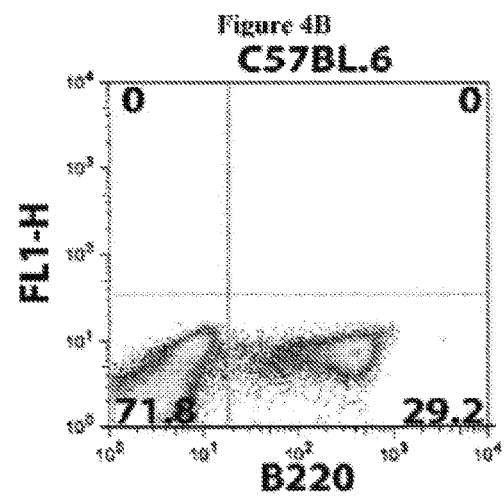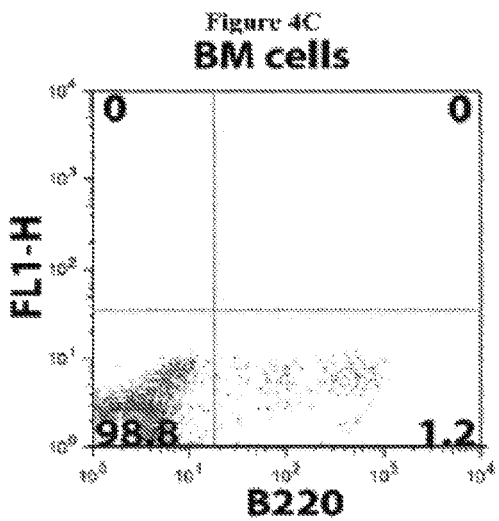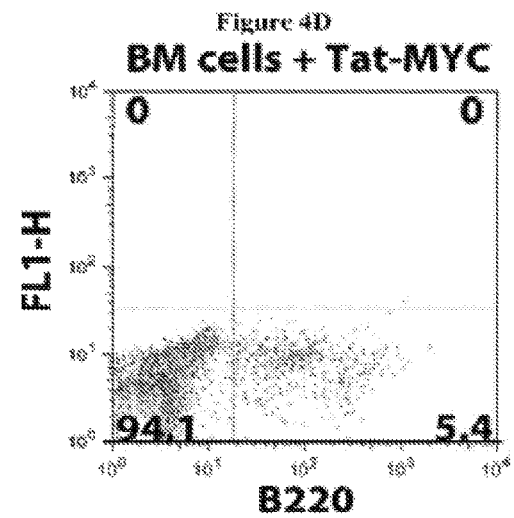

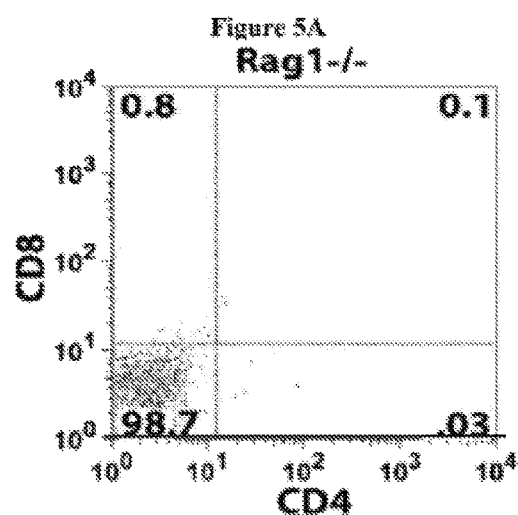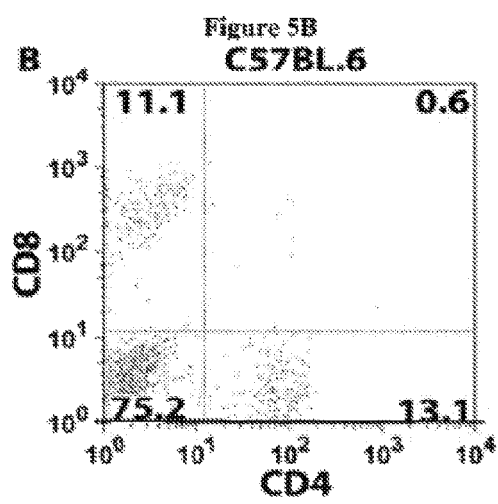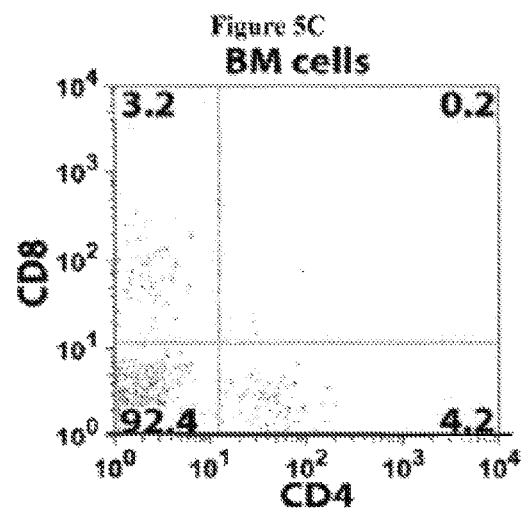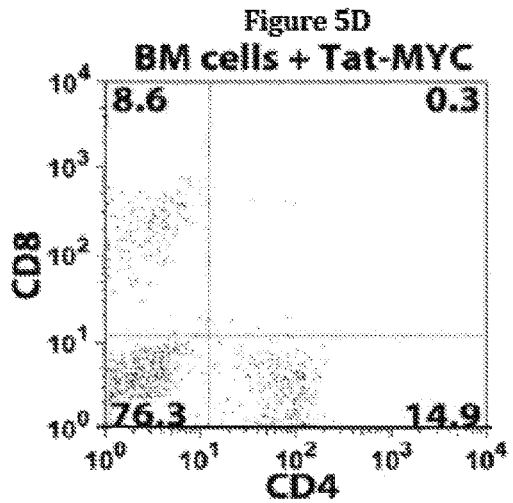

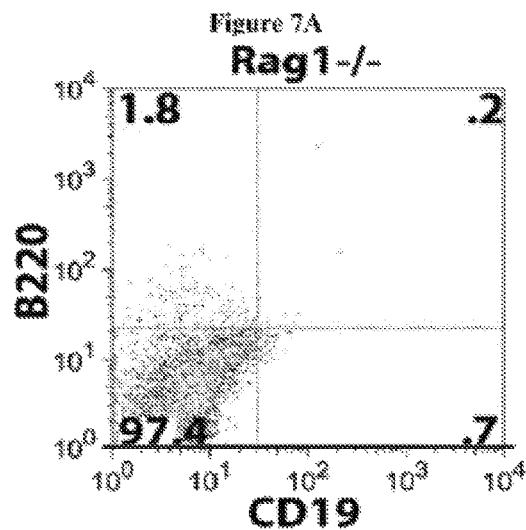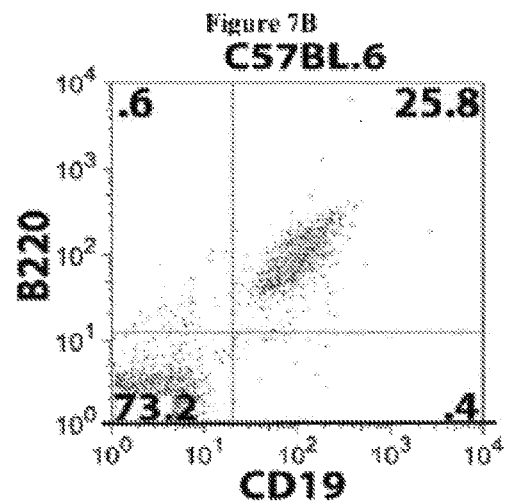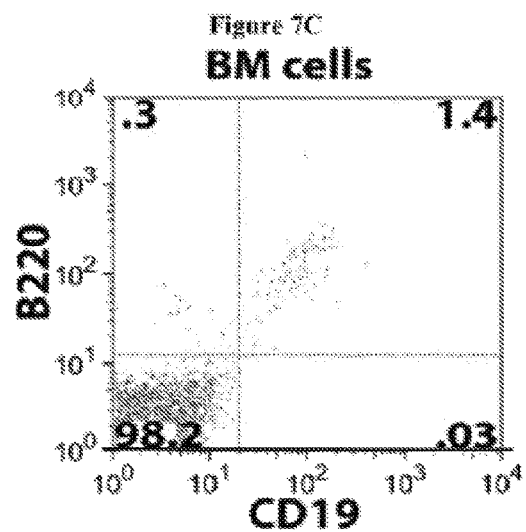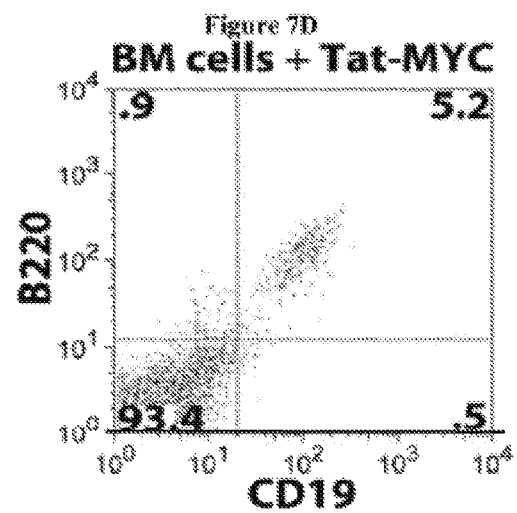

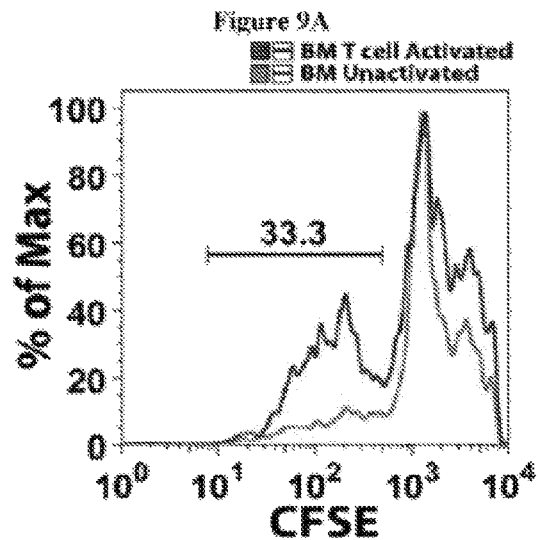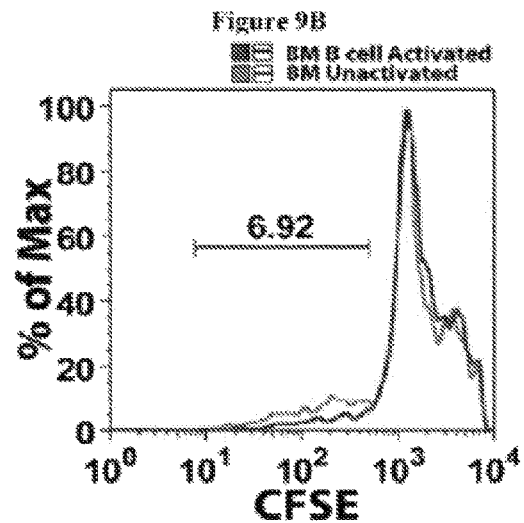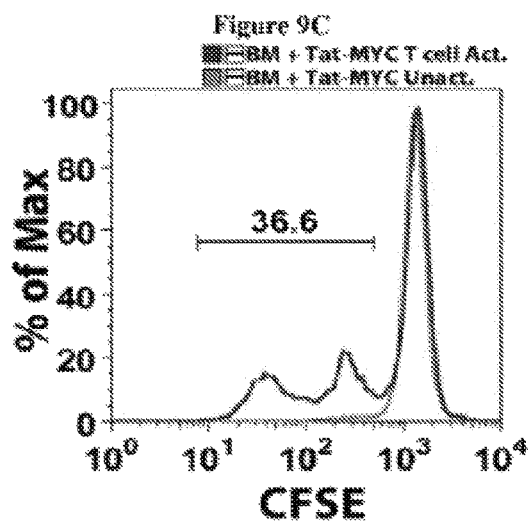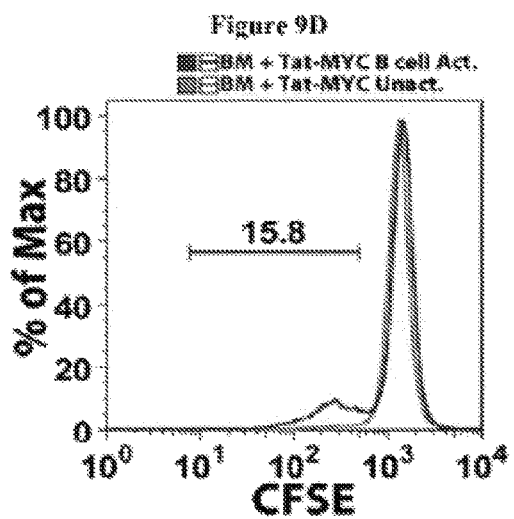

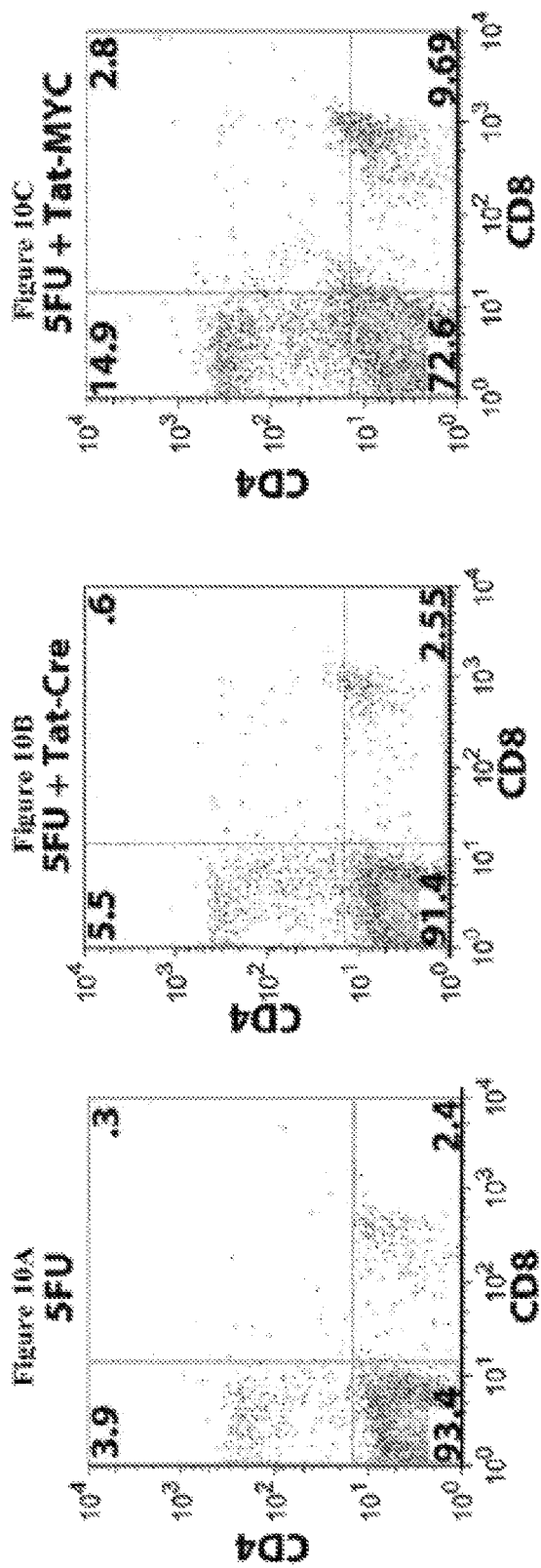

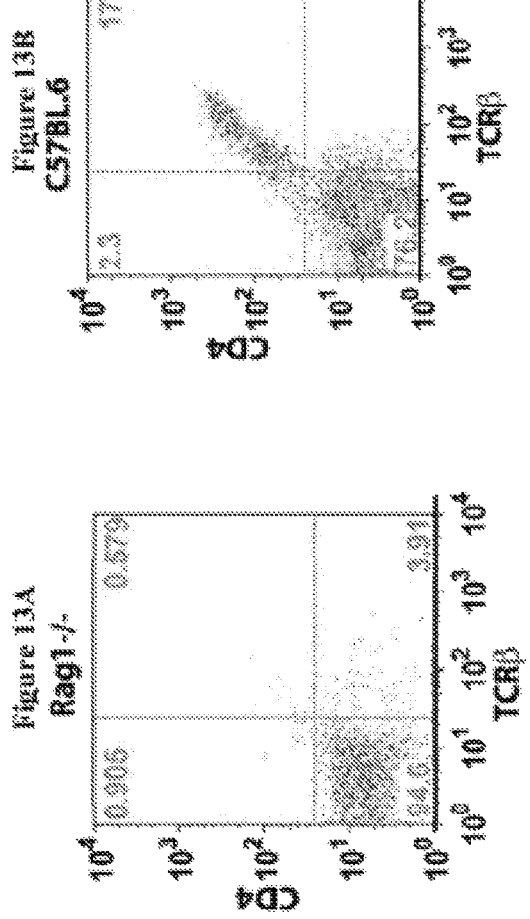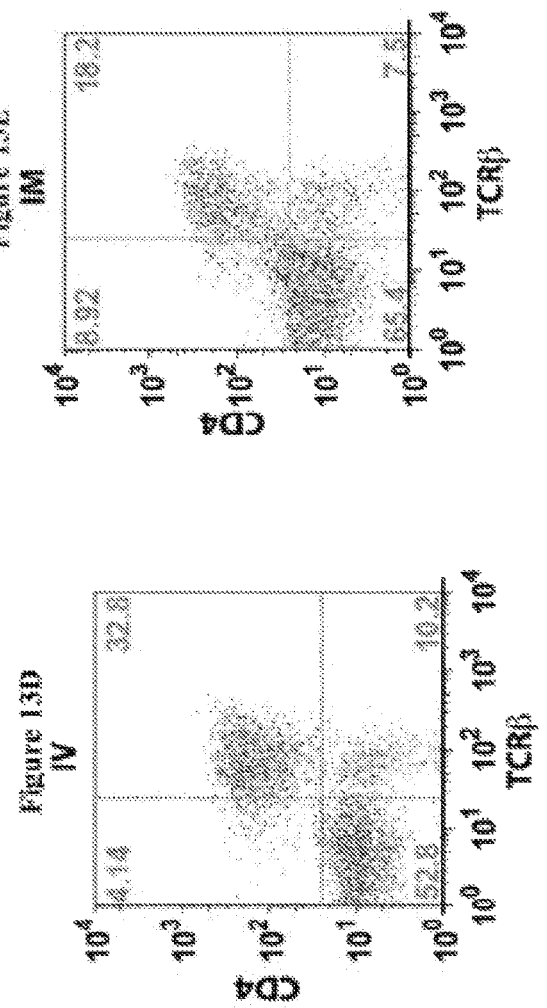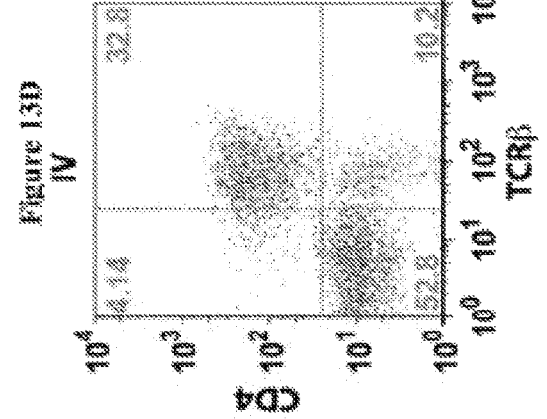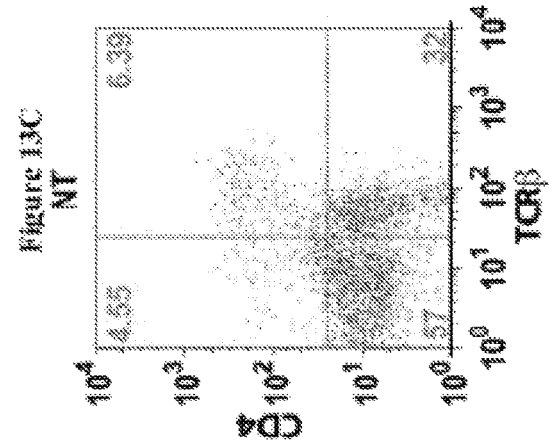

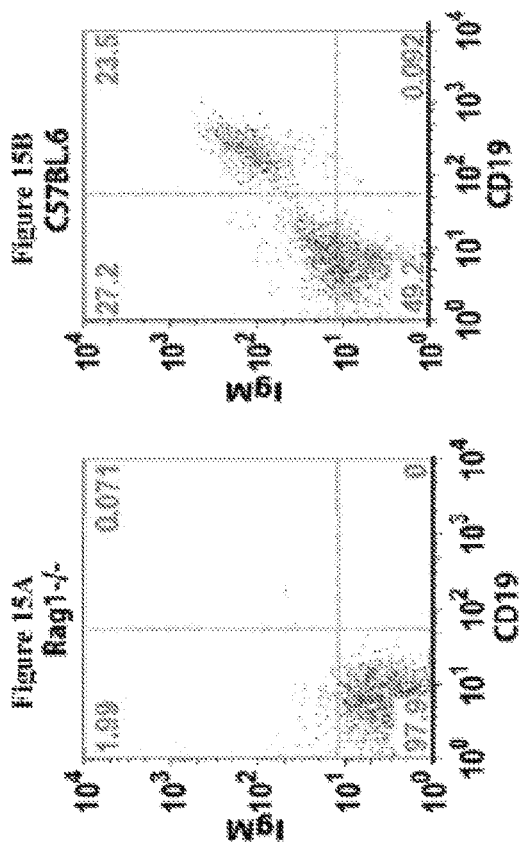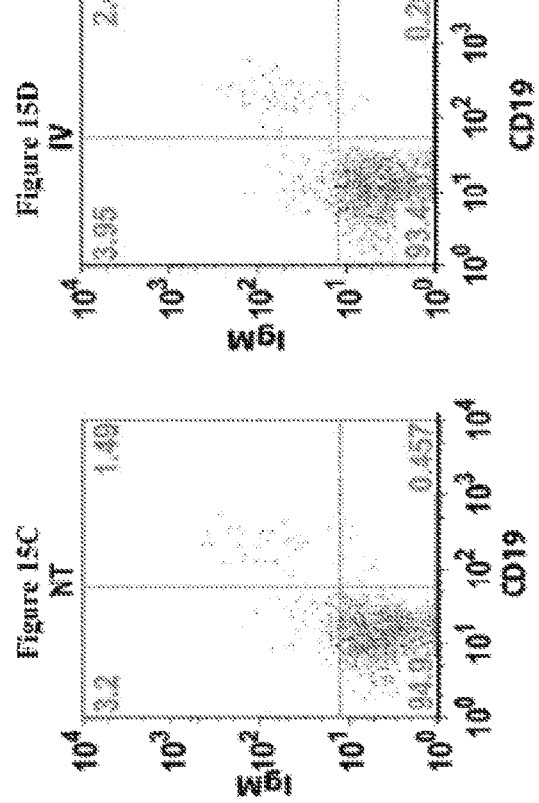

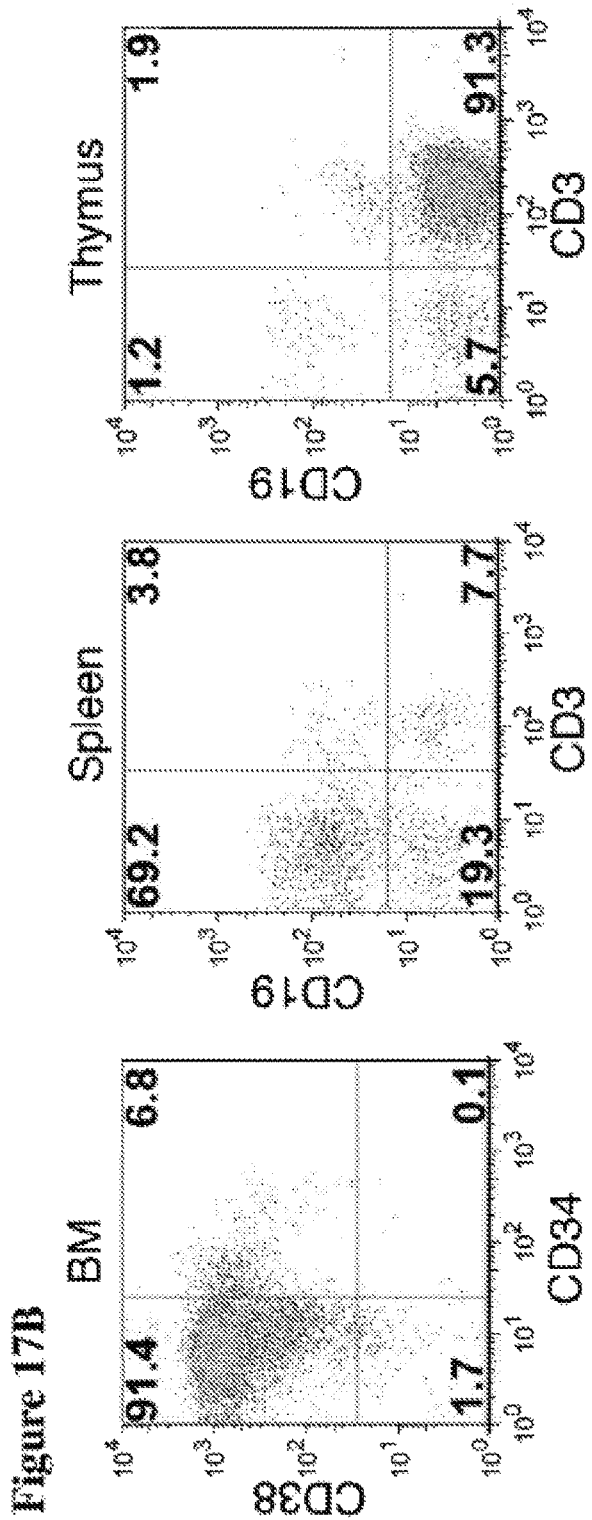

5x10^5 TC

1x10^6 TC

1x10^6 TM

5x10^6 TM

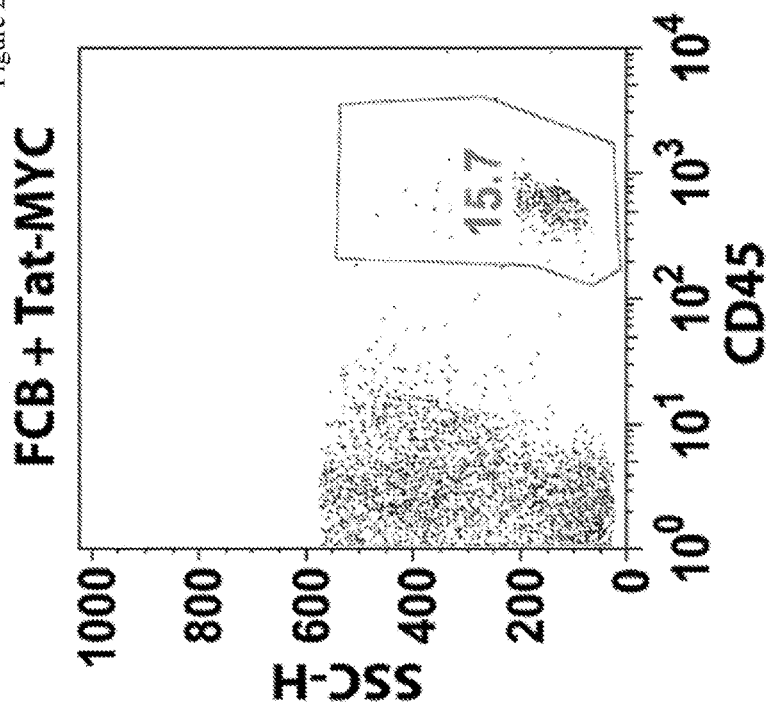
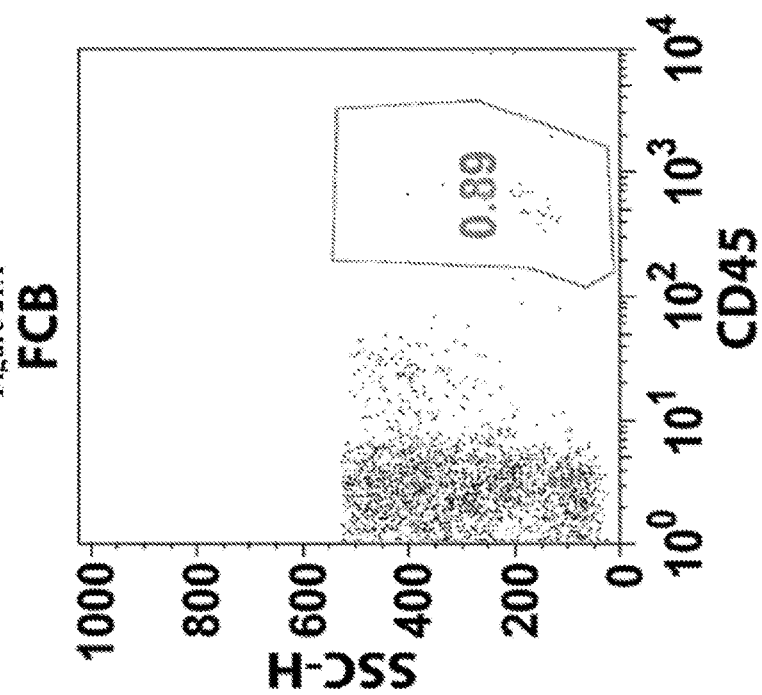

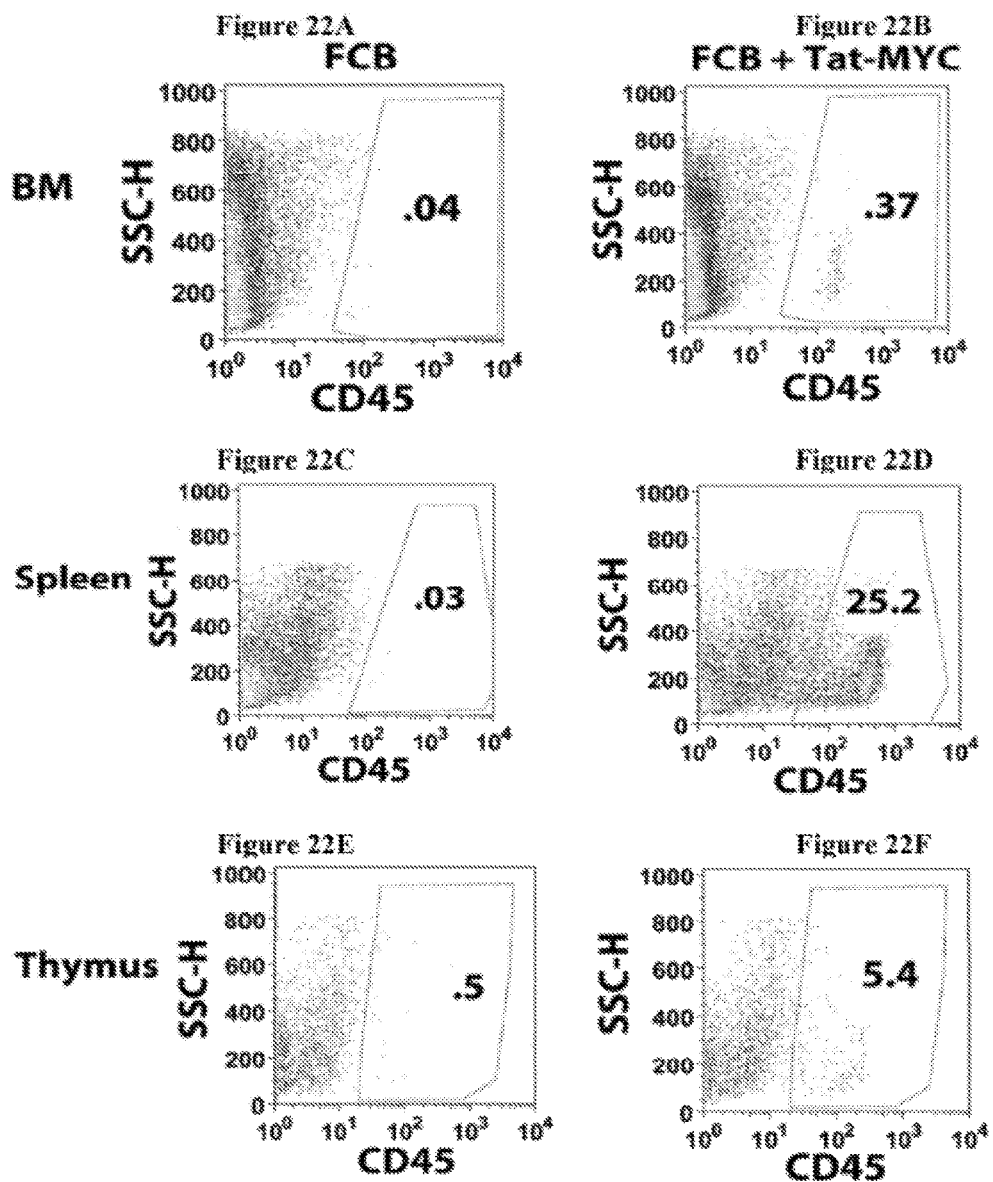

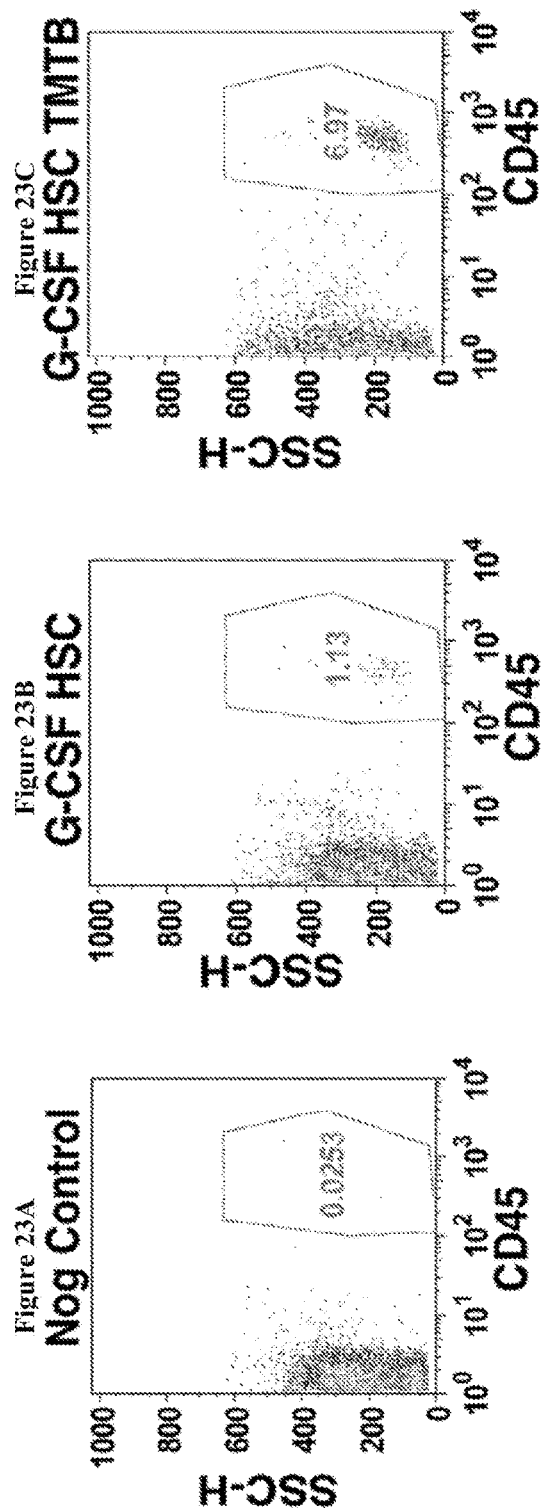

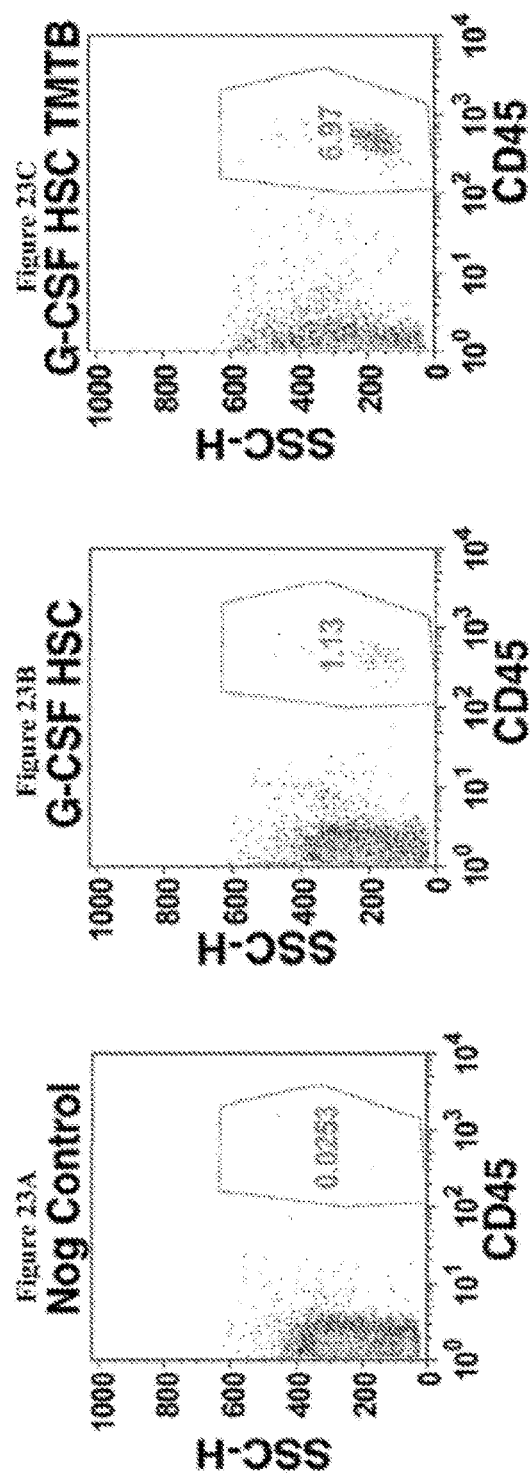

TAT-MYC Amino Acid sequence (SEQ ID NO: 1)

MRKKRRQRRRMPLNVSFTNRNYDLDYDSVQPYFYCDEEENFYQQQQQSELQPP
APSEDIWKKFELLPTPPLSPSRRSGLCSPSYVAVTPFSLRGDNDGGGGSFSTADQL
EMVTELLGGDMVNQSFICDPDDETFIKNIIQDCMWSGFSAAAKLVSEKLASYQA
ARKDSGSPNPARGHSVCSTSSLYLQDLSAAASECIDPSVVFPYPLNDSSSPKSCAS
QDSSAFSPSSDSLLSSTESSPQGSPEPLVLHEETPPTTSSDSEEEQEDEEEIDVVSVE
KRQAPGKRSESGSPSAGGHSKPPHSPLVLKRCHVSTHQHNYAAPPSTRKDYPAA
KRVKLDSVRVLRQISNNRKCTSPRSSDTEENVKRRTHNVLERQRRNELKRSFFAL
RDQIPELENNEKAPKVVILKKATAYILSVQAEEQKLISEEDLLRKRREQLKHKLEQ
LRKGELNSKLEGKPIPNPLLGLDSTRTGHHHHHH

Amino acids 2-10 are the HIV Tat protein transduction domain
Amino acids 11-454 are c-Myc
Amino acids 455-468 are the 14 amino acid V5 epitope
Amino acids 472-477 are the 6 Histidine tag TAT-MYC Nucleotide sequence (SEQ ID NO: 2)

ATGAGGAAGAAGCGGAGACAGCGACGAAGAATGCCCCTCAACGTTAGCTTC
ACCAACAGGAACTATGACCTCGACTACGACTCGGTGCAGCCGTATTTCTACT
GCGACGAGGAGGAGAACTTCTACCAGCAGCAGCAGCAGAGCGAGCTGCAGC
CCCCGGCGCCCAGCGAGGATATCTGGAAGAAATTCGAGCTGCTGCCCACCCC
GCCCCTGTCCCCTAGCCGCCGCTCCGGGCTCTGCTCGCCCTCCTACGTTGCGG
TCACACCCTTCTCCCTTCGGGGAGACAACGACGGCGGTGGCGGGAGCTTCTC
CACGGCCGACCAGCTGGAGATGGTGACCGAGCTGCTGGGAGGAGACATGGT
GAACCAGAGTTTCATCTGCGACCCGGACGACGAGACCTTCATCAAAAACATC
ATCATCCAGGACTGTATGTGGAGCGGCTTCTCGGCCGCCGCCAAGCTCGTCTC
AGAGAAGCTGGCCTCCTACCAGGCTGCGCGCAAAGACAGCGGCAGCCCGAA
CCCCGCCCGCGGCCACAGCGTCTGCTCCACCTCCAGCTTGTACCTGCAGGATC
TGAGCGCCGCCGCCTCAGAGTGCATCGACCCCTCGGTGGTCTTCCCCTACCCT
CTCAACGACAGCAGCTCGCCCAAGTCCTGCGCCTCGCAAGACTCCAGCGCCT
TCTCTCCGTCCTCGGATTCTCTGCTCTCCTCGACGGAGTCCTCCCCGCAGGGC
AGCCCCGAGCCCCTGGTGCTCCATGAGGAGACACCGCCCACCACCAGCAGCG
ACTCTGAGGAGGAACAAGAAGATGAGGAAGAAATCGATGTTGTTTCTGTGGA
AAAGAGGCAGGCTCCTGGCAAAAGGTCAGAGTCTGGATCACCTTCTGCTGGA
GGCCACAGCAAACCTCCTCACAGCCCACTGGTCCTCAAGAGGTGCCACGTCT
CCACACATCAGCACAACTACGCAGCGCCTCCCTCCACTCGGAAGGACTATCC
TGCTGCCAAGAGGGTCAAGTTGGACAGTGTCAGAGTCCTGAGACAGATCAGC
AACAACCGAAAATGCACCAGCCCCAGGTCCTCGGACACCGAGGAGAATGTC
AAGAGGCGAACACACAACGTCTTGGAGCGCCAGAGGAGGAACGAGCTAAAA
CGGAGCTTTTTTGCCCTGCGTGACCAGATCCCGGAGTTGGAAAACAATGAAA
AGGCCCCCAAGGTAGTTATCCTTAAAAAAGCCACAGCATACATCCTGTCCGT
CCAAGCAGAGGAGCAAAAGCTCATTTCTGAAGAGGACTTGTTGCGGAAACGA

Figure 24

TAT-Bcl2Δ Amino Acid sequence (SEQ ID NO: 3)

MRKKRRQRRRMAHAGRSGYDNREIVMKYIHYKLSQRATSGISIEAAGPALSPVP
PVVHLTLRQAGDDFSRRYRRDFAEMSSQLHLTPFTARGCFATVVEELFRDGVNW
GRIVAFFEFGGVMCVESVNREMSPLVDNIALWMTEYLNRHLHTWIQDNGGWDA
FVELYGPSMRPLFDFSWLSLKTLLSLALVGACITLGAYLSHKKGELNSKLEGKPIP
NPLLGLDSTRTG

Amino acids 2-10 are the HIV Tat protein transduction domain

Amino acids 11-212 are Bcl2Δ

Amino acids 213-226 are the 14 amino acid V5 epitope

Amino acids 230-235 are the 6 Histidine tag

TAT-Bcl2Δ Nucleotide sequence (SEQ ID NO: 4)

atgaggaagaagcggagacagcgacgaagaatggcgcacgctgggagaagtggttacgataaccgggagatagtgatgaa
gtacatccattataagctgtcgcagagggctacgagtgggatctcgatcgaggccgcggggcctgcgctcagcccggtgccac
ctgtggtccacctgaccctccgccaggccggcgacgacttctcccgccgctaccgccgcgacttcgccgagatgtccagccag
ctgcacctgacgcccttcaccgcgcgggggatgctttgccacggtggtggaggagctcttcagggacggggtgaactggggga
ggattgtggccttctttgagttcggtggggtcatgtgtgtggagagcgtcaaccgggagatgtcgcccctggtggacaacatcgc
cctgtggatgactgagtacctgaaccggcacctgcacacctggatccaggataacggaggctgggatgcctttgtggaactgta
cggccccagcatgcggcctctgtttgatttctcctggctgtctctgaagactctgctcagtttggcccctggtgggagcttgcatcac
cctgggtgcctatctgagccacaagaagggcgagctcaattcgaagcttgaaggtaagcctatccctaaccctctcctcggtctc
gattctacgcgtaccggtcatcatcaccatcaccattga

Figure 25

ENHANCED RECONSTITUTION AND AUTORECONSTITUTION OF THE HEMATOPOIETIC COMPARTMENT

CROSS-REFERENCE TO RELATED PATENT APPLICATIONS

This application claims the benefit of U.S. Provisional Application No. 61/674,224, filed Jul. 20, 2012, and U.S. Provisional Application No. 61/785,691, filed Mar. 14, 2013, both of which are hereby incorporated by reference in their entirety.

SUBMISSION OF SEQUENCE LISTING AS ASCII TEXT FILE

The content of the following submission on ASCII text file is incorporated herein by reference in its entirety: a computer readable form (CRF) of the Sequence Listing (file name: 691772000840SeqList.txt, date recorded: Jul. 19, 2013, size: 9 KB).

FIELD

The present disclosure generally relates to hematopoietic compartment cell formation, cell survival, and cell proliferation by hematopoietic stem cells. In particular, the present disclosure relates to the acceleration of hematopoietic compartment reconstitution and to the enhancement of hematopoietic compartment autoreconstitution.

BACKGROUND

The use of hematopoietic stem cells for bone marrow transplantation has revolutionized the approaches used to treat a large number of hematological malignancies (e.g., leukemias), as well as several widespread autoimmune diseases, and is a critical treatment for immunodeficiencies (Buckley, R H, *Annu Rev Immunol* 22, 625-655, 2004). The use of hematopoietic stem cell transplantations has also been successful in mitigating the effects of exposure to high levels of radiation in several instances (Bishop, M R, *Stem Cells* 15 Suppl 2, 305-310, 1997). In addition, hematopoietic stem cell transplantations have been used to enable the administration of high doses of cytotoxic chemotherapeutic agents to patients who suffer from a number of solid organ tumors, thus enabling the repopulation of the bone marrow following drug-induced toxicity (Crivellari, G et al., *Oncologist* 12, 79-89, 2007). The use of hematopoietic stem cell transplantation to improve the rate of engraftment of solid organ transplantations is another recent application of this medical procedure (Delis, S et al., *Pancreas* 32, 1-8, 2006). Recent studies also indicate that bone marrow transplantation may have value in the treatment of heart disease (Engelmann, M G et al., *Curr Opin Mol Ther* 8, 396-414, 2006). Although the basis of this effect is unknown, these findings raise the possibility that hematopoietic stem cells may be reprogrammed to give rise to other tissues (Kiel, M J et al., *Dev Biol* 283, 29-39, 2005). Accordingly, adult hematopoietic stem cells may have a much broader utility than, and may provide an alternative to, controversial embryonic stem cell therapy. These therapeutic applications of hematopoietic stem cell transplantation demonstrate the medical and economic impact of improving hematopoietic stem cell transplantation.

Several problems have limited the therapeutic application of hematopoietic stem cell (HSC) transplantation. For example, one major problem is the low number of HSCs available for transplants. Patients who suffer from bone marrow failure, autoimmune diseases, congenital immunodeficiencies, or hematological malignancies do not provide a good source of HSCs for autologous transplantation (Linker, C, *Best Pract Res Clin Haematol* 20, 77-84, 2007). In addition, some bone marrow failure patients and cancer patients require multiple rounds of HSC transplantation in order to achieve full HSC engraftment following radiation or chemotherapy treatment (Oliansky, D M et al., *Biol Blood Marrow Transplant* 13, 1-25, 2007). In cases where autologous HSC transplantation is not possible, there is the additional problem of identifying an appropriately histocompatible bone marrow donor. This is generally accomplished using registries that have enrolled more than 6 million potential donors (de Mello, A N et al., *Telemed. Telecare* 12 Suppl3, 64-6, 2006). Additionally, once selected, the donor must undergo a grueling and painful process to mobilize HSCs into the blood followed by 4-5 days of leukapheresis to isolate rare long-term HSCs (Nervi, B et al., *J Cell Biochem* 99, 690-705, 2006). There have been a number of novel approaches aimed at solving the problem of low numbers of HSCs available for transplants, by expanding HSCs ex vivo after isolation, but the ability to generate large numbers of long-term repopulating HSCs that remain available and bioactive over a period of years has remained elusive (Hoffman, R, *Curr Opin Hematol* 6, 184-91, 1999).

Another problem that limits the therapeutic application of HSC transplantation is the time required for the transplanted HSCs to reconstitute the functional and mature hematopoietic lineages (i.e., the hematopoietic compartment) after the ablation of the transplant recipient's resident immune system. One of the elements required to promote the successful engraftment of transplanted HSCs is the removal of the resident immune system. This is routinely done by total body irradiation or chemical ablation. The end result of this process is an almost completely immunocompromised patient that is highly susceptible to opportunistic infection by environmental microorganisms that humans routinely interact with during normal activities, such as breathing and eating. This problem is of greater concern with the significant increase in the variety and heterogeneity of iatrogenic infectious agents, many of which are highly resistant to existing antibiotics. The time required for recovery of mature hematopoietic lineages after an HSC transplant significantly affects the risk of the transplant recipient developing and ultimately succumbing to opportunistic infections.

The time required to repopulate mature hematopoietic lineages in an HSC transplant recipient is affected by several variables. One such variable is the differing recovery times required to repopulate the different hematopoietic lineages following an HSC transplant. For example, the myeloid compartment, which is composed of monocytes, neutrophils, and basophils, usually requires 4-8 weeks to recover following HSC transplantation. The lymphoid compartment requires a significantly longer recovery time in humans. For example, T-cells, NK cells, and NKT-cells require between 4-8 months to recover, while B-cells require over 12 months to recover in most individuals. The recovery time of the myeloid lineage cells is critical for the minimal required defenses against food-borne and environmental microorganisms. Another variable affecting the time required to repopulate mature hematopoietic lineages in an HSC transplant recipient is the number of HSCs available for transplantation and the size/weight of the recipient. A further variable is the nature of other treatments that an HSC transplant patient may have been subjected to prior to the transplantation. In most patients with some form of cancer, the patient will have been given several rounds of chemotherapy prior to receiving an HSC transplant. The use of such cytotoxic drugs can impact the bone marrow niches to which the transplanted HSCs home to and begin the differentiation process. In some instances where the niches have been destroyed by cytotoxic drugs, several HSC transplants may be required to initially reconstitute the niches and subsequently seed the niches with pluripotent HSCs.

Moreover, the recovery time of mature hematopoietic lineages following HSC transplantation is largely dependent of the ability of the donor HSCs to find their way to bone marrow niches. Once the HSCs arrive at the bone marrow niches, they need to establish a molecular crosstalk with the niche-resident cells. This cross talk is thought to regulate the nature and levels of cell-intrinsic signals within the HSCs that regulate their survival, proliferation, self-renewal, and differentiation. Thus, failure of HSCs to find their way to bone marrow niches, home properly, or correctly establish such molecular crosstalk with the niches can result in HSC engraftment failure. Additionally, failure of HSCs to find their way to bone marrow niches can also result in only a short term recovery of mature hematopoietic lineages or only a partial reconstitution of mature hematopoietic lineages that will slowly subside as a result of long-term bone marrow failure.

The lag time between ablation of a patient's resident immune system and hematopoietic lineage reconstitution by HSC transplantation is thus one of the major risk factors for the development of potentially fatal complications, such as opportunistic infections or HSC engraftment failure. Several approaches have been attempted to decrease the time required to reconstitute mature hematopoietic lineages following HSC transplantation. Examples of such approaches include the use of higher numbers of HSCs for transplantation, partial resident immune system ablation and multiple transplants of smaller numbers of HSCs, pre-conditioning of donor bone marrow to retain its resident T-cells, growth factor treatment of the patient following HSC transplantation, and the use of monoclonal antibodies and/or small molecule modifiers that target enzymes affecting E-selectin expression in order to improve HSC homing to bone marrow niches after HSC transplantation (Adams G B and Scadden D T, *Gene Ther* 15, 96-99, 2008; Campbell T B and Broxmeyer H E, *Front. Biosc.* 13, 1795-1805, 2008; Rocha V and Boxmeyer H, *Biology of Bone marrow transplantation* 16, S126-S132, 2009; and Hogatt J. et al., *Blood* 113, 5444-55, 2009). However, these solutions only provide a modest improvement over current approaches without significantly affecting the frequency of fatal opportunistic infections in the patient population.

BRIEF SUMMARY

Accordingly, there is a need for improved approaches for accelerating hematopoietic compartment reconstitution in a hematopoietic stem cell (HSC) transplant recipient that result in one or more of the following: increase the number of HSCs available for transplantation, increase the number of HSCs that productively home to bone marrow niches, reduce the risk of opportunistic infections, and reduce the risk of HSC engraftment failure. There is also a need for improved approaches for enhancing hematopoietic compartment autoreconstitution in a subject in need of hematopoietic compartment autoreconstitution.

In order to meet the above needs, the present disclosure provides novel methods of enhancing hematopoietic compartment reconstitution (e.g., HSC engraftment) in a subject by treating a population of HSCs with a MYC-composition, such as a protein transduction domain-MYC (PTD-MYC) fusion protein, a Bcl-2-composition, such as a PTD-Bcl-2 fusion protein, or both, prior to transplanting the HSCs into the subject; and to novel methods of enhancing hematopoietic compartment cell formation in a subject by administering a composition having a MYC-composition, such as a protein transduction domain-MYC (PTD-MYC) fusion protein, a Bcl-2-composition, such as a protein transduction domain-Bcl-2 (PTD-Bcl-2) fusion protein, or both. Certain aspects relate to methods of accelerating hematopoietic compartment reconstitution in a hematopoietic stem cell (HSC) transplant recipient by administering a composition having a MYC-composition, such as a protein transduction domain-MYC (PTD-MYC) fusion protein, a Bcl-2-composition, such as a protein transduction domain-Bcl-2 (PTD-Bcl-2) fusion protein, or both in combination with the HSC transplantation. Advantageously, such novel methods of accelerating hematopoietic compartment reconstitution may increase the number of HSCs that productively home to bone marrow niches of the transplant recipient and/or may enhance the rate of myeloid and lymphoid compartment reconstitution, thereby reducing the risk of opportunistic infections in the transplant recipient and reducing the risk of HSC engraftment failure.

Additionally, the present disclosure is based, at least in part, on the surprising discovery that administering a composition having a fusion protein containing a MYC polypeptide and a protein transduction domain (PTD), such as the HIV TAT protein transduction domain, (TAT-MYC fusion protein) after HSC transplantation accelerates the recovery time of mature hematopoietic lineages in an HSC transplant recipient. Without wishing to be bound by theory, it is believed that administering a MYC-composition, such as a PTD-MYC fusion protein to an HSC transplant recipient increases MYC activity in the hematopoietic compartment of the recipient, resulting in enhanced HSC homing to bone marrow niches in the recipient, and enhanced survival of the HSCs after transplantation resulting in a higher likelihood of HSC homing. Enhanced HSC homing improves the number of transplanted HSCs that can successfully interact with the cell matrix at bone marrow niches (i.e., productive homing), improves the number of transplanted HSCs at bone marrow niches that self-renew and produce the relevant progenitor cell types, and improves the kinetics of homing to bone marrow niches, which results in the acceleration of hematopoietic compartment reconstitution. Without wishing to be bound by theory, it is also believed that administering a MYC-composition, such as a PTD-MYC fusion protein to an HSC transplant recipient increases MYC activity in the transplanted HSCs, which increases the number of HSCs that self-renew and produce the relevant progenitor cell types and subtypes for reconstituting the functional and mature hematopoietic lineages (i.e., the hematopoietic compartment). Moreover, treating HSCs to be transplanted with a MYC-composition, such as a PTD-MYC fusion protein approximately from about 10 minutes to about 24 hours prior to transplantation also accelerates the recovery time of mature hematopoietic lineages in an HSC transplant recipient. In some embodiments, the amount of time required to transduce or otherwise introduce the MYC-composition into the HSCs is sufficient to achieve an acceleration in the recovery time of mature hematopoietic lineages in an HSC transplant recipient.

Other aspects of the present disclosure also relate to novel methods of enhancing hematopoietic compartment autoreconstitution in a subject in need of hematopoietic compartment autoreconstitution by administering a composition having a MYC-composition, such as a protein transduction domain-MYC (PTD-MYC) fusion protein, a Bcl-2-composition, such as a protein transduction domain-Bcl-2 (PTD-Bcl-2) fusion protein, or both, which induce endogenous HSCs to autoreconstitute the hematopoietic compartment in the subject. Advantageously, such novel methods of enhancing hematopoietic compartment autoreconstitution may protect patients, or facilitate recovery, from insults to the hematopoietic compartment, such as chemotherapy and radiation therapy. Such novel methods may also be used to treat bone marrow failure syndromes. Without wishing to be bound by theory, it is believed that administering a MYC-composition, such as a PTD-MYC fusion protein, a Bcl-2-composition, such as a PTD-Bcl-2 fusion protein, or both to a subject in need of hematopoietic compartment autoreconstitution increases MYC activity, Bcl-2 activity, or both in the endogenous HSCs, which increases the number of HSCs that self-renew and produce the relevant progenitor cell types and subtypes for autoreconstituting the functional and mature hematopoietic lineages (i.e., the hematopoietic compartment). Furthermore, without wishing to be bound by theory, it is also believed that MYC activity also enhances HSC localization to bone marrow niches.

While Refaeli et al. state that the protooncogene MYC can break B cell tolerance (Refaeli et al. Proc Nat Acad Sci 102(11):4097-4102, 2005), Refaeli et al. provide no guidance regarding the use of PTD-MYC fusion proteins, or the role of MYC in enhancing the ability of HSCs to form hematopoietic compartment cells. Moreover, while US2007/0116691, US2010/0297763, WO2007/047583, US2010/0047217, and WO2010/011644 disclose conditionally immortalized long-term stem cells and methods for preparing differentiated cells, none of these applications disclose that MYC enhances the ability of exogenously added HSCs to reconstitute the hematopoietic compartment in an HSC transplant recipient, or the ability of endogenous HSCs to autoreconstitute the hematopoietic compartment in a subject.

In contrast to Refaeli et al., US2007/0116691, US2010/0297763, WO2007/047583, US2010/0047217, and WO2010/011644, the inventors have surprisingly shown that administering a MYC-composition, such as a PTD-MYC fusion protein in HSC transplant recipients 24 hours after accelerates hematopoietic compartment reconstitution by reducing the time required for recovery of mature hematopoietic lineages by at least 50%. The inventors have also surprisingly shown that administering a MYC-composition, such as a PTD-MYC fusion protein in a subject having a reduction in their hematopoietic compartment enhances autoreconstitution in the subject.

Accordingly, the present disclosure relates to a method of enhancing hematopoietic compartment reconstitution to a subject in need of hematopoietic stem cell transplantation, by: treating a population of hematopoietic stem cells with a composition containing a MYC-composition, a composition containing a Bcl-2-composition, or both, for less than about 13 days; and administering to the subject, a therapeutically effective amount of the treated population of hematopoietic stem cells to reconstitute the hematopoietic compartment of the subject, wherein hematopoietic compartment reconstitution is enhanced compared to hematopoietic compartment reconstitution in a subject that is administered a population of hematopoietic stem cells that were not treated with the composition containing a MYC-composition, the composition containing a Bcl-2-composition, or both. Advantageously, a composition of the present disclosure containing a MYC-composition, a Bcl-2 composition, or both may also be administered to the subject receiving the pre-treated hematopoietic stem cells to maintain and/or further enhance hematopoietic compartment reconstitution in the subject.

In certain embodiments that may be combined with any of the preceding embodiments, the population of hematopoietic stem cells is treated with the composition containing a MYC-composition, the composition containing a Bcl-2-composition, or both, for less than about 12 days, less than about 11 days, less than about 10 days, less than about 9 days, less than about 8 days, less than about 7 days, less than about 6 days, less than about 5 days, less than about 4 days, less than about 2 days, or less than about 1 day. In certain embodiments that may be combined with any of the preceding embodiments, the population of hematopoietic stem cells is treated with the composition containing a MYC-composition, the composition containing a Bcl-2-composition, or both, for less than about 24 hours, less than about 23 hours, less than about 22 hours, less than about 21 hours, less than about 20 hours, less than about 19 hours, less than about 18 hours, less than about 17 hours, less than about 16 hours, less than about 15 hours, less than about 14 hours, less than about 13 hours, less than about 12 hours, less than about 11 hours, less than about 10 hours, less than about 9 hours, less than about 8 hours, less than about 7 hours, less than about 6 hours, less than about 5 hours, less than about 4 hours, less than about 3 hours, less than about 2 hours, or less than about 1 hour. In certain embodiments that may be combined with any of the preceding embodiments, the population of hematopoietic stem cells is treated with the composition containing a MYC-composition, the composition containing a Bcl-2-composition, or both, for less than about 60 minutes, less than about 55 minutes, less than about 50 minutes, less than about 45 minutes, less than about 40 minutes, less than about 35 minutes, less than about 30 minutes, less than about 29 minutes, less than about 28 minutes, less than about 27 minutes, less than about 26 minutes, less than about 25 minutes, less than about 24 minutes, less than about 23 minutes, less than about 22 minutes, less than about 21 minutes, less than about 20 minutes, less than about 19 minutes, less than about 18 minutes, less than about 17 minutes, less than about 16 minutes, less than about 15 minutes, less than about 14 minutes, less than about 13 minutes, less than about 12 minutes, less than about 11 minutes, or less than about 10 minutes. In certain embodiments that may be combined with any of the preceding embodiments, the population of hematopoietic stem cells is treated with the composition containing a MYC-composition. In certain embodiments that may be combined with any of the preceding embodiments, the population of hematopoietic stem cells is treated with the composition containing a Bcl-2-composition. In certain embodiments that may be combined with any of the preceding embodiments, the population of hematopoietic stem cells is treated with the composition containing a MYC-composition and the composition containing a Bcl-2-composition. In certain embodiments that may be combined with any of the preceding embodiments, the therapeutically effective amount of the composition containing a MYC-composition is at least 0.5 µ/ml, at least 0.6 µ/ml, at least 0.7 µml, at least 0.8 µ/ml, at least 0.9 µ/ml, at least 1 µ/ml, at least 2 µ/ml, at least 3 µ/ml, at least 4 µ/ml, at least 5 µ/ml, at least 6 µ/ml, at least 7 µ/ml, at least 8 µ/ml, at least 9 µ/ml, at least 10 µ/ml, at least 15 µ/ml, at least 20 µ/ml, at least 25 µ/ml, at least 30 µ/ml, at least 35 μ/ml, at least 40 μ/ml, at least 45 μ/ml, at least 50 μ/ml, at least 55 μ/ml, at least 60 μ/ml, at least 65 μ/ml, at least 70 μ/ml, at least 75 μ/ml, at least 80 μ/ml, at least 85 μ/ml, at least 90 μ/ml, at least 95 μ/ml, or at least 100 μ/ml. In certain embodiments that may be combined with any of the preceding embodiments, the Bcl-2-composition contains a Bcl-2 polypeptide, a homologue thereof, an analogue thereof, or a biologically active fragment thereof. In certain embodiments that may be combined with any of the preceding embodiments, the Bcl-2-composition contains a protein transduction domain (PTD). In certain embodiments that may be combined with any of the preceding embodiments, the Bcl-2-composition is a PTD-Bcl-2 fusion protein. In certain embodiments that may be combined with any of the preceding embodiments, the Bcl-2-composition is a TAT-Bcl-2 fusion protein. In certain embodiments that may be combined with any of the preceding embodiments, the therapeutically effective amount of the composition containing a Bcl-2-composition is at least 0.5 μ/ml, at least 0.6 μ/ml, at least 0.7 μ/ml, at least 0.8 μ/ml, at least 0.9 μ/ml, at least 1 μ/ml, at least 2 μ/ml, at least 3 μ/ml, at least 4 μ/ml, at least 5 μ/ml, at least 6 μ/ml, at least 7 μ/ml, at least 8 μ/ml, at least 9 μ/ml, at least 10 μ/ml, at least 15 μ/ml, at least 20 μ/ml, at least 25 μ/ml, at least 30 μ/ml, at least 35 μ/ml, at least 40 μ/ml, at least 45 μ/ml, at least 50 μ/ml, at least 55 μ/ml, at least 60 μ/ml, at least 65 μ/ml, at least 70 μ/ml, at least 75 μ/ml, at least 80 μ/ml, at least 85 μ/ml, at least 90 μ/ml, at least 95 μ/ml, or at least 100 μ/ml. In certain embodiments that may be combined with any of the preceding embodiments, the composition containing a MYC-composition further contains a pharmaceutically acceptable carrier. In certain embodiments that may be combined with any of the preceding embodiments, the population of hematopoietic stem cells is washed prior to being administered to the subject in need thereof. In certain embodiments that may be combined with any of the preceding embodiments, the population of hematopoietic stem cells is administered to the subject in need thereof without washing the population of hematopoietic stem cells. In certain embodiments that may be combined with any of the preceding embodiments, the subject has or had a hematological malignancy, a myeloma, multiple myeloma, a leukemia, acute lymphoblastic leukemia, chronic lymphocytic leukemia, a lymphoma, indolent lymphoma, non-Hodgkin lymphoma, diffuse B cell lymphoma, follicular lymphoma, mantle cell lymphoma, T cell lymphoma, Hodgkin lymphoma, a neuroblastoma, a retinoblastoma, Shwachman Diamond syndrome, a brain tumor, Ewing's Sarcoma, a Desmoplastic small round cell tumor, a relapsed germ cell tumor, a hematological disorder, a hemoglobinopathy, an autoimmune disorder, juvenile idiopathic arthritis, systemic lupus erythematosus, severe combined immunodeficiency, congenital neutropenia with defective stem cells, severe aplastic anemia, a sickle-cell disease, a myelodysplastic syndrome, chronic granulomatous disease, a metabolic disorder, Hurler syndrome, Gaucher disease, osteopetrosis, malignant infantile osteopetrosis, heart disease, HIV, or AIDS. In certain embodiments that may be combined with any of the preceding embodiments, the subject has had an organ transplant. In certain embodiments that may be combined with any of the preceding embodiments, the population of hematopoietic stem cells were obtained from bone marrow, from peripheral blood cells, from peripheral blood cells that have undergone apheresis, from peripheral blood cells that have undergone leukapheresis, from umbilical cord blood, from amniotic fluid, from cultured HSC cells, from an immortalized HSC cell line, or from a conditionally immortalized HSC cell line. In certain embodiments that may be combined with any of the preceding embodiments, the treated population of hematopoietic stem cells is administered as a step in a hematopoietic stem cell (HSC) transplantation procedure. In certain embodiments that may be combined with any of the preceding embodiments, the HSC transplantation procedure is a myeloablative HSC transplantation procedure. In certain embodiments that may be combined with any of the preceding embodiments, the HSC transplantation procedure is a non-myeloablative HSC transplantation procedure. In certain embodiments that may be combined with any of the preceding embodiments, the HSC transplantation is an autologous HSC transplantation or an allogenic HSC transplantation. In certain embodiments that may be combined with any of the preceding embodiments, administration of the treated population of hematopoietic stem cells accelerates hematopoietic compartment reconstitution after HSC transplantation in the subject. In certain embodiments that may be combined with any of the preceding embodiments, administering the treated population of hematopoietic stem cells achieves an at least 50% acceleration in hematopoietic compartment reconstitution, compared to hematopoietic compartment reconstitution in a subject that is administered a population of hematopoietic stem cells that were not treated with the composition containing a MYC-composition, the composition containing a Bcl-2-composition, or both. In certain embodiments that may be combined with any of the preceding embodiments, the accelerated hematopoietic compartment reconstitution in the subject results in T cell compartment reconstitution that is accelerated by at least 50%, compared to T cell reconstitution in a subject that is administered a population of hematopoietic stem cells that were not treated with the composition containing a MYC-composition, the composition containing a Bcl-2-composition, or both. In certain embodiments that may be combined with any of the preceding embodiments, the accelerated hematopoietic compartment reconstitution in the subject results in B cell compartment reconstitution that is accelerated by at least 50%, compared to B cell reconstitution in a subject that is administered a population of hematopoietic stem cells that were not treated with the composition containing a MYC-composition, the composition containing a Bcl-2-composition, or both. In certain embodiments that may be combined with any of the preceding embodiments, the accelerated hematopoietic compartment reconstitution in the subject results in NK-cell compartment reconstitution that is accelerated by at least 50%, compared to NK-cell reconstitution in a subject that is administered a population of hematopoietic stem cells that were not treated with the composition containing a MYC-composition, the composition containing a Bcl-2-composition, or both. In certain embodiments that may be combined with any of the preceding embodiments, he accelerated hematopoietic compartment reconstitution in the subject results in myeloid cell compartment reconstitution that is accelerated by at least 50%, compared to myeloid cell compartment reconstitution in a subject that is administered a population of hematopoietic stem cells that were not treated with the composition containing a MYC-composition, the composition containing a Bcl-2-composition, or both. In certain embodiments that may be combined with any of the preceding embodiments, the accelerated hematopoietic compartment reconstitution in the subject results in neutrophil recovery that is accelerated by at least 50%, compared to neutrophil recovery in a subject that is administered a population of hematopoietic stem cells that were not treated with the composition containing a MYC-composition, the composition containing a Bcl-2-composition, or both. In certain embodiments that may be combined with any of the preceding embodiments, administration of the composition containing a MYC-composition results in a 50% increase in HSC productive homing to bone marrow niches in the subject, compared to a subject that is administered a population of hematopoietic stem cells that were not treated with the composition containing a MYC-composition, the composition containing a Bcl-2-composition, or both. In certain embodiments that may be combined with any of the preceding embodiments, further including administering a third composition containing a MYC-composition, a Bcl-2-composition, or both; and optionally at least one cytokine, growth factor, antibody, and/or small molecule modifier. In certain embodiments that may be combined with any of the preceding embodiments, the third composition further includes a pharmaceutically acceptable carrier. In certain embodiments that may be combined with any of the preceding embodiments, the population of hematopoietic stem cells is a population of human hematopoietic stem cells. In certain embodiments that may be combined with any of the preceding embodiments, the MYC-composition contains a MYC polypeptide, a homologue thereof, an analogue thereof, or a biologically active fragment thereof. In certain embodiments that may be combined with any of the preceding embodiments, the MYC-compound contains a protein transduction domain (PTD). In certain embodiments that may be combined with any of the preceding embodiments, the MYC-composition is a PTD-MYC fusion protein. In certain embodiments that may be combined with any of the preceding embodiments, the MYC-composition is a TAT-MYC fusion protein. In certain embodiments that may be combined with any of the preceding embodiments, the subject is a human patient. In certain embodiments that may be combined with any of the preceding embodiments, the subject is a non-human animal.

Other aspects of the present disclosure relate to a method of enhancing hematopoietic compartment cell formation in a subject, by: administering a therapeutically effective amount of a composition containing a MYC-composition, a Bcl-2-composition, or both to a subject in need thereof, where hematopoietic compartment formation is enhanced compared to hematopoietic compartment formation in a subject that is not administered the composition.

In certain embodiments that may be combined with any of the preceding embodiments, the composition contains a MYC-composition. In certain embodiments that may be combined with any of the preceding embodiments, the composition contains a Bcl-2-composition. In certain embodiments that may be combined with any of the preceding embodiments, the composition contains a MYC-composition and a Bcl-2-composition. In certain embodiments that may be combined with any of the preceding embodiments, the Bcl-2-composition contains a Bcl-2 polypeptide, a homologue thereof, an analogue thereof, or a biologically active fragment thereof. In certain embodiments that may be combined with any of the preceding embodiments, the Bcl-2-composition comprises a protein transduction domain (PTD). In certain embodiments that may be combined with any of the preceding embodiments, the Bcl-2-composition is a PTD-Bcl-2 fusion protein. In certain embodiments that may be combined with any of the preceding embodiments, the Bcl-2-composition is a TAT-Bcl-2 fusion protein. In certain embodiments that may be combined with any of the preceding embodiments, the MYC-composition contains a MYC polypeptide, a homologue thereof, an analogue thereof, or a biologically active fragment thereof. In certain embodiments that may be combined with any of the preceding embodiments, the MYC-compound contains a protein transduction domain (PTD). In certain embodiments that may be combined with any of the preceding embodiments, the MYC-composition is a PTD-MYC fusion protein. In certain embodiments that may be combined with any of the preceding embodiments, the MYC-composition is a TAT-MYC fusion protein. In certain embodiments that may be combined with any of the preceding embodiments, the subject is in need or was in need of hematopoietic stem cell (HSC) transplantation. In certain embodiments, the subject has or had a hematological malignancy, a myeloma, multiple myeloma, a leukemia, acute lymphoblastic leukemia, chronic lymphocytic leukemia, a lymphoma, indolent lymphoma, non-Hodgkin lymphoma, diffuse B cell lymphoma, follicular lymphoma, mantle cell lymphoma, T cell lymphoma, Hodgkin lymphoma, a neuroblastoma, a retinoblastoma, Shwachman Diamond syndrome, a brain tumor, Ewing's Sarcoma, a Desmoplastic small round cell tumor, a relapsed germ cell tumor, a hematological disorder, a hemoglobinopathy, an autoimmune disorder, juvenile idiopathic arthritis, systemic lupus erythematosus, severe combined immunodeficiency, congenital neutropenia with defective stem cells, severe aplastic anemia, a sickle-cell disease, a myelodysplastic syndrome, chronic granulomatous disease, a metabolic disorder, Hurler syndrome, Gaucher disease, osteopetrosis, malignant infantile osteopetrosis, heart disease, HIV, or AIDS. In certain embodiments, the subject has had an organ transplant. In certain embodiments that may be combined with any of the preceding embodiments, the method further includes administering a therapeutically effective amount of a second composition containing HSCs to achieve hematopoietic compartment reconstitution in the subject. In certain embodiments, the composition containing a MYC-composition, a Bcl-2-composition, or both, a Bcl-2-composition, or both is administered before, after, or concurrently with the administering of the second composition. In certain embodiments, the composition containing a MYC-composition, a Bcl-2-composition, or both, a Bcl-2-composition, or both is administered at least 5 days, at least 4 days, at least 3 days, at least 2 days, or at least 1 day before the administering of the second composition. In certain embodiments, the composition containing a MYC-composition, a Bcl-2-composition, or both, a Bcl-2-composition, or both is administered concurrently with the administering of the second composition. In certain embodiments, the composition containing a MYC-composition, a Bcl-2-composition, or both, a Bcl-2-composition, or both is administered at least 1 day, at least 2 days, at least three days, at least 4 days, at least 5 days, at least 6 days, at least 1 week, at least 2 weeks, or at least 3 weeks after the administering of the second composition. In certain embodiments that may be combined with any of the preceding embodiments, administration of the composition containing a MYC-composition, a Bcl-2-composition, or both, a Bcl-2-composition, or both results in an expansion of the HSCs contained in the second composition. In certain embodiments that may be combined with any of the preceding embodiments, the second composition containing HSCs was cultured in the presence of a MYC-composition, a Bcl-2-composition, or both, before the administering of the second composition. In certain embodiments, culturing the second composition in the presence of the MYC-composition, Bcl-2-composition, or both conditionally immortalized the HSCs. In certain embodiments, immortalization of the HSCs resulted in an expansion of the HSCs. In certain embodiments that may be combined with any of the preceding embodiments, the second composition as administered includes the MYC-composition, Bcl-2-composition, or both as a result of being cultured in the presence of the MYC-composition, Bcl-2-composition, or both. In certain embodiments that may be combined with any of the preceding embodiments, the HSCs were obtained from bone marrow, from peripheral blood cells, from peripheral blood cells that have undergone apheresis, from peripheral blood cells that have undergone leukapheresis, from umbilical cord blood, from amniotic fluid, from cultured HSC cells, from an immortalized HSC cell line, or from a conditionally immortalized HSC cell line. In certain embodiments that may be combined with any of the preceding embodiments, the HSCs are present in bone marrow, in peripheral blood cells, in peripheral blood cells that have undergone apheresis, in peripheral blood cells that have undergone leukapheresis, in umbilical cord blood, or in amniotic fluid. In certain embodiments that may be combined with any of the preceding embodiments, the second composition is administered as a step in an HSC transplantation procedure. In certain embodiments, the HSC transplantation procedure is a myeloablative HSC transplantation procedure. In certain embodiments, the HSC transplantation procedure is a non-myeloablative HSC transplantation procedure. In certain embodiments that may be combined with any of the preceding embodiments, the HSC transplantation is an autologous HSC transplantation or an allogenic HSC transplantation. In certain embodiments that may be combined with any of the preceding embodiments, administration of the composition containing a MYC-composition, a Bcl-2-composition, or both, a Bcl-2-composition, or both accelerates hematopoietic compartment reconstitution after HSC transplantation in the subject. In certain embodiments, administering the composition containing a MYC-composition, a Bcl-2-composition, or both, a Bcl-2-composition, or both achieves an at least 50% acceleration in hematopoietic compartment reconstitution compared to hematopoietic compartment reconstitution in a subject that is not administered the composition. In certain embodiments that may be combined with any of the preceding embodiments, the accelerated hematopoietic compartment reconstitution in the subject results in T cell compartment reconstitution that is accelerated by at least 50% compared to T cell reconstitution in a subject that is not administered the composition. In certain embodiments that may be combined with any of the preceding embodiments, the accelerated hematopoietic compartment reconstitution in the subject results in B cell compartment reconstitution that is accelerated by at least 50% compared to B cell reconstitution in a subject that is not administered the composition. In certain embodiments that may be combined with any of the preceding embodiments, the accelerated hematopoietic compartment reconstitution in the subject results in NK-cell compartment reconstitution that is accelerated by at least 50% compared to NK-cell reconstitution in a subject that is not administered the composition. In certain embodiments that may be combined with any of the preceding embodiments, the accelerated hematopoietic compartment reconstitution in the subject results in myeloid cell compartment reconstitution that is accelerated by at least 50% compared to myeloid cell compartment reconstitution in a subject that is not administered the composition. In certain embodiments that may be combined with any of the preceding embodiments, the accelerated hematopoietic compartment reconstitution in the subject results in neutrophil recovery that is accelerated by at least 50% compared to neutrophil recovery in a subject that is not administered the composition. In certain embodiments that may be combined with any of the preceding embodiments, administration of the composition containing a MYC-composition, a Bcl-2-composition, or both, a Bcl-2-composition, or both results in a 50% increase in HSC productive homing to bone marrow niches in the subject. In certain embodiments that may be combined with any of the preceding embodiments, the therapeutically effective amount of the second composition administered to the subject is less when the composition containing a MYC-composition, a Bcl-2-composition, or both, a Bcl-2-composition, or both is administered compared to the amount required when the composition containing a MYC-composition, a Bcl-2-composition, or both, a Bcl-2-composition, or both is not administered. In certain embodiments that may be combined with any of the preceding embodiments, further including administering a third composition containing at least one cytokine, growth factor, antibody, and/or small molecule modifier. In certain embodiments, the third composition further contains a pharmaceutically acceptable carrier. In certain embodiments that may be combined with any of the preceding embodiments, the HSCs contained in the second composition are human HSCs. In certain embodiments, the subject is in need or was in need of hematopoietic compartment autoreconstitution. In certain embodiments, the MYC-composition, Bcl-2-composition, or both induces endogenous hematopoietic stem cells (HSCs) to autoreconstitute the hematopoietic compartment in the subject. In certain embodiments that may be combined with any of the preceding embodiments, the hematopoietic compartment autoreconstitution is enhanced compared to hematopoietic compartment autoreconstitution in a subject that is not administered the composition containing a MYC-composition, a Bcl-2-composition, or both, a Bcl-2-composition, or both. In certain embodiments that may be combined with any of the preceding embodiments, the enhanced hematopoietic compartment autoreconstitution in the subject results in enhanced T cell compartment autoreconstitution, enhanced B cell compartment autoreconstitution, enhanced NK-cell compartment autoreconstitution, enhanced myeloid cell compartment autoreconstitution, or neutrophil recovery. In certain embodiments that may be combined with any of the preceding embodiments, administration of the composition containing a MYC-composition, a Bcl-2-composition, or both, a Bcl-2-composition, or both results in an expansion of endogenous HSCs. In certain embodiments that may be combined with any of the preceding embodiments, the subject is undergoing or has undergone chemotherapy. In certain embodiments, administration of the composition containing a MYC-composition, a Bcl-2-composition, or both, a Bcl-2-composition, or both prevents a decrease in hematopoietic compartment cells due to the chemotherapy. In certain embodiments that may be combined with any of the preceding embodiments, administration of the composition containing a MYC-composition, a Bcl-2-composition, or both prevents a decrease in the amount of endogenous HSCs due to the chemotherapy. In certain embodiments that may be combined with any of the preceding embodiments, the subject is undergoing or has undergone radiation therapy. In certain embodiments, administration of the composition containing a MYC-composition, a Bcl-2-composition, or both prevents a decrease in hematopoietic compartment cells due to the radiation therapy. In certain embodiments that may be combined with any of the preceding embodiments, administration of the composition containing a MYC-composition, a Bcl-2-composition, or both prevents a decrease in the amount of endogenous HSCs due to the radiation therapy. In certain embodiments that may be combined with any of the preceding embodiments, the subject has a bone marrow failure syndrome. In certain embodiments, the bone marrow failure syndrome is aplastic anemia or Gulf War syndrome. In certain embodiments, the bone marrow failure syndrome is an inherited bone marrow failure syndrome (IBMFS). In certain embodiments, the IBMFS is selected from amegakaryocytic thrombocytopenia, Diamond-Blackfan anemia, dyskeratosis congenita, fanconi anemia, Pearson syndrome, severe congenital neutropenia, Shwachman-Diamond syndrome, and thrombocytopenia absent radii, IVIC syndrome, WT syndrome, radio-ulnar synostosis, and ataxia pancytopenia. In certain embodiments that may be combined with any of the preceding embodiments, administration of the composition containing a MYC-composition, a Bcl-2-composition, or both prevents a decrease in hematopoietic compartment cells due to the bone marrow failure syndrome. In certain embodiments that may be combined with any of the preceding embodiments, administration of the composition containing a MYC-composition, a Bcl-2-composition, or both prevents a decrease in the amount of endogenous HSCs due to the bone marrow failure syndrome. In certain embodiments that may be combined with any of the preceding embodiments, the therapeutically effective amount of the composition containing a MYC-composition is at least 0.1 mg/kg, at least 0.2 mg/kg, at least 0.3 mg/kg, at least 0.4 mg/kg, at least 0.5 mg/kg, at least 0.6 mg/kg, at least 0.7 mg/kg, at least 0.8 mg/kg, at least 0.9 mg/kg, at least 1 mg/kg, at least 2 mg/kg, at least 3 mg/kg, at least 4 mg/kg, at least 5 mg/kg, at least 6 mg/kg, at least 7 mg/kg, at least 8 mg/kg, at least 9 mg/kg, at least 10 mg/kg, at least 20 mg/kg, at least 30 mg/kg, at least 40 mg/kg, or at least 50 mg/kg of the subject's weight. In certain embodiments that may be combined with any of the preceding embodiments, the therapeutically effective amount of the composition comprising a Bcl-2-composition is at least 0.1 mg/kg, at least 0.2 mg/kg, at least 0.3 mg/kg, at least 0.4 mg/kg, at least 0.5 mg/kg, at least 0.6 mg/kg, at least 0.7 mg/kg, at least 0.8 mg/kg, at least 0.9 mg/kg, at least 1 mg/kg, at least 2 mg/kg, at least 3 mg/kg, at least 4 mg/kg, at least 5 mg/kg, at least 6 mg/kg, at least 7 mg/kg, at least 8 mg/kg, at least 9 mg/kg, at least 10 mg/kg, at least 20 mg/kg, at least 30 mg/kg, at least 40 mg/kg, or at least 50 mg/kg of the subject's weight. In certain embodiments that may be combined with any of the preceding embodiments, the composition containing a MYC-composition, a Bcl-2-composition, or both further contains a pharmaceutically acceptable carrier. In certain embodiments that may be combined with any of the preceding embodiments, the subject is a human patient. In certain embodiments that may be combined with any of the preceding embodiments, the subject is a non-human animal.

Other aspects of the present disclosure relate to a method of accelerating hematopoietic compartment reconstitution after hematopoietic stem cell (HSC) transplantation in a subject, by: a) administering a therapeutically effective amount of a first composition containing HSCs to achieve hematopoietic compartment reconstitution in a subject in need thereof; and b) administering a second composition containing a MYC-composition, a Bcl-2-composition, or both to the subject, where administering the second composition achieves an at least 50% acceleration in hematopoietic compartment reconstitution compared to hematopoietic compartment reconstitution in a subject that is not administered the second composition.

Other aspects of the present disclosure relate to a method of enhancing hematopoietic compartment autoreconstitution in a subject, by: administering a therapeutically effective amount of a composition containing a MYC-composition, a Bcl-2-composition, or both to a subject in need of hematopoietic compartment autoreconstitution, where the MYC-composition, the Bcl-2-composition, or both induces endogenous hematopoietic stem cells (HSCs) to autoreconstitute the hematopoietic compartment in the subject, and where hematopoietic compartment autoreconstitution is enhanced compared to hematopoietic compartment autoreconstitution in a subject that is not administered the composition.

Other aspects of the present disclosure relate to a method of treating a decrease in hematopoietic compartment cells due to chemotherapy, by: administering a therapeutically effective amount of a composition containing a MYC-composition, a Bcl-2-composition, or both to a subject that is undergoing or has undergone chemotherapy, where the MYC-composition, Bcl-2-composition, or both induces endogenous hematopoietic stem cells (HSCs) to autoreconstitute the hematopoietic compartment in the subject.

Other aspects of the present disclosure relate to a method of treating a decrease in hematopoietic compartment cells due to radiation therapy, by: administering a therapeutically effective amount of a composition containing a MYC-composition, a Bcl-2-composition, or both to a subject that is undergoing or has undergone radiation therapy, where the MYC-composition, Bcl-2-composition, or both induces endogenous hematopoietic stem cells (HSCs) to autoreconstitute the hematopoietic compartment in the subject.

Other aspects of the present disclosure relate to a method of treating a bone marrow failure syndrome, by: administering a therapeutically effective amount of a composition containing a MYC-composition, a Bcl-2-composition, or both to a subject having a bone marrow failure syndrome, where the MYC-composition, Bcl-2-composition, or both induces endogenous hematopoietic stem cells (HSCs) to autoreconstitute the hematopoietic compartment in the subject.

Other aspects of the present disclosure relate to a use of a composition containing a MYC-composition, a Bcl-2-composition, or both in a subject that is in need or was in need of hematopoietic compartment cell formation to enhance hematopoietic compartment cell formation, where use of the composition enhances hematopoietic compartment formation compared to hematopoietic compartment formation in a patient that does not receive the composition.

In certain embodiments that may be combined with any of the preceding embodiments, the subject is in need or was in need of hematopoietic stem cell (HSC) transplantation. In certain embodiments, the subject has or had a hematological malignancy, a myeloma, multiple myeloma, a leukemia, acute lymphoblastic leukemia, chronic lymphocytic leukemia, a lymphoma, indolent lymphoma, non-Hodgkin lymphoma, diffuse B cell lymphoma, follicular lymphoma, mantle cell lymphoma, T cell lymphoma, Hodgkin lymphoma, a neuroblastoma, a retinoblastoma, Shwachman Diamond syndrome, a brain tumor, Ewing's Sarcoma, a Desmoplastic small round cell tumor, a relapsed germ cell tumor, a hematological disorder, a hemoglobinopathy, an autoimmune disorder, juvenile idiopathic arthritis, systemic lupus erythematosus, severe combined immunodeficiency, congenital neutropenia with defective stem cells, severe aplastic anemia, a sickle-cell disease, a myelodysplastic syndrome, chronic granulomatous disease, a metabolic disorder, Hurler syndrome, Gaucher disease, osteopetrosis, malignant infantile osteopetrosis, heart disease, HIV, or AIDS. In certain embodiments, the subject has had an organ transplant. In certain embodiments that may be combined with any of the preceding embodiments, the subject is undergoing or underwent and HSC transplant. In certain embodiments, the composition containing a MYC-composition, a Bcl-2-composition, or both is administered before, after, or concurrently with the HSC transplant. In certain embodiments, the composition containing a MYC-composition, a Bcl-2-composition, or both is administered at least 5 days, at least 4 days, at least 3 days, at least 2 days, or at least 1 day before HSC transplantation. In certain embodiments, the composition containing a MYC-composition, a Bcl-2-composition, or both is administered concurrently with HSC transplantation. In certain embodiments, the composition containing a MYC-composition, a Bcl-2-composition, or both is administered at least 1 day, at least 2 days, at least three days, at least 4 days, at least 5 days, at least 6 days, at least 1 week, at least 2 weeks, or at least 3 weeks after the HSC transplantation. In certain embodiments that may be combined with any of the preceding embodiments, administration of the composition containing a MYC-composition, a Bcl-2-composition, or both results in an expansion of the transplanted HSCs. In certain embodiments that may be combined with any of the preceding embodiments, the transplanted HSCs were cultured in the presence of a MYC-composition, a Bcl-2-composition, or both prior to HSC transplantation. In certain embodiments, culturing the HSCs in the presence of the MYC-composition, Bcl-2-composition, or both conditionally immortalized the HSCs. In certain embodiments, immortalization of the HSCs resulted in an expansion of the HSCs. In certain embodiments that may be combined with any of the preceding embodiments, the transplanted HSCs included the MYC-composition, Bcl-2-composition, or both as a result of being cultured in the presence of the MYC-composition, Bcl-2-composition, or both. In certain embodiments that may be combined with any of the preceding embodiments, the transplanted HSCs were obtained from bone marrow, from peripheral blood cells, from peripheral blood cells that have undergone apheresis, from peripheral blood cells that have undergone leukapheresis, from umbilical cord blood, from amniotic fluid, from cultured HSC cells, from an immortalized HSC cell line, or from a conditionally immortalized HSC cell line. In certain embodiments that may be combined with any of the preceding embodiments, the HSC transplantation procedure is or was a myeloablative HSC transplantation procedure. In certain embodiments that may be combined with any of the preceding embodiments, the HSC transplantation procedure is or was a non-myeloablative HSC transplantation procedure. In certain embodiments that may be combined with any of the preceding embodiments, the HSC transplantation is or was an autologous HSC transplantation. In certain embodiments that may be combined with any of the preceding embodiments, the HSC transplantation is or was an allogenic HSC transplantation. In certain embodiments that may be combined with any of the preceding embodiments, administration of the composition containing a MYC-composition, a Bcl-2-composition, or both accelerates hematopoietic compartment reconstitution after HSC transplantation in the subject. In certain embodiments, administering the composition containing a MYC-composition, a Bcl-2-composition, or both achieves an at least 50% acceleration in hematopoietic compartment reconstitution compared to hematopoietic compartment reconstitution in a subject that is not administered the composition. In certain embodiments that may be combined with any of the preceding embodiments, the accelerated hematopoietic compartment reconstitution in the subject results in T cell compartment reconstitution that is accelerated by at least 50% compared to T cell reconstitution in a subject that is not administered the composition. In certain embodiments that may be combined with any of the preceding embodiments, the accelerated hematopoietic compartment reconstitution in the subject results in B cell compartment reconstitution that is accelerated by at least 50% compared to B cell reconstitution in a subject that is not administered the composition. In certain embodiments that may be combined with any of the preceding embodiments, the accelerated hematopoietic compartment reconstitution in the subject results in NK-cell compartment reconstitution that is accelerated by at least 50% compared to NK-cell reconstitution in a subject that is not administered the composition. In certain embodiments that may be combined with any of the preceding embodiments, the accelerated hematopoietic compartment reconstitution in the subject results in myeloid cell compartment reconstitution that is accelerated by at least 50% compared to myeloid cell compartment reconstitution in a subject that is not administered the composition. In certain embodiments that may be combined with any of the preceding embodiments, the accelerated hematopoietic compartment reconstitution in the subject results in neutrophil recovery that is accelerated by at least 50% compared to neutrophil recovery in a subject that is not administered the composition. In certain embodiments that may be combined with any of the preceding embodiments, administration of the composition containing a MYC-composition, a Bcl-2-composition, or both results in a 50% increase in HSC productive homing to bone marrow niches in the subject. In certain embodiments that may be combined with any of the preceding embodiments, further including administering a second composition containing at least one cytokine, growth factor, antibody, and/or small molecule modifier. In certain embodiments, the third composition further contains a pharmaceutically acceptable carrier. In certain embodiments that may be combined with any of the preceding embodiments, the transplanted HSCs are human HSCs. In certain embodiments, the subject is in need or was in need of hematopoietic compartment autoreconstitution. In certain embodiments, the MYC-composition, Bcl-2-composition, or both induces endogenous hematopoietic stem cells (HSCs) to autoreconstitute the hematopoietic compartment in the subject. In certain embodiments that may be combined with any of the preceding embodiments, the hematopoietic compartment autoreconstitution is enhanced compared to hematopoietic compartment autoreconstitution in a subject that is not administered the composition containing a MYC-composition, a Bcl-2-composition, or both. In certain embodiments that may be combined with any of the preceding embodiments, the enhanced hematopoietic compartment autoreconstitution in the subject results in enhanced T cell compartment autoreconstitution, enhanced B cell compartment autoreconstitution, enhanced NK-cell compartment autoreconstitution, enhanced myeloid cell compartment autoreconstitution, or neutrophil recovery. In certain embodiments that may be combined with any of the preceding embodiments, administration of the composition containing a MYC-composition, a Bcl-2-composition, or both results in an expansion of endogenous HSCs. In certain embodiments that may be combined with any of the preceding embodiments, the subject is undergoing or has undergone chemotherapy. In certain embodiments, administration of the composition containing a MYC-composition, a Bcl-2-composition, or both prevents a decrease in hematopoietic compartment cells due to the chemotherapy. In certain embodiments that may be combined with any of the preceding embodiments, administration of the composition containing a MYC-composition, a Bcl-2-composition, or both prevents a decrease in the amount of endogenous HSCs due to the chemotherapy. In certain embodiments that may be combined with any of the preceding embodiments, the subject is undergoing or has undergone radiation therapy. In certain embodiments, administration of the composition containing a MYC-composition, a Bcl-2-composition, or both prevents a decrease in hematopoietic compartment cells due to the radiation therapy. In certain embodiments that may be combined with any of the preceding embodiments, administration of the composition containing a MYC-composition, a Bcl-2-composition, or both prevents a decrease in the amount of endogenous HSCs due to the radiation therapy. In certain embodiments that may be combined with any of the preceding embodiments, the subject has a bone marrow failure syndrome. In certain embodiments, the bone marrow failure syndrome is aplastic anemia or Gulf War Syndrome. In certain embodiments, the bone marrow failure syndrome is an inherited bone marrow failure syndrome (IBMFS). In certain embodiments, the IBMFS is selected from amegakaryocytic thrombocytopenia, Diamond-Blackfan anemia, dyskeratosis congenita, fanconi anemia, Pearson syndrome, severe congenital neutropenia, Shwachman-Diamond syndrome, and thrombocytopenia absent radii, IVIC syndrome, WT syndrome, radio-ulnar synostosis, and ataxia pancytopenia. In certain embodiments that may be combined with any of the preceding embodiments, administration of the composition containing a MYC-composition, a Bcl-2-composition, or both prevents a decrease in hematopoietic compartment cells due to the bone marrow failure syndrome. In certain embodiments that may be combined with any of the preceding embodiments, administration of the composition containing a MYC-composition, a Bcl-2-composition, or both prevents a decrease in the amount of endogenous HSCs due to the bone marrow failure syndrome. In certain embodiments that may be combined with any of the preceding embodiments, the MYC-composition is TAT-MYC. In certain embodiments that may be combined with any of the preceding embodiments, the therapeutically effective amount of the composition containing a MYC-composition is at least 0.1 mg/kg, at least 0.2 mg/kg, at least 0.3 mg/kg, at least 0.4 mg/kg, at least 0.5 mg/kg, at least 0.6 mg/kg, at least 0.7 mg/kg, at least 0.8 mg/kg, at least 0.9 mg/kg, at least 1 mg/kg, at least 2 mg/kg, at least 3 mg/kg, at least 4 mg/kg, at least 5 mg/kg, at least 6 mg/kg, at least 7 mg/kg, at least 8 mg/kg, at least 9 mg/kg, at least 10 mg/kg, at least 20 mg/kg, at least 30 mg/kg, at least 40 mg/kg, or at least 50 mg/kg of the subject's weight. In certain embodiments that may be combined with any of the preceding embodiments, the Bcl-2-composition is TAT-Bcl-2.

In certain embodiments that may be combined with any of the preceding embodiments, the therapeutically effective amount of the composition comprising a Bcl-2-composition is at least 0.1 mg/kg, at least 0.2 mg/kg, at least 0.3 mg/kg, at least 0.4 mg/kg, at least 0.5 mg/kg, at least 0.6 mg/kg, at least 0.7 mg/kg, at least 0.8 mg/kg, at least 0.9 mg/kg, at least 1 mg/kg, at least 2 mg/kg, at least 3 mg/kg, at least 4 mg/kg, at least 5 mg/kg, at least 6 mg/kg, at least 7 mg/kg, at least 8 mg/kg, at least 9 mg/kg, at least 10 mg/kg, at least 20 mg/kg, at least 30 mg/kg, at least 40 mg/kg, or at least 50 mg/kg of the subject's weight. In certain embodiments that may be combined with any of the preceding embodiments, the composition containing a MYC-composition, a Bcl-2-composition, or both further contains a pharmaceutically acceptable carrier. In certain embodiments that may be combined with any of the preceding embodiments, the composition containing a MYC-composition, the subject is a human patient. In certain embodiments that may be combined with any of the preceding embodiments, the subject is a non-human animal.

Other aspects of the present disclosure relate to a use of a composition containing a MYC-composition, a Bcl-2-composition, or both in a patient who has had or will receive a hematopoietic stem cell (HSC) transplant to accelerate hematopoietic compartment reconstitution, where use of the composition achieves an at least 50% acceleration in hematopoietic compartment reconstitution in the patient compared to hematopoietic compartment reconstitution in a subject that does not receive the composition.

Other aspects of the present disclosure relate to a use of a composition containing a MYC-composition, a Bcl-2-composition, or both in a patient who has or has had a decrease in hematopoietic compartment cells to enhance hematopoietic compartment autoreconstitution, where the MYC-composition, Bcl-2-composition, or both induces endogenous hematopoietic stem cells (HSCs) to autoreconstitute the hematopoietic compartment in the patient, and where use of the composition enhances hematopoietic compartment autoreconstitution compared to hematopoietic compartment autoreconstitution in a patient that does not receive the composition.

BRIEF DESCRIPTION OF THE DRAWINGS

FIGS. 1A-1D depict the results of FACS staining showing the development of T-cells in mice 4 weeks after transplant with expanded bone marrow cells and treatment with TAT-MYC. The panels show flow cytometry of TCRβ positive PBMCs. FIG. 1A and FIG. 1B depict flow cytometry of cells from Rag-1$^{-/-}$ (FIG. 1A) and C57BL/6 (FIG. 1B) control mice that did not receive a cell transplant or treatment with TAT-MYC. FIG. 1C and FIG. 1D depict flow cytometry of cells from Rag-1$^{-/-}$ mice injected with 5×10$^3$ expanded bone marrow cells alone (FIG. 1C), or also receiving a 10 µg injection Tat-MYC 24 hours post-transplant (FIG. 1D).

FIGS. 2A-2D depict the results of FACS staining showing the development of B-cells in mice 4 weeks after transplant with expanded bone marrow cells and treatment with TAT-MYC. The panels show flow cytometry of B220 positive PBMCs. FIG. 2A and FIG. 2B depict flow cytometry of cells from Rag-1$^{-/-}$ (FIG. 2A) and C57BL/6 (FIG. 2B) control mice that did not receive a cell transplant or treatment with TAT-MYC. FIG. 2C and FIG. 2D depict flow cytometry of cells from Rag-1$^{-/-}$ mice injected with 5×10$^3$ expanded bone marrow cells alone (FIG. 2C), or also receiving a 10 µg injection Tat-MYC 24 hours post-transplant (FIG. 2D).

FIGS. 3A-3D depict the results of FACS staining showing the development of T-cells in mice 8 weeks after transplant with expanded bone marrow cells and treatment with TAT-MYC. The panels show flow cytometry of TCRβ positive PBMCs. FIG. 3A and FIG. 3B depict flow cytometry of cells from Rag-1$^{-/-}$ (FIG. 3A) and C57BL/6 (FIG. 3B) control mice that did not receive a cell transplant or treatment with TAT-MYC. FIG. 3C and FIG. 3D depict flow cytometry of cells from Rag-1$^{-/-}$ mice injected with 5×10$^3$ expanded bone marrow cells alone (FIG. 3C), or also receiving a 10 µg injection Tat-MYC 24 hours post-transplant (FIG. 3D).

FIGS. 4A-4D depict the results of FACS staining showing the development of B-cells in mice 8 weeks after transplant with expanded bone marrow cells and treatment with TAT-MYC. The panels show flow cytometry of B220 positive PBMCs. FIG. 4A and FIG. 4B depict flow cytometry of cells from Rag-1$^{-/-}$ (FIG. 4A) and C57BL/6 (FIG. 4B) control mice that did not receive a cell transplant or treatment with TAT-MYC. FIG. 4C and FIG. 4D depict flow cytometry of cells from Rag-1$^{-/-}$ mice injected with 5×10$^3$ expanded bone marrow cells alone (FIG. 4C), or also receiving a 10 μg injection Tat-MYC 24 hours post-transplant (FIG. 4D).

FIGS. 5A-5D depict the results of FACS staining showing the development of T-cells in mice 4 weeks after transplant with freshly isolated whole bone marrow cells and treatment with TAT-MYC. The panels show flow cytometry of isolated PBMCs gated for CD8×CD4 positive cells. FIG. 5A and FIG. 5B depict flow cytometry of cells from Rag-1$^{-/-}$ (FIG. 5A) and C57BL/6 (FIG. 5B) control mice that did not receive a cell transplant or treatment with TAT-MYC. FIG. 5C and FIG. 5D depict flow cytometry of cells from Rag-1$^{-/-}$ mice injected with 1×10$^6$ whole bone marrow cells alone (FIG. 5C), or also receiving a 10 μg injection Tat-MYC 24 hours post-transplant (FIG. 5D).

FIG. 6A shows the % CD4 positive T cells in C57BL/6 control mice (untreated; first column), Rag-1$^{-/-}$ mice treated with 10$^6$ BM cells only (middle column); and Rag-1$^{-/-}$ mice treated with 10$^6$ BM cells followed 24 hours later with 10 μg TAT-MYC (last column). FIG. 6B shows the % CD8 T cells in C57BL/6 control mice (untreated; first column), Rag-1$^{-/-}$ mice treated with 10$^6$ BM cells only (middle column); and Rag-1$^{-/-}$ mice treated with 10$^6$ BM cells followed 24 hours later with 10 μg TAT-MYC (last column).

FIGS. 7A-7D depict the results of FACS staining showing the development of B-cells in mice 4 weeks after transplant with freshly isolated whole bone marrow cells and treatment with TAT-MYC. The panels show flow cytometry of isolated PBMCs gated for B220×CD19 positive cells. FIG. 7A and FIG. 7B depict flow cytometry of cells from Rag-1$^{-/-}$ (FIG. 7A) and C57BL/6 (FIG. 7B) control mice that did not receive a cell transplant or treatment with TAT-MYC. FIG. 7C and FIG. 7D depict flow cytometry of cells from Rag-1$^{-/-}$ mice injected with 1×10$^6$ whole bone marrow cells alone (FIG. 7C), or also receiving a 10 μg injection Tat-MYC 24 hours post-transplant (FIG. 7D).

FIGS. 9A-9D graphically depict activation of splenic T-cells and B-cells from Rag-1$^{-/-}$ mice cohorts shown in FIGS. 5-8. FIG. 9A and FIG. 9B show the activation of T cells (FIG. 9A) and B cells (FIG. 9B) from Rag-1$^{-/-}$ mice transplanted with 10$^6$ fresh bone marrow cells, but not treated with TAT-MYC. FIG. 9C and FIG. 9D show the activation of T cells (FIG. 9C) and B cells (FIG. 9D) from Rag-1$^{-/-}$ mice treated with 10 μg TAT-MYC following transplantation with fresh bone marrow cells.

FIGS. 10A-10C depict the results of FACS staining showing the reconstitution of T-cells in mice 2 weeks after non-lethal challenge with 5FU followed by treatment with TAT-MYC. The panels show flow cytometry of isolated PBMCs gated for CD8×CD4 positive cells. FIG. 10A depicts flow cytometry of cells from C57BL/6 control mice that did not receive treatment with TAT-MYC. FIG. 10B depicts flow cytometry of cells from C57BL/6 mice treated with 10 μg TAT-CRE. FIG. 10C depicts flow cytometry of cells from C57BL/6 mice treated with 10 μg Tat-MYC 24 hours post-5FU challenge.

FIGS. 13A-13E depict the results of FACS staining showing the reconstitution of T-cells in mice 4 weeks after sub-lethal irradiation followed transplantation of freshly-isolated whole bone marrow and treatment with TAT-MYC. The panels show flow cytometry of isolated PBMCs gated for CD4×TCRβ positive cells. FIG. 13A and FIG. 13B depict flow cytometry of cells from Rag-1$^{-/-}$ (FIG. 13A) and C57BL/6 (FIG. 13B) control mice that did not receive a cell transplant or treatment with TAT-MYC. FIG. 13C, FIG. 13D, and FIG. 13E depict flow cytometry of cells from Rag-1$^{-/-}$ mice injected with 1×10$^6$ whole bone marrow cells alone (FIG. 13C), or also receiving an intravenous (FIG. 13D) or intramuscular (FIG. 13E) injection of 10 μg Tat-MYC 24 hours post-transplant.

FIGS. 15A-15E depict the results of FACS staining showing the reconstitution of B-cells in mice 4 weeks after sub-lethal irradiation followed by transplantation of freshly isolated whole bone marrow and treatment with TAT-MYC. The panels show flow cytometry of isolated PBMCs gated for IgM×CD19 positive cells. FIG. 15A and FIG. 15B depict flow cytometry of cells from Rag-1$^{-/-}$ (FIG. 15A) and C57BL/6 (FIG. 15B) control mice that did not receive a cell transplant or treatment with TAT-MYC. FIG. 15C, FIG. 15D, and FIG. 15E depict flow cytometry of cells from Rag-1$^{-/-}$ mice injected with 1×10$^6$ whole bone marrow cells alone (FIG. 15C), or also receiving an intravenous (FIG. 15D) or intramuscular (FIG. 15E) injection of 10 μg Tat-MYC 24 hours post-transplant.

FIGS. 17A-17G depict shows a functional analysis of human cord blood derived protein-transduced long term (ptlt)-HSC in vivo. FIG. 17A depicts the results of FACS analysis showing reconstitution of the bone marrow of cohorts of sublethally irradiated NSG mice given transplants of 10$^6$ cord blood cells expanded in vitro in a cocktail of cytokines (first panel; FCB), or expanded in a cocktail of cytokines supplemented with Tat-Myc and Tat-Bcl-2 (second panel; FCB TMTB), or 5×10$^6$ fresh un-manipulated cord blood cells (third panel; Fresh FCB). FIG. 17B depicts the results of FACS analysis of bone marrow, spleen and thymus cells from the xenochimaeric mice reconstituted with ptlt-HSC shown in the second panel of FIG. 17A. All cells were stained for human CD45. Gating on CD45+ cells showed human CD34+CD3810 cells in the bone marrow (first panel; BM); human CD19+ and human CD3+ lymphocytes in the spleen (second panel; spleen); and human CD3+ cells in the thymus (third panel; thymus). FIG. 17C depicts the results of FACS analysis of human splenic B cells that developed in the NSG mouse shown in the second panel of FIG. 17A. The splenic B cells were labeled with CFSE and cultured in the presence of monoclonal antibodies to human CD40 and IgM. Human B cells from this mouse underwent proliferation following stimulation of their antigen receptor. FIG. 17D shows a graphical representation of the quantification of myeloerythroid colonies (Burst Forming Unit Erythroid (BFU-E), Colony Forming Units Megakaryocyte (CFU-M), Colony Forming Units Granulocyte (CFU-G), and Colony Forming Units Granulocyte Monocyte (CFU-GM)) from human CD34+ CD38$^{lo}$ cells after plating on methycellulose. The human CD34+ CD38$^{lo}$ cells were obtained from the bone marrow of the NSG xenochimaeric mouse shown in FIG. 17A second panel further analyzed in FIG. 17B first panel. FIG. 17E shows a graphical representation of the quantification of the development of myeloerythroid colonies following replating on methycellulose. FIG. 17F shows a graphical representation of the quantification of myeloid and lymphoid cell differentiation (CD11b, CD33, CD3, and CD19 expression) in the CD45 positive population of bone marrow cells from the NSG mouse shown in FIG. 17A second panel. FIG. 17G shows a graphical representation of the quantification of myeloid and lymphoid cell differentiation (CD11b, CD33, CD3, and CD19 expression) in the CD45 positive population of spleen cells from the NSG mouse shown in FIG. 17A second panel.

FIGS. 18A-18C depict flow cytometry of cells from NSG mice that received 5×10$^5$ (FIG. 18A), 1×10$^6$ (FIG. 18B), or 5×10$^6$ (FIG. 18C) freshly isolated fetal cord blood cells followed 24 hours later by an injection of 10 Tat-Cre. FIGS. 18D-18F depict flow cytometry of cells from NSG mice that received 5×10$^5$ (FIG. 18D), 1×10$^6$ (FIG. 18E), or 5×10$^6$ (FIG. 18F) freshly isolated fetal cord blood cells followed 24 hours later by an injection of 10 µg Tat-MYC.

FIGS. 19A-19C depict flow cytometry of cells from NSG mice that received 5×10$^5$ (FIG. 19A), 1×10$^6$ (FIG. 19B), or 5×10$^6$ (FIG. 19C) freshly isolated fetal cord blood cells followed 24 hours later by an injection of 10 µg Tat-Cre. FIGS. 19D-19F depict flow cytometry of cells from NSG mice that received 5×10$^5$ (FIG. 19D), 1×10$^6$ (FIG. 19E), or 5×10$^6$ (FIG. 19F) freshly isolated fetal cord blood cells followed 24 hours later by an injection of 10 µg Tat-MYC.

FIGS. 20A-20C depict flow cytometry of cells from NSG mice that received 5×10$^5$ (FIG. 20A), 1×10$^6$ (FIG. 20B), or 5×10$^6$ (FIG. 20C) freshly isolated fetal cord blood cells followed 24 hours later by an injection of 10 µg Tat-Cre. FIGS. 20D-20F depict flow cytometry of cells from NSG mice that received 5×10$^5$ (FIG. 20D), 1×10$^6$ (FIG. 20E), or 5×10$^6$ (FIG. 20F) freshly isolated fetal cord blood cells followed 24 hours later by an injection of 10 µg Tat-MYC.

FIGS. 21A and 21B depict the results of FACS staining showing the reconstitution of the peripheral blood in NSG mice 8 weeks after sub-lethal irradiation followed transplantation of fresh fetal cord blood cells that were treated in vitro for 1 hour with TAT-MYC prior to injecting into mice. The panels show flow cytometry of isolated PBMCs gated for human CD45 positive cells. FIG. 21A depicts flow cytometry of cells from NSG mice that received 5×10$^6$ freshly isolated fetal cord blood cells. FIG. 21B depicts flow cytometry of cells from NSG mice that received 5×10$^6$ freshly isolated fetal cord blood cells treated in vitro with Tat-MYC for 1 hour prior to injecting the cells into mice.

FIGS. 22A-22F depict the results of FACS staining showing the long-term reconstitution of the bone marrow, spleen and thymus in NSG mice 8 months after sub-lethal irradiation followed transplantation of fresh fetal cord blood cells that were treated in vitro for 1 hour with TAT-MYC prior to injecting into mice. The panels show flow cytometry of isolated bone marrow, spleen and thymus cells gated for human CD45 positive cells. FIG. 22A depicts flow cytometry of bone marrow cells from NSG mice that received 5×10$^6$ freshly isolated fetal cord blood cells. FIG. 22B depicts flow cytometry of bone marrow cells from NSG mice that received 5×10$^6$ freshly isolated fetal cord blood cells treated in vitro with Tat-MYC for 1 hour prior to injecting the cells into mice. FIG. 22C depicts flow cytometry of spleen cells from NSG mice that received 5×10$^6$ freshly isolated fetal cord blood cells. FIG. 22D depicts flow cytometry of Spleen cells from NSG mice that received 5×10$^6$ freshly isolated fetal cord blood cells treated in vitro with Tat-MYC for 1 hour prior to injecting the cells into mice. FIG. 22E depicts flow cytometry of thymus cells from NSG mice that received 5×10$^6$ freshly isolated fetal cord blood cells. FIG. 22F depicts flow cytometry of thymus cells from NSG mice that received 5×10$^6$ freshly isolated fetal cord blood cells treated in vitro with Tat-MYC for 1 hour prior to injecting the cells into mice.

FIGS. 23A-23C depict a FACS analysis of the peripheral blood from a control NSG mouse (FIG. 23A), a sublethally irradiated NSG mouse given transplants of 5×10$^6$ C-GSF mobilized adult blood cells expanded in vitro in a cocktail of cytokines (FIG. 23B), or 5×10$^6$ C-GSF mobilized adult blood cells expanded in a cocktail of cytokines supplemented with Tat-MYC and Tat-Bcl-2 (FIG. 23C).

FIG. 24 depicts the amino acid and nucleic acid sequences for some embodiments of the Tat-Myc polypeptide.

FIG. 25 depicts the amino acid and nucleic acid sequences for some embodiments of the Bcl-2 domain polypeptide.

DETAILED DESCRIPTION

The present disclosure relates, in part, to enhancing hematopoietic compartment cell formation in a subject in need thereof by administering a composition containing a MYC-composition, such as a protein transduction domain- MYC (PTD-MYC) fusion protein, a composition containing a Bcl-2-composition, such as a protein transduction domain-Bcl-2 (PTD-Bcl-2) fusion protein, or both. In certain aspects, the present disclosure relates to accelerating hematopoietic stem cell (HSC) engraftment and hematopoietic compartment reconstitution in an HSC transplant recipient by administering a composition containing a MYC-composition, such as a protein transduction domain-MYC (PTD-MYC) fusion protein, a composition containing a Bcl-2-composition, such as a protein transduction domain-Bcl-2 (PTD-Bcl-2) fusion protein, or both. In some embodiments, the HSC transplant recipient is also administered a composition containing a MYC-composition, such as a protein transduction domain-MYC (PTD-MYC) fusion protein, a composition containing a Bcl-2-composition, such as a protein transduction domain-Bcl-2 (PTD-Bcl-2) fusion protein, or both to maintain and/or further accelerate HSC engraftment and hematopoietic compartment reconstitution in the HSC transplant recipient. As used herein, HSC transplantation includes, without limitation, bone marrow transplantation.

Moreover, the present disclosure is based, at least in part, on the discovery that administering a composition having a fusion protein containing a MYC polypeptide and a PTD, such as the HIV TAT protein transduction domain, after bone transplantation reduced the time required for recovery of mature hematopoietic lineages after bone marrow transplantation. For example, it was shown that the time required for T-cell recovery was reduced from about 9 weeks to about 4 weeks, and the time required for B-cell recovery was reduced from about 10 weeks to about 4 weeks in lethally irradiated mice that were administered a MYC-composition after bone marrow transplantation (Example 1). Accordingly, one aspect of the present disclosure provides methods of accelerating hematopoietic compartment reconstitution after hematopoietic stem cell (HSC) transplantation in a subject, by: a) administering a therapeutically effective amount of a first composition containing HSCs to achieve hematopoietic compartment reconstitution in a subject in need thereof; and b) administering a second composition containing a MYC-composition, a Bcl-2-composition, or both to the subject, where administering the second composition achieves an at least 50% acceleration in hematopoietic compartment reconstitution compared to hematopoietic compartment reconstitution in a subject that is not administered the second composition.

Figure 14:
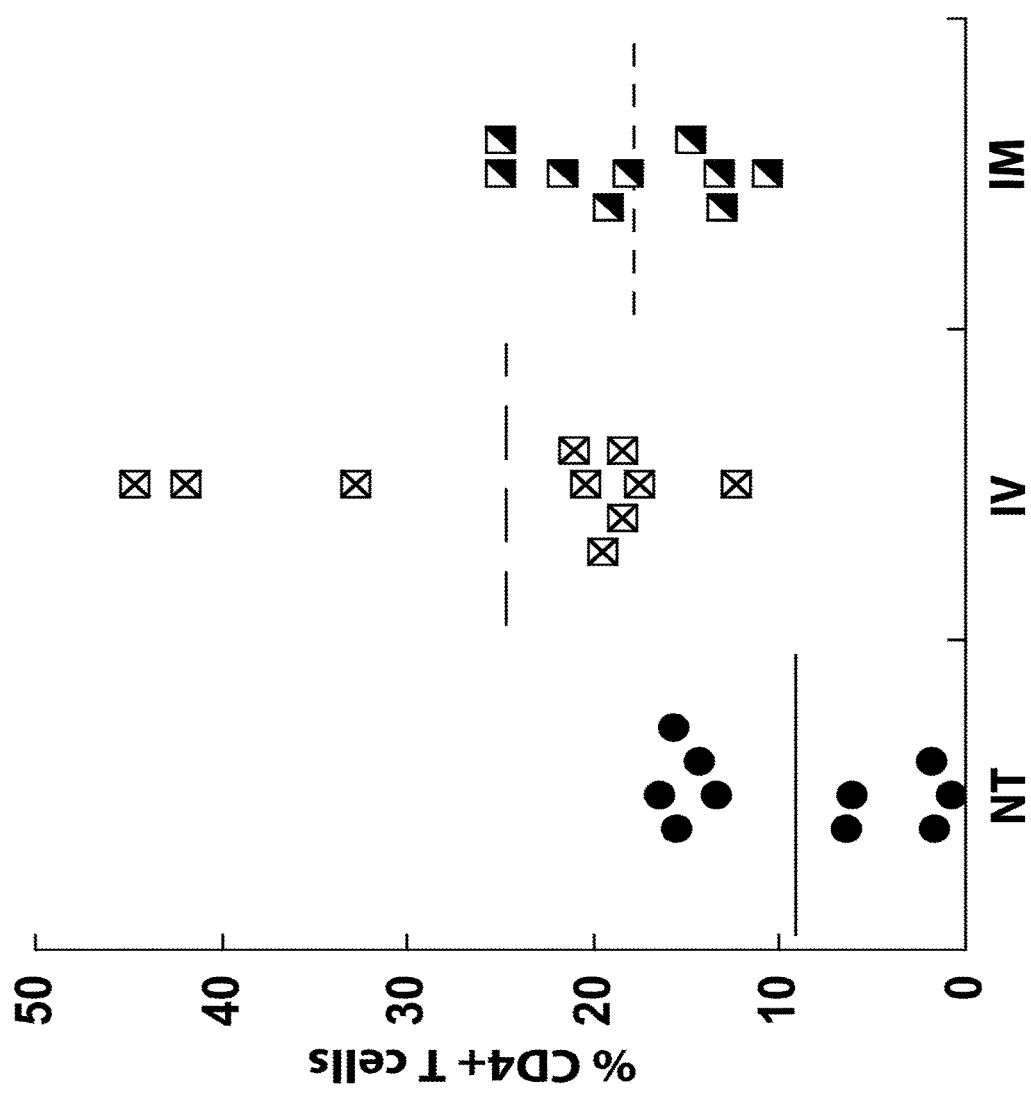
FIG. 14 graphically depicts the percentage of reconstituted CD4 T cells for the full cohort of 5FU challenged mice shown in FIG. 13. The graph shows the % CD4 positive T cells in Rag-1$^{-/-}$ control mice (untreated; first column), Rag-1$^{-/-}$ mice treated with 10 μg TAT-MYC intravenously (middle column); and Rag-1$^{-/-}$ mice treated with 10 μg TAT-CRE intramuscularly (last column).

In other aspects, the present disclosure relates to enhancing hematopoietic compartment autoreconstitution in a subject in need thereof by administering a composition having a protein transduction domain-MYC (PTD-MYC) fusion protein. The present disclosure is also based, at least in part, on the novel discovery that administration of a MYC-composition can enhance recovery in a subject undergoing chemotherapy and/or radiation therapy after suffering a decrease hematopoietic compartment cells due to the therapy. For example, it was shown that administration of a MYC-composition to a subject after treatment with the chemotherapeutic drug 5-fluorouracil accelerated recovery of hematopoietic compartment cells (e.g., CD8$^-$ T-cells) following the reduction due to the 5-fluorouracil treatment (FIG. 14).

Another aspect of the present disclosure provides methods of enhancing hematopoietic compartment autoreconstitution in a subject, by: administering a therapeutically effective amount of a composition containing a MYC-composition, a composition containing a Bcl-2-composition, or both to a subject in need of hematopoietic compartment autoreconstitution, where the MYC-composition, the Bcl-2-composition, or both induces endogenous HSCs to autoreconstitute the hematopoietic compartment in the subject, and where hematopoietic compartment autoreconstitution is enhanced compared to hematopoietic compartment autoreconstitution in a subject that is not administered the composition.

In other aspects, the present disclosure relates, in part, to enhancing hematopoietic compartment reconstitution in a subject in need of hematopoietic stem cell transplantation by pre-treating a population of HSCs with a MYC-composition, such as a protein transduction domain-MYC (PTD-MYC) fusion protein; a Bcl-2 composition, such as a PTD-Bcl-2 fusion protein; or both, prior to administering the HSCs to the subject. In certain aspects, the present disclosure relates to accelerating hematopoietic stem cell (HSC) engraftment and hematopoietic compartment reconstitution in an HSC transplant recipient by pre-treating HSCs with a protein transduction domain-MYC (PTD-MYC) fusion protein, a protein transduction domain-Bcl-2 (PTD-Bcl-2) fusion protein, or both prior to administering the HSCs to the subject. Surprisingly, pre-treating HSCs for at least as little as 1 hour prior to transplantation (and perhaps as little as about 10 minutes) is sufficient for the MYC-composition, the Bcl-2 composition, or both to achieve an enhancement in hematopoietic compartment reconstitution.

Accordingly, certain preferred embodiments relate to methods of enhancing hematopoietic compartment reconstitution to a subject in need of hematopoietic stem cell transplantation, by treating a population of hematopoietic stem cells with a composition containing a MYC-composition, a composition containing a Bcl-2-composition, or both, for less than about 13 days; and administering to the subject, a therapeutically effective amount of the treated population of hematopoietic stem cells to reconstitute the hematopoietic compartment of the subject, wherein hematopoietic compartment reconstitution is enhanced compared to hematopoietic compartment reconstitution in a subject that is administered a population of hematopoietic stem cells that were not treated with the composition containing a MYC-composition, the composition containing a Bcl-2-composition, or both. In some embodiments, the population of hematopoietic stem cells is treated with the composition containing a MYC-composition, the composition containing a Bcl-2-composition, or both, for less than about or about 12 days to less than about or about 1 days, for example, less than about or about 12 days, less than about or about 11 days, less than about or about 10 days, less than about or about 9 days, less than about or about 8 days, less than about or about 7 days, less than about or about 6 days, less than about or about 5 days, less than about or about 4 days, less than about or about 2 days, or less than about or about 1 day. In some embodiments, the population of hematopoietic stem cells is treated with the composition containing a MYC-composition, the composition containing a Bcl-2-composition, or both, for less than about or about 24 hours to less than about or about 1 hour, for example, less than about or about 24 hours, less than about or about 23 hours, less than about or about 22 hours, less than about or about 21 hours, less than about or about 20 hours, less than about or about 19 hours, less than about or about 18 hours, less than about or about 17 hours, less than about or about 16 hours, less than about or about 15 hours, less than about or about 14 hours, less than about or about 13 hours, less than about or about 12 hours, less than about or about 11 hours, less than about or about 10 hours, less than about or about 9 hours, less than about or about 8 hours, less than about or about 7 hours, less than about or about 6 hours, less than about or about 5 hours, less than about or about 4 hours, less than about or about 3 hours, less than about or about 2 hours, or less than about or about 1 hour. In some embodiments, the population of hematopoietic stem cells is treated with the composition containing a MYC-composition, the composition containing a Bcl-2-composition, or both, for less than about or about 60 minutes to less than about or about 10 minutes, for example, less than about or about 60 minutes, less than about or about 55 minutes, less than about or about 50 minutes, less than about or about 45 minutes, less than about or about 40 minutes, less than about or about 35 minutes, less than about or about 30 minutes, less than about or about 29 minutes, less than about or about 28 minutes, less than about or about 27 minutes, less than about or about 26 minutes, less than about or about 25 minutes, less than about or about 24 minutes, less than about or about 23 minutes, less than about or about 22 minutes, less than about or about 21 minutes, less than about or about 20 minutes, less than about or about 19 minutes, less than about or about 18 minutes, less than about or about 17 minutes, less than about or about 16 minutes, less than about or about 15 minutes, less than about or about 14 minutes, less than about or about 13 minutes, less than about or about 12 minutes, less than about or about 11 minutes, or less than about or about 10 minutes.

As used herein, the term "hematopoietic compartment" refers to the cell compartment in a subject that contains all blood cell lineages, including without limitation, the myeloid lineage, which includes, without limitation, monocytes, macrophages, neutrophils, basophils, eosinophils, erythrocytes, megakaryocytes, platelets, and dendritic cells; and the lymphoid lineage, which includes, without limitation, T-cells, B-cells, NKT-cells, and NK cells. The "hematopoietic compartment" can contain all immature, mature, undifferentiated, and differentiated white blood cell populations and sub-populations, including tissue-specific and specialized varieties.

As used herein, the term "hematopoietic compartment cell formation" in a subject refers to the production and/or expansion of one or more cells of any blood cell lineages of the hematopoietic compartment in the hematopoietic compartment from hematopoietic stem cell (HSC) differentiation, HSC proliferation, and/or HSC survival. "Hematopoietic compartment cell formation" may be the result of HSC engraftment by exogenous HSCs, such as hematopoietic compartment reconstitution in an HSC transplant recipient. Alternatively, hematopoietic compartment cell formation" may be the result of endogenous HSC differentiation, endogenous HSC proliferation, and/or endogenous HSC survival, such as from hematopoietic compartment autoreconstitution in a subject. In some embodiments, "hematopoietic compartment cell formation" includes, without limitation, one or more of myeloid lineage formation, myeloid lineage progenitor cell formation, monocyte cell formation, macrophage cell formations, neutrophil cell formation, basophil cell formation, eosinophil cell formation, erythrocyte cell formation, megakaryocyte cell formation, platelet cell formation, dendritic cell formation, lymphoid lineage formation, lymphoid lineage progenitor cell formation, T-cell formation, B-cell formation, NKT-cell formation, and NK cell formation.

As used herein, "enhancing hematopoietic compartment cell formation" in a subject refers to one or more of: i) increasing the rate of hematopoietic compartment cell formation (e.g., accelerating hematopoietic compartment reconstitution with exogenous HSCs or accelerating autoreconstitution with endogenous HSCs) by at least about or about 5% to at least about or about 500%, as compared to the rate of hematopoietic compartment cell formation in a subject that is administered exogenous HSCs that have not been treated with a MYC-composition, a Bcl-2 composition, or both, or as compared to the rate of hematopoietic compartment cell formation from HSCs in a subject that is not administered a MYC-composition; ii) increasing the amount of hematopoietic compartment cells that are formed in the hematopoietic compartment of the subject from either exogenous or endogenous HSCs by at least about or about 5% to at least about or about 500%, as compared to the amount of hematopoietic compartment cells that are formed in the hematopoietic compartment in a subject that is administered exogenous HSCs that have not been treated with a MYC-composition, a Bcl-2 composition, or both, or as compared to the amount of hematopoietic compartment cells that are formed in the hematopoietic compartment in a subject that is not administered a MYC-composition, a Bcl-2 composition, or both; or iii) reducing loss of hematopoietic compartment cells in the subject by at least about or about 5% to at least about or about 500%, as compared to the amount of hematopoietic compartment cells that are lost in a subject that is administered exogenous HSCs that have not been treated with a MYC-composition, a Bcl-2 composition, or both, or as compared to the amount of hematopoietic compartment cells that are lost in a subject that is not administered a MYC-composition, a Bcl-2 composition or both. Moreover, "enhancing hematopoietic compartment cell formation" in a subject includes, without limitation, enhancing hematopoietic compartment reconstitution from exogenous HSCs (e.g., HSC engraftment), and enhancing hematopoietic compartment autoreconstitution from endogenous HSCs. As used herein, "loss of hematopoietic compartment cells" in a subject refers to a reduction in the amount of hematopoietic compartment cells due to cell necrosis, apoptosis, and the like.

Similarly, hematopoietic compartment cell formation in a subject is enhanced when: i) the rate of hematopoietic compartment cell formation is increased (e.g., hematopoietic compartment reconstitution with exogenous HSCs is accelerated or autoreconstitution with endogenous HSCs is accelerated), for example, by at least about or about 5% to at least about or about 500%, as compared to the rate of hematopoietic compartment cell formation in a subject that is administered exogenous HSCs that have not been treated with a MYC-composition, a Bcl-2-composition, or both, or as compared to the rate of hematopoietic compartment cell formation from HSCs in a subject that is not administered a MYC-composition; ii) the amount of hematopoietic compartment cells that are formed in the hematopoietic compartment of the subject is increased, for example, by at least about or about 5% to at least about or about 500%, as compared to the amount of hematopoietic compartment cells that are formed in the hematopoietic compartment in a subject that is administered exogenous HSCs that have not been treated with a MYC-composition, a Bcl-2-composition, or both, or as compared to the amount of hematopoietic compartment cells that are formed in the hematopoietic compartment in a subject that is not administered a MYC-composition; and/or iii) loss of hematopoietic compartment cells in the subject is reduced, for example, by at least about or about 5% to at least about or about 500%, as compared to the amount of hematopoietic compartment cells that are lost in a subject that is administered exogenous HSCs that have not been treated with a MYC-composition, a Bcl-2-composition, or both, or as compared to the amount of hematopoietic compartment cells that are lost in a subject that is not administered a MYC-composition.

Any method known in the art and disclosed herein for measuring the rate of hematopoietic compartment cell formation (e.g., hematopoietic compartment reconstitution or autoreconstitution) from HSCs, for measuring the amount of hematopoietic compartment cells that are formed in the hematopoietic compartment of a subject, and/or for measuring loss of hematopoietic compartment cells in a subject may be used. In one non-limiting example, fluorescent-tagged antibodies specific for blood cell lineage marker and fluorescence-activated flow cytometry (FACS) analysis is utilized.

In certain embodiments, the rate of hematopoietic compartment cell formation is considered to be increased when the rate of hematopoietic compartment cell formation is increased, for example, by at least about or about 5%, at least about or about 10%, at least about or about 15%, at least about or about 20%, at least about or about 25%, at least about or about 30%, at least about or about 31%, at least about or about 32%, at least about or about 33%, at least about or about 34%, at least about or about 35%, at least about or about 40%, at least about or about 45%, at least about or about 50%, at least about or about 55%, at least about or about 60%, at least about or about 65%, at least about or about 66%, at least about or about 67%, at least about or about 68%, at least about or about 69%, at least about or about 70%, at least about or about 75%, at least about or about 80%, at least about or about 90%, at least about or about 95%, at least about or about 100%, at least about or about 150%, at least about or about 200%, at least about or about 250%, at least about or about 300%, at least about or about 400%, at least about or about 500%, or a higher percentage, as compared to the rate of hematopoietic compartment cell formation in a subject that is administered exogenous HSCs that have not been treated with a MYC-composition, a Bcl-2-composition, or both, or as compared to the rate of hematopoietic compartment cell formation from HSCs in a subject that is not administered a MYC-composition.

In certain embodiments, the amount of hematopoietic compartment cells that are formed in the hematopoietic compartment of a subject is considered to be increased when the amount of hematopoietic compartment cells formed is increased, for example, by at least about or about 5%, at least about or about 10%, at least about or about 15%, at least about or about 20%, at least about or about 25%, at least about or about 30%, at least about or about 31%, at least about or about 32%, at least about or about 33%, at least about or about 34%, at least about or about 35%, at least about or about 40%, at least about or about 45%, at least about or about 50%, at least about or about 55%, at least about or about 60%, at least about or about 65%, at least about or about 66%, at least about or about 67%, at least about or about 68%, at least about or about 69%, at least about or about 70%, at least about or about 75%, at least about or about 80%, at least about or about 90%, at least about or about 95%, at least about or about 100%, at least about or about 150%, at least about or about 200%, at least about or about 250%, at least about or about 300%, at least about or about 400%, at least about or about 500%, or a higher percentage, as compared to the amount of hematopoietic compartment cells that are formed in the hematopoietic compartment in a subject that is administered exogenous HSCs that have not been treated with a MYC-composition, a Bcl-2-composition, or both, or as compared to the amount of hematopoietic compartment cells that are formed in the hematopoietic compartment in a subject that is not administered a MYC-composition.

In certain embodiments, loss of hematopoietic compartment cells in a subject is considered to be decreased when the loss of cells is reduced, for example, by at least about or about 5%, at least about or about 10%, at least about or about 15%, at least about or about 20%, at least about or about 25%, at least about or about 30%, at least about or about 31%, at least about or about 32%, at least about or about 33%, at least about or about 34%, at least about or about 35%, at least about or about 40%, at least about or about 45%, at least about or about 50%, at least about or about 55%, at least about or about 60%, at least about or about 65%, at least about or about 66%, at least about or about 67%, at least about or about 68%, at least about or about 69%, at least about or about 70%, at least about or about 75%, at least about or about 80%, at least about or about 90%, at least about or about 95%, at least about or about 100%, at least about or about 150%, at least about or about 200%, at least about or about 250%, at least about or about 300%, at least about or about 400%, at least about or about 500%, or a higher percentage, as compared to the amount of hematopoietic compartment cells that are lost in a subject that is administered exogenous HSCs that have not been treated with a MYC-composition, a Bcl-2-composition, or both, or as compared to the amount of hematopoietic compartment cells that are lost in a subject that is not administered a MYC-composition.

MYC-Compositions

Certain aspects of the present disclosure relate to treating a population of hematopoietic stem cells (HSCs) with a composition containing a MYC-composition to enhance hematopoietic compartment reconstitution. HSCs of the present disclosure may be treated with the MYC-composition alone, or in combination with a Bcl-2-composition of the present disclosure. Any method of treating cells with a composition, such as fusion protein, known in the art and disclosed herein may be used. For example, a population of hematopoietic stem cells may be cultured in the presence of the MYC-composition. Other aspect of the present disclosure relate to administering to a subject in need thereof, a composition containing a MYC-composition to enhance hematopoietic compartment formation in the subject.

As used herein, a "MYC-composition" refers to a MYC polypeptide; a variant or mutant of a MYC polypeptide, a modified MYC polypeptide, a homologue of a MYC polypeptide; an analogue of a MYC polypeptide; a biologically active fragment of a MYC polypeptide; a downstream target of a MYC polypeptide, a homologue thereof, an analogue thereof, or a biologically active fragment thereof; and a fusion protein containing a MYC polypeptide, a homologue thereof, an analogue thereof, and a biologically active fragment thereof. A MYC-composition of the present disclosure includes any MYC polypeptide, variant thereof, mutant thereof, homologue thereof, analogue thereof, or biologically active fragment thereof known in the art (e.g., US Patent Application Publication Nos. US 2007/0116691, US 2009/0291094, US 2010/0047217, US 2010/0055129, and US 2010/0279351).

In certain preferred embodiments, MYC-compositions of the present disclosure are fusion proteins that contain a MYC polypeptide, variant thereof, mutant thereof, homologue thereof, analogue thereof, or biologically active fragment thereof that has been coupled (e.g., fused) to a protein transduction domain (PTD).

MYC Polypeptides

In some embodiments, a MYC-composition of the present disclosure is a MYC polypeptide. A MYC polypeptide of the present disclosure includes, without limitation, any polypeptide having one or more activities of a full-length MYC protein.

As used herein, "MYC" and "MYC protein" are used interchangeably and refer to a protein that is a member of the MYC family of bHLH (basic helix-loop-helix) transcription factors. MYC proteins of the present disclosure are transcription factors that regulate expression of MYC responsive genes, and as such are required to enter the nucleus of a cell to function as transcription factors. MYC activity can activate expression of certain MYC responsive genes, while repressing expression of other MYC responsive genes. MYC activity can regulate various cellular functions including, without limitation, cell proliferation, cell growth, and apoptosis.

MYC-compositions of the present disclosure allow for an increase in MYC activity in a subject in need of hematopoietic compartment cell formation by the exogenous addition of MYC, without the need for overexpressing endogenous MYC or recombinantly expressing MYC via genetic manipulation.

MYC polypeptides of the present disclosure include, without limitation, full-length MYC proteins, fragments of MYC proteins that retain at least one activity of a full-length MYC protein, homologs thereof that retain at least one activity of a full-length MYC protein, and analogs thereof that retain at least one activity of a full-length MYC protein. MYC polypeptides of the present disclosure may be produced by any suitable method known in the art. For example, a MYC polypeptide may be purified from a native source, may be recombinantly expressed, or may be chemically synthesized.

MYC Proteins

Examples of full-length MYC proteins suitable for use in any of the methods of the present disclosure include, without limitation, c-Myc, N-Myc, L-Myc, and S-Myc.

In certain preferred embodiments, the MYC polypeptide is a full-length c-Myc polypeptide. The c-Myc polypeptide may have one or more of the following features: the polypeptide may be a polymer of 439 amino acids, the polypeptide may have a molecular weight of 48,804 kDa, the polypeptide may contain a basic Helix-Loop-Helix Leucine Zip-per (bHLH/LZ) domain, or the polypeptide may bind to a sequence containing CACGTG (i.e., an E-box sequence). Preferably, the c-Myc polypeptide is the human c-Myc polypeptide having NCBI Accession Number NP_002458.2. Moreover, a c-Myc polypeptide of the present disclosure may be a c-Myc polypeptide that has not undergone any post-translational modifications. Alternatively, a c-Myc polypeptide of the present disclosure may be a c-Myc polypeptide that has undergone post-translational modifications.

In some embodiments, the MYC polypeptide is a fusion protein containing a protein transduction domain (PTD). In certain embodiments, the MYC polypeptide is a fusion protein containing a TAT protein, or fragment thereof, of the present disclosure. In some embodiments, the MYC polypeptide is a TAT-MYC fusion protein with the following amino acid sequence (SEQ ID NO: 1):

MRKKRRQRRRMPLNVSFTNRNYDLDYDSVQPYFYCDEEENFYQQQQQSEL

QPPAPSEDIWKKFELLPTPPLSPSRRSGLCSPSYVAVTPFSLRGDNDGGG

GSFSTADQLEMVTELLGGDMVNQSFICDPDDETFIKNIIIQDCMWSGFSA

-continued
AAKLVSEKLASYQAARKDSGSPNPARGHSVCSTSSLYLQDLSAAASECID

PSVVFPYPLNDSSSPKSCASQDSSAFSPSSDSLLSSTESSPQGSPEPLVL

HEETPPTTSSDSEEEQEDEEEIDVVSVEKRQAPGKRSESGSPSAGGHSKP

PHSPLVLKRCHVSTHQHNYAAPPSTRKDYPAAKRVKLDSVRVLRQISNNR

KCTSPRSSDTEENVKRRTHNVLERQRRNELKRSFFALRDQIPELENNEKA

PKVVILKKATAYILSVQAEEQKLISEEDLLRKRREQLKHKLEQLRKGELN

SKLEGKPIPNPLLGLDSTRTGHHHHHH

In the TAT-MYC polypeptide of SEQ ID NO: 1, amino acids 2-10 correspond to the HIV TAT protein transduction domain, amino acids 11-454 correspond to the amino acid sequence of c-Myc, amino acids 455-468 correspond to a 14 amino acid V5 epitope, and amino acids 472-477 correspond to a 6 Histidine tag.

Biologically Active MYC Fragments

In other embodiments, a MYC-composition of the present disclosure is a biologically active fragment of a full-length MYC protein that retains at least one activity of a full-length MYC protein. The MYC polypeptide may be a fragment of c-Myc, N-Myc, L-Myc, or S-Myc.

A MYC fragment of the present disclosure may contain at least 10, at least 15, at least 20, at least 25, at least 30, at least 35, at least 40, at least 45, at least 50, at least 55, at least 60, at least 65, at least 70, at least 75, at least 80, at least 85, at least 90, at least 95, at least 100, at least 150, at least 200, at least 250, at least 300, at least 350, at least 400, or more consecutive amino acid residues of the amino acid sequence of a MYC protein.

MYC Homologues

In other embodiments, a MYC-composition of the present disclosure is a homologue of a MYC protein, or a homologue of a fragment thereof that retains at least one activity of a full-length MYC protein.

For example, a MYC polypeptide of the present disclosure may include an amino acid sequence that is at least 40% to 100% identical, e.g., at least 40%, 45%, 50%, 55%, 60%, 65%, 70%, 75%, 80%, 85%, 86%, 87%, 88%, 90%, 91%, 92%, 94%, 95%, 96%, 97%, 98%, or any other percent from about 40% to about 100% identical to a MYC protein or fragments thereof. In certain embodiments, the MYC polypeptide is a homologue of c-Myc, N-Myc, L-Myc, S-Myc, or fragments thereof.

MYC polypeptides of the present disclosure also include functional homologs or analogs of the human c-Myc polypeptide having NCBI Accession Number NP_002458.2, or fragment thereof. In certain embodiments, the c-Myc homolog or analog contains an amino acid sequence that is at least 40% to 100% identical, e.g., at least 40%, 45%. 50%, 55%, 60%, 65%, 70%, 75%, 80%, 85%, 86%, 87%, 88%, 90%, 91%, 92%, 94%, 95%, 96%, 97%, 98%, or any other percent from about 40% to about 100% identical to the c-Myc polypeptide sequence of NCBI Accession Number NP_002458.2 or a fragment thereof.

In other embodiments, the c-Myc homolog or analog contains a polypeptide sequence of at least 10 amino acids, at least 20 amino acids, at least 30 amino acids, at least 40 amino acids, at least 50 amino acids, at least 60 amino acids, at least 70 amino acids, at least 80 amino acids, at least 90 amino acids, at least 100 amino acids, at least 150 amino acids, at least 200 amino acids, at least 250 amino acids, at least 300 amino acids, at least 350 amino acids, at least 400 amino acids, or more in length that is at least 50% to 100% identical, e.g., at least 50%, 55%, 60%, 65%, 70%, 75%, 80%, 85%, 86%, 87%, 88%, 90%, 91%, 92%, 94%, 95%, 96%, 97%, 98%, or any other percent from about 50% to about 100% identical to the c-Myc polypeptide sequence of NCBI Accession Number NP_002458.2 or a fragment thereof.

As used herein, a "homologue" refers to a protein or polypeptide having amino acid sequence similarity between a reference sequence and at least a fragment of a second sequence. Homologues may be identified by any method known in the art, preferably, by using the BLAST tool to compare a reference sequence to a single second sequence or fragment of a sequence or to a database of sequences. As described below, BLAST will compare sequences based upon percent identity and similarity.

The terms "identical" or percent "identity," in the context of two or more sequences (e.g., amino acid sequences), refer to two or more sequences or subsequences that are the same. Two sequences are substantially identical if two sequences have a specified percentage of amino acid residues or nucleotides that are the same (i.e., 29% identity, optionally 30%, 40%, 45%, 50%, 55%, 60%, 65%, 70%, 75%, 80%, 85%, 90%, 95%, 99% or 100% identity over a specified region, or, when not specified, over the entire sequence), when compared and aligned for maximum correspondence over a comparison window, or designated region as measured using one of the following sequence comparison algorithms or by manual alignment and visual inspection. Optionally, the identity exists over a region that is at least about 10 amino acids in length, or more preferably over a region that is 20, 50, 200, or more amino acids in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters. When comparing two sequences for identity, it is not necessary that the sequences be contiguous, but any gap would carry with it a penalty that would reduce the overall percent identity. For blastp, the default parameters are Gap opening penalty=11 and Gap extension penalty=1. For blastn, the default parameters are Gap opening penalty=5 and Gap extension penalty=2.

As used herein, a "comparison window" includes reference to a segment of any one of the number of contiguous positions including, but not limited to from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well known in the art. Optimal alignment of sequences for comparison can be conducted, e.g., by the local homology algorithm of Smith and Waterman (1981), by the homology alignment algorithm of Needleman and Wunsch (1970) J Mol Biol 48(3):443-453, by the search for similarity method of Pearson and Lipman (1988) Proc Natl Acad Sci USA 85(8): 2444-2448, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection [see, e.g., Brent et al., (2003) Current Protocols in Molecular Biology, John Wiley & Sons, Inc. (Ringbou Ed)].

Two examples of algorithms that are suitable for determining percent sequence identity and sequence similarity are the BLAST and BLAST 2.0 algorithms, which are described in Altschul et al. (1997) Nucleic Acids Res 25(17): 3389-3402 and Altschul et al. (1990) J. Mol Biol 215(3)-403-410, respectively. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always>0) and N (penalty score for mismatching residues; always<0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. For amino acid sequences, the BLASTP program uses as defaults a wordlength of 3, and expectation (E) of 10, and the BLOSUM62 scoring matrix [see Henikoff and Henikoff, (1992) Proc Natl Acad Sci USA 89(22):10915-10919] alignments (B) of 50, expectation (E) of 10, M=5, N=−4, and a comparison of both strands. For nucleotide sequences, the BLASTN program uses as defaults a wordlength (W) of 11, an expectation (E) or 10, M=5, N=−4, and a comparison of both strands.

The BLAST algorithm also performs a statistical analysis of the similarity between two sequences (see, e.g., Karlin and Altschul, (1993) Proc Natl Acad Sci USA 90(12):5873-5877).

One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

Other than percentage of sequence identity noted above, another indication that two polypeptides are substantially identical is that the first polypeptide is immunologically cross-reactive with antibodies raised against the second polypeptide. Thus, a polypeptide is typically substantially identical to a second polypeptide, for example, where the two peptides differ only by conservative substitutions.

As disclosed herein, suitable MYC polypeptides also include conservatively modified variants of MYC polypeptides of the present disclosure. "Conservatively modified variants" as used herein include individual substitutions, deletions, or additions to an encoded amino acid sequence which result in the substitution of an amino acid with a chemically similar amino acid. Conservative substitution tables providing functionally similar amino acids are well known in the art. The following eight groups contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1984)).

MYC Analogues,

In other embodiments, a MYC-composition of the present disclosure is an analogue of a MYC protein, or an analogue of a fragment thereof that retains at least one activity of a full-length MYC protein. In certain embodiments, the MYC polypeptide is an analogue of c-Myc, N-Myc, L-Myc, S-Myc, or fragments thereof.

As used herein, an "analogue" refers to a protein that structurally or functionally resembles a protein of interest, such as a MYC polypeptide. Compared to the starting protein, an analogue may exhibit the same, similar, or improved activity and/or function. Methods of screening for analogues and/or synthesizing analogues are well known in the art.

Suitable MYC analogues of the present disclosure include, without limitation, HIF-1a and ICN-1.

Proteins Downstream of MYC

In other embodiments, a MYC-composition of the present disclosure is a protein that is downstream of MYC in a MYC pathway. Any protein downstream known in the art is suitable for use with the methods of the present disclosure. Examples of suitable proteins that are downstream of MYC include, without limitation, AKT and AKT-related proteins, such as PDK-1, mTORC2, PI3K-delta. The protein downstream of MYC t may further include a protein transduction domain (PTD). Accordingly, in certain embodiments, the protein downstream of MYC is an AKT-PTD fusion protein, a PTD-PDK-1 fusion protein, a PTD-mTORC2 fusion protein, or a PTD-PI3K-delta fusion protein.

In other embodiments, hematopoietic compartment reconstitution is enhanced in a subject in need thereof by administering HSCs that have been pre-treated with an inhibitor (e.g., genetic, chemical, small molecule, etc.) that inhibits a protein that antagonizes HSC survival and/or proliferation and that is downstream of MYC. Similarly, hematopoietic compartment formation is enhanced in a subject in need thereof by administering a therapeutically effective amount of a composition containing inhibitor (e.g., genetic, chemical, small molecule, etc.) that inhibits a protein that antagonizes HSC survival and/or proliferation and that is downstream of MYC. Methods of administering therapeutically effective amounts of compositions, such as those containing inhibitors, and determining therapeutic amounts are well known in the art and described herein. Examples of proteins that antagonize HSC survival and/or proliferation and that are downstream of MYC include, without limitation, of pTEN, PP2A, PHLPP, CTMP. Any method known in the art for inhibiting protein and/or gene expression, activity, and/or function may be used, including without limitation the methods disclosed herein. Non-limiting examples include genetic inhibitors, small molecule inhibitors, RNA interference, and antibodies.

Activities of Full-Length MYC Proteins

In other embodiments, a MYC-composition of the present disclosure contains a full-length MYC polypeptide having at least one MYC activity, a fragment of a MYC protein that retains at least one activity of a full-length MYC protein, a homologue of a MYC protein that retains at least one activity of a full-length MYC protein, or an analogue of a MYC protein that retains at least one activity of a full-length MYC protein.

Full-length MYC proteins of the present disclosure have numerous activities. Examples of such activities include, without limitation, transcription factor activity, protein binding activity, nucleic acid binding activity, cell proliferation regulation activity, cell growth regulation activity, apoptosis regulation activity, morphogenesis regulation activity, development regulation activity, and enhanced hematopoietic compartment reconstitution activity.

In some embodiments a MYC-composition of the present disclosure has a MYC activity that enhances hematopoietic compartment reconstitution in an HSC transplant recipient, including, without limitation, a bone marrow transplant recipient. Without wishing to be bound by theory, it is believed that MYC activity enhances productive homing of the transplanted HSCs to bone marrow niches in the recipient. The recovery time of mature hematopoietic lineages following HSC transplantation is largely dependent of the ability of the administered HSCs to home to bone marrow niches. Once the HSCs arrive at the bone marrow niches, they need to establish a molecular crosstalk with the niche-resident cells. This crosstalk is thought to regulate the nature and levels of cell-intrinsic signals within the HSCs that regulate their survival, proliferation, self-renewal, and differentiation. While the full extent of the surface molecules that regulate the homing and polarized cell division process between bone marrow niches and HSCs is not yet fully understood, it is clear that several adhesion molecules, such as P-selectin and E-selectin, are involved in this process. Without wishing to be bound by theory, it is believed that MYC is a key regulator of expression of P-selectin and E-selectin, in addition to PSGL1, VLA4, VLA5, LFA1, and CD26 in the homing and maintenance of HSCs at bone marrow niches. It is also believed that MYC is a regulator of survival and differentiation signals within the HSCs. Further, it is believed that MYC regulates the expression and/or function of several additional pathways, such as the Wnt pathway, that are involved in the maintenance of HSC pluripotency and self-renewal. This molecular interplay enables the HSCs to resume a near-quiescent state that supports their asymmetric cell division, allowing for the generation of short-term HSCs that give rise to mature hematopoietic lineages, and for a long-term HSC compartment that enables the successful reconstitution of the hematopoietic lineages for the lifetime of the HSC transplant recipient. Thus, administering a MYC-composition of the present disclosure to an HSC transplant recipient results in an at least a 50% increase in HSC productive homing to bone marrow niches in the recipient.

In further embodiments, a MYC-composition of the present disclosure contains a MYC polypeptide whose activity enhances hematopoietic compartment autoreconstitution in a subject in need of hematopoietic compartment autoreconstitution. Without wishing to be bound by theory, it is believed that MYC activity enhances the ability of endogenous HSCs to self-renew and to differentiate into all hematopoietic compartment lineages, thus enhancing hematopoietic compartment autoreconstitution. Without wishing to be bound by theory, it is also believed that MYC activity enhances HSC homing to their bone marrow niches.

Advantageously, administering MYC in the form of a MYC-composition results in transient MYC activity in a subject. This transient MYC activity avoids the potentially negative effects of prolonged MYC activity, such as oncogenicity.

Additionally, MYC-compositions of the present disclosure can increase the intracellular levels of MYC in both endogenous and exogenously transplanted HSCs and committed lineage precursors. Thus, in certain embodiments, administering a MYC-composition of the present disclosure to a subject in need of hematopoietic compartment autoreconstitution results in an expansion of endogenous HSCs. In other embodiments, administering a MYC-composition of the present disclosure to an HSC transplant recipient, such as a bone marrow transplant recipient, results in an expansion of the transplanted HSCs.

As disclosed herein, a therapeutically effective amount a MYC-composition of the present disclosure is at least about or about 0.5 µ/ml to at least about or about 100 µ/ml, for example at least about or about 0.5 µ/ml, at least about or about 0.6 µ/ml, at least about or about 0.7 µ/ml, at least about or about 0.8 µ/ml, at least about or about 0.9 µ/ml, at least about or about 1 µ/ml, at least about or about 2 µ/ml, at least about or about 3 µ/ml, at least about or about 4 µ/ml, at least about or about 5 µ/ml, at least about or about 6 µ/ml, at least 7 about or about µ/ml, at least about or about 8 µ/ml, at least about or about 9 µ/ml, at least about or about 10 µ/ml, at least about or about 15 µ/ml, at least about or about 20 µ/ml, at least about or about 25 µ/ml, at least about or about 30 µ/ml, at least about or about 35 µ/ml, at least about or about 40 µ/ml, at least about or about 45 µ/ml, at least about or about 50 µ/ml, at least about or about 55 µ/ml, at least about or about 60 µ/ml, at least about or about 65 µ/ml, at least about or about 70 µ/ml, at least about or about 75 µ/ml, at least about or about 80 µ/ml, at least about or about 85 µ/ml, at least about or about 90 µ/ml, at least about or about 95 µ/ml, or at least about or about 100 µ/ml of the MYC-composition.

Bcl-2-Compositions

Certain aspects of the present disclosure relate to treating a population of hematopoietic stem cells (HSCs) with a composition containing a Bcl-2-composition to enhance hematopoietic compartment reconstitution. HSCs of the present disclosure may be treated with the Bcl-2-composition alone, or in combination with a MYC-composition of the present disclosure. Any method of treating cells with a composition, such as fusion protein, known in the art and disclosed herein may be used. For example, a population of hematopoietic stem cells may be cultured in the presence of the Bcl-2-composition. In some embodiments, a population of hematopoietic stem cells may be treated with a combination of a MYC composition of the present disclosure along with a Bcl-2-composition of the present disclosure. Other aspect of the present disclosure relate to administering to a subject in need thereof, a composition containing a Bcl-2-composition to enhance hematopoietic compartment formation in the subject.

In some embodiments, a composition containing a Bcl-2-composition of the present disclosure may be administered to a subject in need thereof, to enhance hematopoietic compartment formation in the subject. Without wishing to be bound by theory, it is believed that the Bcl-2-composition may keep more exogenous and/or endogenous hematopoietic stem cells alive (i.e., increase cell survival) long enough to enhance hematopoietic cell compartment formation (e.g., hematopoietic compartment reconstitution and/or engraftment by exogenous HSCs or autoreconstitution by endogenous HSCs). Exemplary methods of determining hematopoietic cell compartment formation are disclosed herein and known in the art. The Bcl-2-composition may be administered in addition to or instead of a MYC-composition of the present disclosure.

As used herein, a "Bcl-2-composition" refers to a Bcl-2 polypeptide; a variant or mutant of a Bcl-2 polypeptide, a modified Bcl-2 polypeptide, a homologue of a Bcl-2 polypeptide; an analogue of a Bcl-2 polypeptide; a biologically active fragment of a Bcl-2 polypeptide; a downstream target of a Bcl-2 polypeptide, a homologue thereof, an analogue thereof, or a biologically active fragment thereof; and a fusion protein containing a Bcl-2 polypeptide, a homologue thereof, an analogue thereof, and a biologically active fragment thereof. A Bcl-2-composition of the present disclosure includes any Bcl-2 polypeptide, variant thereof, mutant thereof, homologue thereof, analogue thereof, or biologically active fragment thereof known in the art (e.g., US Patent Application Publication Nos. US 2007/0116691, US 2010/0047217, and US 2010/0279351).

In certain preferred embodiments, Bcl-2-compositions of the present disclosure are fusion proteins that contain a Bcl-2 polypeptide, variant thereof, mutant thereof, homologue thereof, analogue thereof, or biologically active fragment thereof that has been coupled (e.g., fused) to a protein transduction domain (PTD).

Bcl-2 Polypeptides

In some embodiments, a Bcl-2-composition of the present disclosure is a Bcl-2 polypeptide. A Bcl-2 polypeptide of the present disclosure includes, without limitation, any polypeptide having the activity of a Bcl-2 protein.

As used herein, "Bcl-2," "Bcl-2 polypeptide," and "Bcl-2 protein" are used interchangeably and refer to a protein that is a member of the Bcl-2 protein family that has one or more and/or all Bcl-2 homology (BH) domains, such as but not limited to, BH1, BH2, BH3, and BH4. Members of the bcl-2 protein family typically form heterodimer or homodimers, and function as regulators of apoptosis. In certain preferred embodiments, Bcl-2 polypeptides of the present disclosure have anti-apoptotic activity.

Bcl-2-compositions of the present disclosure may allow for an increase in Bcl-2 activity in a subject in need of hematopoietic compartment cell formation by the exogenous addition of Bcl-2, without the need for overexpressing endogenous Bcl-2 or recombinantly expressing Bcl-2 via genetic manipulation.

Bcl-2 polypeptides of the present disclosure include, without limitation, full length Bcl-2 proteins, fragments that retain the activity of a full-length Bcl-2 protein, homologues thereof, and analogues thereof. In some embodiments, Bcl-2 fragments that retain the activity of a full-length Bcl-2 protein include a truncated form of Bcl-2 that has been deleted for the unstructured loop domain (Anderson, M., et al. (1999). Refolding, purification and characterization of a loop deletion mutant of human Bcl-2 from bacterial inclusion bodies. Prot Expr. Purif. 15, 162-70). Bcl-2 polypeptides of the present disclosure may be produced by any suitable method known in the art. For example, a Bcl-2 polypeptide may be purified from a native source, may be recombinantly expressed, or may be chemically synthesized.

Bcl-2 Proteins

Examples of full length Bcl-2 proteins suitable for use in any of the methods of the present disclosure include, without limitation, Bcl-2, Bcl-x, Bcl-XL, Mcl-1, CED-9, Bcl-2 related protein A1, Bfl-1, and Bcl-w.

In certain preferred embodiments, the Bcl-2 polypeptide is a full-length human Bcl-2 polypeptide that has been deleted for the unstructured loop domain. The human Bcl-2 polypeptide may have one or more of the following features: the polypeptide may be a polymer of 239 amino acids, the polypeptide may have a molecular weight of approximately 26.3 kDa, or the polypeptide may contain at least one Bcl-2 homology (BH) domain, such as BH1, BH2, BH3, and BH4. Preferably, the human Bcl-2 polypeptide is the Bcl-2 polypeptide having NCBI Accession Number NP_000624.2. Moreover, a Bcl-2 polypeptide of the present disclosure may be a Bcl-2 polypeptide that has not undergone any post-translational modifications. Alternatively, a Bcl-2 polypeptide of the present disclosure may be a Bcl-2 polypeptide that has undergone post-translational modifications.

In some embodiments, the Bcl-2 polypeptide is a fusion protein containing a protein transduction domain (PTD). In certain embodiments, the Bcl-2 polypeptide is a fusion protein containing a TAT protein, or fragment thereof, of the present disclosure. In some embodiments, the Bcl-2 polypeptide is a TAT-Bcl-2Δ fusion protein, where the Bcl-2 polypeptide has a deletion of the unstructured loop domain. In certain embodiments, the TAT-Bcl-2Δ fusion protein has the following amino acid sequence (SEQ ID NO: 3):

MRKKRRQRRRMAHAGRSGYDNREIVMKYIHYKLSQRATSGISIEAAGPAL

SPVPPVVHLTLRQAGDDFSRRYRRDFAEMSSQLHLTPFTARGCFATVVEE

LFRDGVNWGRIVAFFEFGGVMCVESVNREMSPLVDNIALWMTEYLNRHLH

TWIQDNGGWDAFVELYGPSMRPLFDFSWLSLKTLLSLALVGACITLGAYL

SHKKGELNSKLEGKPIPNPLLGLDSTRTGHHHHHH

In the TAT-Bcl-2Δ polypeptide of SEQ ID NO: 3, amino acids 2-10 correspond to the HIV TAT protein transduction domain, amino acids 11-212 correspond to the amino acid sequence of Bcl-2A, amino acids 4213-226 correspond to a 14 amino acid V5 epitope, and amino acids 230-235 correspond to a 6 Histidine tag.

Biologically Active Bcl-2 Fragments

In other embodiments, a Bcl-2-composition of the present disclosure is a biologically active fragment of a full-length Bcl-2 protein that retains at least one activity of a full-length Bcl-2 protein. The Bcl-2 polypeptide may be a fragment of Bcl-2, Bcl-x, Bcl-XL, Mcl-1, CED-9, Bcl-2 related protein A1, Bfl-1, or Bcl-w.

A Bcl-2 fragment of the present disclosure may contain at least 10, at least 15, at least 20, at least 25, at least 30, at least 35, at least 40, at least 45, at least 50, at least 55, at least 60, at least 65, at least 70, at least 75, at least 80, at least 85, at least 90, at least 95, at least 100, at least 110, at least 120, at least 130, at least 140, at least 150, at least 160, at least 170, at least 180, at least 190, at least 200, at least 210, at least 220, at least 230, or more consecutive amino acid residues of the amino acid sequence of a Bcl-2 protein.

Bcl-2 Homologues and Analogues

In other embodiments, a Bcl-2-composition of the present disclosure is a homologue or analogue of a Bcl-2 protein or fragment thereof. For example, a Bcl-2 polypeptide of the present disclosure may include an amino acid sequence that is at least 40% to 100% identical, e.g., at least 40%, 45%, 50%, 55%, 60%, 65%, 70%, 75%, 80%, 85%, 86%, 87%, 88%, 90%, 91%, 92%, 94%, 95%, 96%, 97%, 98%, or any other percent from about 40% to about 100% identical to a Bcl-2 protein or fragments thereof. In certain embodiments, the Bcl-2 polypeptide is a homologue or analogue of Bcl-2, Bcl-x, Bcl-XL, Mcl-1, CED-9, Bcl-2 related protein A1, Bfl-1, Bcl-w, or fragments thereof.

Bcl-2 polypeptides of the present disclosure also include functional homologues or analogues of the human Bcl-2 polypeptide having NCBI Accession Number NP_00624.2, or a fragment thereof. In certain embodiments, the Bcl-2 homologue or analogue contains an amino acid sequence that is at least 40% to 100% identical, e.g., at least 40%, 45%, 50%, 55%, 60%, 65%, 70%, 75%, 80%, 85%, 86%, 87%, 88%, 90%, 91%, 92%, 94%, 95%, 96%, 97%, 98%, or any other percent from about 40% to about 100% identical to the Bcl-2 polypeptide sequence of NCBI Accession Number NP_00624.2 or fragment thereof.

In other embodiments, the Bcl-2 homologue or analogue contains a polypeptide sequence of at least 10 amino acids, at least 20 amino acids, at least 30 amino acids, at least 40 amino acids, at least 50 amino acids, at least 60 amino acids, at least 70 amino acids, at least 80 amino acids, at least 90 amino acids, at least 100 amino acids, at least 110 amino acids, at least 120 amino acids, at least 130 amino acids, at least 140 amino acids, at least 150 amino acids, at least 160 amino acids, at least 170 amino acids, at least 180 amino acids, at least 190 amino acids, at least 200 amino acids, at least 210 amino acids, at least 220 amino acids, at least 230 amino acids, or more in length that is at least 50% to 100% identical, e.g., at least 50%, 55%, 60%, 65%, 70%, 75%, 80%, 85%, 86%, 87%, 88%, 90%, 91%, 92%, 94%, 95%, 96%, 97%, 98%, or any other percent from about 50% to about 100% identical to the Bcl-2 polypeptide sequence of NCBI Accession Number NP_00624.2 or fragment thereof.

As disclosed herein, suitable Bcl-2 polypeptides also include conservatively modified variants of Bcl-2 polypeptides of the present disclosure.

Activities of Full-Length Bcl-2 Proteins

In other embodiments, a Bcl-2-composition of the present disclosure contains a full-length Bcl-2 polypeptide having at least one Bcl-2 activity, a fragment of a Bcl-2 protein that retains at least one activity of a full-length Bcl-2 protein, a homologue of a Bcl-2 protein that retains at least one activity of a full-length Bcl-2 protein, or an analogue of a Bcl-2 protein that retains at least one activity of a full-length Bcl-2 protein.

Full-length Bcl-2 proteins of the present disclosure have numerous activities. Examples of such activities include, without limitation, apoptosis regulation activity, cell survival regulation activity, protein binding activity, mitochondrial membrane permeability regulation activity, caspase regulation activity, voltage-dependent anion channel regulation activity, G2 checkpoint regulation activity, outer mitochondrial membrane channel (VDAC) regulation activity, mitochondrial membrane potential regulation activity, protein channel activity, and cytochrome C regulation activity.

In some embodiments a Bcl-2-composition of the present disclosure has a Bcl-2 activity that either alone or in combination with a MYC-composition enhances hematopoietic compartment reconstitution in an HSC transplant recipient, including, without limitation, a bone marrow transplant recipient, when the HSCs are treated with the compositions prior to HSC transplantation.

As disclosed herein, a therapeutically effective amount a Bcl-2-composition of the present disclosure is at least about or about 0.5 μ/ml to at least about or about 100 μ/ml, for example at least about or about 0.5 μ/ml, at least about or about 0.6 μ/ml, at least about or about 0.7 μ/ml, at least about or about 0.8 μ/ml, at least about or about 0.9 μ/ml, at least about or about 1 μ/ml, at least about or about 2 μ/ml, at least about or about 3 μ/ml, at least about or about 4 μ/ml, at least about or about 5 μ/ml, at least about or about 6 μ/ml, at least 7 about or about μ/ml, at least about or about 8 μ/ml, at least about or about 9 μ/ml, at least about or about 10 μ/ml, at least about or about 15 μ/ml, at least about or about 20 μ/ml, at least about or about 25 μ/ml, at least about or about 30 μ/ml, at least about or about 35 µ/ml, at least about or about 40 µ/ml, at least about or about 45 µ/ml, at least about or about 50 µ/ml, at least about or about 55 µ/ml, at least about or about 60 µ/ml, at least about or about 65 µ/ml, at least about or about 70 µ/ml, at least about or about 75 µ/ml, at least about or about 80 µ/ml, at least about or about 85 µ/ml, at least about or about 90 µ/ml, at least about or about 95 µ/ml, or at least about or about 100 µ/ml of the Bcl-2-composition.

Protein Transduction Domains

Certain aspects of the present disclosure relate to fusion proteins containing a protein transduction domain. In some embodiments a MYC-composition of the present disclosure is a fusion protein containing a protein transduction domain fused to a MYC polypeptide. In other embodiments, a Bcl-2-composition of the present disclosure is a fusion protein containing a protein transduction domain fused to a Bcl-2 polypeptide.

As used herein, the terms "peptide transduction domain," "protein transduction domain," and "PTD" are used interchangeably and refer to a peptide sequence or domain of a protein that promotes penetration of protein into a mammalian cell and/or compartment(s) within a mammalian cell. In one non-limiting example, a PTD promotes penetration of a coupled peptide and/or protein into the nucleus of a cell.

PTDs of the present disclosure may be isolated from a PTD-containing protein by any method of isolating a protein domain known in the art, such as standard molecular biology and biochemical techniques. Alternatively, PTDs of the present disclosure may be synthesized. Suitable PTDs of the present disclosure may be about 8 to about 30 amino acid residues in length, and enriched in basic amino acid residues, such as argentine (Arg) and lysine (Lys).

Suitable PTDs of the present disclosure are not strongly immunogenic, and as such do not induce a strong immune response when administered to a subject. Moreover, PTDs of the present disclosure also do not induce an immune response when administered to an immunocompromised subject, such a subject who has received, is receiving, or will receive a bone marrow or HSC transplant.

As disclosed herein, PTDs of the present disclosure are coupled (e.g., fused, conjugated, cross-linked, etc.) to a peptide and/or protein in order to facilitate the penetration of the peptide and/or protein into a mammalian cell and/or compartment within a mammalian cell. For example, in certain embodiments a PTD of the present disclosure is coupled to a MYC protein.

Protein transduction domains suitable for use in any of the methods of the present disclosure include any PTD known in the art (e.g., U.S. Patent Application Publication Nos. US 2007/0116691 and US 2010/0055129). For example, suitable PTDs may be obtained or derived from proteins that include, without limitation, lentiviral TAT (Trans-Activator of Transcription) proteins, lentiviral VPR proteins, herpesviral VP22 proteins, and homeoproteins.

Examples of suitable PTDs obtained or derived from lentiviral TAT proteins include, without limitation, the PTD from a TAT protein of a TAT protein-containing virus, the PTD from a TAT protein of a TAT protein-containing lentivirus, the PTD from the HIV-1 TAT protein, the PTD from the HIV-2 TAT protein, the PTD from the SIV TAT protein, the PTD from a primate lentivirus TAT protein, the PTD from an ovine lentivirus TAT protein, the PTD from a bovine lentivirus TAT protein, the PTD from an equine lentivirus TAT protein, the PTD from a feline lentivirus TAT protein, a PTD from the TAT protein of a subvariant of HIV, SIV, primate lentivirus, ovine lentivirus, bovine lentivirus, equine lentivirus, or feline lentivirus, and homologs thereof. In certain embodiments, the PTD is amino acid residues 48-57 of the HIV TAT protein ($TAT_{[48-57]}$). In other embodiments, the PTD is amino acid residues 57-48 of the HIV TAT protein ($TAT_{[57-48]}$).

Examples of suitable PTDs that may obtained or derived from lentiviral VPR proteins include, without limitation, the PTD from a VPR protein of a VPR protein-containing virus, the PTD from a VPR protein of a VPR protein-containing lentivirus, the PTD from the HIV-1 VPR protein, the PTD from the HIV-2 VPR protein, the PTD from the SIV VPR protein, the PTD from a primate lentivirus VPR protein, the PTD from an ovine lentivirus VPR protein, the PTD from a bovine lentivirus VPR protein, the PTD from an equine lentivirus VPR protein, the PTD from a feline lentivirus VPR protein, a PTD from the VPR protein of a subvariant of HIV, SIV, primate lentivirus, ovine lentivirus, bovine lentivirus, equine lentivirus, or feline lentivirus, and homologs thereof.

Examples of suitable PTDs that may obtained or derived from herpesviral VP22 proteins include, without limitation, the PTD from the human herpesvirus 1(HSV-1) VP22 protein, the PTD from the human herpesvirus 2 (HSV-2) VP22 protein, the PTD from the BHV-1 VP22 protein, the PTD from the Psittacid herpesvirus 1VP22 protein, the PTD from the Equine herpesvirus 1 VP22 protein, the PTD from the Equine herpesvirus 4 VP22 protein, the PTD from the Gallid herpesvirus 2 VP22 protein, the PTD from the Varicella-zoster virus VP22 protein, and homologs thereof.

Examples of suitable PTDs that may be obtained or derived from homeodomain transcription factors include, without limitation, the homeodomain (HD) from the *Drosophila* Antennapedia (Antp) protein, the HD from the *Drosophila* Fushi tarazu (Ftz) protein, the HD from the *Drosophila* Engrailed (En) protein, the HD from the chick Engrailed-2 protein, the HD from mammalian homeoproteins, the HD from human homeoproteins, the HD from human Hox-A5 homeoprotein, the HD from human Hox-A4 homeoprotein, the HD from human Hox-B5 homeoprotein, the HD from human Hox-B6 homeoprotein, the HD from human Hox-B7 homeoprotein, the HD from human HOX-D3 homeoprotein, the HD from human GOX homeoprotein, the HD from human MOX-2 homeoprotein, the HD from human Hoxc-8 homeoprotein, the HD from human Islet-1 (Is1-1) homeoprotein, and homologs thereof.

Additionally, suitable PTDs include, without limitation, the PTD derived from Kaposi-FGF (K-FGF or FGF-4), the PTD derived from FGF-2, the PTD derived from FGF-1, and the PTD from other members of the FGF-family of proteins.

Other suitable PTDs include synthetic PTDs (e.g., Beerens, AMJ et al. *Curr Gene Ther.* 2003 October; 3(5):486-94).

Further suitable PTDs include, without limitation, a CHARIOT™ peptide (Active Motif, Carlsbad, Calif.).

In some embodiments, PTDs of the present disclosure are produced recombinantly, while in others the PTDs are produced synthetically or are purified from a native source.

PTD Fusion Protein Modifications

In some embodiments, PTD-containing fusion proteins of the present disclosure include PTD-MYC fusion proteins and PTD-Bcl-2 fusion proteins that contain one or more molecules that link the PTD to the MYC or Bcl-2 polypeptide. In some embodiments, the one or more linker molecules are amino acid peptides.

PTD-containing fusion proteins of the present disclosure may further contain at least one amino acid sequence that facilitates purification of the fusion proteins. For example, the PTD-MYC fusion proteins may contain a protein tag, such as a polyhistidine tag, such as a six histidine epitope tag. Alternatively, the PTD-containing fusion proteins may contain a V5 domain. Accordingly, in certain embodiments, PTD-containing fusion proteins of the present disclosure further contain a polyhistidine tag. Preferably, the polyhistidine tag is a 6-histidine tag. More preferably, the histidine tag contains the sequence HHHHHH. Additionally, the histidine tag may be added to a PTD-containing fusion protein of the present disclosure by any suitable method known in the art. For example, a sequence may be cloned into an expression vector encoding a polyhistidine tag. Alternatively, a polyhistidine tag may be added by PCR (i.e., the PCR primers contain a polyhistidine sequence).

Moreover, a PTD-containing fusion protein of the present disclosure may also contain at least one protein tag. In some embodiments, the at least one protein tag is an epitope tag. Preferably, the epitope tag is a V5 epitope tag. In some embodiments, the V5 epitope tag contains the amino acid sequence: GKPIPNPLLGLDST, while in other the V5 epitope tag contains the amino acid sequence: IPNPLLGLD. The amino acids may be either in the D formation, or in the L formation. In some embodiments, a first plurality of amino acids is in the D formation and a second plurality is in the L formation. Additionally, aV5 epitope tag of the present disclosure may be added to a PTD-containing fusion protein of the present disclosure by any suitable method known in the art. For example, a PTD-containing fusion protein sequence may be cloned into an expression vector encoding a V5 epitope tag. Alternatively, aV5 epitope tag may be added by PCR (i.e., the PCR primers contain a V5 epitope sequence).

In certain embodiments, a PTD-containing fusion protein of the present disclosure further contains a polyhistidine tag and an epitope tag. Preferably, the PTD-containing fusion protein contains a 6-histidine tag and a V5 epitope tag.

In some embodiments, a PTD-containing fusion protein of the present disclosure can be arranged in any desired order. In some embodiments, the PTD-containing fusion protein can be arranged in order of a) the protein transduction domain connected in frame to the Myc or Bcl-2 polypeptide, b) the Mycor Bcl-2 polypeptide connected in frame to the V5 domain, and c) the V5 domain connected in frame to the six histidine epitope tag. In some embodiments, the PTD-containing fusion protein has an order of components of a) the Myc or Bcl-2 polypeptide connected in frame to the protein transduction domain, b) the protein transduction domain connected in frame to the V5 domain, and c) the V5 domain connected in frame to the six histidine epitope tag. In some embodiments, additional intervening amino acid sequences can be included between each of the sequences. In some embodiments, additional amino acid sequences can be included at the start and/or end of the sequences.

In some embodiments, the PTD-containing fusion protein contains a protein transduction domain, a Myc or Bcl-2 polypeptide, and a short peptide domain. The short peptide domain can be varied. In some embodiments, the short peptide domain is selected from at least one of a V5, a histidine-tag, HA (hemagglutinin) tags, FLAG tag, CBP (calmodulin binding peptide), CYD (covalent yet dissociable NorpD peptide), StrepII, or HPC (heavy chain of protein C). In some embodiments, the short peptide domain is about 10 or 20 amino acids long. In some embodiments, the short peptide domain is 2-20, for example 6-20 amino acids in length. In some embodiments, two of the above listed items (for example, V5 and the his-tag) can be used together as the short peptide domain.

Construction of PTD-Containing Fusion Proteins

PTD-containing fusion proteins of the present disclosure may be constructed by any suitable method known in the art (e.g., U.S. Patent Application Publication No. US 2010/0055129).

In one non-limiting example, a nucleic acid sequence encoding a PTD-MYC fusion protein of the present disclosure may be generated by PCR. This may be accomplished by designing a forward primer for a MYC sequence that contains an in frame PTD sequence, such as the RKKRRQRRR 9-amino-acid sequence of TAT, and a reverse primer for the MYC sequence that is designed to remove the stop codon. The PCR product from a PCR reaction using such primers may then be cloned into any suitable expression vector known in the art.

In one non-limiting example, a nucleic acid sequence encoding a PTD-Bcl-2 fusion protein of the present disclosure may be generated by PCR. This may be accomplished by designing a forward primer for a Bcl-2 sequence that contains an in frame PTD sequence, such as the RKKRRQRRR 9-amino-acid sequence of TAT, and a reverse primer for the Bcl-2 sequence that is designed to remove the stop codon. The PCR product from a PCR reaction using such primers may then be cloned into any suitable expression vector known in the art. The Bcl-2 unstructured loop may be removed from the BCL-2 coding sequence using a site directed mutagenesis kit.

PTD-Containing Compositions

In other embodiments, PTD-containing fusion proteins of the present disclosure are included in a composition. For therapeutic methods, such fusion protein-containing compositions may include a pharmaceutically acceptable carrier, which includes pharmaceutically acceptable excipients and/or delivery vehicles, for delivering a PTD-containing fusion protein to a subject, such as an HSC transplant recipient.

In some embodiments, the PTD-containing fusion protein is a PTD-MYC, and a therapeutically effective amount of the PTD-MYC fusion protein-containing composition (PTD-MYC composition) is administered to a subject to achieve an at least 50% acceleration in hematopoietic compartment reconstitution compared to hematopoietic compartment reconstitution in a subject that is not administered the second composition. In other embodiments, a therapeutically effective amount of a PTD-MYC composition is administered to a subject to achieve enhanced hematopoietic compartment autoreconstitution compared to hematopoietic compartment autoreconstitution in a subject that is not administered the PTD-MYC composition. Advantageously, PTD-MYC compositions of the present disclosure have low toxicity when administered to a subject. Accordingly, a PTD-MYC composition may be administered in an amount that ranges from about 0.1 to about 50 mg/kg of the weight of the subject. In certain embodiments, a therapeutically effective amount of a composition containing a PTD-MYC fusion protein is at least 0.1 mg/kg, at least 0.2 mg/kg, at least 0.3 mg/kg, at least 0.4 mg/kg, at least 0.5 mg/kg, at least 0.6 mg/kg, at least 0.7 mg/kg, at least 0.8 mg/kg, at least 0.9 mg/kg, at least 1 mg/kg, at least 2 mg/kg, at least 3 mg/kg, at least 4 mg/kg, at least 5 mg/kg, at least 6 mg/kg, at least 7 mg/kg, at least 8 mg/kg, at least 9 mg/kg, at least 10 mg/kg, at least 20 mg/kg, at least 30 mg/kg, at least 40 mg/kg, or at least 50 mg/kg of the weight of the subject.

In other embodiments, the PTD-containing fusion protein is a PTD-Bcl-2, and a therapeutically effective amount of the PTD-Bcl-2 fusion protein-containing composition (PTD-Bcl-2-composition) is administered to a subject to achieve an at least 50% acceleration in hematopoietic compartment reconstitution compared to hematopoietic compartment reconstitution in a subject that is not administered the second composition. In other embodiments, a therapeutically effective amount of a PTD-Bcl-2-composition is administered to a subject to achieve enhanced hematopoietic compartment autoreconstitution compared to hematopoietic compartment autoreconstitution in a subject that is not administered the PTD-Bcl-2-composition. Advantageously, PTD-Bcl-2-compositions of the present disclosure have low toxicity when administered to a subject. Accordingly, a PTD-Bcl-2-composition may be administered in an amount that ranges from about 0.1 to about 50 mg/kg of the weight of the subject. In certain embodiments, a therapeutically effective amount of a composition containing a PTD-Bcl-2 fusion protein is at least 0.1 mg/kg, at least 0.2 mg/kg, at least 0.3 mg/kg, at least 0.4 mg/kg, at least 0.5 mg/kg, at least 0.6 mg/kg, at least 0.7 mg/kg, at least 0.8 mg/kg, at least 0.9 mg/kg, at least 1 mg/kg, at least 2 mg/kg, at least 3 mg/kg, at least 4 mg/kg, at least 5 mg/kg, at least 6 mg/kg, at least 7 mg/kg, at least 8 mg/kg, at least 9 mg/kg, at least 10 mg/kg, at least 20 mg/kg, at least 30 mg/kg, at least 40 mg/kg, or at least 50 mg/kg of the weight of the subject.

PTD-MYC compositions of the present disclosure and/or PTD-Bcl-2-compositions of the present disclosure can be administered at least once a day, at least twice a day, at least three times a day, at least four times a day, at least five times a day, or more times a day. Alternatively, PTD-MYC compositions of the present disclosure and/or PTD-Bcl-2-compositions of the present disclosure can be administered at least once every two days, at least once every three days, at least once every four days, at least once every five days, or at least once every six days, at least once every week, at least once every two weeks, at least once every three weeks, or at least once every four weeks.

Advantageously, PTD-MYC compositions of the present disclosure and/or PTD-Bcl-2-compositions of the present disclosure can accelerate hematopoietic compartment reconstitution from HSC transplantation (e.g., HSC engraftment), such as from bone marrow transplantation, in a subject when administered from at least about or about 5 days to at least about or about 12 hours before an HSC transplant, concurrently with an HSC transplant, or from at least about or about 12 hours to at least about or about 3 weeks after an HSC transplant. A PTD-MYC composition of the present disclosure and/or a PTD-Bcl-2-composition of the present disclosure may be administered at any suitable location, including, without limitation, the same location where the HSC transplantation occurs, a clinic or doctor's office that is separate from the location where the HSC transplantation occurs, and the home or residence of the subject receiving the HSC transplantation. Any method of administering PTD-MYC compositions of the present disclosure and/or PTD-Bcl-2-compositions of the present disclosure known in the art and disclosed herein may be used. In some embodiments, the PTD-MYC composition and/or the PTD-Bcl-2-composition is administered together with any suitable pharmaceutically acceptable carrier known in the art and disclosed herein. In other embodiments, the PTD-MYC composition and/or the PTD-Bcl-2-composition is administered as a suitable formulation known in the art, including, without limitation, an intravenous formulation.

As used herein, administering a PTD-MYC composition of the present disclosure and/or a PTD-Bcl-2-composition of the present disclosure occurs "concurrently" with an HSC transplantation when it is administered either in the same mixture and/or formulation as the HSCs to be transplanted, or in a separate mixture and/or formulation as that of the HSCs to be transplanted. When the PTD-MYC composition and/or the PTD-Bcl-2-composition is administered in a separate mixture and/or formulation, administering a PTD-MYC composition of the present disclosure occurs and/or a PTD-Bcl-2-composition of the present disclosure "concurrently" with an HSC transplantation includes, without limitation, administering the PTD-MYC composition and/or the PTD-Bcl-2-composition from at least about or about 11 hours to at least about or about 1 minute before HSC transplantation, or from at least about or about 1 minute to at least about or about 11 hours after HSC transplantation. As used herein, administering a PTD-MYC composition of the present disclosure and/or a PTD-Bcl-2-composition of the present disclosure occurs "before" an HSC transplantation when it is administered in a separate mixture and/or formulation as that of the HSCs to be transplanted from at least about or about 5 days to at least about or about 12 hours before the HSC transplantation. As used herein, administering a PTD-MYC composition of the present disclosure occurs and/or a PTD-Bcl-2-composition of the present disclosure "after" an HSC transplantation when it is administered in a separate mixture and/or formulation as that of the HSCs to be transplanted from at least about or about 12 hours to at least about or about 3 weeks after the HSC transplantation.

Accordingly, in certain embodiments, a PTD-MYC composition of the present disclosure and/or a PTD-Bcl-2-composition of the present disclosure is administered before, after, or concurrently with an HSC transplant in a subject. In some embodiments, the PTD-MYC composition and/or the PTD-Bcl-2-composition is administered at least about or about 5 days, at least about or about 4 days, at least about or about 3 days, at least about or about 2 days, at least about or about 1 day, at least about or about 23 hours, at least about or about 22 hours, at least about or about 21 hours, at least about or about 20 hours, at least about or about 19 hours, at least about or about 18 hours, at least about or about 17 hours, at least about or about 16 hours, at least about or about 15 hours, at least about or about 14 hours, at least about or about 13 hours, or at least about or about 12 hours before an HSC transplant. In other embodiments, the PTD-MYC composition and/or the PTD-Bcl-2-composition is administered concurrently with an HSC transplant. In further embodiments, the PTD-MYC composition and/or the PTD-Bcl-2-composition is administered at least about or about 12 hours, at least about or about 13 hours, at least about or about 14 hours, at least about or about 15 hours, at least about or about 16 hours, at least about or about 17 hours, at least about or about 18 hours, at least about or about 19 hours, at least about or about 20 hours, at least about or about 21 hours, at least about or about 22 hours, or at least about or about 23 hours, at least about or about 1 day, at least about or about 2 days, at least about or about three days, at least about or about 4 days, at least about or about 5 days, at least about or about 6 days, at least about or about 1 week, at least about or about 2 weeks, or at least about or about 3 weeks after an HSC transplant.

Therapeutic Uses

PTD-MYC compositions of the present disclosure and/or PTD-Bcl-2-compositions of the present disclosure find many therapeutic uses in the treatment of various conditions, diseases, and syndromes. Such uses include, without limitation, accelerating hematopoietic compartment reconstitution in an HSC transplant recipient, such as a bone marrow transplant recipient; enhancing hematopoietic compartment autoreconstitution; treating decreases in the hematopoietic compartment due to chemotherapy or radiation therapy;

treating bone marrow failure syndromes; and treating long-term HSC engraftment failure.

As used herein, a "preventing a decrease in hematopoietic compartment cells" due to chemotherapy, radiation therapy, bone marrow failure, and/or any other condition that leads to loss of hematopoietic compartment cells, refers to reducing and/or inhibiting the reduction in the amount of any hematopoietic compartment cells of the present disclosure that are lost due to cell necrosis, apoptosis, or the like as a result of the chemotherapy, radiation therapy, bone marrow failure, and/or condition that leads to loss of hematopoietic compartment cells. Any method known in the art and disclosed herein for quantifying cell loss (e.g., quantifying cell necrosis, apoptosis, etc.) may be used. In one non-limiting example DNA-intercalating dyes are used to quantify cell loss. In some embodiments, "preventing a decrease in hematopoietic compartment cells" may include, without limitation, an at least about or about 25% to an at least about or about 99%, or more reduction in hematopoietic compartment cell loss due to chemotherapy, radiation therapy, bone marrow failure, and/or condition that leads to loss of hematopoietic compartment cells.

In certain embodiments, PTD-MYC compositions of the present disclosure and/or PTD-Bcl-2-compositions of the present disclosure may be used to reduce the risk of engraftment failure and opportunistic infections in an HSC transplant recipient by accelerating hematopoietic compartment reconstitution in the recipient.

Alternatively, PTD-MYC compositions of the present disclosure and/or PTD-Bcl-2-compositions of the present disclosure may be used to treat bone marrow failure syndromes in a subject. Bone marrow failure syndromes can be inherited, or can occur as a result of, for example, an infectious disease, or chronic fatigue syndrome. Additionally, bone marrow failure in an HSC transplant recipient can occur as result of, for example, a transplant of an insufficient number of HSCs, a transplant of mismatched HSCs, or the health status of the recipient.

Acquired bone marrow failure syndromes may include, without limitation, aplastic anemia and Gulf War Syndrome.

Inherited bone marrow failure syndromes (IBMFS) may include, without limitation, amegakaryocytic thrombocytopenia, Diamond-Blackfan anemia, dyskeratosis congenita, fanconi anemia, Pearson syndrome, severe congenital neutropenia, Shwachman-Diamond syndrome, and thrombocytopenia absent radii, IVIC syndrome, WT syndrome, radio-ulnar synostosis, and ataxia pancytopenia.

In further embodiments, PTD-MYC compositions of the present disclosure and/or PTD-Bcl-2-compositions of the present disclosure may be used in treating an HSC transplant recipient whose hematopoietic chimaerism is failing after an initial engraftment of transplanted HSCs (i.e., failure of long-term HSC engraftment).

Exposure to toxins, such as chemicals, chemotherapeutic drugs, or radiation may lead to a decrease or loss in a subject's hematopoietic compartment. As used herein, a decrease in the hematopoietic compartment may occur when there is a decrease in the total amount cells in the hematopoietic compartment or a decrease in a specific population or sub-population of cells in the hematopoietic compartment. Examples of specific populations or sub-populations of cells in the hematopoietic compartment include, without limitation, myeloid cells, monocytes, macrophages, neutrophils, basophils, eosinophils, erythrocytes, megakaryocytes, platelets, dendritic cells, lymphocytes, T-cell progenitors, pro-T-cells, pre-T-cells, double positive T-cells, immature T-cells, mature T-cells, B-cell progenitors, pro-B-cells, early pro-B-cells, late-pro B-cells, large pre-B-cells, small pre-B-cells, immature B-cells, mature B-cells, NKT-cells, and NK-cells.

Accordingly, in certain embodiments, PTD-MYC compositions of the present disclosure and/or PTD-Bcl-2-compositions of the present disclosure may be used to treat subjects that have been exposed to such toxins. In some embodiments, treating subjects with a PTD-MYC composition of the present disclosure and/or a PTD-Bcl-2-composition of the present disclosure prevents a decrease or loss in hematopoietic compartment cells in subjects that are undergoing or have undergone chemotherapy or radiation therapy. In other embodiments, treating subjects with a PTD-MYC composition of the present disclosure and/or a PTD-Bcl-2-composition of the present disclosure prevents a decrease or loss in the amount of endogenous HSCs in subjects that are undergoing or have undergone chemotherapy or radiation therapy.

Hematopoietic Stem Cells

Other aspects of the present disclosure relate to treating a population of hematopoietic stem cells (HSCs) with a MYC-composition of the present disclosure, a Bcl-2-composition of the present disclosure, or both prior to transplanting the HSCs in a subject in need thereof to enhance hematopoietic compartment reconstitution. Other aspects of the present disclosure relate to enhancing hematopoietic compartment cell formation in a subject in need thereof by administering a MYC-composition of the present disclosure, a Bcl-2-composition of the present disclosure, or both to induce HSCs to generate hematopoietic compartment cells. A "subject", "patient", or "host" to be treated by the methods of the present disclosure may be a human or non-human such as any of the non-human animal disclosed herein, in need of hematopoietic compartment cell formation (e.g., hematopoietic compartment reconstitution or autoreconstitution) enhancement. As disclosed herein HSCs of the present disclosure pre-treated with a MYC-composition of the present disclosure, a Bcl-2-composition of the present disclosure, or both may be washed prior to being administered to a subject in need of hematopoietic compartment reconstitution. Alternatively, the pre-treated HSCs may be administered to the subject without being washed prior to administration as the transient effects of the MYC-composition and/or Bcl-2-composition are not harmful to the subject. Any suitable solution known in the art as disclosed herein may be used to wash the pre-treated HSCs. In one non-limiting example, a pH-balanced saline solution is used to wash the pre-treated HSCs prior to administering the HSCs to the subject. The pre-treated HSCs may be washed from less than about or about 1 minute to about 1 hour, about 4 hours, about 6 hours, about 8 hours, about 12 hours, about 24 hours or more prior administering to the subject.

HSCs of the present disclosure are able to give rise to all cell types of the hematopoietic compartment, including, without limitation the myeloid lineage, which includes, without limitation, monocytes, macrophages, neutrophils, basophils, eosinophils, erythrocytes, megakaryocytes, platelets, and dendritic cells; and the lymphoid lineage, which includes, without limitation, T-cells, B-cells, NKT-cells, and NK cells.

In some embodiments, a MYC-composition of the present disclosure accelerates hematopoietic compartment reconstitution in HSC transplant recipients. As disclosed herein, HSC transplant recipients may receive a bone marrow transplant, an HSC-enriched bone marrow transplant, a transplant of cord blood, a transplant of HSC-enriched cord blood, a transplant of placenta-derived blood, a transplant of purified or partially-purified HSCs, a transplant of HSCs derived from an HSC cell line, or a transplant of conditionally immortalized HSCs. In such embodiments, HSCs may be administered as a step in the process of an HSC transplantation procedure. As disclosed herein, the HSCs may be included, without limitation, in transplanted bone marrow, transplanted cord blood, or in transplanted cell lines. In certain preferred embodiments, the transplant recipient is a human subject. Suitable HSCs may be obtained by any suitable technique known in the art. For example, HSCs may be found in the bone marrow of a donor, which includes femurs, hip, ribs, sternum, and other bones. Any method known in the art for extracting or harvesting bone marrow cells may be used. In one non-limiting example, HSCs may be obtained directly from the marrow cavity of the hip using a needle and syringe to aspirate cells from the marrow cavity. Rich marrow may be obtained from the hip by performing multiple small aspirations.

HSCs suitable for use with the methods of the present disclosure may be produced from embryonic stem (ES) cells and/or induced pluripotent stem (iPS) cells. Any method of producing HSCs from ES cells and/or iPS cells known in the art may be used (e.g., Keller, G. *Genes Dev.* 2005 19:1129-1155; and Papapetrou Sadelain, *F1000 Med Rep.* 2010 Jun. 16; 2). For example, HSCs may be produced from ES cells by patterning the hematopoietic development of ES cell culture on the hematopoietic commitment in the early embryo (e.g., Keller, G. *Genes Dev.* 2005 19:1129-1155).

Additionally, HSCs suitable for use with the methods of the present disclosure may be obtained by any suitable technique known in the art. For example, HSCs may be found in the bone marrow of a donor, which includes femurs, hip, ribs, sternum, and other bones. Any method known in the art for extracting or harvesting bone marrow cells may be used. In one non-limiting example, HSCs may be obtained directly from the marrow cavity of the hip using a needle and syringe to aspirate cells from the marrow cavity. Rich marrow may be obtained from the hip by performing multiple small aspirations.

Suitable HSCs may also be obtained from peripheral blood cells found in the blood of a donor, often following pre-treatment with cytokines, such as G-CSF (granulocyte colony-stimulating factors), that induce HSCs to be released from the bone marrow compartment of the donor. HSCs may also be obtained from peripheral blood that has undergone an apheresis procedure to enrich for HSC. Any apheresis procedure known in the art may be used. In certain embodiments, the apheresis procedure is a leukapheresis procedure.

Additionally, suitable HSCs may be obtained from umbilical cord blood, placenta, and mobilized peripheral blood. For experimental purposes, fetal liver, fetal spleen, and AGM (Aorta-gonad-mesonephros) of animals are also useful sources of HSCs. Additionally, HSCs may be procured from a source that obtained HSCs from the bone marrow, peripheral blood, umbilical cord, or fetal tissue of a donor. Alternatively, the HSCs may be included in a bone marrow, peripheral blood, umbilical cord, or fetal tissue sample of a donor.

In some embodiments, HSCs are obtained from a human umbilical cord or placenta. Another source of HSCs that may be utilized is the developing blood-producing tissues of fetal animals. In humans, HSCs may be found in the circulating blood of a human fetus by about 12 to 18 weeks. In some embodiments, human HSCs are obtained from any source, e.g., the bone marrow, umbilical cord, peripheral blood, or fetal tissue of blood, of type A+, A−, B+, B−, O+, O−, AB+, and AB−donors. In other embodiments, human HSCs are obtained from any source, e.g., the bone marrow, umbilical cord, peripheral blood, or fetal tissue of blood, of universal donors or donors having a rare blood type. Rare blood types are known in the art and include, without limitation, Oh, CDE/CDE, CdE/CdE, C$^w$D−/C$^w$D−, −D−/−D−, R$_{null}$, Rh:−51, LW(a−b+), LW(a−b−), −S−s−U−, S−s−U(+), pp, Pk, Lu(a+b−), Lu(a−b−), Kp(a+b−), Kp(a−b−), Js(a+b−), Ko, K:−11, Fy(a−b−), Jk(a−b−), Di(b−), I−, Yt(a−), Sc:−1, Co(a−), Co(a−b−), Do(a−), Vel−, Ge−, Lan−, Lan(+), Gy(a−), Hy−, At(a−), Jr(a−), In(b−), Tc(a−), Cr(a−), Er(a−), Ok(a−), JMH−, and En(a−).

In other embodiments, human HSCs are obtained from any source, e.g., the bone marrow, umbilical cord, peripheral blood, or fetal tissue of blood, of donors having an autoimmune disorder, immune deficiency, or any other disease or disorder that would benefit from a transplantation of HSCs. Such donors may also be the recipients. Advantageously, HSCs obtained from such donor may be used for personalized HSC therapy.

In one non-limiting example, human HSCs may be obtained by anesthetizing the stem cell donor, puncturing the posterior superior iliac crest with a needle, and performing aspiration of bone marrow cells with a syringe. In another non-limiting example, HSCs may be obtained from the peripheral blood of a donor, where a few days prior to harvesting the stem cells form the peripheral blood, the donor is injected with G-CSF in order to mobilize the stem cells to the peripheral blood.

Accordingly, in some embodiments, HSCs are obtained from an autologous donor, that is the donor will also be the recipient of the HSCs derived from such HSCs. Any methods known in the art and described herein may be used to obtain HSCs from the autologous donor. The HSCs and/or any therapeutic products derived or produced therefrom are then transplanted, administered, and or transfused back to the original donor. Similarly, HSCs may be obtained from an allogenic donor, such as a sibling, parent, or other relative of a subject in need of an HSC transplantation. In one non-limiting example, allogenic HSCs are obtained by collecting HSCs from different blood groups or major histocompatibility complex (MHC) or human leukocyte antigen (HLA) matching sources. Autologous and/or allogenic HSC transplantation may occur at any time after the donation, such as days later, months later, or even years later. Autologous donation may be particularly useful in cases where the subject in need of HSCs would have a negative, deleterious, or toxic reaction to transplantation and/or transfusion of HSCs from any other donor, including allogenic and/or universal donors. Examples of patients that may benefit from autologous and/or allogenic donation are well known in the art and include, without limitation, those suffering from an autoimmune disorder, blood disease or disorder, immune disease or disorder, or other related diseases or conditions.

Cells obtained from, for example, bone marrow, peripheral blood, or cord blood, are typically processed after extraction or harvest. Any method known in the art for processing extracted or harvest cells may be used. Examples of processing steps include, without limitation, filtration, centrifugation, screening for hematopathologies, screening for viral and/or microbial infection, erythrocyte depletion, T-cell depletion to reduce incidence of graft-versus-host disease in allogenic stem cell transplant recipients, volume reduction, cell separation, resuspension of cells in culture medium or a buffer suitable for subsequent processing, separation of stem cells from non-stem cells e.g., stem cell enrichment), ex vivo or in vitro stem cell expansion with growth factors, cytokines, and/or hormones, and cryopreservation.

Any suitable method for stem cell enrichment known in the art may be used. Examples of stem cell enrichment methods include, without limitation, fluorescence activated cell sorting (FACS) and magnetic activated cell sorting (MACS).

Accordingly, in certain embodiments, HSCs suitable for use in the methods of the present disclosure are human HSCs. In other embodiments, HSCs suitable for use in the methods of the present disclosure are autologous to the subject. In further embodiments, HSCs suitable for use in the methods of the present disclosure are allogenic to the subject.

HSCs obtained from a donor may be identified and/or enriched by any suitable method of stem cell identification and enrichment known in the art, such as by utilizing certain phenotypic or genotypic markers. For example, in some embodiments, identification of HSCs includes using cell surface markers associated with HSCs or specifically associated with terminally differentiated cells of the system. Suitable surface markers may include, without limitation, one or more of c-kit, Sca-1, CD4, CD34, CD38, Thy1, CD2, CD3, CD4, CD5, CD8, CD43, CD45, CD59, CD90, CD105, CD133, CD135, ABCG2, NK1.1, B220, Ter-119, Flk-2, CDCP1, Endomucin, Gr-1, CD46, Mac-1, Thy1.1, and the signaling lymphocyte activation molecule (SLAM) family of receptors. Examples of SLAM receptors include, without limitation, CD150, CD48, and CD244.

Additionally, HSCs obtained from a donor may be separated from non-stem cells by any suitable method known in the art including, without limitation, fluorescence activated cell sorting (FACS) and magnetic activated cell sorting (MACS).

In one non-limiting example, human peripheral blood cells are incubated with antibodies recognizing c-kit, Sca-1, CD34, CD38, Thy1, CD2, CD3, CD4, CD5, CD8, CD43, CD45, CD59, CD90, CD105, CD133, ABCG2, NK1.1, B220, Ter-119, Flk-2, CDCP1, Endomucin, or Gr-1. Antibodies for CD2, CD3, CD4, CD5, CD8, NK1.1, B220, Ter-119, and Gr-1 are conjugated with magnetic beads. The cells expressing CD2, CD3, CD4, CD5, CD8, NK1.1, B220, Ter-119, or Gr-1 are retained in the column equipped to trap magnetic beads and cells attached to magnetic bead conjugated antibodies. The cells that are not captured by the MACS column are subjected to FACS analysis. Antibodies for c-kit, Sca-1, CD34, CD38, Thy1, are conjugated with fluorescent materials known in the art. The cells that are CD34+, CD38$^{low/-}$, c-kit$^{-/low}$, Thy1$^+$ are separated from the rest of sample by virtue of the types of fluorescent antibodies associated with the cells. These cells are provided as human long-term HSCs suitable for use with any of the methods of the present disclosure.

In another non-limiting example, cells obtained from a subject are labeled with the same set of magnetic bead conjugated antibodies as described above (antibodies against one or more of CD2, CD3, CD4, CD5, CD8, NK1.1, B220, Ter-119, or Gr-1) and fluorescent conjugated CD150, CD244 and/or CD48 antibodies. After removing cells captured by the magnetic bead conjugated antibodies from the sample, the sample is analyzed by FACS and CD150$^+$, CD244$^-$ and CD48$^-$ cells are retained as long-term HSCs.

In some embodiments, HSCs utilized in the methods of the present disclosure contain one or more of the markers: c-kit$^-$, Sca-1$^+$, CD34$^{low/-}$, CD38$^+$, Thy1$^{+/low}$, CD34$^+$, CD38$^{low/-}$, c-kit$^{-/low}$, and/or Thy1$^+$. In some embodiments, the HSCs utilized in the methods of the present disclosure lack one or more of the markers: CD2, CD3, CD4, CD5, CD8, NK1.1, B220, Ter-119, and/or Gr-1. In certain embodiments, the HSCs utilized in the methods of the present disclosure are of an A$^+$, A$^-$, B$^+$, B$^-$, O$^+$, O$^-$, AB$^+$, or AB$^-$ type.

Alternatively, suitable HSCs may be obtained from a non-human source. Suitable non-human HSCs may be isolated from, femurs, hip, ribs, sternum, and other bones of a non-human animal, including, without limitation, laboratory/research animals, rodents, pets, livestock, farm animals, work animals, pack animals, rare or endangered species, racing animals, and zoo animals. Further examples of suitable non-human animals include, without limitation, monkeys, primates, mice, rats, guinea pigs, hamsters, dogs, cats, horses, cows, pigs, sheep, goats, and chickens. For example, HSCs may be obtained from murine bone marrow cells, by incubating the bone marrow cells with antibodies recognizing cell surface molecules such as one or more of c-kit, Sca-1, CD34, CD38, Thy1, CD2, CD3, CD4, CD5, CD8, CD43, CD45, CD59, CD90, CD105, CD133, ABCG2, NK1.1, B220, Ter-119, Flk-2, CDCP1, Endomucin, or Gr-1. Antibodies for CD2, CD3, CD4, CD5, CDS, NK1.I, B220, Ter-119, and Gr-1 are conjugated with magnetic beads. In MACS equipment, the cells harboring CD2, CD3, CD4, CD5, CD8, NK1.1, B220, Ter-119, or Gr-1 on their surface are retained in the column equipped to trap magnetic beads and the cells attached to magnetic bead conjugated antibodies. The cells that are not captured by MACS column are subjected to FACS analysis. For FACS analysis, Antibodies for surface molecules such as c-kit, Sca-1, CD34, CD38, Thy1, are conjugated with fluorescent materials. The cells that are c-kit$^+$, Sca-1$^-$, CD34$^{low/-}$, CD38$^+$, Thy1$^{+/low}$ are separated from the rest of the sample by virtue of the types of fluorescent antibodies associated with the cells. These cells are provided as murine long-term HSCs suitable for use with any of the methods of the present disclosure. In other embodiments, different sets of marker are used to separate murine long-term HSCs from cells of bone marrow, umbilical cord blood, fetal tissue, and peripheral blood.

In some embodiments, obtaining HSCs from bone marrow includes first injecting the HSC donor, such as a mouse, with 5-fluorouracil (5-FU) to induce the HSCs to proliferate in order to enrich for HSCs in the bone marrow of the donor.

Moreover, HSCs suitable for use with any of the methods of the present disclosure, whether obtained from, or present in cord blood, bone marrow, peripheral blood, or other source, may be grown or expanded in any suitable, commercially available or custom defined medium, with or without serum, as desired (e.g., Hartshorn et al., *Cell Technology for Cell Products*, pages 221-224, R. Smith, Editor; Springer Netherlands, 2007). For example, serum free medium may utilize albumin and/or transferrin, which have been shown to be useful for the growth and expansion of CD34$^+$ cells in serum free medium. Also, cytokines may be included, such as Flt-3 ligand, stem cell factor (SCF), and thrombopoietin (TPO), among others. HSCs may also be grown in vessels such as bioreactors (e.g., Liu et al., *Journal of Biotechnology* 124:592-601, 2006). A suitable medium for ex vivo expansion of HSCs may also contain HSC supporting cells, such as stromal cells (e.g., lymphoreticular stromal cells), which can be derived, for example, from the disaggregation of lymphoid tissue, and which have been shown to support the in vitro, ex vivo, and in vivo maintenance, growth, and differentiation of HSCs, as well as their progeny.

HSC growth or expansion may be measured in vitro or in vivo according to routine techniques known in the art. For example, WO 2008/073748, describes methods for measuring in vivo and in vitro expansion of HSCs, and for distinguishing between the growth/expansion of HSCs and the growth/expansion of other cells in a potentially heterogeneous population (e.g., bone marrow), such as intermediate progenitor cells.

HSC Cell Lines

In other embodiments, HSCs suitable for use in any of the methods of the present disclosure may also be derived from an HSC cell line. Suitable HSC cell lines include any cultured hematopoietic stem cell line known in the art. Non-limiting examples include the conditionally immortalized long-term stem cell lines described in U.S. Patent Application Publication Nos. US 2007/0116691 and US 2010/0047217.

In certain embodiments, HSCs suitable for use in the methods of the present disclosure are conditionally immortalized before administering the HSCs to a subject. For example, HSCs obtained by any method disclosed herein may be treated with a regulatable (e.g., inducible, controllable) protooncogene that promotes cell survival and proliferation, such as MYC, and/or with a protein that inhibits apoptosis of the HSCs, such as Bcl-2 (e.g., U.S. Patent Application Publication No. US 2007/0116691). In some embodiments, the regulatable protooncogene is a MYC-composition. Preferably, the MYC-composition is a TAT-MYC fusion protein. The protein that inhibits apoptosis of the HSCs may also be regulatable. For example, the regulatable protein may be a PTD-Bcl-2 fusion protein, such as a TAT-Bcl-2 fusion protein.

In other embodiments, HSCs suitable for use in the methods of the present disclosure are cultured in the presence of a MYC-composition (e.g., a TAT-MYC protein fusion) of the present disclosure, a Bcl-2-composition (e.g., a TAT-BC1-2 protein fusion) of the present disclosure, or both before administering the HSCs to a subject. Preferably, culturing the first composition in the presence of the MYC-composition and/or Bcl-2-composition conditionally immortalizes the HSCs, which results in an expansion of the cultured HSCs.

As used herein, an "expansion of hematopoietic stem cells" or an "expansion of HSCs" refers to an increase in cell proliferation and/or cell survival, as compared to HSCs that have not been cultured or treated with a MYC-composition of the present disclosure, a Bcl-2-composition of the present disclosure, or both. For example, HSC expansion occurs when HSC proliferation, HSC survival, or both is increased by at least about or about 10% to at least about or about 500%. Any method known in the art and disclosed herein for measuring an increase in HSC proliferation and/or survival may be used.

Accordingly, HSCs suitable for use in any of the methods of the present disclosure may be obtained from bone marrow, from an apheresis procedure, from peripheral blood cells, from peripheral blood cells that have undergone leukapheresis, from umbilical cord blood, from amniotic fluid, from cultured HSC cells, from an immortalized HSC cell line, or from a conditionally immortalized HSC cell line. Alternatively, HSCs suitable for use in any of the methods of the present disclosure may be present in bone marrow, in peripheral blood cells, in peripheral blood cells that have undergone leukapheresis, in umbilical cord blood, in amniotic fluid, and in cell lines.

Transgenic Approach

In some embodiments, conditionally immortalized HSCs for use in the methods of the present disclosure are established using any transgenic approach known in the art (e.g., U.S. Patent Application Publication Nos. US 2007/0116691 and US 2010/0047217. For example, HSCs may be immortalized by obtaining an expanded population of HSCs, transfecting (transducing) the HSCs with a vector that encodes, for example, a MYC polypeptide and/or a Bcl-2 polypeptide (e.g., inducible and/or controllable), transfecting (transducing) the HSCs with a vector encoding the MYC polypeptide and/or the Bcl-2 polypeptide, and expanding the transfected HSCs in the presence of a combination of stem cell growth factors under conditions where the MYC polypeptide and/or Bcl-2 polypeptide is induced and/or active.

The MYC polypeptide and/or Bcl-2 polypeptide is regulatable (e.g., inducible or controllable), so that the polypeptide can be activated and deactivated (i.e., turned on or turned off) as desired to either maintain the HSCs in an immortalized state or to allow it to differentiate into a desired cell type.

In some embodiments, the MYC polypeptide and/or Bcl-2 polypeptide has been modified such that activity is inducible or repressible. For example, the MYC polypeptide and/or Bcl-2 polypeptide may further contain an inducible receptor. In certain embodiments, the recombinant proteins contain an estrogen receptor (ER). In certain embodiments, the recombinant protein that promotes cell survival and/or proliferation and that contains an estrogen receptor is a MYC-ER polypeptide and/or a Bcl-2-ER polypeptide. In certain embodiments, the proteins containing an estrogen receptor are induced by 4-hydroxytamoxifen (4-OHT). Alternatively, the proteins may contain a glucocorticoid receptor (GR), e.g., a glucocorticoid receptor that is sensitive to mifepristone (MIFEPREX). In certain embodiments, the protein that contains a glucocorticoid receptor is a MYC-GR polypeptide and/or a Bcl-2-GR polypeptide.

Any method known in the art for obtaining an expanded population of HSCs known in the art may be used. For example, HSCs may be cultured with one or more growth factor that promotes cell proliferation and/or cell division.

Preferably, the vectors are an integrating vector, which has the ability to integrate into the genome of a cell (e.g., a retroviral vector). The HSCs can be transfected and/or transduce with the vectors using any suitable method of transfecting cells, and particularly mammalian cells, including by using combinations of techniques. Examples of suitable vectors, include without limitation, retroviral vectors, lentivirus vectors, parvovirus vectors, vaccinia virus vectors, coronavirus vectors, calicivirus vectors, papilloma virus vectors, flavivirus vectors, orthomixovirus vectors, togavirus vectors, picornavirus vectors, adenoviral vectors, and modified and attenuated herpesviruses vectors. Any such virus vector can further be modified with specific surface expressed molecules that target these to HSCs, such as membrane bound SCF, or other stem-cell specific growth factor ligands. Other methods of transfection of mammalian cells include, but are not limited to, direct electroporation of mammalian expression vectors, such as by using NUCLEOFECTOR™ technology (AMAXA Biosystems). This technology is a highly efficient non-viral gene transfer method for most primary cells and for hard-to-transfect cell lines, which is an improvement on the long-known method of electroporation, based on the use of cell-type specific combinations of electrical current and solutions to transfer polyanionic macromolecules directly into the nucleus. Additionally, suitable methods of transfection can include any bacterial, yeast, or other artificial methods of gene delivery that are known in the art.

Enhancement of Endogenous Expression

In some embodiments, conditionally immortalized HSCs for use in the methods of the present disclosure may be established by enhancing the expression of endogenous proteins that promote cell survival and/or proliferation, including, without limitation, any MYC protein of the present disclosure. Additionally, conditionally immortalized HSCs for use in the methods of the present disclosure may be established by also enhancing the expression of endogenous proteins that inhibit apoptosis, including, without limitation, any Bcl-2 protein of the present disclosure.

Protein Transduction Approach

In some embodiments, HSCs obtained and/or produced by any method disclosed herein may be treated with a gene product that promotes cell survival and/or proliferation, including, but not limited to any MYC protein of the present disclosure, and/or with a protein that inhibits apoptosis of the HSCs, including, but limited to a Bcl-2 protein of the present disclosure. In some embodiments, the MYC protein is a fusion protein containing a PTD. In some embodiments, the Bcl-2 protein is a fusion protein containing a PTD. In some embodiments, HSCs obtained and/or produced by any method disclosed herein may be treated with one or more compound (optionally an exogenous protein) that enables the transient upregulation of at least one function of a MYC protein of the present disclosure. In some embodiments, the MYC protein is a PTD-MYC fusion protein. In certain embodiments, the PTD-MYC fusion protein is a TAT-MYC fusion protein.

In some embodiments, HSCs obtained by any method disclosed herein may be treated with one or more compound (optionally an exogenous protein) that enables the transient upregulation of at least one function of a Bcl-2 protein of the present disclosure. In some embodiments, the exogenous Bcl-2 protein is a PTD-Bcl-2 fusion protein. In some embodiments, the PTD-Bcl-2 fusion protein is a TAT-Bcl-2 fusion protein.

In other embodiments, HSCs suitable for use in any of the methods of the present disclosure are treated with a composition containing a fusion protein containing a MYC protein of the present disclosure fused to a PTD (e.g., a PTD-MYC fusion protein), a composition containing a fusion protein containing a Bcl-2 protein of the present disclosure fused to a PTD (e.g., a PTD-Bcl-2 fusion protein), or both.

Accordingly, HSCs suitable for use in any of the methods of the present disclosure may be obtained from embryonic stem cells (ES cells), fetal stem cells, induced pluripotent stem cells (iPS cells), bone marrow, from peripheral blood cells, from peripheral blood cells that have undergone apheresis, from peripheral blood cells that have undergone leukapheresis, from umbilical cord blood, from amniotic fluid, from cultured HSC cells, from an immortalized HSC cell line, or from a conditionally immortalized HSC cell line.

HSC Compositions

In other embodiments, HSCs suitable for use in any of the methods of the present disclosure are included in a composition. Suitable HSC-containing compositions may contain, without limitation, isolated and/or purified HSCs; whole bone marrow; bone marrow enriched for HSCs (e.g., 5-FU treated bone marrow); peripheral blood; and umbilical cord blood. In some embodiments, such compositions include a pharmaceutically acceptable carrier. Suitable pharmaceutically acceptable carriers may include pharmaceutically acceptable excipients and/or delivery vehicles, for delivering the HSCs to a subject, such as a patient. Additionally, pharmaceutically acceptable carriers may contain a cell culture medium that supports HSC viability. The medium will generally be serum-free in order to avoid provoking an immune response in the recipient. The carrier will generally be buffered and/or pyrogen-free.

In some embodiments, a therapeutically effective amount of a composition containing HSCs is administered to a subject to achieve hematopoietic compartment reconstitution in the subject. Generally, administering $10^4$ to $10^6$ HSCs is sufficient to achieve hematopoietic compartment reconstitution. In certain embodiments, administering a MYC-composition of the present disclosure, a Bcl-2-composition of the present disclosure, or both to an HSC transplant recipient can reduce the number of HSCs required to achieve hematopoietic compartment reconstitution. For example, administering a therapeutically effective amount of a MYC-composition of the present disclosure, a Bcl-2-composition of the present disclosure, or both to an HSC transplant recipient can reduce the therapeutically effective amount of HSCs in an HSC composition of the present disclosure required to achieve hematopoietic compartment reconstitution by at least about or about 10% to least about or about 75%, compared to the amount of HSCs required to achieve hematopoietic compartment reconstitution in an HSC transplant recipient that is not administered the MYC-composition and/or Bcl-2-composition.

In certain embodiments, administering a therapeutically effective amount of a MYC-composition of the present disclosure, a Bcl-2-composition of the present disclosure, or both to an HSC transplant recipient can reduce the therapeutically effective amount of HSCs in an HSC composition of the present disclosure required to achieve hematopoietic compartment reconstitution by at least about or about 10% to at least about or about 75%, for example, by at least about or about 10%, at least about or about 15%, at least about or about 20%, at least about or about 25%, at least about or about 30%, at least about or about 35%, at least about or about 40%, at least about or about 50%, at least about or about 55%, at least about or about 60%, at least about or about 65%, at least about or about 70%, at least about or about 75%, or a higher percentage less, as compared to the amount of HSCs required to achieve hematopoietic compartment reconstitution in an HSC transplant recipient that is not administered the MYC-composition and/or Bcl-2-composition.

In certain embodiments, treating a population with a therapeutically effective amount of a MYC-composition, a Bcl-2-composition, or both to a population of HSCs prior to the HSCs being transplanted to subject in need thereof can reduce the therapeutically effective amount of HSCs required to achieve hematopoietic compartment reconstitution by at least about or about 10% to at least about or about 75%, for example, by at least about or about 10%, at least about or about 15%, at least about or about 20%, at least about or about 25%, at least about or about 30%, at least about or about 35%, at least about or about 40%, at least about or about 50%, at least about or about 55%, at least about or about 60%, at least about or about 65%, at least about or about 70%, at least about or about 75%, or a higher percentage less, as compared to the amount of HSCs required to achieve hematopoietic compartment reconstitution in an HSC transplant recipient that does receive HSCs that were pre-treated with a MYC-composition of the present disclosure, a Bcl-2-composition of the present disclosure, or both.

HSC compositions and populations of HSCs of the present disclosure are generally administered into the body of a subject, such as a patient, by any suitable methods known in the art, including without limitation, injection and implantation. For example, HSC may be directly injected into the tissue in which they are intended to act using a syringe containing an HSC composition of the present disclosure. Alternatively, an HSC composition of the present disclosure may be delivered via a catheter, such as a central venous catheter, attached to a syringe containing the HSC composition.

HSC Transplantation

In further embodiments, HSC-containing compositions and populations of HSCs of the present disclosure are administered to a subject in need of hematopoietic stem cell (HSC) transplantation as a step in the process of an HSC transplantation procedure. In certain preferred embodiments, the subject is a human patient in need of a HSC transplant. In other embodiments, the subject is any non-human animal, including, without limitation, laboratory/research animals, rodents, pets, livestock, farm animals, work animals, pack animals, rare or endangered species, racing animals, zoo animals, monkeys, primates, mice, rats, guinea pigs, hamsters, dogs, cats, horses, cows, pigs, sheep, goats, and chickens.

The HSC transplantation procedure may be a myeloablative HSC transplant. Myeloablation generally refers to the ablation or suppression of the endogenous hematopoietic compartment of an HSC transplant recipient. Myeloablation occurs prior to HSC transplantation. In HSC transplant recipients suffering from a hematological disease, such as a hematological cancer, myeloablation may be performed to help eradicate the disease. Myeloablation may also be performed to suppress the endogenous immune system of the HSC transplant recipient in order to help reduce the risk of rejection of the transplanted HSCs (e.g., graft-versus-host disease). Any method known in the art for myeloablation may be used. Examples of myeloablation procedures include, without limitation, chemotherapy, irradiation, and combinations thereof.

Alternatively, the HSC transplantation procedure may be non-myeloablative. In non-myeloablative procedures lower doses of chemotherapy and/or radiation are used in the recipient prior to HSC transplantation.

Subjects in need of an HSC transplant include subjects presenting with an HSC transplant indication. Examples of HSC transplant indications include, without limitation, a hematological malignancy, a myeloma, multiple myeloma, a leukemia, acute lymphoblastic leukemia, chronic lymphocytic leukemia, a lymphoma, indolent lymphoma, non-Hodgkin lymphoma, diffuse B cell lymphoma, follicular lymphoma, mantle cell lymphoma, T cell lymphoma, Hodgkin lymphoma, a neuroblastoma, a retinoblastoma, Shwachman Diamond syndrome, a brain tumor, Ewing's Sarcoma, a Desmoplastic small round cell tumor, a relapsed germ cell tumor, a hematological disorder, a hemoglobinopathy, an autoimmune disorder, juvenile idiopathic arthritis, systemic lupus erythematosus, severe combined immunodeficiency, congenital neutropenia with defective stem cells, severe aplastic anemia, a sickle-cell disease, a myelodysplastic syndrome, chronic granulomatous disease, a metabolic disorder, Hurler syndrome, Gaucher disease, osteopetrosis, malignant infantile osteopetrosis, heart disease, HIV, and AIDS. Additionally, a subject in need of an HSC transplant can also include a subject that has had an organ transplant.

Enhancing Hematopoietic Compartment Cell Formation

Other aspects of the present disclosure relate to enhancing hematopoietic compartment cell formation in a subject in need thereof by administering a MYC-composition of the present disclosure, a Bcl-2-composition of the present disclosure, or both; and/or administering a population of HSCs that has been pre-treated with a MYC-composition of the present disclosure, a Bcl-2-composition of the present disclosure, or both. In some embodiments, enhancing hematopoietic compartment cell formation includes enhancing hematopoietic compartment reconstitution. In some embodiments, enhancing hematopoietic compartment cell formation includes enhancing hematopoietic compartment autoreconstitution.

Enhancing Hematopoietic Compartment Reconstitution

In certain embodiments, administering a population of HSCs that have been pre-treated with a MYC-composition of the present disclosure, a Bcl-2-composition of the present disclosure, or both, to a subject in need of HSC transplantation enhances hematopoietic compartment reconstitution in the subject. In other embodiments, administering a MYC-composition of the present disclosure, a Bcl-2-composition of the present disclosure, or both to a subject that has received or will receive an HSC transplant enhances hematopoietic compartment reconstitution in the subject. For example, pre-treating HSCs with the MYC-composition, the Bcl-2-composition, or both, and then administering the HSCs; or administering the MYC-composition, the Bcl-2-composition, or both may improve the rate of hematopoietic compartment reconstitution, increase the amount of hematopoietic compartment cells that are formed, or reduce loss of hematopoietic compartment cells in the subject, as compared to a subject that is administered HSCs that were not pre-treated with the MYC-composition, the Bcl-2-composition, or both; or was not administered the MYC-composition, the Bcl-2-composition, or both.

Preferably, pre-treating the HSCs with the MYC-composition, the Bcl-2-composition, or both prior to administering the HSCs to a subject; or administering the MYC-composition, the Bcl-2-composition, or both to the subject accelerates (i.e., increases the rate of) hematopoietic compartment reconstitution in the subject, as compared to hematopoietic compartment reconstitution in a subject that has not been administered the pre-treated HSCs or the MYC-composition, the Bcl-2-composition, or both.

As used herein, an "acceleration in hematopoietic compartment reconstitution" refers to a reduction in the time required to reconstitute at least about or about 25% to about 100% of one or more of the blood cell lineages in the hematopoietic compartment, including, without limitation, monocytes, macrophages, neutrophils, basophils, eosinophils, erythrocytes, megakaryocytes, platelets, and dendritic cells; and the lymphoid lineage, which includes, without limitation, T-cells, B-cells, NKT-cells, and NK cells. For example, a reduction from 8 weeks to 4 weeks in the time required to reconstitute the hematopoietic compartment would constitute an acceleration of 50%.

Pre-treatment with a MYC-composition of the present disclosure, a Bcl-2-composition of the present disclosure, or both; or administration of a MYC-composition of the present disclosure, a Bcl-2-composition of the present disclosure, or both may achieve an at least about or about 25% to art least about or about 500%, for example, an at least about or about 25%, at least about or about 30%, at least about or about 31%, at least about or about 32%, at least about or about 33%, at least about or about 34%, at least about or about 35%, at least about or about 40%, at least about or about 45%, at least about or about 50%, at least about or about 55%, at least about or about 60%, at least about or about 65%, at least about or about 66%, at least about or about 67%, at least about or about 68%, at least about or about 69%, at least about or about 70%, at least about or about 75%, at least about or about 80%, at least about or about 90%, at least about or about 95%, at least about or about 100%, at least about or about 150%, at least about or about 200%, at least about or about 250%, at least about or about 300%, at least about or about 400%, at least about or about 500%, or a higher percentage acceleration in hematopoietic compartment reconstitution in a subject that has received or will receive an HSC transplant, compared to hematopoietic compartment reconstitution in a subject that is not administered the pre-treated HSCs; or the MYC-composition, the Bcl-2-composition, or both.

As disclosed herein, hematopoietic compartment reconstitution includes, without limitation, T-cell compartment reconstitution, B-cell compartment reconstitution, NK-cell compartment reconstitution, myeloid cell compartment reconstitution, and neutrophil recovery. As used herein, the term "T-cell compartment" refers to the cell compartment in a subject that contains all immature, mature, undifferentiated and differentiated B-cells. The "T-cell compartment" includes, without limitation, T-cell progenitors, pro-T-cells, pre-T-cells, double positive T-cells, immature T-cells, mature T-cells, helper T-cells, cytotoxic T-cells, memory T-cells, regulatory T-cells, natural killer T-cells (NKT-cells), and gamma delta T-cells. As used herein, the term "B-cell compartment" refers to the cell compartment in a subject that contains all immature, mature, undifferentiated and differentiated B-cells. The "B-cell compartment" includes, without limitation, B-cell progenitors, pro-B-cells, early pro-B-cells, late-pro B-cells, large pre-B-cells, small pre-B-cells, immature B-cells, mature B-cells, plasma B-cells, memory B-cells, B-1 cells, B-2 cells, marginal-zone B-cells, and follicular B-cells. As used herein, the term "NK cell compartment" refers to the cell compartment in a subject that contains all progenitor, immature, mature, undifferentiated and differentiated natural killer (NK) cells. The "NK cell compartment" NK cells. As used herein, the term "myeloid cell compartment" refers to the cell compartment in a subject that contains all progenitor, immature, mature, undifferentiated and differentiated myeloid cell populations. The "myeloid cell compartment" includes, without limitation, monocytes, macrophages, neutrophils, basophils, eosinophils, erythrocytes, megakaryocytes, platelets, and dendritic cells.

Accordingly, in certain embodiments, the accelerated hematopoietic compartment reconstitution in an HSC transplant recipient that has been administered HSCs pre-treated with a MYC-composition of the present disclosure, a Bcl-2-composition of the present disclosure, or both; or administered a MYC-composition of the present disclosure, a Bcl-2-composition of the present disclosure, or both results in T-cell compartment reconstitution that is accelerated by at least about or about 25% to art least about or about 500%, for example, at least about or about 25%, at least about or about 30%, at least about or about 31%, at least about or about 32%, at least about or about 33%, at least about or about 34%, at least about or about 35%, at least about or about 40%, at least about or about 45%, at least about or about 50%, at least about or about 55%, at least about or about 60%, at least about or about 65%, at least about or about 66%, at least about or about 67%, at least about or about 68%, at least about or about 69%, at least about or about 70%, at least about or about 75%, at least about or about 80%, at least about or about 90%, at least about or about 95%, at least about or about 100%, at least about or about 150%, at least about or about 200%, at least about or about 250%, at least about or about 300%, at least about or about 400%, at least about or about 500%, or a higher percentage more, compared to T-cell compartment reconstitution in a subject that is not administered the pre-treated HSCs; or the MYC-composition, the Bcl-2-composition, or both.

In other embodiments, the accelerated hematopoietic compartment reconstitution in an HSC transplant recipient that has been administered HSCs pre-treated with a MYC-composition of the present disclosure, a Bcl-2-composition of the present disclosure, or both; or administered a MYC-composition of the present disclosure, a Bcl-2-composition of the present disclosure, or both results in NKT-cell reconstitution that is accelerated by at least about or about 25% to art least about or about 500%, for example, at least about or about 25%, at least about or about 30%, at least about or about 31%, at least about or about 32%, at least about or about 33%, at least about or about 34%, at least about or about 35%, at least about or about 40%, at least about or about 45%, at least about or about 50%, at least about or about 55%, at least about or about 60%, at least about or about 65%, at least about or about 66%, at least about or about 67%, at least about or about 68%, at least about or about 69%, at least about or about 70%, at least about or about 75%, at least about or about 80%, at least about or about 90%, at least about or about 95%, at least about or about 100%, at least about or about 150%, at least about or about 200%, at least about or about 250%, at least about or about 300%, at least about or about 400%, at least about or about 500%, or a higher percentage more, compared to NKT-cell reconstitution in a subject that is not administered the pre-treated HSCs; or the MYC-composition, the Bcl-2-composition, or both.

In other embodiments, the accelerated hematopoietic compartment reconstitution in an HSC transplant recipient that has been administered HSCs pre-treated with a MYC-composition of the present disclosure, a Bcl-2-composition of the present disclosure, or both; or administered a MYC-composition of the present disclosure, a Bcl-2-composition of the present disclosure, or both results in B-cell compartment reconstitution that is accelerated by at least about or about 25% to art least about or about 500%, for example, at least about or about 25%, at least about or about 30%, at least about or about 31%, at least about or about 32%, at least about or about 33%, at least about or about 34%, at least about or about 35%, at least about or about 40%, at least about or about 45%, at least about or about 50%, at least about or about 55%, at least about or about 60%, at least about or about 65%, at least about or about 66%, at least about or about 67%, at least about or about 68%, at least about or about 69%, at least about or about 70%, at least about or about 75%, at least about or about 80%, at least about or about 90%, at least about or about 95%, at least about or about 100%, at least about or about 150%, at least about or about 200%, at least about or about 250%, at least about or about 300%, at least about or about 400%, at least about or about 500%, or a higher percentage more, compared to B-cell compartment reconstitution in a subject that is not administered the pre-treated HSCs; or the MYC-composition, the Bcl-2-composition, or both.

In other embodiments, the accelerated hematopoietic compartment reconstitution in an HSC transplant recipient that has been administered HSCs pre-treated with a MYC-composition of the present disclosure, a Bcl-2-composition of the present disclosure, or both; or administered a MYC-composition of the present disclosure, a Bcl-2-composition of the present disclosure, or both results in NK-cell compartment reconstitution that is accelerated by at least about or about 25% to art least about or about 500%, for example, at least about or about 25%, at least about or about 30%, at least about or about 31%, at least about or about 32%, at least about or about 33%, at least about or about 34%, at least about or about 35%, at least about or about 40%, at least about or about 45%, at least about or about 50%, at least about or about 55%, at least about or about 60%, at least about or about 65%, at least about or about 66%, at least about or about 67%, at least about or about 68%, at least about or about 69%, at least about or about 70%, at least about or about 75%, at least about or about 80%, at least about or about 90%, at least about or about 95%, at least about or about 100%, at least about or about 150%, at least about or about 200%, at least about or about 250%, at least about or about 300%, at least about or about 400%, at least about or about 500%, or a higher percentage more, compared to NK-cell compartment reconstitution in a subject that is not administered the pre-treated HSCs; or the MYC-composition, the Bcl-2-composition, or both.

In other embodiments, the accelerated hematopoietic compartment reconstitution in an HSC transplant recipient that has been administered HSCs pre-treated with a MYC-composition of the present disclosure, a Bcl-2-composition of the present disclosure, or both; or administered a MYC-composition of the present disclosure, a Bcl-2-composition of the present disclosure, or both results in myeloid cell compartment reconstitution that is accelerated by at least about or about 25% to art least about or about 500%, for example, at least about or about 25%, at least about or about 30%, at least about or about 31%, at least about or about 32%, at least about or about 33%, at least about or about 34%, at least about or about 35%, at least about or about 40%, at least about or about 45%, at least about or about 50%, at least about or about 55%, at least about or about 60%, at least about or about 65%, at least about or about 66%, at least about or about 67%, at least about or about 68%, at least about or about 69%, at least about or about 70%, at least about or about 75%, at least about or about 80%, at least about or about 90%, at least about or about 95%, at least about or about 100%, at least about or about 150%, at least about or about 200%, at least about or about 250%, at least about or about 300%, at least about or about 400%, at least about or about 500%, or a higher percentage more, compared to myeloid cell compartment reconstitution in a subject that is not administered the pre-treated HSCs; or the MYC-composition, the Bcl-2-composition, or both.

In other embodiments, the accelerated hematopoietic compartment reconstitution in an HSC transplant recipient that has been administered HSCs pre-treated with a MYC-composition of the present disclosure, a Bcl-2-composition of the present disclosure, or both; or administered a MYC-composition of the present disclosure, a Bcl-2-composition of the present disclosure, or both results in monocyte reconstitution that is accelerated by at least about or about 25% to art least about or about 500%, for example, at least about or about 25%, at least about or about 30%, at least about or about 31%, at least about or about 32%, at least about or about 33%, at least about or about 34%, at least about or about 35%, at least about or about 40%, at least about or about 45%, at least about or about 50%, at least about or about 55%, at least about or about 60%, at least about or about 65%, at least about or about 66%, at least about or about 67%, at least about or about 68%, at least about or about 69%, at least about or about 70%, at least about or about 75%, at least about or about 80%, at least about or about 90%, at least about or about 95%, at least about or about 100%, at least about or about 150%, at least about or about 200%, at least about or about 250%, at least about or about 300%, at least about or about 400%, at least about or about 500%, or a higher percentage more, compared to monocyte reconstitution in a subject that is not administered the pre-treated HSCs; or the MYC-composition, the Bcl-2-composition, or both.

In other embodiments, the accelerated hematopoietic compartment reconstitution in an HSC transplant recipient that has been administered HSCs pre-treated with a MYC-composition of the present disclosure, a Bcl-2-composition of the present disclosure, or both; or administered a MYC-composition of the present disclosure, a Bcl-2-composition of the present disclosure, or both results in macrophage reconstitution that is accelerated by at least about or about 25% to art least about or about 500%, for example, at least about or about 25%, at least about or about 30%, at least about or about 31%, at least about or about 32%, at least about or about 33%, at least about or about 34%, at least about or about 35%, at least about or about 40%, at least about or about 45%, at least about or about 50%, at least about or about 55%, at least about or about 60%, at least about or about 65%, at least about or about 66%, at least about or about 67%, at least about or about 68%, at least about or about 69%, at least about or about 70%, at least about or about 75%, at least about or about 80%, at least about or about 90%, at least about or about 95%, at least about or about 100%, at least about or about 150%, at least about or about 200%, at least about or about 250%, at least about or about 300%, at least about or about 400%, at least about or about 500%, or a higher percentage more, compared to macrophage reconstitution in a subject that is not administered the pre-treated HSCs; or the MYC-composition, the Bcl-2-composition, or both.

In other embodiments, the accelerated hematopoietic compartment reconstitution in an HSC transplant recipient that has been administered HSCs pre-treated with a MYC-composition of the present disclosure, a Bcl-2-composition of the present disclosure, or both; or administered a MYC-composition of the present disclosure, a Bcl-2-composition of the present disclosure, or both results in basophil reconstitution that is accelerated by at least about or about 25% to art least about or about 500%, for example, at least about or about 25%, at least about or about 30%, at least about or about 31%, at least about or about 32%, at least about or about 33%, at least about or about 34%, at least about or about 35%, at least about or about 40%, at least about or about 45%, at least about or about 50%, at least about or about 55%, at least about or about 60%, at least about or about 65%, at least about or about 66%, at least about or about 67%, at least about or about 68%, at least about or about 69%, at least about or about 70%, at least about or about 75%, at least about or about 80%, at least about or about 90%, at least about or about 95%, at least about or about 100%, at least about or about 150%, at least about or about 200%, at least about or about 250%, at least about or about 300%, at least about or about 400%, at least about or about 500%, or a higher percentage more, compared to basophil reconstitution in a subject that is not administered the pre-treated HSCs; or the MYC-composition, the Bcl-2-composition, or both.

In other embodiments, the accelerated hematopoietic compartment reconstitution in an HSC transplant recipient that has been administered HSCs pre-treated with a MYC-composition of the present disclosure, a Bcl-2-composition of the present disclosure, or both; or administered a MYC-composition of the present disclosure, a Bcl-2-composition of the present disclosure, or both results in eosinophil reconstitution that is accelerated by at least about or about 25% to art least about or about 500%, for example, at least about or about 25%, at least about or about 30%, at least about or about 31%, at least about or about 32%, at least about or about 33%, at least about or about 34%, at least about or about 35%, at least about or about 40%, at least about or about 45%, at least about or about 50%, at least about or about 55%, at least about or about 60%, at least about or about 65%, at least about or about 66%, at least about or about 67%, at least about or about 68%, at least about or about 69%, at least about or about 70%, at least about or about 75%, at least about or about 80%, at least about or about 90%, at least about or about 95%, at least about or about 100%, at least about or about 150%, at least about or about 200%, at least about or about 250%, at least about or about 300%, at least about or about 400%, at least about or about 500%, or a higher percentage more, compared to eosinophil reconstitution in a subject that is not administered the pre-treated HSCs; or the MYC-composition, the Bcl-2-composition, or both.

In other embodiments, the accelerated hematopoietic compartment reconstitution in an HSC transplant recipient that has been administered HSCs pre-treated with a MYC-composition of the present disclosure, a Bcl-2-composition of the present disclosure, or both; or administered a MYC-composition of the present disclosure, a Bcl-2-composition of the present disclosure, or both results in erythrocyte reconstitution that is accelerated by at least about or about 25% to art least about or about 500%, for example, at least about or about 25%, at least about or about 30%, at least about or about 31%, at least about or about 32%, at least about or about 33%, at least about or about 34%, at least about or about 35%, at least about or about 40%, at least about or about 45%, at least about or about 50%, at least about or about 55%, at least about or about 60%, at least about or about 65%, at least about or about 66%, at least about or about 67%, at least about or about 68%, at least about or about 69%, at least about or about 70%, at least about or about 75%, at least about or about 80%, at least about or about 90%, at least about or about 95%, at least about or about 100%, at least about or about 150%, at least about or about 200%, at least about or about 250%, at least about or about 300%, at least about or about 400%, at least about or about 500%, or a higher percentage more, compared to erythrocyte reconstitution in a subject that is not administered the pre-treated HSCs; or the MYC-composition, the Bcl-2-composition, or both.

In other embodiments, the accelerated hematopoietic compartment reconstitution in an HSC transplant recipient that has been administered HSCs pre-treated with a MYC-composition of the present disclosure, a Bcl-2-composition of the present disclosure, or both; or administered a MYC-composition of the present disclosure, a Bcl-2-composition of the present disclosure, or both results in megakaryocyte reconstitution that is accelerated by at least about or about 25% to art least about or about 500%, for example, at least about or about 25%, at least about or about 30%, at least about or about 31%, at least about or about 32%, at least about or about 33%, at least about or about 34%, at least about or about 35%, at least about or about 40%, at least about or about 45%, at least about or about 50%, at least about or about 55%, at least about or about 60%, at least about or about 65%, at least about or about 66%, at least about or about 67%, at least about or about 68%, at least about or about 69%, at least about or about 70%, at least about or about 75%, at least about or about 80%, at least about or about 90%, at least about or about 95%, at least about or about 100%, at least about or about 150%, at least about or about 200%, at least about or about 250%, at least about or about 300%, at least about or about 400%, at least about or about 500%, or a higher percentage more, compared to megakaryocyte reconstitution in a subject that is not administered the pre-treated HSCs; or the MYC-composition, the Bcl-2-composition, or both.

In other embodiments, the accelerated hematopoietic compartment reconstitution in an HSC transplant recipient that has been administered HSCs pre-treated with a MYC-composition of the present disclosure, a Bcl-2-composition of the present disclosure, or both; or administered a MYC-composition of the present disclosure, a Bcl-2-composition of the present disclosure, or both results in platelet reconstitution that is accelerated by at least about or about 25% to art least about or about 500%, for example, at least about or about 25%, at least about or about 30%, at least about or about 31%, at least about or about 32%, at least about or about 33%, at least about or about 34%, at least about or about 35%, at least about or about 40%, at least about or about 45%, at least about or about 50%, at least about or about 55%, at least about or about 60%, at least about or about 65%, at least about or about 66%, at least about or about 67%, at least about or about 68%, at least about or about 69%, at least about or about 70%, at least about or about 75%, at least about or about 80%, at least about or about 90%, at least about or about 95%, at least about or about 100%, at least about or about 150%, at least about or about 200%, at least about or about 250%, at least about or about 300%, at least about or about 400%, at least about or about 500%, or a higher percentage more, compared to platelet reconstitution in a subject that is not administered the pre-treated HSCs; or the MYC-composition, the Bcl-2-composition, or both.

In other embodiments, the accelerated hematopoietic compartment reconstitution in an HSC transplant recipient that has been administered HSCs pre-treated with a MYC-composition of the present disclosure, a Bcl-2-composition of the present disclosure, or both; or administered a MYC-composition of the present disclosure, a Bcl-2-composition of the present disclosure, or both results in dendritic cell reconstitution that is accelerated by at least about or about 25% to art least about or about 500%, for example, at least about or about 25%, at least about or about 30%, at least about or about 31%, at least about or about 32%, at least about or about 33%, at least about or about 34%, at least about or about 35%, at least about or about 40%, at least about or about 45%, at least about or about 50%, at least about or about 55%, at least about or about 60%, at least about or about 65%, at least about or about 66%, at least about or about 67%, at least about or about 68%, at least about or about 69%, at least about or about 70%, at least about or about 75%, at least about or about 80%, at least about or about 90%, at least about or about 95%, at least about or about 100%, at least about or about 150%, at least about or about 200%, at least about or about 250%, at least about or about 300%, at least about or about 400%, at least about or about 500%, or a higher percentage more, compared to dendritic cell reconstitution in a subject that is not administered the pre-treated HSCs; or the MYC-composition, the Bcl-2-composition, or both.

In other embodiments, the accelerated hematopoietic compartment reconstitution in an HSC transplant recipient that has been administered HSCs pre-treated with a MYC-composition of the present disclosure, a Bcl-2-composition of the present disclosure, or both; or administered a MYC-composition of the present disclosure, a Bcl-2-composition of the present disclosure, or both results in neutrophil recovery that is accelerated by at least about or about 25% to art least about or about 500%, for example, at least about or about 25%, at least about or about 30%, at least about or about 31%, at least about or about 32%, at least about or about 33%, at least about or about 34%, at least about or about 35%, at least about or about 40%, at least about or about 45%, at least about or about 50%, at least about or about 55%, at least about or about 60%, at least about or about 65%, at least about or about 66%, at least about or about 67%, at least about or about 68%, at least about or about 69%, at least about or about 70%, at least about or about 75%, at least about or about 80%, at least about or about 90%, at least about or about 95%, at least about or about 100%, at least about or about 150%, at least about or about 200%, at least about or about 250%, at least about or about 300%, at least about or about 400%, at least about or about 500%, or a higher percentage more, compared to neutrophil recovery in a subject that is not administered the pre-treated HSCs; or the MYC-composition, the Bcl-2-composition, or both.

Enhanced Hematopoietic Compartment Autoreconstitution

In other embodiments, administering a MYC-composition of the present disclosure to a subject in need of autoreconstitution enhances hematopoietic compartment autoreconstitution in the subject. For example, administering the MYC-composition may improve the rate of autoreconstitution, increase the amount of hematopoietic compartment cells that are formed, or reduce loss of hematopoietic compartment cells in the subject, as compared to a subject that is not administered the MYC-composition.

Administration of a MYC-composition of the present disclosure, a Bcl-2-composition of the present disclosure, or both may enhance hematopoietic compartment autoreconstitution by at least about or about 25% to art least about or about 500%, for example, at least about or about 25%, at least about or about 30%, at least about or about 31%, at least about or about 32%, at least about or about 33%, at least about or about 34%, at least about or about 35%, at least about or about 40%, at least about or about 45%, at least about or about 50%, at least about or about 55%, at least about or about 60%, at least about or about 65%, at least about or about 66%, at least about or about 67%, at least about or about 68%, at least about or about 69%, at least about or about 70%, at least about or about 75%, at least about or about 80%, at least about or about 90%, at least about or about 95%, at least about or about 100%, at least about or about 150%, at least about or about 200%, at least about or about 250%, at least about or about 300%, at least about or about 400%, at least about or about 500%, or more, compared to hematopoietic compartment autoreconstitution in a subject that is not administered the MYC-composition composition, the Bcl-2-composition, or both.

As disclosed herein, hematopoietic compartment autoreconstitution includes, without limitation, T-cell compartment autoreconstitution, B-cell compartment autoreconstitution, NKT-cell autoreconstitution, and NK-cell compartment autoreconstitution; myeloid cell compartment autoreconstitution, such as monocyte autoreconstitution, macrophage autoreconstitution, basophil autoreconstitution, eosinophil autoreconstitution, erythrocyte autoreconstitution, megakaryocyte autoreconstitution, platelet autoreconstitution, and dendritic cell autoreconstitution; and neutrophil recovery.

Composition Formulations

Certain aspects of the present disclosure relate to compositions containing a MYC-composition of the present disclosure, a Bcl-2-composition of the present disclosure, or both for pre-treating HSCs of the present disclosure, and for treating subjects in need of an HSC transplant. Other aspects relate to a first composition containing HSCs for achieving hematopoietic compartment reconstitution in a subject in need thereof, and a second composition containing a MYC-composition of the present disclosure, a Bcl-2-composition of the present disclosure, or both for enhancing hematopoietic compartment reconstitution in the subject. Other aspects of the present disclosure relate to a composition containing a MYC-composition of the present disclosure, a Bcl-2-composition of the present disclosure, or both for enhancing hematopoietic compartment autoreconstitution in a subject in need thereof.

In some embodiments, compositions of the present disclosure are formulated in a conventional manner using one or more physiologically acceptable carriers including, e.g., excipients and auxiliaries which facilitate processing of the active compounds into preparations which are suitable for pharmaceutical use. Suitable pharmaceutically acceptable carriers include, without limitation, saline, aqueous buffer solutions, solvents and/or dispersion media. The use of such carriers is well known in the art. The carrier is preferably sterile. In some embodiments, the carrier is stable under the conditions of manufacture and storage and preserved against the contaminating action of microorganisms, such as bacteria and fungi, through the use of, for example and without limitation, parabens, chlorobutanol, phenol, ascorbic acid, or thimerosal.

Examples of materials and solutions that can serve as pharmaceutically acceptable carriers include, without limitation: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; and (22) other non-toxic compatible substances employed in pharmaceutical formulations.

Proper formulation of the compositions of the present disclosure may be dependent upon the route of administration chosen. A summary of pharmaceutical compositions described herein is found, for example, in *Remington: The Science and Practice of Pharmacy*, Nineteenth Ed (Easton, Pa.: Mack Publishing Company, 1995); Hoover, John E., *Remington's Pharmaceutical Sciences*, Mack Publishing Co., Easton, Pa. 1975; Liberman, H. A. and Lachman, L., Eds., *Pharmaceutical Dosage Forms*, Marcel Decker, New York, N.Y., 1980; and Pharmaceutical Dosage Forms and Drug Delivery Systems, Seventh Ed. (Lippincott Williams & Wilkins 1999).

The compositions of the present disclosure can facilitate administration of a compound of the present disclosure (e.g., HSCs or a MYC-composition or a Bcl-2-composition) to a subject or cell. In certain embodiments of the methods of the present disclosure, therapeutically effective amounts of compounds described herein are administered in a pharmaceutical composition to a subject having a disorder, disease, or condition to be treated. In some embodiments, the subject is a human patient. In other embodiments, the subject is a non-human animal, including without limitation, a dog, cat, horse, cow, pig, sheep, goat, chicken, monkey, rat, mouse, or the like.

The HSC compositions, MYC-composition-containing compositions, and/or Bcl-2-composition-containing compositions of the present disclosure may be utilized either alone or in combination with one or more additional therapeutic agents. For example, cytokines, growth factors, antibodies, and/or small molecule modifiers that are known to aid in reducing the time required to reconstitute mature hematopoietic lineages after HSC transplantation, may administered in combination with the HSC, MYC-composition-containing, and/or Bcl-2-composition-containing compositions. For example, monoclonal antibodies and/or small molecule modifiers that target enzymes affecting E-selectin expression can improve HSC homing to bone marrow niches after an HSC transplantation. Other examples include, without limitation, antibodies or small molecules that affect adhesion proteins such and β6 integrin, G-MCSF, G-CSF is the same, and Epo. Accordingly, certain embodiments of the methods of the present disclosure further include administering a third composition containing at least one cytokine, growth factor, antibody, and/or small molecule modifier. In some embodiments, the cytokine and/or growth factor composition further contains a pharmaceutically acceptable carrier.

The compositions of the present disclosure may be administered to a subject in any suitable manner, including, without limitation, one or more of multiple administration routes, such as, oral, parenteral (e.g., intravenous, subcutaneous, intramuscular), intranasal, buccal, rectal, or transdermal administration routes.

Composition formulations of the present disclosure include, without limitation, aqueous liquid dispersions, oil emulsions, self-emulsifying dispersions, solid solutions, liposomal dispersions, aerosols, solid dosage forms, powders, immediate release formulations, controlled release formulations, fast melt formulations, tablets, capsules, pills, delayed release formulations, extended release formulations, pulsatile release formulations, multiparticulate formulations, and mixed immediate and controlled release formulations.

Pharmaceutical compositions of the present disclosure (e.g., a PTD-MYC composition, a PTD-Bcl-2 composition, or a cytokine and/or growth factor composition) are optionally manufactured in a conventional manner, including, without limitation, conventional mixing, dissolving, granulating, dragee-making, levigating, emulsifying, encapsulating, entrapping or compression processes.

In some embodiments, pharmaceutical compositions of the present disclosure (e.g., a PTD-MYC composition, a PTD-Bcl-2 composition, or a cytokine and/or growth factor composition) are in unit dosage forms suitable for single administration of precise dosages. In unit dosage form, the formulation is divided into unit doses containing appropriate quantities of one or more compound. In some embodiments, the unit dosage is in the form of a package containing discrete quantities of the formulation. Non-limiting examples include packaged tablets or capsules, and powders in vials or ampoules. Aqueous suspension compositions are optionally packaged in single-dose non-reclosable containers. In some embodiments, multiple-dose re-closeable containers are used. In certain embodiments, multiple dose containers contain a preservative in the composition. Formulations for parenteral injection may be presented in unit dosage forms, which include, without limitation, ampoules or in multi-dose containers with an added preservative.

The following Examples are merely illustrative and are not meant to limit any aspects of the present disclosure in any way.

EXAMPLES

Example 1: Accelerated Hematopoietic Reconstitution In Mice

The following example describes the results of treating mice with a TAT-MYC fusion protein after transplantation with expanded bone marrow cells (e.g. protein transduced longterm hematopoietic stem cells (ptlt-HSCs)).

Materials and Methods

Cohorts of 4-6 week old female C57BL/6J mice were obtained from Jackson Laboratories (Bar Harbor, Me.). The mice were treated with 5 mg/mouse of 5-fluorouracil (5FU), intravenously. Bone marrow (BM) cells were collected from the tibia and femur bones 5 days after 5FU treatment. The red blood cells were lysed by incubation in 5 ml sterile TAC buffer (135 mM NH4CL, 17 mM Tris Ph 7.65). The bone marrow cells were expanded in BM Medium (DMEM containing 15% FCS, 100 units per ml Penn/Strep, MEM NEAA (Gibco), 10 mM HEPES, recombinant murine IL-3, IL-6, and SCF) supplemented with 5 µ/ml recombinant Tat-Myc, and 10 µ/ml recombinant Tat-Bcl-2. Cells were cultured for 21 days with a BM medium change every 48 hr to refresh the Tat-fusion proteins.

Cytokines were prepared by plating 293FT cells in 150 mm plates at $12\times10^6$ cells per plate in D10 media (DMEM, 10% FBS, 100 units per ml Penn/Strep, MEM NEAA (Gibco), 2 mM L-glutamine (Gibco)). The cells were transfected with 30 µg total DNA per plate consisting of 10 µg pcDNA3.1-SCF, 10 µg pcDNA3.1-IL3, and 10 µg pcDNA3.1-IL6 or 10 µg pcDNA3.1-TPO, 10 µg pcDNA3.1-Flt3-L, and 10 µg pcDNA3.1-GM-CSF using calcium phosphate (Young, R. M., et al. (2008). Future Oncology, 4, 591-4.). The following day, the media was removed and was replaced with 100 ml D10 media. Cells were incubated at 37° C./5% CO2 for 4-5 days. The media was collected, sterile filtered, and frozen at −20° C. in 30 ml aliquots.

After 21 days, $5\times10^3$ expanded bone marrow cells were transplanted into sublethally irradiated Rag-1$^{-/-}$ mice on a C57/BL6 background (Jackson Laboratory) that received 350 Rads of radiation just prior to injection of the BM cells via the tail vein. The expanded cells were washed 3 times in PBS prior to injection via the tail vein in 200 µl PBS.

After 24 hours, one cohort of mice was injected intramuscularly with 10 µg TAT-MYC emulsified in corn oil. The emulsion is prepared by adding 30 µg Tat-MYC into 1ml of corn oil. Just prior to injection, the corn oil containing the Tat-MYC is passed several times from 1 syringe to a second syringe through a 2-way stopcock. 300 ul of the emulsion containing 10 µg of Tat-MYC is injected IM into the mouse, just to the side of the tail.

Reconstitution of the lymphoid compartment was monitored by flow cytometric analysis (FACS) of peripheral blood samples obtained by venipuncture of the tail at 4 weeks and 8 weeks following transplant. Peripheral blood mononuclear cells (PBMCs) were monitored by FACS for TCRβ and for B220 expression.

Results

As shown in FIGS. 1 and 3, accelerated development of T-cells was seen in mice treated with TAT-MYC following bone marrow transplant with ex vivo expanded bone marrow cells. Cohorts of Rag-1$^{-/-}$ mice were sub-lethally irradiated and given transplants of 5×10$^3$ expanded bone marrow cells (FIGS. 1C and 1D; FIGS. 3C and 3D). Half of the irradiated and transplanted mice in each cohort were injected with 10 µg TAT-MYC 24 hours after the transplant (FIGS. 1D and 3D). FACS analysis of wild-type (untreated and non-irradiated) Rag-1$^{-/-}$ mice (FIGS. 1A, 0.9% TCRβ+ cells and 3A, 0.8% TCRβ$^+$ cells) and C57BL/6 mice (FIGS. 1B, 34.3% TCRβ$^+$ cells and 3B, 34.3% TCRβ$^+$ cells) are also provided as a control.

Mice were tested for T cell reconstitution at 4 weeks (FIG. 1) and 8 weeks (FIG. 3) by FACS analysis of their peripheral blood. FIG. 1D shows the 4-week levels of T cells in the peripheral blood of mice treated with TAT-MYC (5.6% TCRβ$^+$ cells), as compared to the control (FIG. 1C) that was not injected with TAT-MYC (0.2% TCRβ$^+$ cells). FIG. 3D shows the 8-week levels of T cells in the peripheral blood of mice treated with TAT-MYC (13.1% TCRβ$^+$ cells), as compared to the control (FIG. 3C) that was not injected with TAT-MYC (4.2% TCRβ$^-$ cells). At 4 weeks, the TAT-MYC injected mice showed T cell levels similar to those of control mice not injected with TAT-MYC at 8 weeks. As the average time to T-cell recovery is 8-10 weeks, this represents an acceleration of about 50-60%.

As shown in FIGS. 2 and 4, accelerated development of B cells was also seen in mice treated with TAT-MYC following bone marrow transplant with expanded bone marrow cells. Cohorts of Rag-1$^{-/-}$ mice on a C57/BL6 background were sub-lethally irradiated and given transplants of 5×10$^3$ expanded bone marrow cells. Half of the irradiated and transplanted mice in each cohort were injected with 10 µg TAT-MYC 24 hours after the transplant (FIGS. 2D and 4D). FACS analysis of wild-type (untreated and non-irradiated) Rag-1$^{-/-}$ mice (FIGS. 2A, 1.15% B220$^+$ cells and 4A, 1% B220$^+$ cells) and C57BL/6 mice are also provided as a control (FIGS. 2B, 21.4% B220$^+$ cells and 4B, 29.2% B220$^+$ cells).

Mice were tested for B cell reconstitution at 4 weeks (FIG. 2) and 8 weeks (FIG. 4) by FACS analysis of their peripheral blood. FIG. 2D shows the 4-week levels of B cells in the peripheral blood of mice treated with TAT-MYC (12.1% B220$^+$ cells), as compared to the control (FIG. 2C) that was not injected with TAT-MYC (0.3% B220$^+$ cells). FIG. 4D shows the 8-week levels of B cells in the peripheral blood of mice treated with TAT-MYC (5.4% B220$^+$ cells), as compared to the control (FIG. 4C) that was not injected with TAT-MYC (1.2% B220$^+$ cells). At 4 weeks, the TAT-MYC injected mice showed B cell levels higher than those of control mice not injected with TAT-MYC at 8 weeks. As the average time to B-cell recovery is 8-12 weeks, this represents an acceleration of about 50-67%.

Example 2: Accelerated Hematopoietic Reconstitution In Mice

The following example describes the results of treating mice with a TAT-MYC fusion protein following freshly isolated whole bone marrow transplantation.

Materials and Methods

For whole bone marrow transplantations in mice, donors and recipients were both on a C57/BL6 background.

Bone marrow cells were flushed from femurs and tibial bones obtained from two donor wild type C57/BL6 mice. The harvested cells were transferred into D10 complete medium (DMEM supplemented with 10% heat inactivated fetal calf serum, 100 units/ml penicillin/streptomycin, 10 µg/ml L-glutamine, as well as MEM NEAA). The bone marrow aspirates were dissociated into single cell suspensions and pelleted by centrifugation. The red blood cells were lysed by incubation of the cell suspension in a hypotonic buffer (135 mM NH$_4$Cl, 17 mM Tris, pH 7.65). The remaining cells were then washed in D10 medium followed by two washes with PBS and kept cold until transplantation into Rag-1$^{-/-}$ mice the same day.

The recipient Rag-1$^{-/-}$ mice were irradiated with 350 Rads (whole body irradiation). Recipient mice were given 1×10$^6$ whole bone marrow cells via tail vein injection. 24 hours after the bone marrow cell transplant, mice were given 10 µg of TAT-MYC emulsified in 300 µl of corn oil as described in Example 1. The TAT-MYC was delivered via intramuscular injection.

Reconstitution of the lymphoid compartment was monitored by flow cytometric analysis (FACS) of peripheral blood samples obtained by venipuncture of the tail. Specifically, samples were monitored for the appearance of CD4 or CD8 expressing T-cells (TCRβ), as well as B-cells (CD19 and B220 expressing cells).

Spleen cell samples from chimeric mice were also measured for the ability to respond to mitogenic stimulation. Spleen-derived T-cells and B-cells were labeled with CFSE and activated with either antibodies to CD3 (T-cells), or antibodies to IgM and CD40 (B-cells). The cells were evaluated for proliferation, as determined by dilution of the CFSE signal, using FACS, 72 hours after stimulation.

Results

Cohorts of 5 mice each (Rag-1$^{-/-}$ mice) were sub-lethally irradiated and given transplants of 10$^6$ whole BM cells obtained from female C57/BL6 donor mice. The transplant recipient mice were then either injected with TAT-MYC 24 hours later or not treated. The chimaeric mice were maintained in the vivarium for observation for 4 weeks. At that point, the mice were euthanized, and PBMCs and spleens were collected. The spleens were used to generate single cell suspension. Those cells were then stained with fluoresceinated antibodies to murine CD4 and CD8, and analyzed by flow cytometry.

FIGS. 5 and 6 show the accelerated development of T cells in mice treated with TAT-MYC following freshly isolated whole bone marrow transplant. Cohorts of Rag-1$^{-/-}$ mice on a C57/BL6 background were sub-lethally irradiated and given transplants of 1×10$^6$ whole bone marrow cells. Half of the transplanted cohorts were injected with TAT-MYC 24 hours after the transplant.

FIG. 5A shows the level of peripheral blood CD4 and CD8 T cells in control Rag-1$^{-/-}$ mice that did not receive irradiation, a cell transplant, or treatment with Tat-Myc (0.03% CD4$^+$ and 0.8% CD8$^+$ cells). FIG. 5B shows the level of peripheral blood CD4 and CD8 T cells in untreated and non-irradiated wildtype C57BL/6 mice as a control (13.1% CD4$^+$ and 11.1% CD8$^+$ cells). FIG. 5D shows the detection of both CD4 and CD8 T-cells in the peripheral blood of mice treated with TAT-MYC (14.9% CD4$^+$ and 8.6% CD8 cells), as compared to the mice (FIG. 5C) that were not injected with TAT-MYC (4.2% CD4$^+$ and 3.2% CD8 cells). At 4 weeks, mice treated with TAT-MYC 24 hours after whole bone marrow transplant have approximately the same levels of CD4 and CD8 T cells as wildtype C57BL/6 mice.

Figure 6B:
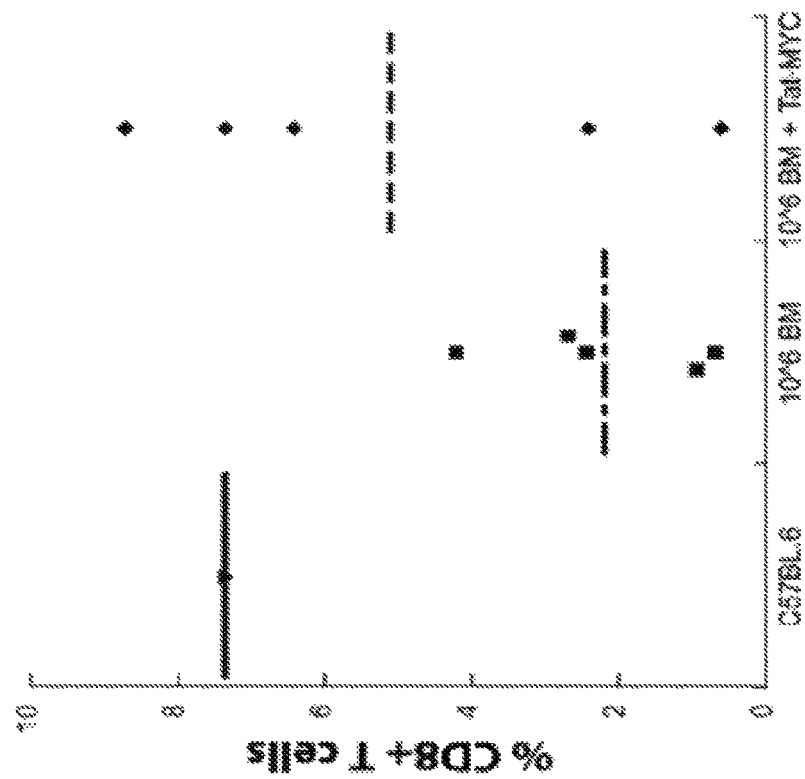
FIGS. 6A and 6B graphically depict the percentage of T cells for the full cohort of mice shown in FIG. 5.
Figure 6A:
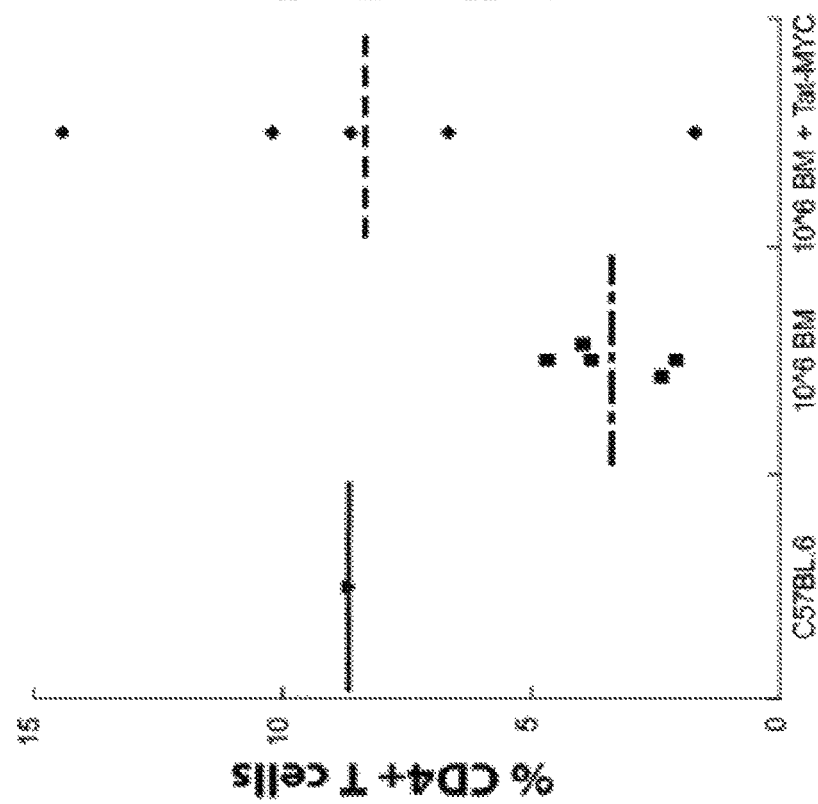

FIG. 6 graphically depicts the percentage of T cells for the full cohort of mice described above and shown in FIG. 5. FIG. 6A shows the percent CD4+ cells in the peripheral blood at 4 weeks post-transplant in wild type C57BL/6 (First column), in Rag-1$^{-/-}$ mice irradiated and transplanted, but not treated with TAT-MYC (Second column), and in Rag-1$^{-/-}$ mice irradiated, transplanted, and injected with 10 µg TAT-MYC (Third column). FIG. 6B shows the percent CD8+ cells in the peripheral blood at 4 weeks post-transplant in wild type C57BL/6 (First column), in Rag-1$^{-/-}$ mice irradiated and transplanted, but not treated with TAT-MYC (Second column), and in Rag-1$^{-/-}$ mice irradiated, transplanted, and injected with 10 TAT-MYC (Third column).

Figure 8:
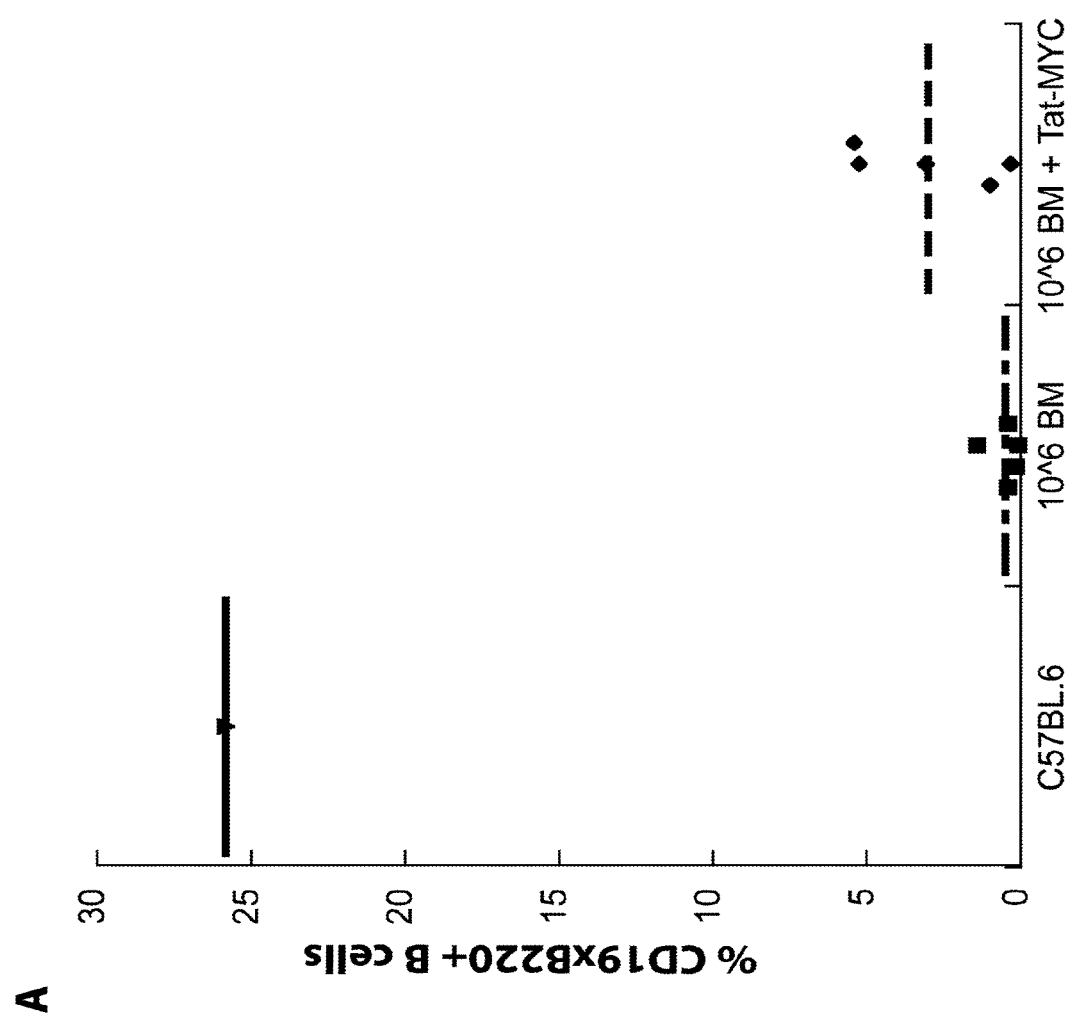
FIG. 8 graphically depicts the percentage of B cells for the full cohort of mice shown in FIG. 7. The graph shows the % CD19×B220 positive B cells in C57BL/6 control mice (untreated; first column), Rag-1$^{-/-}$ mice treated with 10$^6$ BM cells only (middle column); and Rag-1$^{-/-}$ mice treated with 10$^6$ BM cells followed 24 hours later with 10 μg TAT-MYC (last column).

FIGS. 7 and 8 show the accelerated development of B-cells in mice treated with TAT-MYC following freshly isolated bone marrow transplant. Cohorts of Rag-1$^{-/-}$ mice on a C57/BL6 background were sub-lethally irradiated and given transplants of 1×10$^6$ whole bone marrow cells. Half of the transplanted cohorts were injected with TAT-MYC 24 hours after the transplant.

FIG. 7A shows the level of peripheral blood CD19×B220 B cells in control Rag-1$^{-/-}$ mice that did not receive irradiation, a cell transplant, or treatment with TAT-MYC (0.2% CD19+×B220+ cells). FIG. 7B shows the level of peripheral blood CD19×B220 B cells in untreated and non-irradiated wildtype C57BL/6 mice as a control (25.8% CD19+×B220+ cells). FIG. 7D shows the detection of both CD19×B220 B cells in the peripheral blood of mice treated with TAT-MYC (5.2% CD19+×B220+ cells), as compared to the mice (FIG. 7C) that were not injected with TAT-MYC (1.4% CD19+× B220+ cells). At 4 weeks, mice treated with TAT-MYC 24 hours after whole bone marrow transplant have significantly higher levels of CD19×B220 B cells as transplanted control mice not treated with TAT-MYC.

FIG. 8 graphically depicts the percentage of B cells for the full cohort of mice described above and shown in FIG. 7. FIG. 8A shows the percent CD19×B220+ cells in the peripheral blood at 4 weeks post-transplant in wild type C57BL/6 (First column), in Rag-1$^{-/-}$ mice irradiated and transplanted, but not treated with TAT-MYC (Second column), and in Rag-1$^{-/-}$ mice irradiated, transplanted, and injected with 10 µg TAT-MYC (Third column).

FIG. 9 shows that T-cells and B-cells that developed in chimeric mice transplanted with whole bone marrow and treated with TAT-MYC 24 hours after transplant were functional and proliferated following stimulation of their antigen receptors. Spleen-derived T-cells and B-cells were labeled with CFSE and activated with either antibodies to CD3 (T-cells), or antibodies to IgM and CD40 (B-cells). The cells were evaluated for proliferation, as determined by dilution of the CFSE signal, using FACS, 72 hours after stimulation.

As shown in FIG. 9A, 33.3% of the spleen cells from mice given transplants of 1×10$^6$ whole BM cells, but not treated with TAT-MYC, showed T cell blasting upon stimulation with anti-CD3. The spleen cells from the chimeric mouse given transplants of 1×10$^6$ whole BM cells and treated with TAT-MYC showed 36.6% T cells blasting after CD3 stimulation (FIG. 9C). Similarly, FIG. 9B shows 6.92% of the spleen cells from mice given transplants of 1×10$^6$ whole BM cells, but not treated with TAT-MYC showed B cell blasting upon stimulation with anti-CD40 and anti-IgM. The spleen cells from the chimeric mouse given transplants of 1×10$^6$ whole BM cells and treated with TAT-MYC showed 15.8% B cells blasting after CD40 and IgM stimulation (FIG. 9D). These data show that the mature lymphoid cells obtained from HSC chimaeric mice that received TAT-MYC treatment were able to blast and undergo cell division following activation through their antigen receptors.

Example 3: Induction of Hematopoietic Reconstitution In Mice Treated with 5-fluorouracil The following example describes the results of treating mice with a TAT-MYC fusion protein after administration of 5-fluorouracil (5-FU), a chemotherapeutic agent known to be toxic to the hematopoietic compartment.

Introduction

Current approaches for reversing bone marrow failure that arises from various environmental insults or disease, among others, basically rely on the administration of growth factors and red blood cell transfusions for supportive therapy. The ultimate goal of these approaches is to encourage the remaining endogenous HSCs to mobilize and repopulate the hematopoietic compartment (auto-reconstitution). However, the current approaches are inefficient and in many cases simply delay the requirement for a myeloablative bone marrow transplant.

In addition, the sensitivity of HSCs to chemotherapeutic drugs as well as radiation has historically limited the doses of each therapy that can be applied to a patient with a solid tumor, for example. The loss of HSCs and hematopoietic compartment are one of the early signs of therapy-related toxicity in cancer patients. The ability to spare the HSC compartment from the therapeutic agents used for cancer could significantly change the approaches that are currently used to deliver such treatments.

The above results in Examples 1 and 2 utilizing TAT-MYC in the context of transplantation of HSCs with a low number of donor cells showed that TAT-MYC could also be useful in promoting auto-reconstitution of the hematopoietic compartment in patients with bone marrow failure syndrome. Although not intending to be bound by theory, it is believed that treatment with TAT-MYC would target a small number of the remaining resident HSCs and induce such HSCs to divide and give rise to differentiated hematopoietic lineages.

Material and Methods

Cohorts of 4-6 week old female C57/BL6 wild type (WT) mice were used for these experiments. Cohorts of 5 mice were treated intravenously with 5-flouorouracil (5 mg/mouse) alone, or followed by a treatment with either 10 µg/mouse of TAT-MYC or 10 µg/mouse of TAT-Cre (24 hours post-5FU challenge). Both proteins were emulsified in corn oil immediately prior to intramuscular injection. In some experiments, mice were pretreated (48 hours in advance of 5FU challenge) with either 10 µg/mouse of TAT-MYC or TAT-Cre.

Reconstitution of the lymphoid compartment was monitored by flow cytometric analysis (FACS) of peripheral blood samples obtained by venipuncture of the tail. Specifically, samples were monitored for the appearance of CD4 or CD8 expressing T-cells (TCRβ), as well as B-cells (CD19 and B220 expressing cells).

Results

Figure 11:
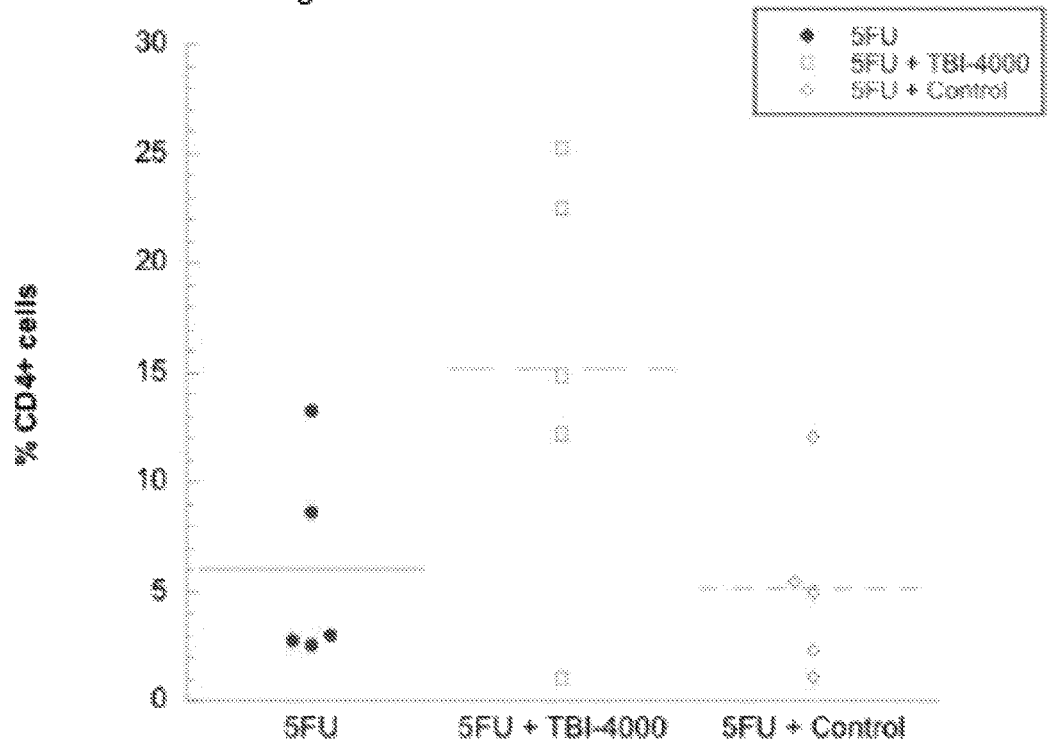
FIG. 11 graphically depicts the percentage of reconstituted CD4 T cells for the full cohort of 5FU challenged mice shown in FIG. 10. The graph shows the % CD4 positive T cells in C57BL/6 control mice (untreated; first column), C57BL/6 mice treated with 10 μg TAT-MYC (middle column); and C57BL/6 mice treated with 10 μg TAT-CRE (last column).
Figure 12:
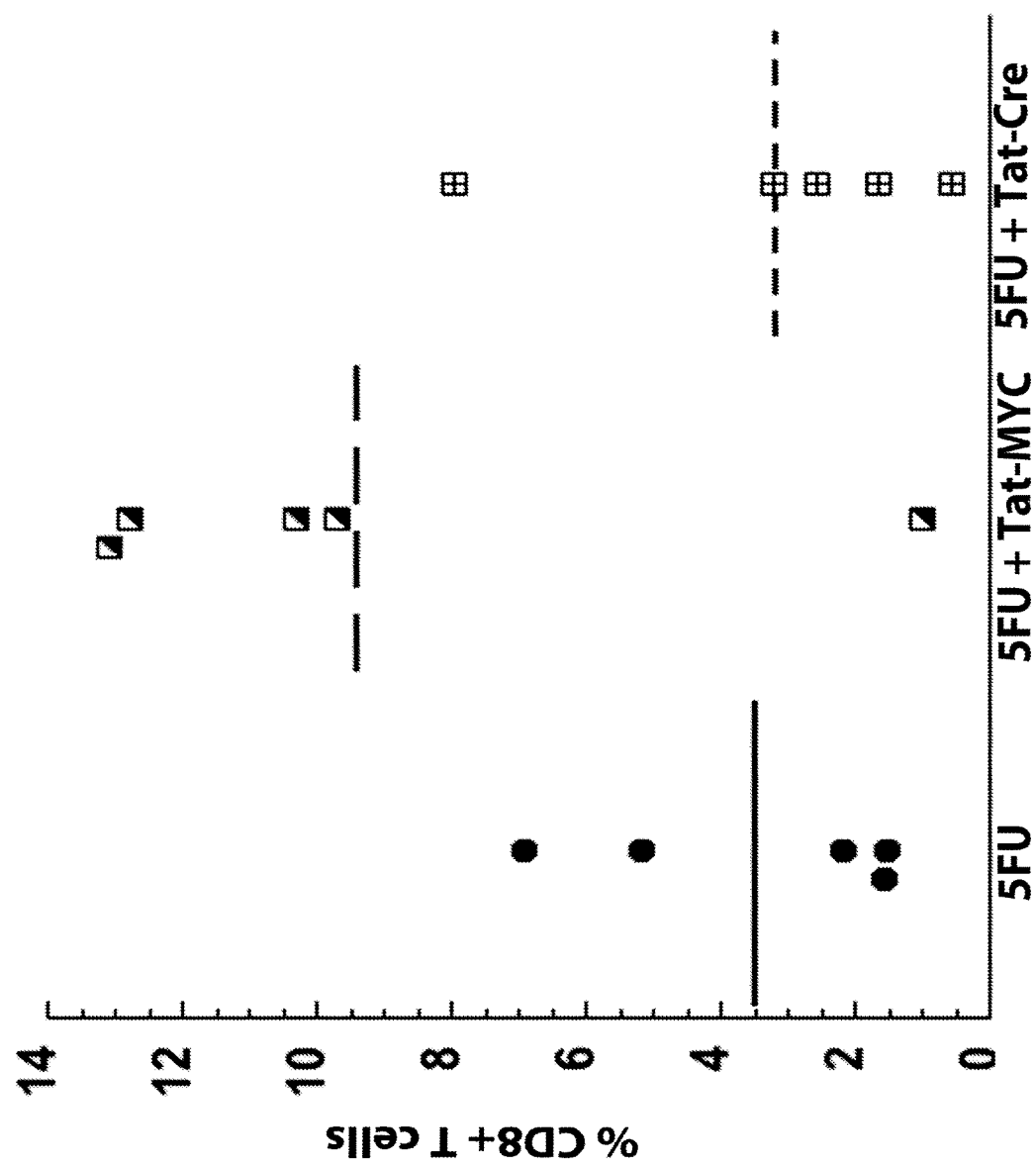
FIG. 12 graphically depicts the percentage of reconstituted CD8 T cells for the full cohort of 5FU challenged mice shown in FIG. 10. The graph shows the % CD8 positive T cells in C57BL/6 control mice (untreated; first column), C57BL/6 mice treated with 10 μg TAT-MYC (middle column); and C57BL/6 mice treated with 10 μg TAT-CRE (last column).

Challenge with 5-flourouracil was used both as a model for environmental insult, and more broadly as a model for treatment of any bone marrow failure. FIGS. 10, 11 and 12 show the accelerated auto-reconstitution of T cells at 2 weeks in mice treated with TAT-MYC 24 hours following 5-fluorouracil challenge. Cohorts of C57BL/6 mice were challenged with 5FU and either left untreated (FIG. 10A), or injected intramuscularly with a control protein TAT-CRE (FIG. 10B) or with TAT-MYC 24 hours after the 5FU challenge (FIG. 10C).

FIG. 10A shows the level of peripheral blood CD4 and CD8 positive T cells at 2 weeks in 5FU challenged C57/BL6 mice that did not receive treatment with TAT-Cre or TAT-MYC following 5FU challenge (3.9% $CD4^+$ and 2.4% $CD8^+$ cells). FIG. 10B shows the level of peripheral blood CD4 and CD8 positive T cells in 5FU challenged C57/BL6 mice that received treatment with 10 µg TAT-Cre following 5FU challenge (5.5% $CD4^+$ and 2.55% $CD8^+$ cells). FIG. 5C shows the level of peripheral blood CD4 and CD8 positive T cells in 5FU challenged C57/BL6 mice that received treatment with 10 µg TAT-MYC following 5FU challenge (14.9% $CD4^+$ and 9.69% $CD8^-$ cells.

FIGS. 11 and 12 graphically depict the percentage of T cells for the full cohort of mice described above and shown in FIG. 10. FIG. 11 shows the percent $CD4^+$ cells in the peripheral blood at 2 weeks post-5FU challenge in C57BL/6 mice not treated with either protein (First column), in C57BL/6 mice injected with 10 µg TAT-MYC (Second column), and in C57BL/6 mice injected with 10 µg TAT-CRE (Third column). FIG. 12 shows the percent $CD8^+$ cells in the peripheral blood at 2 weeks post-5FU challenge in C57BL/6 mice not treated with either protein (First column), in C57BL/6 mice injected with 10 µg TAT-MYC (Second column), and in C57BL/6 mice injected with 10 µg TAT-CRE (Third column).

In other experiments, challenge with 5-flourouracil is used as a model for protection against environmental insult, including for protection for HSCs against side-effects of chemotherapy or radiation therapy.

Cohorts of C57BL/6 mice are left untreated, treated intramuscularly with TAT-MYC, or treated intramuscularly with a control protein (TAT-CRE). Five mg of 5-FU are administered intravenously 24 hours later. At various times after 5FU challenge (optionally Days 3, 5, 7 or more), peripheral blood samples are analyzed by FACS to assess the frequency of T-cells ($CD4^+$ and $CD8^+$ T-cells) in the blood. A comparison between mice pre-treated with TAT-MYC or the control protein TAT-CRE will indicate whether TAT-MYC is able to confer chemoprotection to hematopoietic lineages.

Example 4: Induction of Hematopoietic Reconstitution In Mice Treated with Genotoxic Stress Agents In the following example two forms of genotoxic stresses for HSCs, chemical and radiological, are used. Age and gender matched C57/BL6 mice are treated with either TAT-MYC or a control protein, and then subjected to exposure with either a chemotherapeutic agent such as (5FU) or cyclophosphamide (CTX), or with sub-lethal doses of radiation. Fluctuations in the frequency of mature T-cell and B-cells in the peripheral blood of the mice are monitored, starting 5-7 days after exposure to the specific stimuli.

Use of TAT-MYC to Confer Chemoprotection to Hematopoietic Lineages in vivo

Cohorts of 10 C57/BL6 mice are injected with TAT-MYC, injected with a negative control (e.g. TAT-CRE), or left untreated. 24, 48, or 72 hours later (optionally any time point between 1 and 72 hours), we will treat 5 mice in each cohort with 5 mg/mouse of 5FU or 4 mg/mouse of cyclophosphamide (CTX). The other 5 mice of the cohort will be left with only the initial treatment of TAT-MYC, TAT-CRE, or no injection). Peripheral blood is obtained by venipuncture, and the frequency of mature T-cells and B-cell cells in the blood is analyzed by FACS.

The mice are assessed for reduced changes in the frequency of murine T-cells and B-cells in the peripheral blood of mice treated with TAT-MYC prior to challenge with 5FU, Busulfan A or Cyclophosphamide (CTX), in contrast to the significant decrease in the frequency of mature T-cells and B-cells observed in all other mice exposed to those chemotherapeutic agents. Alternatively, the mice are assessed for deceased recovery time to restore the frequency of murine T-cells and B-cells in the peripheral blood of mice treated with TAT-MYC prior to challenge with either 5FU, Busulfan A or CTX, in compared with the length time needed to see recovery in the frequency of mature T-cells and B-cells observed in all other mice exposed to those chemotherapeutic agents.

Additional studies involve a dose-escalation (or de-escalation) of either 5FU, Busulfan A or CTX on mice that are treated with TAT-MYC to determine the parameters of increases in doses of chemotherapeutic agents that are enabled by TAT-MYC treatment.

Use of TAT-MYC to Confer Radioprotection to Hematopoietic Lineages in vivo

The experimental setup is essentially the same as above. The only difference is that the mice are exposed to a range of doses of radiation rather than to chemotherapeutic agents following treatment with TAT-MYC, TAT-CRE, or no. Accordingly, 350 Rads and 600 Rads may be used for the C57/BL6J mice. The peripheral blood is monitored for the fluctuation of mature lymphoid or myeloid cells in by FACS.

The mice are assessed for reduced changes in the frequency of murine T-cells and B-cells in the peripheral blood of mice treated with TAT-MYC prior to challenge with sub-lethal or lethal radiation, in contrast to the significant decrease in the frequency of mature T-cells and B-cells observed in all other mice exposed to radiation. Alternatively, the mice are assessed for deceased recovery time to restore the frequency of murine T-cells and B-cells in the peripheral blood of mice treated with TAT-MYC prior to challenge with radiation, in compared with the length time needed to see recovery in the frequency of mature T-cells and B-cells observed in all other mice exposed to radiation.

Additional studies involve a dose-escalation (or de-escalation) of doses of radiation on mice that are treated with TAT-MYC to determine the parameters of increases in doses of radiation that are enabled by TAT-MYC treatment, and possible combination of radiation and chemotherapeutic agents.

Example 5: Accelerated Hematopoietic Reconstitution In Mice Following Different Routes of Administration The following example describes the results of treating mice with a TAT-MYC fusion protein administered either intramuscularly or intravenously following freshly isolated whole bone marrow transplantation.

Materials and Methods

Experiments were performed as described in Example 2 accept that TAT-MYC was provided using different routes of administration.

Briefly, mice donors and recipients were both on a C57BL/6 background. Bone marrow cells were flushed from femurs and tibial bones obtained from two donor wild type C57/BL6 mice. The bone marrow aspirates were dissociated into single cell suspensions, pelleted by centrifugation, and the red blood cells lysed. The remaining cells were then washed and kept cold until transplantation into Rag-1$^{-/-}$ mice the same day.

The recipient Rag-1$^{-/-}$ mice were irradiated with 350 Rads (whole body irradiation). Recipient mice were given 1×10$^6$ whole bone marrow cells via tail vein injection. 24 hours after the bone marrow cell transplant, mice received an intravenous injection of 10 µg of TAT-MYC dissolved in 200 µl PBS or intramuscular injection of 10 µg of TAT-MYC emulsified in 300 µl of corn oil as described in Example 1.

Reconstitution of the lymphoid compartment was monitored by flow cytometric analysis (FACS) of peripheral blood samples obtained by venipuncture of the tail. Specifically, samples were monitored for the appearance of CD4 or CD8 expressing T-cells (CD4×TCRβ), as well as B-cells (IgM×CD19 expressing cells).

Results

Cohorts of 5 mice each (Rag-1$^{-/-}$ mice) were sub-lethally irradiated and given transplants of 10$^6$ whole bone marrow cells obtained from female C57/BL6 donor mice. The transplant recipient mice were then either injected with TAT-MYC 24 hours later or not treated. The chimaeric mice were maintained in the vivarium for observation for at least 4 weeks, at which point peripheral blood was obtained by venipuncture and levels of T and B cells were assessed by FACS.

FIGS. 13 and 14 show the accelerated development of T cells in mice treated with TAT-MYC following freshly isolated whole bone marrow transplant. Cohorts of Rag-1$^{-/-}$ mice on a C57/BL6 background were sub-lethally irradiated and given transplants of 1×10$^6$ whole bone marrow cells (FIGS. 13C, 13D, and 13E). Two-thirds of the transplanted mice in the cohort received intravenous (FIG. 13D) or intramuscular (FIG. 13E) injection with 10 µg TAT-MYC 24 hours after the transplant. FACS analysis of wild-type (untreated and non-irradiated) Rag-1$^{-/-}$ mice (FIG. 13A, 0.579% CD4×TCRβ$^+$ cells) and C57BL/6 mice (FIG. 13B, 17.5% CD4×TCRβ$^+$ cells) are also provided as a control.

FIGS. 13D and 13E show the detection of CD4×TCRβ$^+$ T cells in the peripheral blood of mice receiving intravenous TAT-MYC (32.8% CD4×TCRβ$^+$ cells) or intramuscular TAT-MYC (18.2% CD4×TCRβ$^+$ cells), as compared to the control (FIG. 13C) that was not injected with TAT-MYC (6.39% CD4×TCRβ$^+$ cells). TAT-MYC injected by either route resulted in mice having approximately the same levels of CD4×TCRβ$^+$ T cells as wildtype C57BL/6 mice.

FIG. 14 graphically depicts the percentage of T cells for the full cohort of mice described above and shown in FIG. 13. The graph shows the percent CD4$^+$ cells in the peripheral blood at 4 weeks post-transplant in wild type Rag-1$^{-/-}$ mice (NT), in Rag-1$^{-/-}$ mice irradiated, transplanted, and receiving an intravenous injection of TAT-MYC (IV), and in Rag-1$^{-/-}$ mice irradiated, transplanted, and receiving an intramuscular injection of TAT-MYC (IM).

Figure 16:
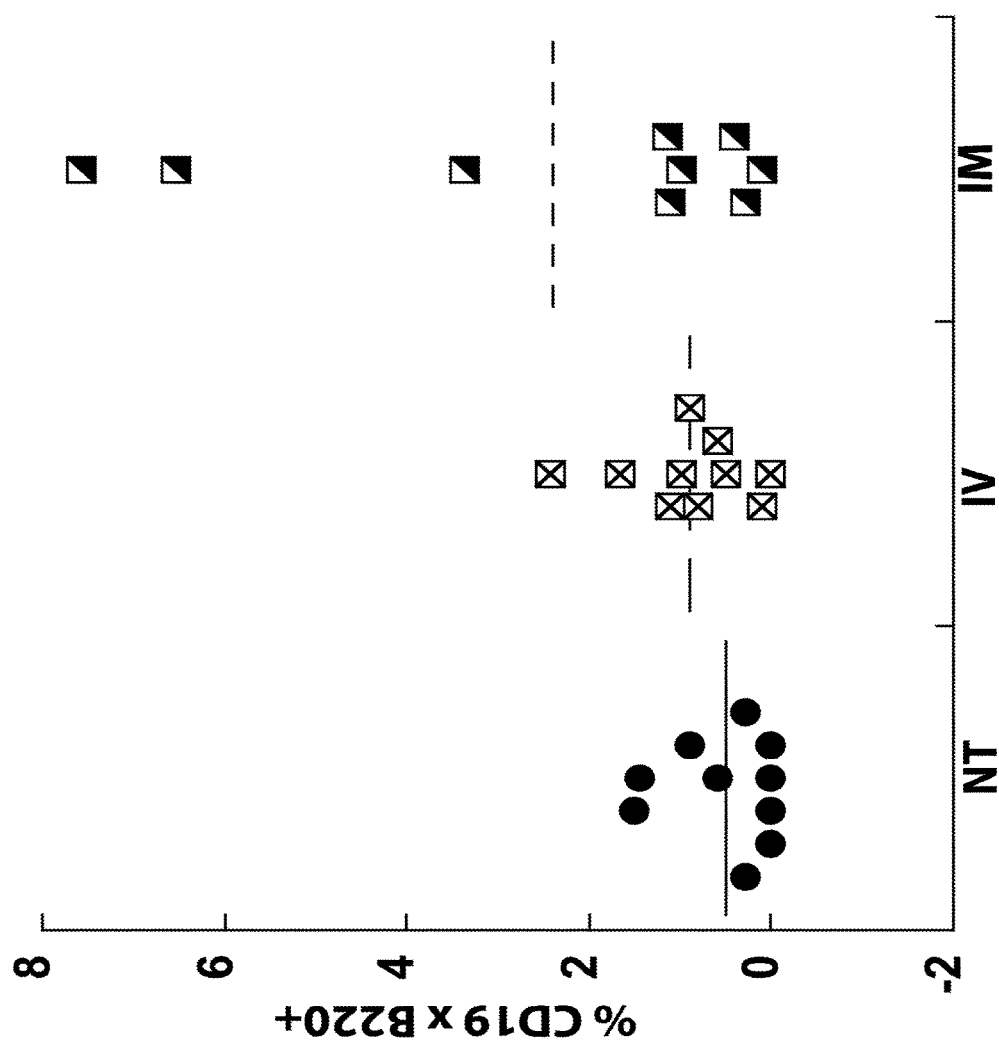
FIG. 16 graphically depicts the percentage of reconstituted B cells for the full cohort of sublethally irradiated mice that were given HSC transplants and then treated with either Tat-MYC or Tat-Cre, or a control 24 hours after the transplant shown in FIG. 15. The graph shows the % CD19×B220 positive B cells in Rag-1$^{-/-}$ control mice (untreated; first column), Rag-1$^{-/-}$ mice treated with 10 μg TAT-MYC intravenously (middle column); and Rag-1$^{-/-}$ mice treated with 10 μg TAT-CRE intramuscularly (last column).

FIGS. 15 and 16 show the accelerated development of B cells in mice treated with TAT-MYC following freshly isolated whole bone marrow transplant. Cohorts of Rag-1$^{-/-}$ mice on a C57/BL6 background were sub-lethally irradiated and given transplants of 1×10$^6$ whole bone marrow cells (FIGS. 15C, 15D and 15E). Two-thirds of the transplanted mice in the cohort received intravenous (FIG. 15D) or intramuscular (FIG. 15E) injection with 10 µg TAT-MYC 24 hours after the transplant. FACS analysis of wild-type (untreated and non-irradiated) Rag-1$^{-/-}$ mice (FIG. 15A, 0.071% IgM×CD19$^+$ cells) and C57BL/6 mice (FIG. 15B, 23.5% IgM×CD19$^-$ cells) are also provided as a control.

FIGS. 15D and 15E show the detection of IgM×CD19$^+$ B cells in the peripheral blood of mice receiving intravenous TAT-MYC (FIG. 15D, 2.41% IgM×CD19$^+$ cells) or intramuscular TAT-MYC (FIG. 15E, 6.53% IgM×CD19$^+$ cells), as compared to the control (FIG. 15C) that was not injected with TAT-MYC (1.49% IgM×CD19$^+$ cells). TAT-MYC injected by either route resulted in mice having higher levels of IgM×CD19$^+$ B cells than Rag-1$^{-/-}$ mice transplanted with whole bone marrow, but not treated with TAT-MYC.

FIG. 16 graphically depicts the percentage of B cells for the full cohort of mice described above and shown in FIG. 15. The graph shows the percent CD19×B220$^+$ cells in the peripheral blood at 4 weeks post-transplant in wild type Rag-1$^{-/-}$ mice (NT), in Rag-1$^{-/-}$ mice irradiated, transplanted, and receiving an intravenous injection of TAT-MYC (IV), and in Rag-1$^{-/-}$ mice irradiated, transplanted, and receiving an intramuscular injection of TAT-MYC (IM).

Example 6: Accelerated Hematopoietic Reconstitution In Mice Transplanted with Human Cord Blood-Derived HSCS Expanded with TAT-MYC and TAT-Bcl-2

The following example describes the results of expanding cord blood derived HSCs in vitro using TAT-MYC and TAT-Bcl-2 to form protein transduced longterm hematopoietic stem cells (ptlt-HSCs), prior to transplantation into sublethally irradiated mice.

Material and Methods

Fresh cord blood cells were obtained from samples that were discarded from a local cord blood bank. All human cells were de-identified and exempt from IRB oversight. The total cord volume was split into 20 ml aliquots and diluted 1:1 in PBS. Diluted cord blood (20 mls) was gently overlaid on 20 mls of Ficoll-Paque Plus (Amersham Biosciences Cat #17-1440-03). The cells were spun at 900× gravity for 60 min. The buffy coat was removed with a glass pipette and was washed twice with PBS. The cells were resuspended in FCB media (Iscove's (Gibco) supplemented with 10% human plasma, 100 units per ml Penn/Strep, 30 ml of media containing SCF, IL3 and IL6 and 30 mls of medium containing TPO, FLT3-L, and GM-CSF described above in Example 1).

Two FCB expansion cultures were initiated. The first culture contained FCB medium alone while the second contained FCB media supplemented with 5 µg/ml recombinant Tat-MYC, and 10 µg/ml recombinant Tat-Bcl-2. The medium on both cultures was replaced every 3 days over a 14 day expansion. The surface phenotype of the in vitro expanded human HSCs was assessed by FACS analysis using antibodies against the human antigens CD45, CD34 and CD38.

Fetal cord blood cells (FCBs) expanded in FCB media or FCB media supplemented with Tat-MYC and Tat-Bcl2 were injected into NOD/SCID/γc−/− mice (NSG) mice (Jackson Laboratory) that received 180 Rads of radiation just prior to injection. Expanded FCBs were washed 3 times in PBS and injected via the tail vein in 200 µl PBS. Eight weeks post-transplant, the bone marrow cells were collected from the tibia and femur bones of the transplant NSG mice. The red blood cells were lysed by incubation in 5 ml sterile TAC buffer (135 mM NH$_4$CL, 17 mM Tris Ph 7.65) followed by 2 washes D10 media. The BM cells were analyzed by flow cytometry using antibodies to the human antigens CD45, CD34, CD38, CD3, CD19, CD11b and CD33.

The spleen and thymus were collected from a euthanized NSG mice and a single cell suspension was generated by mechanical dissociation. The cells were treated with TAC buffer (135 mM NH$_4$CL, 17 mM Tris Ph 7.65) to lyse the red blood cells.

We functionally tested the human HSCs harvested from the BM of NSG mice by plating them on MethoCult Optimum (StemCell Technologies), and examined their ability to give rise to BFU-E, CFU-M, CFU-G and CFU-GM colonies. On the day of the BM harvest, 10,000 BM cells in 300 ul D10 were added to 4 mls of MethoCult. The 4 ml containing the BM cells were divided equally between 2, 30 mM dishes, each containing 5000 cells. The dishes were incubated at 37° in 5% CO$_2$ for 14 days. The colonies were counted and identified based on cell morphology using an inverted microscope.

Results

As shown in FIG. 17, xenochimaeric NSG mice generated by transplanting HSC expanded in FCB media supplemented with Tat-MYC and Tat-Bcl2 (ptlt-HSCs) showed an increase in BM engraftment. Eight weeks post-transplant the NSG mice injected with 1×10$^6$ CD34+/CD38lo cells expanded in FCB media alone had 0.03% of their bone marrow compartment derived from the transplanted cells (FIG. 17A, first panel). NSG mice injected with 1×10$^6$ CD34+/CD38lo cells expanded in FCB media supplemented with Tat-MYC and Tat-Bcl2 had 18.2% of their bone marrow compartment derived from the transplanted cells (FIG. 17A, second panel). An NSG mouse transplanted with 5×10$^6$ fresh cord blood cells was used as a control for engraftment (FIG. 17A, third panel), and showed 2.7% engraftment with transplanted cells.

Human CD45+ cells from the BM, spleen and thymus of xenochimaeric NSG mice generated by transplanting HSC expanded in FCB media supplemented with Tat-MYC and Tat-Bcl2 were analyzed. FACS analysis shows that 6.8% of the human CD45+ population in the BM also stained positive for the hematopoietic stem cell marker CD34 (FIG. 17B, first panel). Human CD45+ cells from the spleen and thymus of these mice were assessed for the B cell marker CD19 and the T cell marker CD3. The majority of the human CD45+ cells from the spleen stained positive for the B cell marker CD19 (FIG. 17B, second panel, 69.2%), compared to the T cell marker CD3 (FIG. 17B, second panel, 7.7%). The majority of CD45+ population in the thymus stained positive for the CD3 T cell marker (FIG. 17B, third panel, 91.3%), compared to the B cell marker CD19 (FIG. 17B, third panel, 1.2%).

Figure 17A:
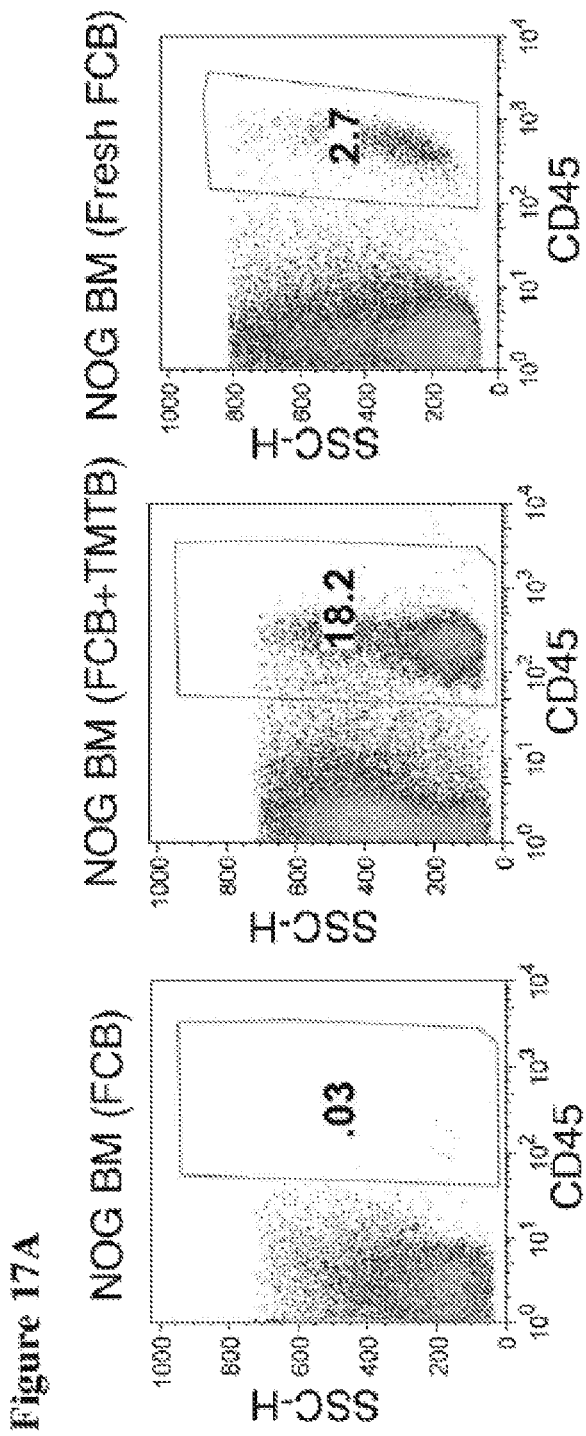
Figure 17C:
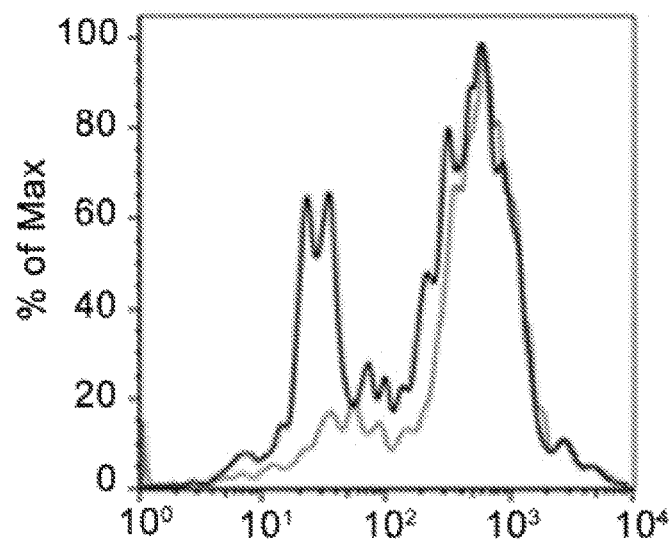

Human CD45+ CD19+ cells from the spleens of xenochimaeric NSG mice transplanted with ptlt-HSCs were labeled with CFSE, and were activated with monoclonal antibodies to human CD40 and IgM. The cells were analyzed at 72 hours by flow cytometry for dilution of CFSE. FIG. 17C shows the proliferation profile of the human B-cells that developed in vivo in xenochimaeric NSG mice. These results demonstration that the B cells derived from the transplanted HSCs that received pretreatment with Tat-MYC and Tat-Bcl2 can be activated through their B cell receptor.

Figure 17D:
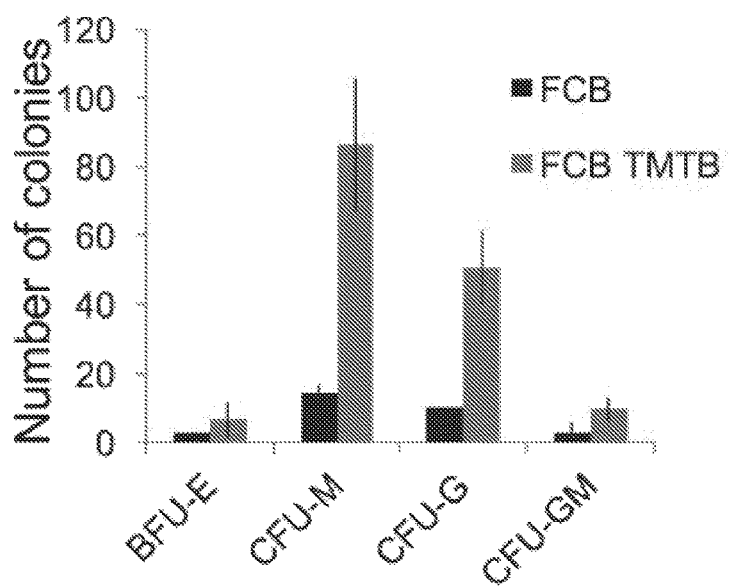
Figure 17E:
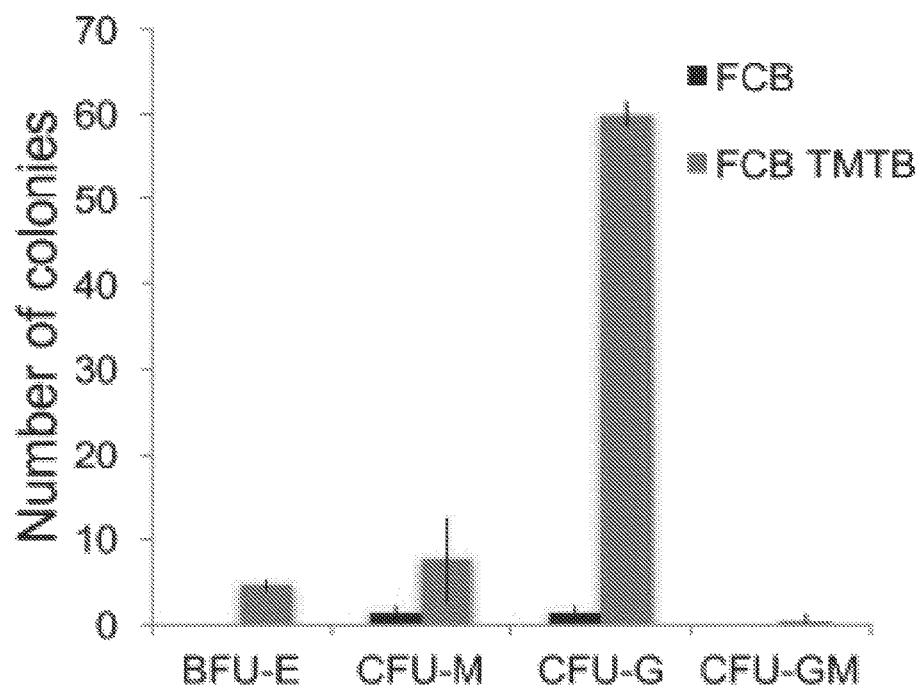
Figure 17F:
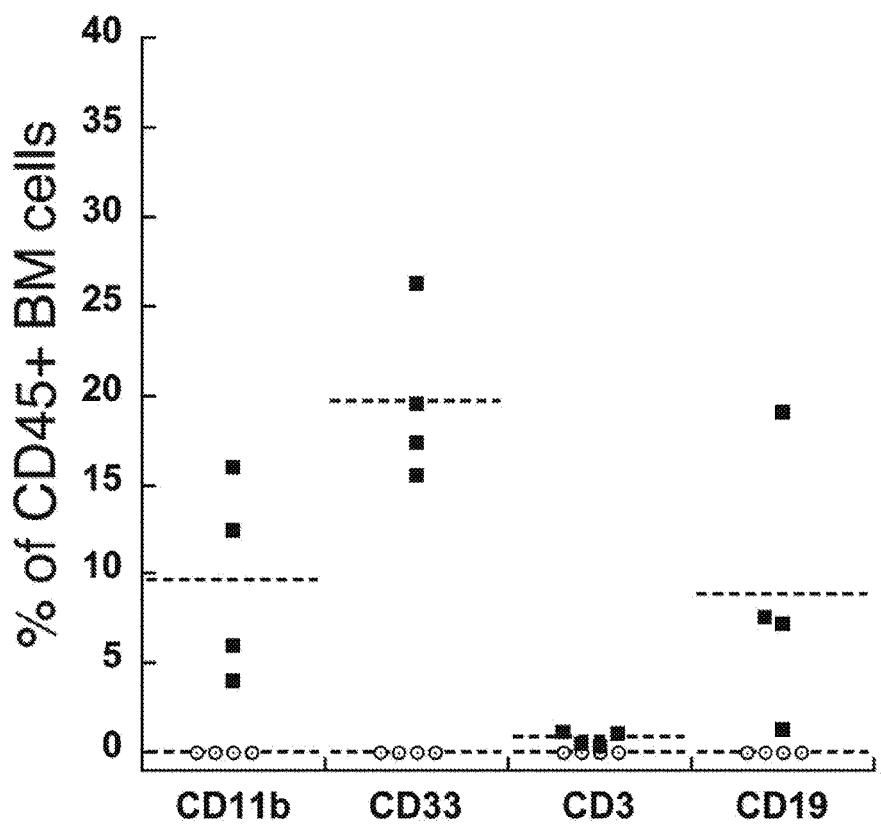
Figure 17G:
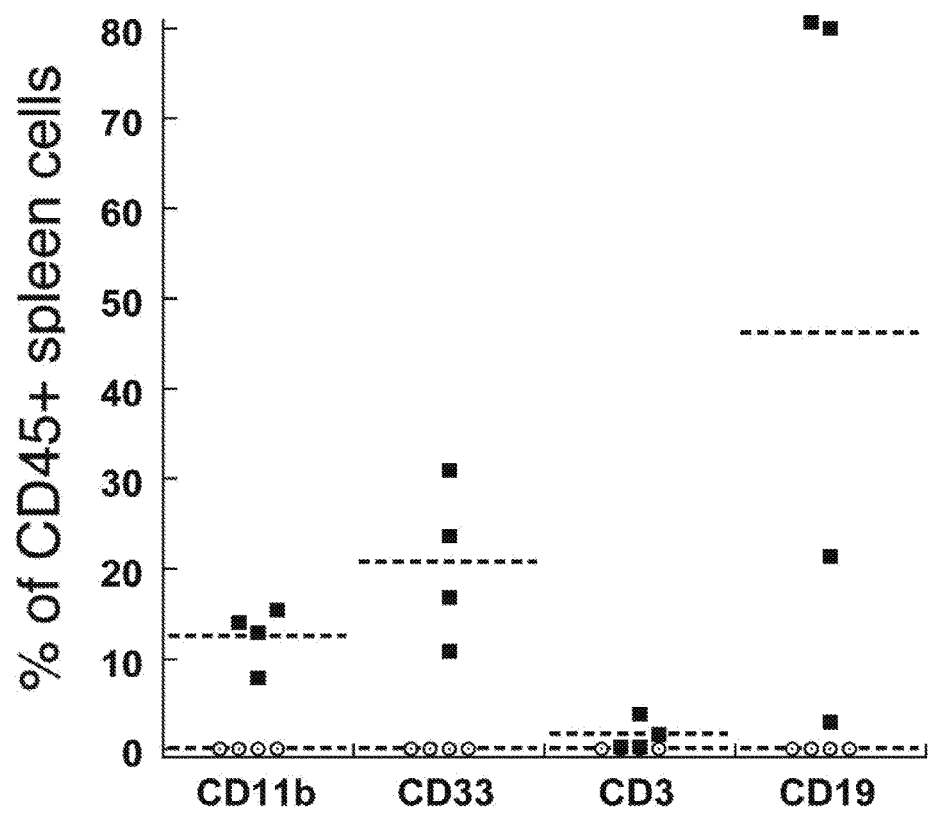
Figure 18A:
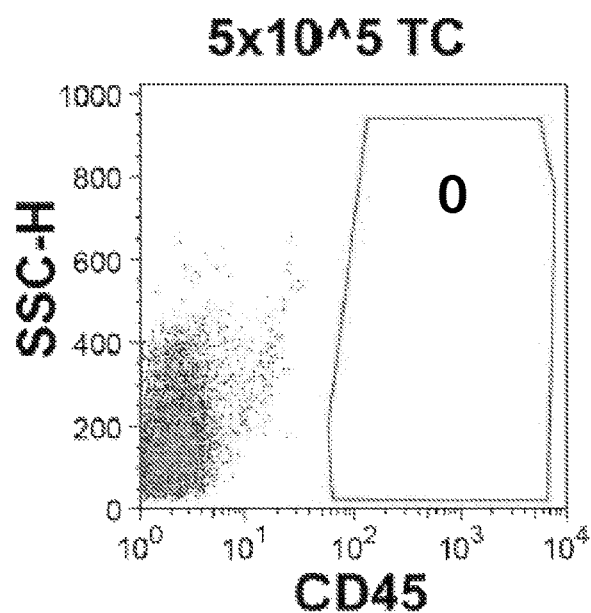
FIGS. 18A-18F depict the results of FACS staining showing the reconstitution of the peripheral blood in NSG mice 8 weeks after sub-lethal irradiation followed by transplantation of fresh fetal cord blood cells and treatment with TAT-MYC or Tat-Cre control protein. The panels show flow cytometry of isolated PBMCs gated for human CD45 positive cells.
Figure 18B:
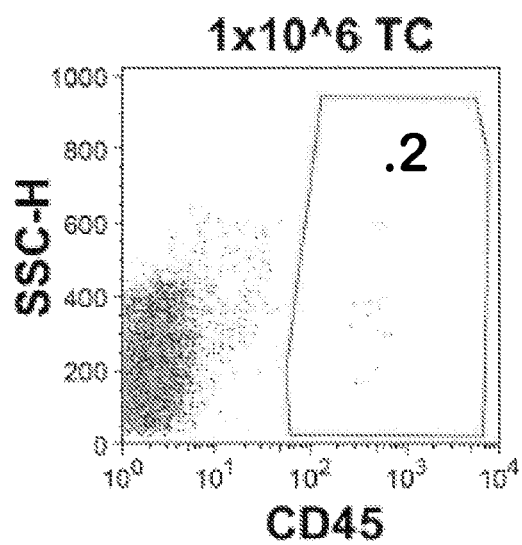
Figure 18C:
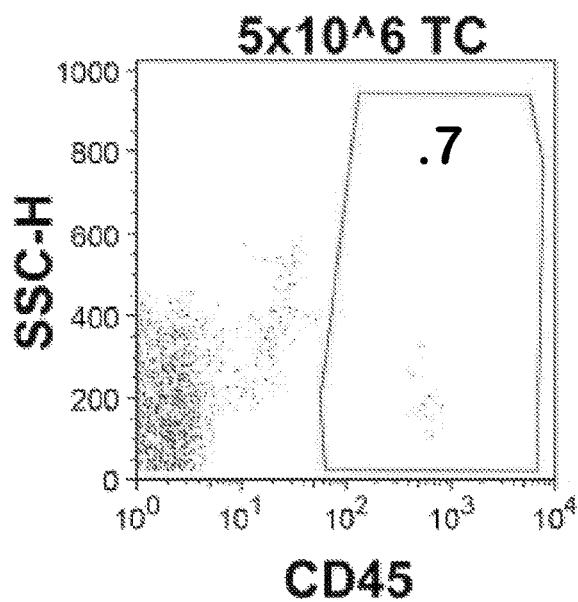
Figure 18D:
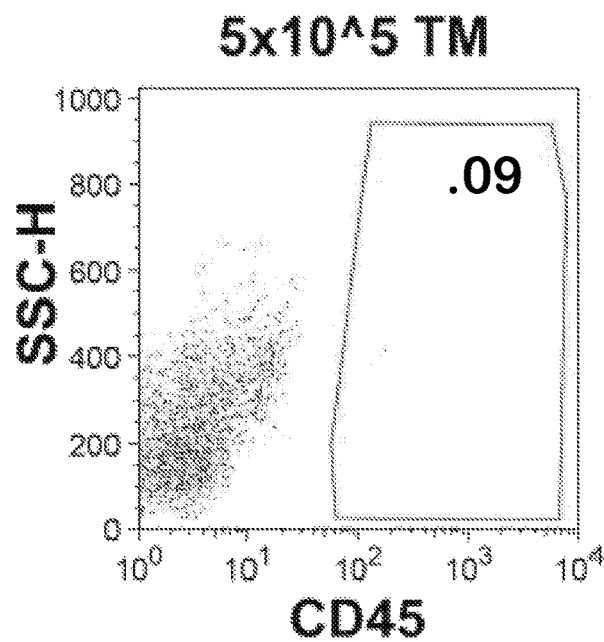
Figure 18E:
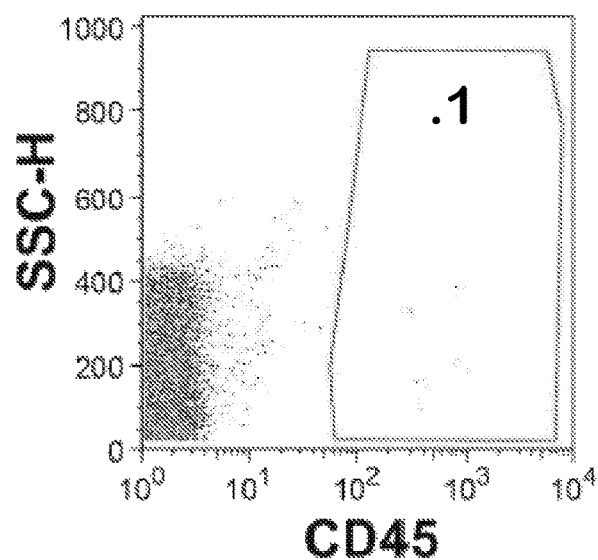
Figure 18F:
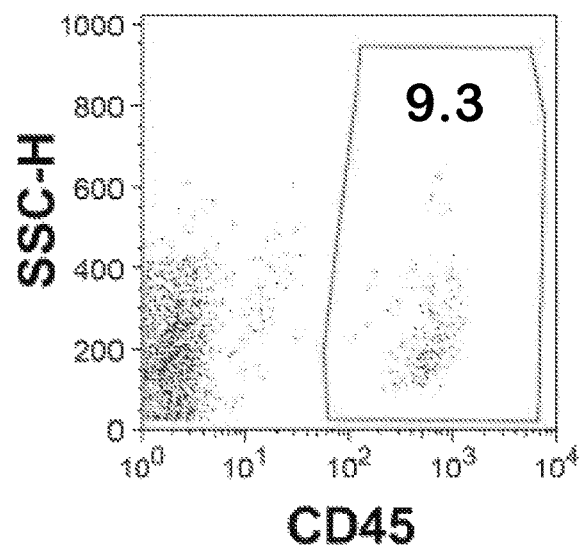
Figure 19A:
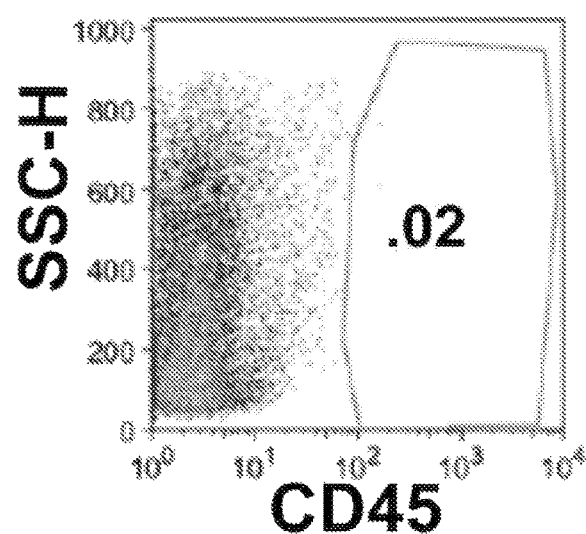
FIGS. 19A-19F depict the results of FACS staining showing the reconstitution of the bone marrow from NSG mice 8 weeks after sub-lethal irradiation followed transplantation of fresh fetal cord blood cells and treatment with TAT-MYC or Tat-Cre control protein. The panels show flow cytometry of isolated bone marrow gated for human CD45 positive cells.
Figure 19B:
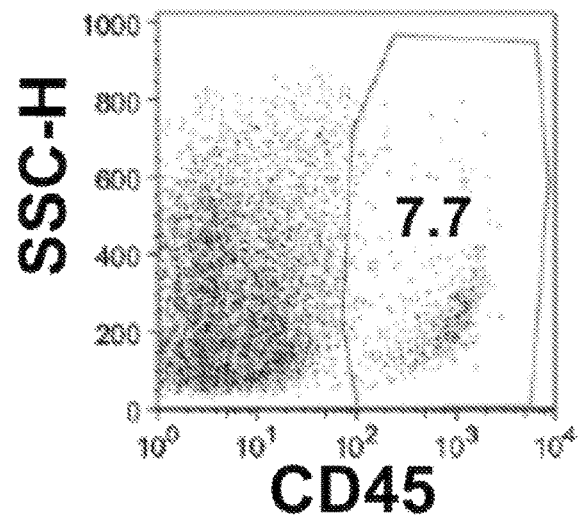
Figure 19C:
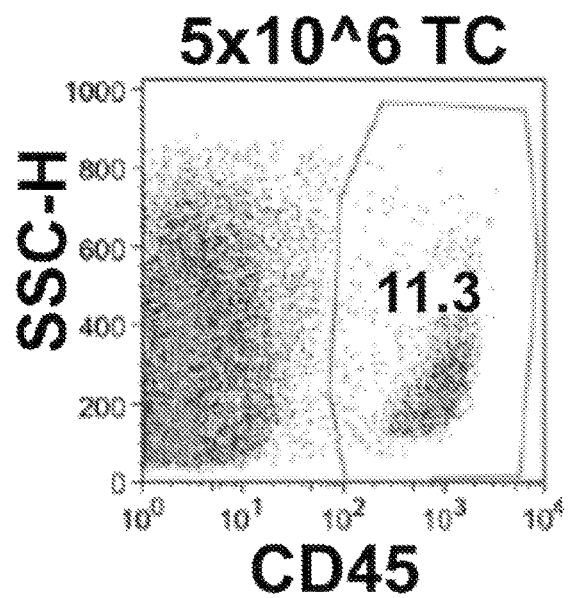
Figure 19D:
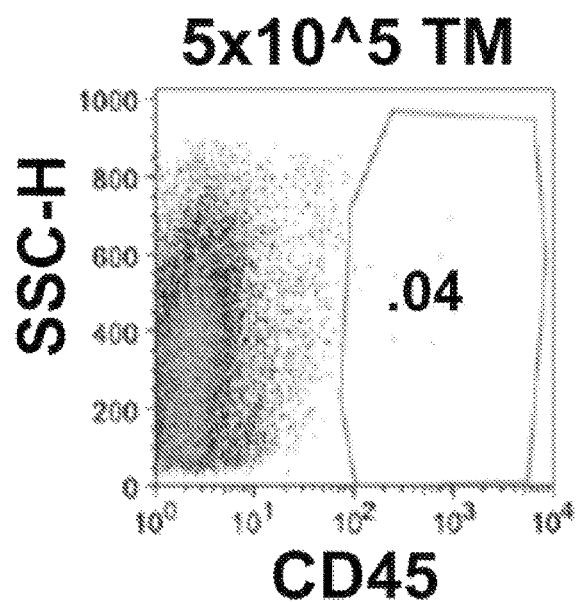
Figure 19E:
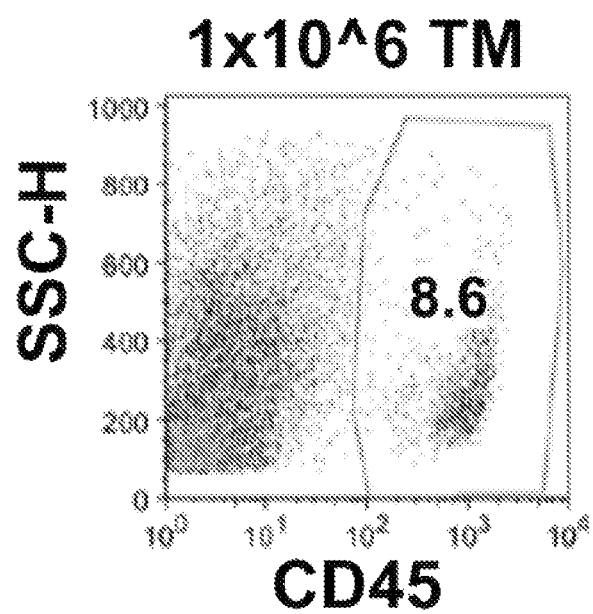
Figure 19F:
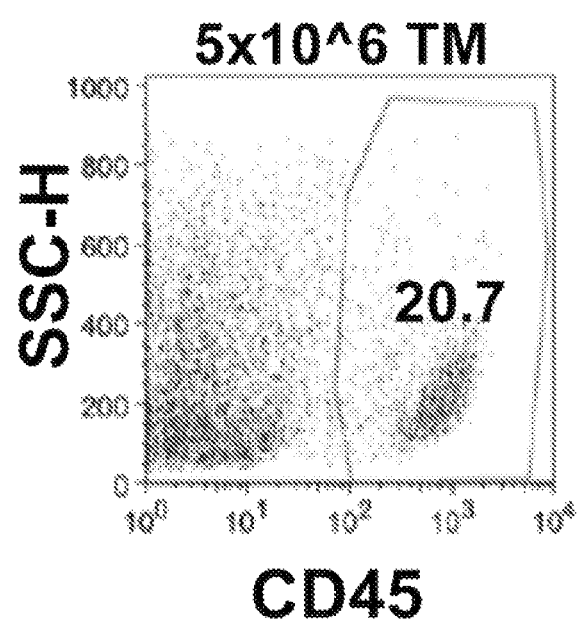
Figure 20A:
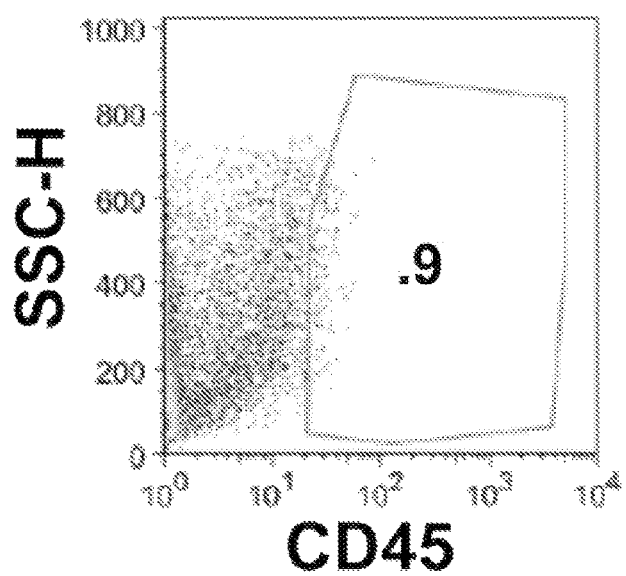
FIGS. 20A-20F depict the results of FACS staining showing the reconstitution of the spleen in NSG mice 8 weeks after sub-lethal irradiation followed transplantation of fresh fetal cord blood cells and treatment with TAT-MYC or Tat-Cre control protein. The panels show flow cytometry of isolated spleen cells gated for human CD45 positive cells.
Figure 20B:
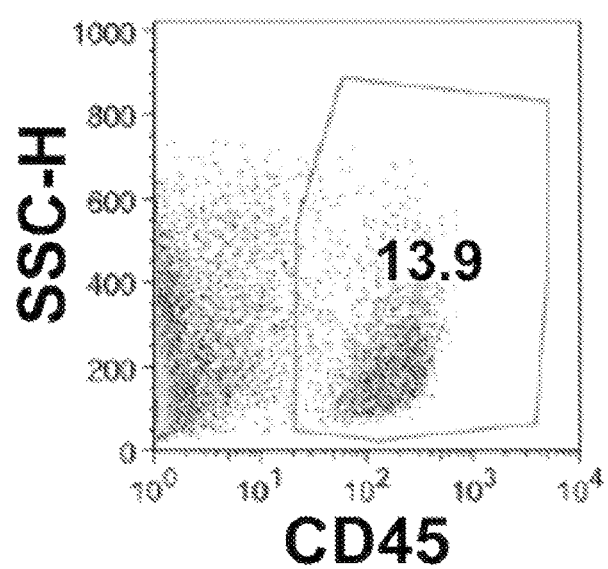
Figure 20C:
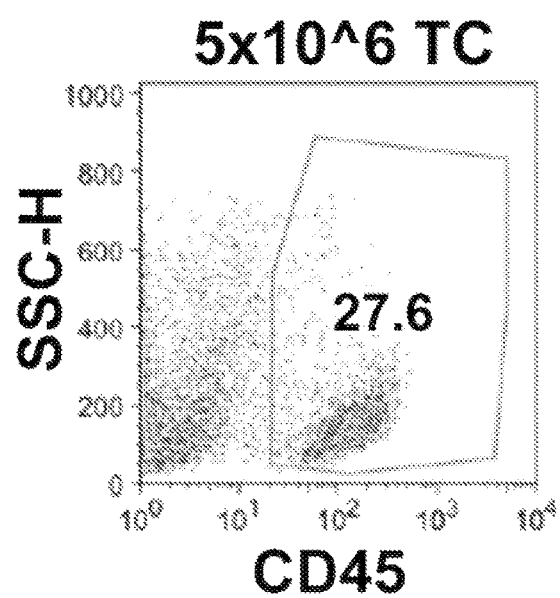
Figure 20D:
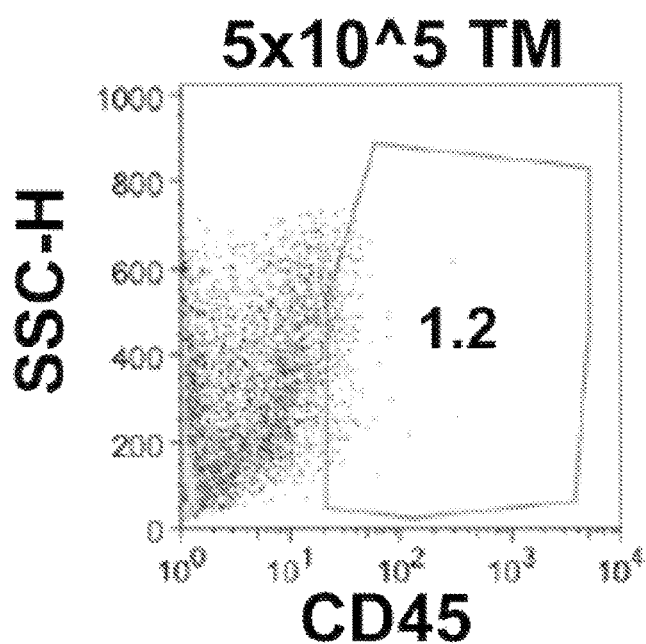
Figure 20E:
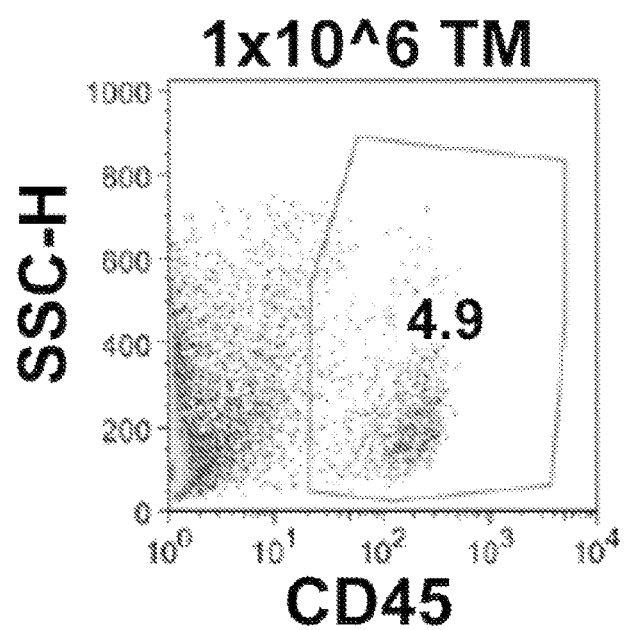
Figure 20F:
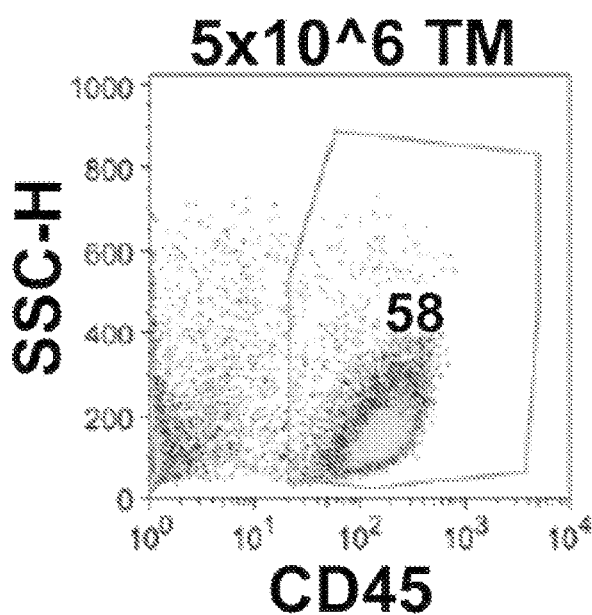

Human CD45+, CD34+ CD38lo HSCs from the bone marrow of xenochimaeric NSG mice transplanted with ptlt-HSCs were used to seed in MethoCult Optimum to assess the presence of myeloerythroid stem cells. These cells from NSG mice transplanted with ptlt-HSCs gave rise to more colonies in MethoCult plates (FIG. 17D, FCB TMTB), as compared to cells from control NSG mice transplanted with cells expanded in media alone (FIG. 17D, FCB). Although colony formation was observed in conditions selective for erythroid (BFU-E), myeloid (CFU-M), granulocyte (CFU-G), and granulocyte macrophage (CFU-GM) lineages, more myeloid and granulocyte growth was observed. In addition, some of the colonies could still be observed following serial replating (FIG. 17E). The number of colonies in both instances was significantly higher for NSG mice reconstituted with human cord blood cells cultured for 14 days with Tat-MYC and Tat-Bcl-2 than for cells obtained from NSG mice reconstituted with fresh, un-manipulated human cord blood cells.

These results show that the CD45+, CD34+CD38lo HSCs from the bone marrow of engrafted mice are hematopoietic stems cell that are able to give rise to all 4 colony types in MethoCult media. Further, the increased colony number observed on plates seeded with bone marrow from NSG mice engrafted with FCBs cultures with Tat-MYC and Tat-Bcl2 is reflective of a greater number of hematopoietic stems cells residing in the bone marrow niche.

In addition, a cohort of xenochimaeric mice, engrafted with 10$^6$ cord blood cells previously expanded in vitro in a cocktail of cytokines supplemented with Tat-MYC and Tat-Bcl-2 (black squares), were assessed for myeloid and lymphoid cell differentiation. The CD45 positive population of bone marrow cells (FIG. 17F) and spleen cells (FIG. 17G) were analyzed for CD11b, CD33, CD3, and CD19 expression. Both myeloid and lymphoid cell differentiation was observed in the bone marrow and spleen of these xenochimaeric mice.

Example 7: Accelerated Hematopoietic Reconstitution In Mice Transplanted with Human Freshly Isolated Whole Cord Blood and Injected with TAT-MYC The following example describes the results of treating mice with a TAT-MYC fusion protein after transplantation with fresh human cord blood cells.

Materials and Methods

Human cord blood cells were obtained, and prepared as described in Example 6. Briefly, the cord blood was separated using Ficoll-hypaque and centrifugation to obtain the buffy coat fraction. Buffy coat cells were removed, washed twice, then resuspended in PBS, and kept cold until transplanted into mice later the same day.

Prior to injecting NOD/SCID/γ$^{-/-}$ (NOG) mice with FCB cells, the mice were irradiated with 180 Rads (whole body irradiation). Each recipient mouse was then given a transplant consisting of 5×10$^5$, 1×10$^6$, or 5×10$^6$ human FCB cells via tail vein injection. 24 hours after the bone marrow cell transplant, mice received an intramuscular injection of 10 μg of TAT-MYC or 10 μg TAT-CRE emulsified in 300 μl of corn oil.

Engraftment was monitored with flow cytometry to assess for the presence of human CD45 positive cells in the peripheral blood, bone marrow, and spleen of the xenochimeric mice eight weeks after transplantation.

Results

As shown in FIGS. 18, 19 and 20, accelerated development of human cells was seen in the peripheral blood (FIG. 18), bone marrow (FIG. 19), and spleen (FIG. 20) of xenochimeric NOD/SCID/βc$^{-/-}$ mice treated with TAT-MYC following xenotransplantation of human fresh fetal cord blood cells. Cohorts of NOD/SCID/βc$^{-/-}$ mice were given a sub-lethal dose of radiation followed by 5×10$^5$ cord blood cells (FIGS. 18A and 18D; FIGS. 19A and 19D; FIGS. 20A and 20D), 1×10$^6$ (FIGS. 18B and 18E; FIGS. 19B and 19E; FIGS. 20B and 20E), or 5×10$^6$ (FIGS. 18C and 18F; FIGS. 19C and 19E; FIGS. 20C and 20E). 24 hours after the transplant, half of the mice in each cohort were injected with TAT-MYC (FIGS. 18D, 18E, and 18F; FIGS. 19D, 19E, and 19F; FIGS. 20D, 20E, and 20F) and the other half were injected with a control protein, TAT-CRE (FIGS. 18A, 18B, and 18C; FIGS. 19A, 19B, and 19C; FIGS. 20A, 20B, and 20C)

FIG. 18 shows that control, sub-lethally irradiated NOD/SCID/βc$^{-/-}$ mice, treated with TAT-CRE following xenotransplantation with human whole cord blood cells, had in their peripheral blood at eight weeks, 0% of CD45$^+$ cells after transplantation of 5×10$^5$ cells (FIG. 18A), 0.2% of CD45$^+$ cells (FIG. 18B) after transplantation of 1×10$^6$ cells, and 0.7% of CD45$^+$ cells (FIG. 18C) after transplantation of 5×10$^6$ cells. Sub-lethally irradiated NOD/SCID/βc$^{-/-}$ mice treated with TAT-MYC following xenotransplantation with human whole cord blood cells, had in their peripheral blood at eight weeks, 0.09% of CD45$^+$ cells after transplantation of 5×10$^5$ cells (FIG. 18D), 0.1% of CD45$^+$ cells (FIG. 18E) after transplantation of 1×10$^6$ cells, and 9.3% of CD45$^+$ cells (FIG. 18F) after transplantation of 5×10$^6$ cells. Accordingly, FIG. 18F shows the detection of human T-cells (hCD45 positive cells) in the peripheral blood of chimeric mice 8 weeks post-transplant. As the average time to T-cell recovery is 12-20 weeks, this represents an acceleration of about 33-60%.

FIG. 19 shows that control, sub-lethally irradiated NOD/SCID/βc$^{-/-}$ mice, treated with TAT-CRE following xenotransplantation with human whole cord blood cells, had in their bone marrow at eight weeks, 0.02% of CD45$^+$ cells after transplantation of 5×10$^5$ cells (FIG. 19A), 7.7% of CD45$^+$ cells (FIG. 19B) after transplantation of 1×10$^6$ cells, and 11.3% of CD45$^+$ cells (FIG. 19C) after transplantation of 5×10$^6$ cells. Sub-lethally irradiated NOD/SCID/βc$^{-/-}$ mice treated with TAT-MYC following xenotransplantation with human whole cord blood cells, had in their bone marrow at eight weeks, 0.04% of CD45$^+$ cells after a transplantation of 5×10$^5$ cells (FIG. 19D), 8.6% of CD45$^+$ cells (FIG. 19E) after a transplantation of 1×10$^6$ cells, and 20.7% of CD45$^+$ cells (FIG. 19F) after a transplantation of 5×10$^6$ cells.

FIG. 20 shows that control, sub-lethally irradiated NOD/SCID/γc$^{-/-}$ mice, treated with TAT-CRE following xenotransplantation with human whole cord blood cells, had in their spleen at eight weeks, 0.9% of CD45$^+$ cells after transplantation of 5×10$^5$ cells (FIG. 20A), 13.9% of CD45$^+$ cells (FIG. 20B) after transplantation of 1×10$^6$ cells, and 27.6% of CD45$^+$ cells (FIG. 20C) after transplantation of 5×10$^6$ cells. Sub-lethally irradiated NOD/SCID/βc$^{-/-}$ mice treated with TAT-MYC following xenotransplantation with human whole cord blood cells, had in their spleen at eight weeks, 1.2% of CD45$^+$ cells after transplantation of 5×10$^5$ cells (FIG. 20D), 4.9% of CD45$^+$ cells (FIG. 20E) after transplantation of 1×10$^6$ cells, and 258% of CD45$^+$ cells (FIG. 20F) after transplantation of 5×10$^6$ cells.

Example 8: Accelerated Hematopoietic Reconstitution In Mice Transplanted with Human Freshly Isolated Cord Blood Cells Pretreated with TAT-MYC and TAT-Bcl-2

The following example describes the results of pre-treating fresh human cord blood cells with TAT-MYC and TAT-Bcl-2 prior to transplantation into mice.

Materials and Methods

Human cord blood cells were obtained and prepared as described in Example 6. Briefly, the cord blood was separated using Ficoll-hypaque and centrifugation to obtain the buffy coat fraction. Buffy coat cells were removed, washed twice, and then resuspended in PBS.

Prior to injection into mice, the isolated cord blood cells were exposed to 5 μg/ml TAT-MYC and 5 μg/ml TAT-Bcl-2 for one hour. After exposure to the fusion proteins, the cells were washed twice with PBS, then resuspended in PBS at 5×10$^6$ cells per 200 ul, and kept cold until injected into mice.

Prior to injecting NOD/SCID/βc$^{-/-}$ (NOG) mice with the FCB cells, the mice were irradiated with 180 Rads (whole body irradiation). Each recipient mouse was then given a transplant consisting of 5×10$^6$ human FCB cells in 200 ul PBS via tail vein injection.

Engraftment was monitored with flow cytometry to assess the presence of CD45 positive cells in the peripheral blood of the xenochimeric mice. The first bleed was done 8 weeks after the FCB transplant.

After eight months, the mice were euthanized and the bone marrow cells were collected from the tibia and femur bones of the xenochimaeric NSG mice. The spleen and thymus were also harvested, and were made into single cell suspensions by pressing the cells through a sterile wire mesh screen. The red blood cells from the BM, spleen and thymus were lysed in 5 ml sterile TAC buffer (135 mM NH$_4$CL, 17 mM Tris Ph 7.65) followed by 2 washes in D10 media. The BM, spleen cells and thymus cells were prepared for FACs analysis to assess the presence of human CD45 positive cells.

Results

FIGS. 21 and 22 show that pre-treatment of human fresh whole cord blood cells with TAT-MYC for one hour prior to transplantation in NOD/SCID/γc$^{-/-}$ (NOG) mice resulted in accelerated development of human CD45 cells in the peripheral blood of the mice, as well as increased longterm persistence of human CD45 cells in the bone marrow, spleen and thymus of the mice. Cohorts of NOD/SCID/γc$^{-/-}$ mice were given a sub-lethal dose of radiation followed by 5×10$^6$ cord blood cells. For half of the mice in each cohort, the cells were pre-treated with 5 μg/ml TAT-MYC and 5 μg/ml TAT-Bcl-2 in FCB media (FIG. 21B; FIGS. 22B, 22D, and 22F); for the other half of the mice in the cohort, the cells were pre-treated in FCB media alone (FIG. 21A; FIGS. 22A, 22C, and 22E).

FIG. 21 shows that control, sub-lethally irradiated NOD/SCID/γc$^{-/-}$ mice, xenotransplanted with human whole cord blood cells pre-treated with FCB media alone, had in their peripheral blood at eight weeks, 0.89% CD45$^+$ cells (FIG. 21A). In contrast, sub-lethally irradiated NOD/SCID/γc$^{-/-}$ mice, xenotransplanted with human whole cord blood cells pre-treated with 5 μg/ml TAT-MYC and 5 μg/ml TAT-Bcl-2 in FCB media, had in their peripheral blood at eight weeks, 15.7% CD45$^+$ cells (FIG. 21B).

FIG. 22 shows that control, sub-lethally irradiated NOD/SCID/γc$^{-/-}$ mice, xenotransplanted with human whole cord blood cells pre-treated with FCB media alone, had at eight months in their bone marrow, 0.04% CD45$^-$ cells (FIG. 22A), in their spleen 0.03% CD45$^+$ cells (FIG. 22C), and in their thymus, 0.5% CD45$^+$ cells (FIG. 22E). In contrast, sub-lethally irradiated NOD/SCID/γc$^{-/-}$ mice, xenotransplanted with human whole cord blood cells pre-treated with 5 μg/ml TAT-MYC and 5 μg/ml TAT-Bcl-2 in FCB media, had at eight months in their bone marrow, 0.37% CD45$^+$ cells (FIG. 22B), in their spleen 25.2% CD45$^+$ cells (FIG. 22D), and in their thymus, 5.4% CD45$^+$ cells (FIG. 22F).

In other experiments, 5 μg/ml TAT-MYC and 5 μg/ml TAT-Bcl-2 are used to pre-treat separate populations of human cord blood cells prior to being transplanted into different cohorts of NOG mice. The inventors expect that separate incubation of cells with TAT-MYC and TAT-Bcl-2 will still afford better engraftment and reconstitution results than transplantation of the same cells without pre-treatment.

Example 9: Accelerated Engraftment with Human G-CSF Mobilized Peripheral Blood HSCs Cultured with Tat-Myc and Tat-Bcl-2

G-CSF mobilized cells were received in a 1 ml volume of elutriated blood from 5 patients who underwent G-CSF mobilization for autologous HSC transplantation. All G-CSF samples were de-identified and no further identifying information is associated with the cells used for these studies. The cells were added drop wise to 10 ml of FCB media. The cells were washed twice in FCB media and treated with 5 µg/ml recombinant Tat-Myc and 5 µg/ml recombinant Tat-Bcl-2 in a 10 ml volume. Cells were cultured for 12 days The cells were expanded in media supplemented with cytokines plus Tat-Myc and Tat-Bcl2 for 12 days. On the $12^{th}$ day half of the cells received an additional treatment with 5 µg/ml Tat-MYC and 5 µg/ml Tat-Bcl2. The other half of the cells were left in FCB media alone. The cells were incubated for 60 minutes in a 37° incubator. The cells were washed three times in PBS, and were resuspended at $5 \times 10^6$ cells per 200 ul. Engraftment was monitored with flow cytometry to assess the presence of CD45 positive cells in the peripheral blood of the xenochimeric mice. The first bleed was done 8 weeks after the HSC transplant.

FIG. 23A shows a FACS analysis of the $CD45^+$ staining of the peripheral blood from control NSG (FIG. 23A), NSG mice transplanted 8 weeks earlier with either $1 \times 10^6$ expanded G-CSF mobilized HSCs (FIG. 23B) or $1 \times 10^6$ expanded G-CSF mobilized HSC treated with Tat-Myc/Tat-Bcl-2 (FIG. 23C). As shown for the peripheral blood, the inventors expect that the BM, spleen and thymus from mice engrafted with G-CSF mobilized cells pretreated with TAT-MYC and TAT-Bcl-2 will afford better engraftment and reconstitution results than transplantation of the same cells without pre-treatment.

Example 10: Accelerated Hematopoietic Reconstitution In Mice Treatment with TAT-MYC Following Transplantation with Human G-CSF Mobilized Cells Pretreated with TAT-MYC and TAT-Bcl-2

The following example describes the results of pre-treating human G-CSF mobilized cells with TAT-MYC and TAT-Bcl-2 prior to transplantation into mice, and then followed by treatment of the mice with TAT-MYC 24 hours later.

Materials and Methods

G-CSF mobilized cells were received in a 1 ml volume of elutriated blood from 5 patients who underwent G-CSF mobilization for autologous HSC transplantation. All G-CSF samples were de-identified and no further identifying information was associated with the cells used for these studies. The cells were added drop wise to 10 ml of FCB media. The cells were washed twice in FCB media and treated with 5 µg/ml recombinant Tat-Myc and 5 µg/ml recombinant Tat-Bcl-2 in a 10 ml volume. The cells were cultured for 12 days.

On Day 12, the expanded G-CSF mobilized cells received a second treatment of 5 µg/ml TAT-MYC and 5 µg/ml TAT-Bcl2 for hour prior to injecting into NSG mice. The cells were washed 3 times with PBS and then injected at $5 \times 10^6$ cell per mouse in 200 µl PBS via the tail vein. Prior to injecting NOD/SCID/$\gamma c^{-/-}$ (NOG) mice with the HSC cells, the mice were irradiated with 180 Rads (whole body irradiation). 24 hours post injection with the expanded HSCs, the mice received 10 µg of Tat-MYC or 10 µg Tat-Cre in corn oil intramuscularly, or no injection. Eight weeks later the mice were bled.

Engraftment was monitored with flow cytometry to assess the presence of CD45 positive cells in the peripheral blood of the xenochimeric mice. The first bleed was done 8 weeks after the HSC transplant.

After eight weeks, the mice are euthanized and the bone marrow cells are collected from the tibia and femur bones of the xenochimaeric NSG mice. The spleen and thymus are also harvested, and are made into single cell suspensions by pressing the cells through a sterile wire mesh screen. The red blood cells from the BM, spleen and thymus are lysed in 5 ml sterile TAC buffer (135 mM $NH_4CL$, 17 mM Tris Ph 7.65) followed by 2 washes in D10 media. The BM, spleen cells and thymus cells are prepared for FACs analysis to assess the presence of human CD45 positive cells.

Results

The data indicate that injection of TAT-MYC 24 hours after transplantation of HSCs pre-treated with TAT-MYC and TAT-Bcl-2 for one hour prior to transplantation in NOD/SCID/$\gamma c^{-/-}$ (NOG) mice did not appear to accelerate development of human CD45 cells in the peripheral blood of the mice, as compared with control mice injected with TAT-CRE or with no Tat-fusion protein injection, but also transplanted with HSCs pre-treated with TAT-MYC and TAT-Bcl2.

At eight weeks, the data show no difference between mice treated with TAT-MYC and TAT-CRE in the levels of CD45+ cells in the peripheral blood. Further investigation is needed to determine if an effect exists at earlier or later time points, or in the BM, spleen, and thymus. At this point, the data indicate that pretreating the cells with TAT-MYC may work just as well as injecting the mice with TAT-MYC after transplant. To date, we have not observed an increased effect by pretreating the cells and also injecting the mice with Tat-MYC after the transplant of treated cells.

Example 11: Generation of Biologically Active Tat-Myc and Tat-Bcl-2 Fusion Proteins Fusion proteins having the HIV-1 Tat protein transduction domain (PTD) and either the ORF for human Myc, or a truncated form of human Bcl-2, that has been deleted for the unstructured loop domain (Anderson, M., et al. (1999). Prot Expr. Purif. 15, 162-70), were generated. The recombinant proteins also encoded a V5 peptide tag and a 6-His tag, to facilitate detection and purification (FIG. 24 and FIG. 25).

pTAT-Myc-V5-6×His ($Amp^R$) and pTAT-Bcl2Δ-V5-6× His($Amp^R$):

plasmid were generated by PCR amplification of a cDNA encoding human cMyc or human Bcl2 using a forward primer encoding an in frame TAT protein transduction domain of HIV (RKKRRQRRR) (SEQ ID NO: 5). The PCR products were cloned into pET101/D-Topo (Invitrogen) vector. The unstructured loop (A.A. #27-80) was removed from the BCL-2 coding sequence using a Quick Change site directed mutagenesis kit (Stratagene #200521-5).

The proteins were synthesized in *E. coli* and purified to homogeneity. SDS-PAGE electrophoresis and Coomassie Staining revealed the level of purity of the final product used for our studies (FIG. 1B). pTAT-Myc-V5-6×His was transformed into BL21-STAR(DE3) cells (Invitrogen) and protein was induced with 0.5 mM IPTG at 37° C. for 3 hrs. The cells were lysed in lysis buffer (8 M urea, 100 mM NaH2PO4, 10 mM Tris pH to 7.0, 10 mM imidazole, pH 7.2). The lysate was diluted to 6M urea and brought to 450 mM NaCl, 50 mM NaH$_2$PO$_4$, 5 mM Tris pH 7.0. The lysate was treated with Benzonase (500 units) at room temp for 1 hour, clarified by centrifugation at 12,000 RPM for 60 min and filtered through a 0.22 μM filter. Myc-V5-6×His was purified on a nickel affinity column (GE) using a GE AKTA purifier 10 FPLC. Myc-V5-6×His was refolded by dialyzing into dialysis buffer (450 mM NaCl, 50 mM NaH$_2$PO$_4$, 5 mM Tris pH 7.0, 5% glycerol, 1 mM DTT). Endotoxin was reduced by passing the purified protein over an Acticlean Etox column (Sterogen).

Bcl2Δ-V5-6×His protein was induced as described above. The cells were lysed in 50 mL of lysis buffer (200 mM NaCl, 200 mM KCL, 50 mM NaH$_2$PO$_4$, 5 mM Tris pH 7.0, 5% glycerol, 1 mM DTT) supplemented with 500 units Benzonase, 1 mM PMSF, 2 μg/ml Leupeptin, 0.015 units/ml Aprotinin, 5 uM Hen Egg Lysozyme (HEL) per 1 L of induced protein, and immediately placed on ice for 1 hour. The cells were sonicated on ice (Duty cycle=50%, Output=5) for 2 sets of 2 minutes. The lysate was cleared by centrifugation at 12,000 RPM for 60 min and was filtered through a 0.22 μM filter. Bcl2Δ-V5-6×His was purified on a nickel affinity column (GE) and endotoxin was removed as described above.

The invention claimed is:

1. A method of enhancing hematopoietic compartment reconstitution in a subject suffering from a decrease in the amount of endogenous hematopoietic stem cells comprising:
administering a therapeutically effective amount of a composition comprising a MYC-composition, a Bcl-2-composition, or both, to a subject suffering from a decrease in the amount of endogenous hematopoietic stem cells, wherein the MYC composition and the Bcl-2 composition each comprises a protein transduction domain (PTD), and wherein hematopoietic compartment reconstitution is enhanced compared to hematopoietic compartment reconstitution in a subject that is not administered the composition.

2. The method of claim 1, wherein the decrease in the amount of endogenous hematopoietic stem cells is due to bone marrow failure syndrome.

3. The method of claim 1, wherein the decrease in the amount of endogenous hematopoietic stem cells is due to chemotherapy or radiation therapy.

4. The method of claim 1, wherein the subject has cancer.

5. The method of claim 1, wherein the subject has a hematological malignancy, a myeloma, multiple myeloma, a leukemia, acute lymphoblastic leukemia, chronic lymphocytic leukemia, a lymphoma, indolent lymphoma, non-Hodgkin lymphoma, diffuse B cell lymphoma, follicular lymphoma, mantle cell lymphoma, T cell lymphoma, Hodgkin lymphoma, a neuroblastoma, a retinoblastoma, Shwachman Diamond syndrome, a brain tumor, Ewing's Sarcoma, a Desmoplastic small round cell tumor, a relapsed germ cell tumor, a hematological disorder, a hemoglobinopathy, an autoimmune disorder, juvenile idiopathic arthritis, systemic lupus erythematosus, severe combined immunodeficiency, congenital neutropenia with defective stem cells, severe aplastic anemia, a sickle-cell disease, a myelodysplasia syndrome, chronic granulomatous disease, a metabolic disorder, Hurler syndrome, Gaucher disease, osteopetrosis, malignant infantile osteopetrosis, heart disease, HIV, or AIDS.

6. The method of claim 1, wherein the subject has received an organ transplant.

7. The method of claim 1, wherein the subject has received a hematopoietic stem cell (HSC) transplant.

8. The method of claim 7, wherein the HSC transplant is autologous HSC transplant or an allogenic HSC transplant.

9. The method of claim 1, wherein the subject has received a myeloablative HSC transplantation procedure.

10. The method of claim 1, wherein the subject has received a non-myeloablative HSC transplantation procedure.

11. The method of claim 1, wherein the MYC-composition is a PTD-MYC fusion protein.

12. The method of claim 11, wherein the MYC-composition is a TAT-MYC fusion protein.

13. The method of claim 1, further comprising administering a therapeutically effective amount of a second composition comprising hematopoietic stem cells (HSCs) to achieve hematopoietic compartment reconstitution in the subject.

14. The method of claim 13, wherein the composition comprising a MYC-composition is administered before, after, or concurrently with the administering of the second composition.

15. The method of claim 13, wherein the composition comprising a MYC-composition is administered at least 1 day after the administering of the second composition.

16. The method of claim 13, wherein the second composition comprising HSCs was cultured in the presence of a MYC-composition, a Bcl-2-composition, or both before the administering of the second composition.

17. The method of claim 13, wherein the second composition comprises conditionally immortalized hematopoietic stem cells (HSCs).

18. The method of claim 1, wherein the enhanced hematopoietic compartment autoreconstitution in the subject results in enhanced T cell compartment autoreconstitution, enhanced B cell compartment autoreconstitution, enhanced NK-cell compartment autoreconstitution, enhanced myeloid cell compartment autoreconstitution, or neutrophil recovery.

19. The method of claim 1, wherein hematopoietic compartment reconstitution is accelerated compared to hematopoietic compartment reconstitution in a subject that is not administered the composition.

20. The method of claim 19, wherein administering the composition comprising a MYC-composition, a Bcl-2-composition, or both achieves an at least 50% acceleration in hematopoietic compartment reconstitution compared to hematopoietic compartment reconstitution in a subject that is not administered the composition.

* * * * *

SEQUENCE LISTING

```
<160> NUMBER OF SEQ ID NOS: 5

<210> SEQ ID NO 1
<211> LENGTH: 477
<212> TYPE: PRT
<213> ORGANISM: Artificial Sequence
<220> FEATURE:
<223> OTHER INFORMATION: Synthetic Construct

<400> SEQUENCE: 1

Met Arg Lys Lys Arg Gln Arg Arg Met Pro Leu Asn Val Ser
 1               5                  10                  15

Phe Thr Asn Arg Asn Tyr Asp Leu Asp Tyr Asp Ser Val Gln Pro Tyr
                 20                  25                  30

Phe Tyr Cys Asp Glu Glu Glu Asn Phe Tyr Gln Gln Gln Gln Gln Ser
             35                  40                  45

Glu Leu Gln Pro Pro Ala Pro Ser Glu Asp Ile Trp Lys Lys Phe Glu
         50                  55                  60

Leu Leu Pro Thr Pro Pro Leu Ser Pro Ser Arg Arg Ser Gly Leu Cys
 65                  70                  75                  80

Ser Pro Ser Tyr Val Ala Val Thr Pro Phe Ser Leu Arg Gly Asp Asn
                 85                  90                  95

Asp Gly Gly Gly Gly Ser Phe Ser Thr Ala Asp Gln Leu Glu Met Val
            100                 105                 110

Thr Glu Leu Leu Gly Gly Asp Met Val Asn Gln Ser Phe Ile Cys Asp
        115                 120                 125

Pro Asp Asp Glu Thr Phe Ile Lys Asn Ile Ile Ile Gln Asp Cys Met
    130                 135                 140

Trp Ser Gly Phe Ser Ala Ala Ala Lys Leu Val Ser Glu Lys Leu Ala
145                 150                 155                 160

Ser Tyr Gln Ala Ala Arg Lys Asp Ser Gly Ser Pro Asn Pro Ala Arg
                165                 170                 175

Gly His Ser Val Cys Ser Thr Ser Ser Leu Tyr Leu Gln Asp Leu Ser
            180                 185                 190

Ala Ala Ala Ser Glu Cys Ile Asp Pro Ser Val Val Phe Pro Tyr Pro
        195                 200                 205

Leu Asn Asp Ser Ser Ser Pro Lys Ser Cys Ala Ser Gln Asp Ser Ser
    210                 215                 220

Ala Phe Ser Pro Ser Ser Asp Ser Leu Leu Ser Ser Thr Glu Ser Ser
225                 230                 235                 240

Pro Gln Gly Ser Pro Glu Pro Leu Val Leu His Glu Glu Thr Pro Pro
                245                 250                 255

Thr Thr Ser Ser Asp Ser Glu Glu Glu Gln Glu Asp Glu Glu Glu Ile
```

```
                     260                 265                 270
Asp Val Val Ser Val Glu Lys Arg Gln Ala Pro Gly Lys Arg Ser Glu
                275                 280                 285

Ser Gly Ser Pro Ser Ala Gly Gly His Ser Lys Pro Pro His Ser Pro
        290                 295                 300

Leu Val Leu Lys Arg Cys His Val Ser Thr His Gln His Asn Tyr Ala
305                 310                 315                 320

Ala Pro Pro Ser Thr Arg Lys Asp Tyr Pro Ala Ala Lys Arg Val Lys
                325                 330                 335

Leu Asp Ser Val Arg Val Leu Arg Gln Ile Ser Asn Asn Arg Lys Cys
        340                 345                 350

Thr Ser Pro Arg Ser Ser Asp Thr Glu Glu Asn Val Lys Arg Arg Thr
                355                 360                 365

His Asn Val Leu Glu Arg Gln Arg Arg Asn Glu Leu Lys Arg Ser Phe
370                 375                 380

Phe Ala Leu Arg Asp Gln Ile Pro Glu Leu Glu Asn Asn Glu Lys Ala
385                 390                 395                 400

Pro Lys Val Val Ile Leu Lys Lys Ala Thr Ala Tyr Ile Leu Ser Val
                405                 410                 415

Gln Ala Glu Glu Gln Lys Leu Ile Ser Glu Glu Asp Leu Leu Arg Lys
                420                 425                 430

Arg Arg Glu Gln Leu Lys His Lys Leu Glu Gln Leu Arg Lys Gly Glu
        435                 440                 445

Leu Asn Ser Lys Leu Glu Gly Lys Pro Ile Pro Asn Pro Leu Leu Gly
        450                 455                 460

Leu Asp Ser Thr Arg Thr Gly His His His His His His
465                 470                 475

<210> SEQ ID NO 2
<211> LENGTH: 1299
<212> TYPE: DNA
<213> ORGANISM: Artificial Sequence
<220> FEATURE:
<223> OTHER INFORMATION: Synthetic Construct

<400> SEQUENCE: 2
atgaggaaga agcggagaca gcgacgaaga atgcccctca acgttagctt caccaacagg     60
aactatgacc tcgactacga ctcggtgcag ccgtatttct actgcgacga ggaggagaac    120
ttctaccagc agcagcagca gagcgagctg cagcccccgg cgcccagcga ggatatctgg    180
aagaaattcg agctgctgcc caccccgccc ctgtccccta gccgccgctc cgggctctgc    240
tcgccctcct acgttgcggt cacacccttc tcccttcggg agacaacga cggcggtggc    300 gggagcttct ccacggccga ccagctggag atggtgaccg agctgctggg aggagacatg    360
gtgaaccaga gtttcatctg cgacccggac gacgagacct tcatcaaaaa catcatcatc    420
caggactgta tgtggagcgg cttctcggcc gccgccaagc tcgtctcaga gaagctggcc    480
tcctaccagg ctgcgcgcaa agacagcggc agcccgaacc ccgcccgcgg ccacagcgtc    540
tgctccacct ccagcttgta cctgcaggat ctgagcgccg ccgcctcaga gtgcatcgac    600
ccctcggtgg tcttccccta ccctctcaac gacagcagct cgcccaagtc ctgcgcctcg    660
caagactcca gcgccttctc tccgtcctcg gattctctgc tctcctcgac ggagtcctcc    720
ccgcagggca gccccgagcc cctggtgctc catgaggaga caccgcccac caccagcagc    780
gactctgagg aggaacaaga agatgaggaa gaaatcgatg ttgtttctgt ggaaaagagg    840
```

```
caggctcctg gcaaaaggtc agagtctgga tcaccttctg ctggaggcca cagcaaacct    900
cctcacagcc cactggtcct caagaggtgc cacgtctcca cacatcagca caactacgca    960
gcgcctccct ccactcggaa ggactatcct gctgccaaga gggtcaagtt ggacagtgtc   1020
agagtcctga cagatcag caacaaccga aaatgcacca gccccaggtc ctcggacacc    1080
gaggagaatg tcaagaggcg aacacacaac gtcttggagc gccagaggag gaacgagcta   1140
aaacggagct tttttgccct gcgtgaccag atcccggagt tggaaaacaa tgaaaaggcc   1200
cccaaggtag ttatccttaa aaaagccaca gcatacatcc tgtccgtcca agcagaggag   1260
caaaagctca tttctgaaga ggacttgttg cggaaacga                          1299
```

<210> SEQ ID NO 3
<211> LENGTH: 235
<212> TYPE: PRT
<213> ORGANISM: Artificial Sequence
<220> FEATURE:
<223> OTHER INFORMATION: Synthetic Construct

<400> SEQUENCE: 3

```
Met Arg Lys Lys Arg Gln Arg Arg Met Ala His Ala Gly Arg
1               5                   10                  15

Ser Gly Tyr Asp Asn Arg Glu Ile Val Met Lys Tyr Ile His Tyr Lys
            20                  25                  30

Leu Ser Gln Arg Ala Thr Ser Gly Ile Ser Ile Glu Ala Ala Gly Pro
        35                  40                  45

Ala Leu Ser Pro Val Pro Pro Val Val His Leu Thr Leu Arg Gln Ala
    50                  55                  60

Gly Asp Asp Phe Ser Arg Arg Tyr Arg Arg Asp Phe Ala Glu Met Ser
65                  70                  75                  80

Ser Gln Leu His Leu Thr Pro Phe Thr Ala Arg Gly Cys Phe Ala Thr
                85                  90                  95

Val Val Glu Glu Leu Phe Arg Asp Gly Val Asn Trp Gly Arg Ile Val
            100                 105                 110

Ala Phe Phe Glu Phe Gly Gly Val Met Cys Val Glu Ser Val Asn Arg
        115                 120                 125

Glu Met Ser Pro Leu Val Asp Asn Ile Ala Leu Trp Met Thr Glu Tyr
    130                 135                 140

Leu Asn Arg His Leu His Thr Trp Ile Gln Asp Asn Gly Gly Trp Asp
145                 150                 155                 160

Ala Phe Val Glu Leu Tyr Gly Pro Ser Met Arg Pro Leu Phe Asp Phe
                165                 170                 175

Ser Trp Leu Ser Leu Lys Thr Leu Leu Ser Leu Ala Leu Val Gly Ala
            180                 185                 190

Cys Ile Thr Leu Gly Ala Tyr Leu Ser His Lys Lys Gly Glu Leu Asn
        195                 200                 205

Ser Lys Leu Glu Gly Lys Pro Ile Pro Asn Pro Leu Leu Gly Leu Asp
    210                 215                 220

Ser Thr Arg Thr Gly His His His His His
225                 230                 235
```

<210> SEQ ID NO 4
<211> LENGTH: 708
<212> TYPE: DNA
<213> ORGANISM: Artificial Sequence
<220> FEATURE:
<223> OTHER INFORMATION: Synthetic Construct

```
<400> SEQUENCE: 4
atgaggaaga agcggagaca gcgacgaaga atggcgcacg ctgggagaag tggttacgat         60
aaccgggaga tagtgatgaa gtacatccat tataagctgt cgcagagggc tacgagtggg        120
atctcgatcg aggccgcggg gcctgcgctc agcccggtgc cacctgtggt ccacctgacc        180
ctccgccagg ccggcgacga cttctcccgc cgctaccgcc gcgacttcgc cgagatgtcc        240
agccagctgc acctgacgcc cttcaccgcg cggggatgct ttgccacggt ggtggaggag        300
ctcttcaggg acggggtgaa ctgggggagg attgtggcct tctttgagtt cggtggggtc        360
atgtgtgtgg agagcgtcaa ccgggagatg tcgcccctgg tggacaacat cgccctgtgg        420
atgactgagt acctgaaccg gcacctgcac acctggatcc aggataacgg aggctgggat        480
gcctttgtgg aactgtacgg ccccagcatg cggcctctgt ttgatttctc ctggctgtct        540
ctgaagactc tgctcagttt ggccctggtg ggagcttgca tcaccctggg tgcctatctg        600
agccacaaga agggcgagct caattcgaag cttgaaggta agcctatccc taaccctctc        660
ctcggtctcg attctacgcg taccggtcat catcaccatc accattga                     708

<210> SEQ ID NO 5
<211> LENGTH: 9
<212> TYPE: PRT
<213> ORGANISM: Artificial Sequence
<220> FEATURE:
<223> OTHER INFORMATION: Synthetic Construct

<400> SEQUENCE: 5

Arg Lys Lys Arg Arg Gln Arg Arg Arg
 1               5
```